(12) United States Patent
Charlton et al.

(10) Patent No.: US 9,115,129 B2
(45) Date of Patent: Aug. 25, 2015

(54) SUBSTITUTED PYRIDO[2,3-B]PYRAZINES AS IP RECEPTOR AGONISTS

(71) Applicants: Steven John Charlton, Horsham (GB); Catherine Leblanc, Basel (CH); Stephen Carl McKeown, Hitchin (GB)

(72) Inventors: Steven John Charlton, Horsham (GB); Catherine Leblanc, Basel (CH); Stephen Carl McKeown, Hitchin (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/371,585

(22) PCT Filed: Jan. 11, 2013

(86) PCT No.: PCT/IB2013/050282
§ 371 (c)(1),
(2) Date: Jul. 10, 2014

(87) PCT Pub. No.: WO2013/105065
PCT Pub. Date: Jul. 18, 2013

(65) Prior Publication Data
US 2014/0357642 A1    Dec. 4, 2014

Related U.S. Application Data

(60) Provisional application No. 61/586,436, filed on Jan. 13, 2012.

(51) Int. Cl.
*A61K 31/4985* (2006.01)
*C07D 487/04* (2006.01)
*C07D 471/04* (2006.01)

(52) U.S. Cl.
CPC .......... *C07D 471/04* (2013.01); *A61K 31/4985* (2013.01)

(58) Field of Classification Search
CPC ........................ A61K 31/4985; C07D 487/04

USPC ................. 514/249; 544/350; 546/199, 268.1
See application file for complete search history.

(56) References Cited

U.S. PATENT DOCUMENTS

| | | | |
|---|---|---|---|
| 8,754,085 B2 | 6/2014 | Charlton |
| 8,937,069 B2 | 1/2015 | Adcock |
| 2010/0280041 A1 | 11/2010 | Chen |
| 2014/0243346 A1 | 8/2014 | Charlton |
| 2014/0357641 A1 | 12/2014 | Bhalay |
| 2014/0378463 A1 | 12/2014 | Leblanc |
| 2015/0005311 A1 | 1/2015 | Charlton |
| 2015/0011555 A1 | 1/2015 | Leblanc |

FOREIGN PATENT DOCUMENTS

| | | | |
|---|---|---|---|
| WO | 2007/017096 | | 2/2007 |
| WO | 2010/008864 | | 1/2010 |
| WO | 2012/007539 | | 1/2012 |
| WO | 2013/105057 | | 7/2013 |
| WO | 2013/105058 | | 7/2013 |
| WO | 2013/105061 | | 7/2013 |
| WO | 2013/105063 | | 7/2013 |
| WO | 2013/105066 | | 7/2013 |
| WO | WO 2013/105065 | * | 7/2013 |
| WO | 2014/125413 | | 8/2014 |

OTHER PUBLICATIONS

Jordan, V. C. Nature Reviews: Drug Discovery, 2, 2003, 205.*
Hackam, et al. JAMA, 296(14), 2006, 1731-1732.*

* cited by examiner

*Primary Examiner* — Douglas M Willis
(74) *Attorney, Agent, or Firm* — Shawn Britt

(57) ABSTRACT

The present invention provides substituted pyrido[2,3-b]pyrazines which activate the IP receptor. Activating the IP receptor signaling pathway is useful to treat many forms of PAH, pulmonary fibrosis and exert beneficial effects in fibrotic conditions of various organs in animal models and in patients. Pharmaceutical compositions comprising such substituted pyride[2,3-b]pyrazines are also encompassed.

7 Claims, No Drawings

SUBSTITUTED PYRIDO[2,3-B]PYRAZINES AS IP RECEPTOR AGONISTS

This application is a U.S. National Phase filing of international Application No. PCT/IB2013/050282 filed 11 Jan. 2013, which claims priority to U.S. Application No. 61/586,436 filed 13 Jan. 2012, the contents of which are incorporated herein by reference in their entirety.

BACKGROUND OF THE INVENTION

Prostacyclin (or PGI2) is a member of the family of lipid molecules known as eicosanoids. It is a potent vasodilator, antiproliferative, anti-thrombotic agent that mediates its effects as an agonist of the IP receptor. The IP receptor is a G-protein coupled receptor that, upon activation by prostacyclin, stimulates the formation of cyclic adenosine monophosphate (cAMP). Prostacyclin counteracts the vasoconstrictor and pro-thrombotic activity of endothelin.

Pulmonary arterial hypertension (PAH) is a life-threatening disease characterized by a progressive pulmonary vasculopathy leading to right ventricular hypertrophy. Exogenous administration of an agonist of the IP receptor has become an important strategy in the treatment of PAH. (See, e.g., Tuder et al., Am. J. Respir. Crit. Care. Med., 1999, 159: 1925-1932; Humbert et al, J. Am. Coll. Cardiol., 2004, 43:13S-24S; Rosenzweig, Expert Opin. Emerging Drugs, 2006, 11:609-619; McLaughlin et al, Circulation, 2006, 114:1417-1431; Rosenkranz, Clin. Res. Cardiol., 2007, 96:527-541; Driscoll et al, Expert Opin. Pharmacother., 2008, 9:65-81.).

The prostacyclin analogue epoprostenol (flolan) is at least as effective as transplantation in terms of survival. Despite this, it is not used as frontline therapy due to significant tolerability, convenience and cost issues. Instead, patients with PAH are often treated first with either endothelin receptor antagonists (e.g. bosentan) and/or PDE5 inhibitors (e.g. sildenafil), which are better tolerated but can have limited efficacy. Prostacyclin analogues are used mainly as add-on treatment as severity of the disease progresses and tolerability and convenience become less of an issue.

Two key issues prevent current prostacyclin analogues being used as frontline therapy in PAH. Firstly, they are very unstable with an extremely short half-life, meaning they must be constantly infused via an in-dwelling intra venous (i.v.) catheter that is both inconvenient for the patient and also associated with a significant risk of infection and sepsis. Secondly, they are associated with significant side effects including nausea, jaw pain, headache and other side effects associated with systemic hypotension.

One solution to these issues is iloprost, which is available as a nebulised formulation that has reduced tolerability issues, but the short half life results in a 6-9 times daily dosing regime. More recently, researchers made efforts to generate stable, orally available IP receptor agonists. These ligands would improve patient convenience and compliance, but high levels of systemic drug is required to achieve pharmacodynamic effects in the lung; thus, possibly generating similar side effects to those observed with i.v. flolan.

The present invention describes stable, highly selective IP receptor agonists that are suitable for oral and inhaled delivery. The present invention offers a significant improvement over existing prostacyclin analogues and enables their use in less-severe patients. In addition, long term activation of the IP receptor has been shown to reverse remodeling associated with PAH; therefore, earlier intervention with the present invention may have significant effects on disease progression and potentially may show reversal.

In addition, pharmaceutical research has considerable interest in developing IP receptor agonists for the treatment of pulmonary fibrosis. IP deficient mice have been shown to be more susceptible to bleomycin-induced lung fibrosis than wild-type animals (Lovgren A K et al. (2006) *Am J Physiol Lung Cell Mol Physiol.* 2911144-56), and the IP receptor agonist iloprost increases survival in bleomycin-treated mice (Zhu et al (2010) Respir. Res. 11(1):34).

Furthermore, IP receptor signaling has been shown to exert beneficial effects in fibrotic conditions of various organs in animal models and in patients. Benefits of IP receptor agonist were shown for fibrosis of the heart, lung, skin, pancreas and liver, and in systemic sclerosis. (Gayraud M (2007) *Joint Bone Spine.* 74(1):e1-8; Hirata Y et al (2009) *Biomed Pharmacother.* 63(10):781-6; Kaneshige T et al (2007) *J Vet Med Sci.* 69(12):1271-6; Sahsivar MO et al (2009) *Shock* 32(5): 498-502; Sato N et al (2010) *Diabetes* 59(4):1092-100; Shouval DS et al (2008) *Clin Exp Rheumatol.* 26(3 Suppl 49): S105-7; Spargias K et al (2009) *Circulation.* 120(18):1793-9; Stratton R et al (2001) *J Clin Invest.* 108(2):241-50; Takenaka M et al (2009) Prostaglandins Leukot Essent Fatty Acids. 80(5-6):263-7; Watanabe M et al (2009) *Am J Nephrol.* 30(1): 1-11; Yano T et al (2005) *Am J Pathol.* 166(5):1333-42; Zardi EM et al (2007) *Expert Opin Biol Ther.* 7(6):785-90; Zardi EM et al (2006) *In Vivo* 20(3):377-80; Rehberger P et al (2009) *Acta Derm Venereol.* 89(3):245-9). Fibrotic conditions can occur in most organs secondary to chronic inflammation indications throughout the body and are likely to share common causes.

Therefore, antifibrotic agents such as IP receptor agonists of the present invention are of potential benefit in all indications that are associated with fibrotic tissue remodeling.

There is considerable interest in developing agonists of the IP receptor for use in the treatment of other diseases, such as atherothrombosis, preeclampsia. It is highly desirable to develop a stable, inhaled agonists of the IP receptor, which may lead to improved management of PAH.

The invention pertains to the compounds as disclosed below, methods for using them, and uses thereof as described herein.

In a first aspect, there is provided a compound selected from the group consisting of
(rac)-6-(2,3-di-p-tolyl-5,6,7,8-tetrahydropyrido[2,3-b] pyrazin-6-yl)hexanoic acid or (S)-6-(2,3-di-p-tolyl-5,6,7,8-tetrahydropyrido[2,3-b]pyrazin-6-yl)hexanoic acid;
(R)-6-(2,3-di-p-tolyl-5,6,7,8-tetrahydropyrido[2,3-b] pyrazin-6-yl)hexanoic acid or (S)-6-(2,3-di-p-tolyl-5,6,7,8-tetrahydropyrido[2,3-b]pyrazin-6-yl)hexanoic acid;
(S)-6-(2,3-di-p-tolyl-5,6,7,8-tetrahydropyrido[2,3-b] pyrazin-6-yl)hexanoic acid; (rac)-7-(7-(2-Hydroxypropan-2-yl)-6-oxo-2,3-di-p-tolyl-7,8-dihydropyrido[2,3-b] pyrazin-5(6H)-yl)heptanoic acid;
(R)-7-(7-(2-hydroxypropan-2-yl)-6-oxo-2,3-di-p-tolyl-7,8-dihydropyrido[2,3-b]pyrazin-5(6H)-yl)heptanoic acid or (S)-7-(7-(2-hydroxypropan-2-yl)-6-oxo-2,3-di-p-tolyl-7,8-dihydropyrido[2,3-b]pyrazin-5(6H)-yl)heptanoic acid;
(S)-7-(7-(2-hydroxypropan-2-yl)-6-oxo-2,3-di-p-tolyl-7,8-dihydropyrido[2,3-b]pyrazin-5(6H)-yl)heptanoic acid or (S)-7-(7-(2-hydroxypropan-2-yl)-6-oxo-2,3-di-p-tolyl-7,8-dihydropyrido[2,3-b]pyrazin-5(6H)-yl)heptanoic acid;
7-(7-Ethyl-2,3-di-p-tolyl-7,8-dihydropyrido[2,3-b]pyrazin-5(6H)-yl)heptanoic acid;
7-(7-Methyl-2-phenyl-3-(p-tolyl)-7,8-dihydropyrido[2,3-b] pyrazin-5(6H)-yl)heptanoic acid;
(rac)-7-(6-Ethyl-2,3-di-p-tolyl-7,8-dihydropyrido[2,3-b] pyrazin-5(6H)-yl)heptanoic acid;

(R)-7-(6-Ethyl-2,3-di-p-tolyl-7,8-dihydropyrido[2,3-b]pyrazin-5(6H)-yl)heptanoic acid;
(S)-7-(6-Ethyl-2,3-di-p-tolyl-7,8-dihydropyrido[2,3-b]pyrazin-5(6H)-yl)heptanoic acid;
7-(6-Methyl-2-phenyl-3-p-tolyl-7,8-dihydropyrido[2,3-b]pyrazin-5(6H)-yl)heptanoic acid;
7-(3-o-Tolyl-2-p-tolyl-7,8-dihydropyrido[3,2-b]pyrazin-5(6H)-yl)heptanoic acid;
7-(2-o-Tolyl-3-p-tolyl-7,8-dihydropyrido[3,2-b]pyrazin-5(6H)-yl)heptanoic acid;
7-(2-(2-Fluorophenyl)-3-p-tolyl-7,8-dihydropyrido[2,3-b]pyrazin-5(6H)-yl)heptanoic acid;
7-(2-(4-Fluorophenyl)-3-p-tolyl-7,8-dihydropyrido[2,3-b]pyrazin-5(6H)-yl)heptanoic acid;
7-(2-(3-Fluorophenyl)-3-p-tolyl-7,8-dihydropyrido[2,3-b]pyrazin-5(6H)-yl)heptanoic acid;
7-(2-(4-Methoxyphenyl)-3-p-tolyl-7,8-dihydropyrido[2,3-b]pyrazin-5(6H)-yl)heptanoic acid;
(rac)-7-(8-Methoxy-2,3-di-p-tolyl-7,8-dihydropyrido[2,3-b]pyrazin-5(6H)-yl)heptanoic acid;
(R)-7-(8-methoxy-2,3-di-p-tolyl-7,8-dihydropyrido[2,3-b]pyrazin-5(6H)-yl)heptanoic acid;
(S)-7-(8-methoxy-2,3-di-p-tolyl-7,8-dihydropyrido[2,3-b]pyrazin-5(6H)-yl)heptanoic acid;
7-(2,3-Bis(2,4-difluorophenyl)-7,8-dihydropyrido[2,3-b]pyrazin-5(6H)-yl)heptanoic acid;
7-(2,3-Bis(6-methylpyridin-3-yl)-7,8-dihydropyrido[2,3-b]pyrazin-5(6H)-yl)heptanoic acid;
7-(2-(6-Methylpyridin-3-yl)-3-p-tolyl-7,8-dihydropyrido[2,3-b]pyrazin-5(6H)-yl)heptanoic acid;
7-(3-(6-Methylpyridin-3-yl)-2-p-tolyl-7,8-dihydropyrido[2,3-b]pyrazin-5(6H)-yl)heptanoic acid;
9-(6-Oxo-2,3-di-p-tolyl-7,8-dihydropyrido[2,3-b]pyrazin-5(6H)-yl)nonanoic acid;
9-(2,3-Di-p-tolyl-7,8-dihydropyrido[2,3-b]pyrazin-5(6H)-yl)nonanoic acid;
(rac)-7-(7-(2-hydroxypropan-2-yl)-2,3-di-p-tolyl-7,8-dihydropyrido[2,3-b]pyrazin-5(6H)-yl)heptanoic acid;
(R)-7-(7-(2-hydroxypropan-2-yl)-2,3-di-p-tolyl-7,8-dihydropyrido[2,3-b]pyrazin-5(6H)-yl)heptanoic acid;
(S)-7-(7-(2-hydroxypropan-2-yl)-2,3-di-p-tolyl-7,8-dihydropyrido[2,3-b]pyrazin-5(6H)-yl)heptanoic acid;
6-(2,3-Di-p-tolyl-7,8-dihydropyrido[2,3-b]pyrazin-5(6H)-yl)hexanoic acid;
(R)-7-(7-hydroxy-6-oxo-2,3-di-p-tolyl-7,8-dihydropyrido[2,3-b]pyrazin-5(6H)-yl)heptanoic acid;
(S)-7-(7-hydroxy-6-oxo-2,3-di-p-tolyl-7,8-dihydropyrido[2,3-b]pyrazin-5(6H)-yl)heptanoic acid; 8-(6-Oxo-2,3-di-p-tolyl-7,8-dihydropyrido[2,3-b]pyrazin-5(6H)-yl)octanoic acid;
7-(2,3-Di-p-tolyl-7,8-dihydropyrido[2,3-b]pyrazin-5(6H)-yl)-N-methoxyheptanamide;
7-(2,3-Di-p-tolyl-7,8-dihydropyrido[2,3-b]pyrazin-5(6H)-yl)-N,N-dimethylheptanamide;
7-(2,3-Di-p-tolyl-7,8-dihydropyrido[2,3-b]pyrazin-5(6H)-yl)-N-hydroxy-N-methylheptanamide;
6-(2,3-Di-p-tolyl-7,8-dihydropyrido[2,3-b]pyrazin-5(6H)-yl)-N-hydroxyhexanamide;
(R)-7-(8-Hydroxy-2,3-di-p-tolyl-7,8-dihydropyrido[3,2-b]pyrazin-5(6H)-yl)-N-(methylsulfonyl)heptanamide;
(S)-7-(8-Hydroxy-2,3-di-p-tolyl-7,8-dihydropyrido[3,2-b]pyrazin-5(6H)-yl)-N-(methylsulfonyl)heptanamide;
(R)—N-(Benzylsulfonyl)-7-(8-hydroxy-2,3-di-p-tolyl-7,8-dihydropyrido[3,2-b]pyrazin-5(6H)-yl)heptanamide;
(S)—N-(Benzylsulfonyl)-7-(8-hydroxy-2,3-di-p-tolyl-7,8-dihydropyrido[3,2-b]pyrazin-5(6H)-yl)heptanamide;
7-(2,3-Di-p-tolyl-7,8-dihydropyrido[2,3-b]pyrazin-5(6H)-yl)-N-(methylsulfonyl)heptanamide;
7-(7-Piperidin-1-yl)-2,3-di-p-tolyl-7,8-dihydropyrido[2,3-b]pyrazin-5(6H)-yl)heptanoic acid;
rac-7-(8-Methoxy-8-methyl-2,3-di-p-tolyl-7,8-dihydropyrido[2,3-b]pyrazin-5(6H)-yl)heptanoic acid;
7-(8-Hydroxy-8-methyl-2,3-di-p-tolyl-7,8-dihydropyrido[2,3-b]pyrazin-5(6H)-yl)heptanoic acid;
rac-7-(2,3-Di-p-tolyl-7,8-dihydropyrido[2,3-b]pyrazin-5(6H)-yl)-3-hydroxyheptanoic acid;
(R)-7-(8-Methoxy-8-methyl-2,3-di-p-tolyl-7,8-dihydropyrido[2,3-b]pyrazin-5(6H)-yl)heptanoic acid;
(S)-7-(8-Methoxy-8-methyl-2,3-di-p-tolyl-7,8-dihydropyrido[2,3-b]pyrazin-5(6H)-yl)heptanoic acid;
(R)-7-(2,3-di-p-tolyl-7,8-dihydropyrido[2,3-b]pyrazin-5(6H)-yl)-3-hydroxyheptanoic acid;
(S)-7-(2,3-di-p-tolyl-7,8-dihydropyrido[2,3-b]pyrazin-5(6H)-yl)-3-hydroxyheptanoic acid;
7-(2,3-Bis(4-chlorophenyl)-6-oxo-7,8-dihydropyrido[2,3-b]pyrazin-5(6H)-yl)heptanoic acid;
7-(2-(4-Chlorophenyl)-6-oxo-3-p-tolyl-7,8-dihydropyrido[2,3-b]pyrazin-5(6H)-yl)heptanoic acid;
7-(3-(4-Chlorophenyl)-6-oxo-2-p-tolyl-7,8-dihydropyrido[2,3-b]pyrazin-5(6H)-yl)heptanoic acid;
N-(Benzylsulfonyl)-7-(2,3-di-p-tolyl-7,8-dihydropyrido[2,3-b]pyrazin-5(6H)-yl)heptanamide;
N-Benzyl-7-(2,3-di-p-tolyl-7,8-dihydro pyrido[2,3-b]pyrazin-5(6H)-yl)heptanamide;
7-(2,3-Di-p-tolyl-7,8-dihydro pyrido[2,3-b]pyrazin-5(6H)-yl)-N-(phenyl sulfonyl) heptanamide;
7-(2,3-Di-p-tolyl-7,8-dihydropyrido[2,3-b]pyrazin-5(6H)-yl)-N-isopropylheptanamide;
7-(2,3-Di-p-tolyl-7,8-dihydropyrido[2,3-b]pyrazin-5(6H)-yl)-N-methylheptanamide;
7-(2,3-Di-p-tolyl-7,8-dihydropyrido[2,3-b]pyrazin-5(6H)-yl)-N-phenylheptanamide;
7-(2,3-Di-p-tolyl-7,8-dihydropyrido[2,3-b]pyrazin-5(6H)-yl)-N-hydroxyheptanamide;
7-(2,3-Di-p-tolyl-7,8-dihydropyrido[2,3-b]pyrazin-5(6H)-yl)-N-(isopropylsulfonyl)heptanamide;
(rac or R or S)-7-(7-hydroxy-7-methyl-2,3-di-p-tolyl-7,8-dihydropyrido[2,3-b]pyrazin-5(6H)-yl)heptanoic acid;
(rac or R or S)-7-(7-(dimethylamino)-2,3-di-p-tolyl-7,8-dihydropyrido[2,3-b]pyrazin-5(6H)-yl)heptanoic acid;
7-(3-(4-chlorophenyl)-2-(p-tolyl)-7,8-dihydropyrido[2,3-b]pyrazin-5(6H)-yl)heptanoic acid;
7-(2-(4-chlorophenyl)-3-(p-tolyl)-7,8-dihydropyrido[2,3-b]pyrazin-5(6H)-yl)heptanoic acid;
7-(2,3-bis(4-chlorophenyl)-7,8-dihydropyrido[2,3-b]pyrazin-5(6H)-yl)heptanoic acid;
7-(6-oxo-2,3-di-p-tolyl-7,8-dihydropyrido[2,3-b]pyrazin-5(6H)-yl)heptanoic acid;
7-(2-(4-chlorophenyl)-6-oxo-3-(p-tolyl)-7,8-dihydropyrido[2,3-b]pyrazin-5(6H)-yl)heptanoic acid;
7-(3-(4-chlorophenyl)-6-oxo-2-(p-tolyl)-7,8-dihydropyrido[2,3-b]pyrazin-5(6H)-yl)heptanoic acid;
7-(7-hydroxy-6-oxo-2,3-di-p-tolyl-7,8-dihydropyrido[2,3-b]pyrazin-5(6H)-yl)heptanoic acid;
7-(2-(4-chlorophenyl)-7-hydroxy-6-oxo-3-(p-tolyl)-7,8-dihydropyrido[2,3-b]pyrazin-5(6H)-yl)heptanoic acid;
7-(3-(4-chlorophenyl)-7-hydroxy-6-oxo-2-(p-tolyl)-7,8-dihydropyrido[2,3-b]pyrazin-5(6H)-yl)heptanoic acid;
7-(2,3-bis(4-chlorophenyl)-7-hydroxy-6-oxo-7,8-dihydropyrido[2,3-b]pyrazin-5(6H)-yl)heptanoic acid;
7-(7-hydroxy-2,3-di-p-tolyl-7,8-dihydropyrido[2,3-b]pyrazin-5(6H)-yl)heptanoic acid;

7-(2-(4-chlorophenyl)-7-hydroxy-3-(p-tolyl)-7,8-dihydro-pyrido[2,3-b]pyrazin-5(6H)-yl)heptanoic acid;

7-(3-(4-chlorophenyl)-7-hydroxy-2-(p-tolyl)-7,8-dihydro-pyrido[2,3-b]pyrazin-5(6H)-yl)heptanoic acid;

7-(2,3-bis(4-chlorophenyl)-7-hydroxy-7,8-dihydropyrido[2,3-b]pyrazin-5(6H)-yl)heptanoic acid;

7-(8-hydroxy-2,3-di-p-tolyl-7,8-dihydropyrido[2,3-b]pyrazin-5(6H)-yl)heptanoic acid;

7-(2-(4-chlorophenyl)-8-hydroxy-3-(p-tolyl)-7,8-dihydro-pyrido[2,3-b]pyrazin-5(6H)-yl)heptanoic acid;

7-(3-(4-chlorophenyl)-8-hydroxy-2-(p-tolyl)-7,8-dihydro-pyrido[2,3-b]pyrazin-5(6H)-yl)heptanoic acid;

7-(2,3-bis(4-chlorophenyl)-8-hydroxy-7,8-dihydropyrido[2,3-b]pyrazin-5(6H)-yl)heptanoic acid;

7-(2,3-di-p-tolyl-7,8-dihydropyrido[2,3-b]pyrazin-5(6H)-yl)-N-(phenylsulfonyl)heptanamide;

7-(2-(4-chlorophenyl)-3-(p-tolyl)-7,8-dihydropyrido[2,3-b]pyrazin-5(6H)-yl)-N-(phenylsulfonyl)heptanamide;

7-(3-(4-chlorophenyl)-2-(p-tolyl)-7,8-dihydropyrido[2,3-b]pyrazin-5(6H)-yl)-N-(phenylsulfonyl)heptanamide;

7-(2,3-bis(4-chlorophenyl)-7,8-dihydropyrido[2,3-b]pyrazin-5(6H)-yl)-N-(phenylsulfonyl)heptanamide;

7-(6-oxo-2,3-di-p-tolyl-7,8-dihydropyrido[2,3-b]pyrazin-5(6H)-yl)-N-(phenylsulfonyl)heptanamide;

7-(2-(4-chlorophenyl)-6-oxo-3-(p-tolyl)-7,8-dihydropyrido[2,3-b]pyrazin-5(6H)-yl)-N-(phenylsulfonyl)heptanamide;

7-(3-(4-chlorophenyl)-6-oxo-2-(p-tolyl)-7,8-dihydropyrido[2,3-b]pyrazin-5(6H)-yl)-N-(phenylsulfonyl)heptanamide;

7-(2,3-bis(4-chlorophenyl)-6-oxo-7,8-dihydropyrido[2,3-b]pyrazin-5(6H)-yl)-N-(phenylsulfonyl)heptanamide;

7-(7-hydroxy-6-oxo-2,3-di-p-tolyl-7,8-dihydropyrido[2,3-b]pyrazin-5(6H)-yl)-N-(phenylsulfonyl)heptanamide;

7-(2-(4-chlorophenyl)-7-hydroxy-6-oxo-3-(p-tolyl)-7,8-dihydropyrido[2,3-b]pyrazin-5(6H)-yl)-N-(phenylsulfonyl)heptanamide;

7-(3-(4-chlorophenyl)-7-hydroxy-6-oxo-2-(p-tolyl)-7,8-dihydropyrido[2,3-b]pyrazin-5(6H)-yl)-N-(phenylsulfonyl)heptanamide;

7-(2,3-bis(4-chlorophenyl)-7-hydroxy-6-oxo-7,8-dihydro-pyrido[2,3-b]pyrazin-5(6H)-yl)-N-(phenylsulfonyl)heptanamide;

7-(7-hydroxy-2,3-di-p-tolyl-7,8-dihydropyrido[2,3-b]pyrazin-5(6H)-yl)-N-(phenylsulfonyl)heptanamide;

7-(2-(4-chlorophenyl)-7-hydroxy-3-(p-tolyl)-7,8-dihydro-pyrido[2,3-b]pyrazin-5(6H)-yl)-N-(phenylsulfonyl)heptanamide;

7-(3-(4-chlorophenyl)-7-hydroxy-2-(p-tolyl)-7,8-dihydro-pyrido[2,3-b]pyrazin-5(6H)-yl)-N-(phenylsulfonyl)heptanamide;

7-(2,3-bis(4-chlorophenyl)-7-hydroxy-7,8-dihydropyrido[2,3-b]pyrazin-5(6H)-yl)-N-(phenylsulfonyl)heptanamide;

7-(8-hydroxy-2,3-di-p-tolyl-7,8-dihydropyrido[2,3-b]pyrazin-5(6H)-yl)-N-(phenylsulfonyl)heptanamide;

7-(2-(4-chlorophenyl)-8-hydroxy-3-(p-tolyl)-7,8-dihydro-pyrido[2,3-b]pyrazin-5(6H)-yl)-N-(phenylsulfonyl)heptanamide;

7-(3-(4-chlorophenyl)-8-hydroxy-2-(p-tolyl)-7,8-dihydro-pyrido[2,3-b]pyrazin-5(6H)-yl)-N-(phenylsulfonyl)heptanamide;

7-(2,3-bis(4-chlorophenyl)-8-hydroxy-7,8-dihydropyrido[2,3-b]pyrazin-5(6H)-yl)-N-(phenylsulfonyl)heptanamide;

N-(benzylsulfonyl)-7-(2,3-bis(4-chlorophenyl)-7,8-dihydropyrido[2,3-b]pyrazin-5(6H)-yl)heptanamide;

N-(benzylsulfonyl)-7-(2-(4-chlorophenyl)-3-(p-tolyl)-7,8-dihydropyrido[2,3-b]pyrazin-5(6H)-yl)heptanamide;

N-(benzylsulfonyl)-7-(3-(4-chlorophenyl)-2-(p-tolyl)-7,8-dihydropyrido[2,3-b]pyrazin-5(6H)-yl)heptanamide;

N-(benzylsulfonyl)-7-(6-oxo-2,3-di-p-tolyl-7,8-dihydropyrido[2,3-b]pyrazin-5(6H)-yl)heptanamide;

N-(benzylsulfonyl)-7-(3-(4-chlorophenyl)-6-oxo-2-(p-tolyl)-7,8-dihydropyrido[2,3-b]pyrazin-5(6H)-yl)heptanamide;

N-(benzylsulfonyl)-7-(3-(4-chlorophenyl)-6-oxo-2-(p-tolyl)-7,8-dihydropyrido[2,3-b]pyrazin-5(6H)-yl)heptanamide;

N-(benzylsulfonyl)-7-(3-(4-chlorophenyl)-6-oxo-2-(p-tolyl)-7,8-dihydropyrido[2,3-b]pyrazin-5(6H)-yl)heptanamide;

N-(benzylsulfonyl)-7-(7-hydroxy-6-oxo-2,3-di-p-tolyl-7,8-dihydropyrido[2,3-b]pyrazin-5(6H)-yl)heptanamide;

N-(benzylsulfonyl)-7-(3-(4-chlorophenyl)-7-hydroxy-6-oxo-2-(p-tolyl)-7,8-dihydropyrido[2,3-b]pyrazin-5(6H)-yl)heptanamide;

N-(benzylsulfonyl)-7-(3-(4-chlorophenyl)-7-hydroxy-6-oxo-2-(p-tolyl)-7,8-dihydropyrido[2,3-b]pyrazin-5(6H)-yl)heptanamide;

N-(benzylsulfonyl)-7-(3-(4-chlorophenyl)-7-hydroxy-6-oxo-2-(p-tolyl)-7,8-dihydropyrido[2,3-b]pyrazin-5(6H)-yl)heptanamide;

N-(benzylsulfonyl)-7-(7-hydroxy-2,3-di-p-tolyl-7,8-dihydropyrido[2,3-b]pyrazin-5(6H)-yl)heptanamide;

N-(benzylsulfonyl)-7-(3-(4-chlorophenyl)-7-hydroxy-2-(p-tolyl)-7,8-dihydropyrido[2,3-b]pyrazin-5(6H)-yl)heptanamide;

N-(benzylsulfonyl)-7-(3-(4-chlorophenyl)-7-hydroxy-2-(p-tolyl)-7,8-dihydropyrido[2,3-b]pyrazin-5(6H)-yl)heptanamide;

N-(benzylsulfonyl)-7-(3-(4-chlorophenyl)-7-hydroxy-2-(p-tolyl)-7,8-dihydropyrido[2,3-b]pyrazin-5(6H)-yl)heptanamide;

N-(benzylsulfonyl)-7-(8-hydroxy-2,3-di-p-tolyl-7,8-dihydropyrido[2,3-b]pyrazin-5(6H)-yl)heptanamide;

N-(benzylsulfonyl)-7-(3-(4-chlorophenyl)-8-hydroxy-2-(p-tolyl)-7,8-dihydropyrido[2,3-b]pyrazin-5(6H)-yl)heptanamide;

N-(benzylsulfonyl)-7-(3-(4-chlorophenyl)-8-hydroxy-2-(p-tolyl)-7,8-dihydropyrido[2,3-b]pyrazin-5(6H)-yl)heptanamide;

N-(benzylsulfonyl)-7-(3-(4-chlorophenyl)-8-hydroxy-2-(p-tolyl)-7,8-dihydropyrido[2,3-b]pyrazin-5(6H)-yl)heptanamide;

7-(2-(4-chlorophenyl)-3-(p-tolyl)-7,8-dihydropyrido[2,3-b]pyrazin-5(6H)-yl)-N-phenylheptanamide;

7-(3-(4-chlorophenyl)-2-(p-tolyl)-7,8-dihydropyrido[2,3-b]pyrazin-5(6H)-yl)-N-phenylheptanamide;

7-(2,3-bis(4-chlorophenyl)-7,8-dihydropyrido[2,3-b]pyrazin-5(6H)-yl)-N-phenylheptanamide;

7-(6-oxo-2,3-di-p-tolyl-7,8-dihydropyrido[2,3-b]pyrazin-5(6H)-yl)-N-phenylheptanamide;

7-(2-(4-chlorophenyl)-6-oxo-3-(p-tolyl)-7,8-dihydropyrido[2,3-b]pyrazin-5(6H)-yl)-N-phenylheptanamide;

7-(3-(4-chlorophenyl)-6-oxo-2-(p-tolyl)-7,8-dihydropyrido[2,3-b]pyrazin-5(6H)-yl)-N-phenylheptanamide;

7-(2,3-bis(4-chlorophenyl)-6-oxo-7,8-dihydropyrido[2,3-b]pyrazin-5(6H)-yl)-N-phenylheptanamide;

7-(7-hydroxy-6-oxo-2,3-di-p-tolyl-7,8-dihydropyrido[2,3-b]pyrazin-5(6H)-yl)-N-phenylheptanamide;

7-(2-(4-chlorophenyl)-7-hydroxy-6-oxo-3-(p-tolyl)-7,8-dihydropyrido[2,3-b]pyrazin-5(6H)-yl)-N-phenylheptanamide;

7-(3-(4-chlorophenyl)-7-hydroxy-6-oxo-2-(p-tolyl)-7,8-dihydropyrido[2,3-b]pyrazin-5(6H)-yl)-N-phenylheptanamide;
7-(2,3-bis(4-chlorophenyl)-7-hydroxy-6-oxo-7,8-dihydropyrido[2,3-b]pyrazin-5(6H)-yl)-N-phenylheptanamide;
7-(7-hydroxy-2,3-di-p-tolyl-7,8-dihydropyrido[2,3-b]pyrazin-5(6H)-yl)-N-phenylheptanamide;
7-(2-(4-chlorophenyl)-7-hydroxy-3-(p-tolyl)-7,8-dihydropyrido[2,3-b]pyrazin-5(6H)-yl)-N-phenylheptanamide;
7-(3-(4-chlorophenyl)-7-hydroxy-2-(p-tolyl)-7,8-dihydropyrido[2,3-b]pyrazin-5(6H)-yl)-N-phenylheptanamide;
7-(2,3-bis(4-chlorophenyl)-7-hydroxy-7,8-dihydropyrido[2,3-b]pyrazin-5(6H)-yl)-N-phenylheptanamide;
7-(8-hydroxy-2,3-di-p-tolyl-7,8-dihydropyrido[2,3-b]pyrazin-5(6H)-yl)-N-phenylheptanamide
7-(2-(4-chlorophenyl)-8-hydroxy-3-(p-tolyl)-7,8-dihydropyrido[2,3-b]pyrazin-5(6H)-yl)-N-phenylheptanamide;
7-(3-(4-chlorophenyl)-8-hydroxy-2-(p-tolyl)-7,8-dihydropyrido[2,3-b]pyrazin-5(6H)-yl)-N-phenylheptanamide;
7-(2,3-bis(4-chlorophenyl)-8-hydroxy-7,8-dihydropyrido[2,3-b]pyrazin-5(6H)-yl)-N-phenylheptanamide;
N-benzyl-7-(2,3-di-p-tolyl-7,8-dihydropyrido[2,3-b]pyrazin-5(6H)-yl)heptanamide;
N-benzyl-7-(2-(4-chlorophenyl)-3-(p-tolyl)-7,8-dihydropyrido[2,3-b]pyrazin-5(6H)-yl)heptanamide;
N-benzyl-7-(3-(4-chlorophenyl)-2-(p-tolyl)-7,8-dihydropyrido[2,3-b]pyrazin-5(6H)-yl)heptanamide;
N-benzyl-7-(2,3-bis(4-chlorophenyl)-7,8-dihydropyrido[2,3-b]pyrazin-5(6H)-yl)heptanamide;
N-benzyl-7-(6-oxo-2,3-di-p-tolyl-7,8-dihydropyrido[2,3-b]pyrazin-5(6H)-yl)heptanamide;
N-benzyl-7-(2-(4-chlorophenyl)-6-oxo-3-(p-tolyl)-7,8-dihydropyrido[2,3-b]pyrazin-5(6H)-yl)heptanamide;
N-benzyl-7-(3-(4-chlorophenyl)-6-oxo-2-(p-tolyl)-7,8-dihydropyrido[2,3-b]pyrazin-5(6H)-yl)heptanamide;
N-benzyl-7-(2,3-bis(4-chlorophenyl)-6-oxo-7,8-dihydropyrido[2,3-b]pyrazin-5(6H)-yl)heptanamide;
N-benzyl-7-(7-hydroxy-6-oxo-2,3-di-p-tolyl-7,8-dihydropyrido[2,3-b]pyrazin-5(6H)-yl)heptanamide;
N-benzyl-7-(2-(4-chlorophenyl)-7-hydroxy-6-oxo-3-(p-tolyl)-7,8-dihydropyrido[2,3-b]pyrazin-5(6H)-yl)heptanamide;
N-benzyl-7-(3-(4-chlorophenyl)-7-hydroxy-6-oxo-2-(p-tolyl)-7,8-dihydropyrido[2,3-b]pyrazin-5(6H)-yl)heptanamide;
N-benzyl-7-(2,3-bis(4-chlorophenyl)-7-hydroxy-6-oxo-7,8-dihydropyrido[2,3-b]pyrazin-5(6H)-yl)heptanamide;
N-benzyl-7-(7-hydroxy-2,3-di-p-tolyl-7,8-dihydropyrido[2,3-b]pyrazin-5(6H)-yl)heptanamide;
N-benzyl-7-(2-(4-chlorophenyl)-7-hydroxy-3-(p-tolyl)-7,8-dihydropyrido[2,3-b]pyrazin-5(6H)-yl)heptanamide;
N-benzyl-7-(3-(4-chlorophenyl)-7-hydroxy-2-(p-tolyl)-7,8-dihydropyrido[2,3-b]pyrazin-5(6H)-yl)heptanamide;
N-benzyl-7-(2,3-bis(4-chlorophenyl)-7-hydroxy-7,8-dihydropyrido[2,3-b]pyrazin-5(6H)-yl)heptanamide;
N-benzyl-7-(8-hydroxy-2,3-di-p-tolyl-7,8-dihydropyrido[2,3-b]pyrazin-5(6H)-yl)heptanamide;
N-benzyl-7-(2-(4-chlorophenyl)-8-hydroxy-3-(p-tolyl)-7,8-dihydropyrido[2,3-b]pyrazin-5(6H)-yl)heptanamide;
N-benzyl-7-(3-(4-chlorophenyl)-8-hydroxy-2-(p-tolyl)-7,8-dihydropyrido[2,3-b]pyrazin-5(6H)-yl)heptanamide;
N-benzyl-7-(2,3-bis(4-chlorophenyl)-8-hydroxy-7,8-dihydropyrido[2,3-b]pyrazin-5(6H)-yl)heptanamide;
7-(2-(4-chlorophenyl)-3-(p-tolyl)-7,8-dihydropyrido[2,3-b]pyrazin-5(6H)-yl)-N-(methylsulfonyl)heptanamide;
7-(3-(4-chlorophenyl)-2-(p-tolyl)-7,8-dihydropyrido[2,3-b]pyrazin-5(6H)-yl)-N-(methylsulfonyl)heptanamide;
7-(2,3-bis(4-chlorophenyl)-7,8-dihydropyrido[2,3-b]pyrazin-5(6H)-yl)-N-(methylsulfonyl)heptanamide;
7-(2-(4-chlorophenyl)-3-(p-tolyl)-7,8-dihydropyrido[2,3-b]pyrazin-5(6H)-yl)-N-(isopropylsulfonyl)heptanamide;
7-(3-(4-chlorophenyl)-2-(p-tolyl)-7,8-dihydropyrido[2,3-b]pyrazin-5(6H)-yl)-N-(isopropylsulfonyl)heptanamide;
7-(2,3-bis(4-chlorophenyl)-7,8-dihydropyrido[2,3-b]pyrazin-5(6H)-yl)-N-(isopropylsulfonyl)heptanamide;
7-(2-(4-chlorophenyl)-3-(p-tolyl)-7,8-dihydropyrido[2,3-b]pyrazin-5(6H)-yl)-N-methylheptanamide;
7-(3-(4-chlorophenyl)-2-(p-tolyl)-7,8-dihydropyrido[2,3-b]pyrazin-5(6H)-yl)-N-methylheptanamide;
7-(2,3-bis(4-chlorophenyl)-7,8-dihydropyrido[2,3-b]pyrazin-5(6H)-yl)-N-methylheptanamide;
7-(2-(4-chlorophenyl)-3-(p-tolyl)-7,8-dihydropyrido[2,3-b]pyrazin-5(6H)-yl)-N-isopropylheptanamide;
7-(3-(4-chlorophenyl)-2-(p-tolyl)-7,8-dihydropyrido[2,3-b]pyrazin-5(6H)-yl)-N-isopropylheptanamide;
7-(2,3-bis(4-chlorophenyl)-7,8-dihydropyrido[2,3-b]pyrazin-5(6H)-yl)-N-isopropylheptanamide;
7-(2-(4-chlorophenyl)-3-(p-tolyl)-7,8-dihydropyrido[2,3-b]pyrazin-5(6H)-yl)-N-hydroxyheptanamide;
7-(3-(4-chlorophenyl)-2-(p-tolyl)-7,8-dihydropyrido[2,3-b]pyrazin-5(6H)-yl)-N-hydroxyheptanamide;
6-(5-methyl-2,3-di-p-tolyl-5,6,7,8-tetrahydropyrido[2,3-b]pyrazin-6-yl)hexanoic acid;
6-(5-isopropyl-2,3-di-p-tolyl-5,6,7,8-tetrahydropyrido[2,3-b]pyrazin-6-yl)hexanoic acid;
5-(2,3-di-p-tolyl-5,6,7,8-tetrahydropyrido[2,3-b]pyrazin-6-yl)pentanoic acid;
5-(5-methyl-2,3-di-p-tolyl-5,6,7,8-tetrahydropyrido[2,3-b]pyrazin-6-yl)pentanoic acid;
5-(5-isopropyl-2,3-di-p-tolyl-5,6,7,8-tetrahydropyrido[2,3-b]pyrazin-6-yl)pentanoic acid;
7-(2,3-di-p-tolyl-5,6,7,8-tetrahydropyrido[2,3-b]pyrazin-6-yl)heptanoic acid;
7-(5-methyl-2-phenyl-3-(p-tolyl)-5,6,7,8-tetrahydropyrido[2,3-b]pyrazin-6-yl)heptanoic acid;
7-(5-isopropyl-2,3-di-p-tolyl-5,6,7,8-tetrahydropyrido[2,3-b]pyrazin-6-yl)heptanoic acid;
6-(7-hydroxy-2,3-di-p-tolyl-5,6,7,8-tetrahydropyrido[2,3-b]pyrazin-6-yl)hexanoic acid;
6-(7-hydroxy-5-methyl-2,3-di-p-tolyl-5,6,7,8-tetrahydropyrido[2,3-b]pyrazin-6-yl)hexanoic acid;
6-(7-hydroxy-5-isopropyl-2,3-di-p-tolyl-5,6,7,8-tetrahydropyrido[2,3-b]pyrazin-6-yl)hexanoic acid;
5-(7-hydroxy-2,3-di-p-tolyl-5,6,7,8-tetrahydropyrido[2,3-b]pyrazin-6-yl)pentanoic acid;
5-(7-hydroxy-5-methyl-2,3-di-p-tolyl-5,6,7,8-tetrahydropyrido[2,3-b]pyrazin-6-yl)pentanoic acid;
5-(7-hydroxy-5-isopropyl-2,3-di-p-tolyl-5,6,7,8-tetrahydropyrido[2,3-b]pyrazin-6-yl)pentanoic acid;
7-(7-hydroxy-2,3-di-p-tolyl-5,6,7,8-tetrahydropyrido[2,3-b]pyrazin-6-yl)heptanoic acid;
7-(7-hydroxy-5-methyl-2-phenyl-3-(p-tolyl)-5,6,7,8-tetrahydropyrido[2,3-b]pyrazin-6-yl)heptanoic acid;
7-(7-hydroxy-5-isopropyl-2,3-di-p-tolyl-5,6,7,8-tetrahydropyrido[2,3-b]pyrazin-6-yl)heptanoic acid;
6-(8-hydroxy-2,3-di-p-tolyl-5,6,7,8-tetrahydropyrido[2,3-b]pyrazin-6-yl)hexanoic acid;
6-(8-hydroxy-5-methyl-2,3-di-p-tolyl-5,6,7,8-tetrahydropyrido[2,3-b]pyrazin-6-yl)hexanoic acid;
6-(8-hydroxy-5-isopropyl-2,3-di-p-tolyl-5,6,7,8-tetrahydropyrido[2,3-b]pyrazin-6-yl)hexanoic acid;
5-(8-hydroxy-2,3-di-p-tolyl-5,6,7,8-tetrahydropyrido[2,3-b]pyrazin-6-yl)pentanoic acid;

5-(8-hydroxy-5-methyl-2,3-di-p-tolyl-5,6,7,8-tetrahydropyrido[2,3-b]pyrazin-6-yl)pentanoic acid;
5-(8-hydroxy-5-isopropyl-2,3-di-p-tolyl-5,6,7,8-tetrahydropyrido[2,3-b]pyrazin-6-yl)pentanoic acid;
7-(8-hydroxy-2,3-di-p-tolyl-5,6,7,8-tetrahydropyrido[2,3-b]pyrazin-6-yl)heptanoic acid;
7-(8-hydroxy-5-methyl-2,3-di-p-tolyl-5,6,7,8-tetrahydropyrido[2,3-b]pyrazin-6-yl)heptanoic acid;
7-(8-hydroxy-5-isopropyl-2,3-di-p-tolyl-5,6,7,8-tetrahydropyrido[2,3-b]pyrazin-6-yl)heptanoic acid; and
7-(2,3-bis(4-chlorophenyl)-7,8-dihydropyrido[2,3-b]pyrazin-5(6H)-yl)-N-hydroxyheptanamide;
or a pharmaceutically acceptable salt thereof.

In an embodiment of the first aspect, the compound is selected from the group consisting of
(rac)-6-(2,3-di-p-tolyl-5,6,7,8-tetrahydropyrido[2,3-b]pyrazin-6-yl)hexanoic acid or (S)-6-(2,3-di-p-tolyl-5,6,7,8-tetrahydropyrido[2,3-b]pyrazin-6-yl)hexanoic acid;
(R)-6-(2,3-di-p-tolyl-5,6,7,8-tetrahydropyrido[2,3-b]pyrazin-6-yl)hexanoic acid or (S)-6-(2,3-di-p-tolyl-5,6,7,8-tetrahydropyrido[2,3-b]pyrazin-6-yl)hexanoic acid;
(S)-6-(2,3-di-p-tolyl-5,6,7,8-tetrahydropyrido[2,3-b]pyrazin-6-yl)hexanoic acid;
(rac)-7-(7-(2-Hydroxypropan-2-yl)-6-oxo-2,3-di-p-tolyl-7,8-dihydropyrido[2,3-b]pyrazin-5(6H)-yl)heptanoic acid;
(R)-7-(7-(2-hydroxypropan-2-yl)-6-oxo-2,3-di-p-tolyl-7,8-dihydropyrido[2,3-b]pyrazin-5(6H)-yl)heptanoic acid or (S)-7-(7-(2-hydroxypropan-2-yl)-6-oxo-2,3-di-p-tolyl-7,8-dihydropyrido[2,3-b]pyrazin-5(6H)-yl)heptanoic acid;
(S)-7-(7-(2-hydroxypropan-2-yl)-6-oxo-2,3-di-p-tolyl-7,8-dihydropyrido[2,3-b]pyrazin-5(6H)-yl)heptanoic acid or (S)-7-(7-(2-hydroxypropan-2-yl)-6-oxo-2,3-di-p-tolyl-7,8-dihydropyrido[2,3-b]pyrazin-5(6H)-yl)heptanoic acid;
7-(7-Ethyl-2,3-di-p-tolyl-7,8-dihydropyrido[2,3-b]pyrazin-5(6H)-yl)heptanoic acid;
7-(7-Methyl-2-phenyl-3-(p-tolyl)-7,8-dihydropyrido[2,3-b]pyrazin-5(6H)-yl)heptanoic acid;
(rac)-7-(6-Ethyl-2,3-di-p-tolyl-7,8-dihydropyrido[2,3-b]pyrazin-5(6H)-yl)heptanoic acid;
(R)-7-(6-Ethyl-2,3-di-p-tolyl-7,8-dihydropyrido[2,3-b]pyrazin-5(6H)-yl)heptanoic acid;
(S)-7-(6-Ethyl-2,3-di-p-tolyl-7,8-dihydropyrido[2,3-b]pyrazin-5(6H)-yl)heptanoic acid;
7-(6-Methyl-2-phenyl-3-(p-tolyl)-7,8-dihydropyrido[2,3-b]pyrazin-5(6H)-yl)heptanoic acid;
7-(3-o-Tolyl-2-p-tolyl-7,8-dihydropyrido[3,2-b]pyrazin-5(6H)-yl)heptanoic acid;
7-(2-o-Tolyl-3-p-tolyl-7,8-dihydropyrido[3,2-b]pyrazin-5(6H)-yl)heptanoic acid;
7-(2-(2-Fluorophenyl)-3-p-tolyl-7,8-dihydropyrido[2,3-b]pyrazin-5(6H)-yl)heptanoic acid;
7-(2-(4-Fluorophenyl)-3-p-tolyl-7,8-dihydropyrido[2,3-b]pyrazin-5(6H)-yl)heptanoic acid;
7-(2-(3-Fluorophenyl)-3-p-tolyl-7,8-dihydropyrido[2,3-b]pyrazin-5(6H)-yl)heptanoic acid;
7-(2-(4-Methoxyphenyl)-3-p-tolyl-7,8-dihydropyrido[2,3-b]pyrazin-5(6H)-yl)heptanoic acid;
(rac)-7-(8-Methoxy-2,3-di-p-tolyl-7,8-dihydropyrido[2,3-b]pyrazin-5(6H)-yl)heptanoic acid;
(R)-7-(8-methoxy-2,3-di-p-tolyl-7,8-dihydropyrido[2,3-b]pyrazin-5(6H)-yl)heptanoic acid;
(S)-7-(8-methoxy-2,3-di-p-tolyl-7,8-dihydropyrido[2,3-b]pyrazin-5(6H)-yl)heptanoic acid;
7-(2,3-Bis(2,4-difluorophenyl)-7,8-dihydropyrido[2,3-b]pyrazin-5(6H)-yl)heptanoic acid;
7-(2,3-Bis(6-methylpyridin-3-yl)-7,8-dihydropyrido[2,3-b]pyrazin-5(6H)-yl)heptanoic acid;
7-(2-(6-Methylpyridin-3-yl)-3-p-tolyl-7,8-dihydropyrido[2,3-b]pyrazin-5(6H)-yl)heptanoic acid;
7-(3-(6-Methylpyridin-3-yl)-2-p-tolyl-7,8-dihydropyrido[2,3-b]pyrazin-5(6H)-yl)heptanoic acid;
9-(6-Oxo-2,3-di-p-tolyl-7,8-dihydropyrido[2,3-b]pyrazin-5(6H)-yl)nonanoic acid;
9-(2,3-Di-p-tolyl-7,8-dihydropyrido[2,3-b]pyrazin-5(6H)-yl)nonanoic acid;
(rac)-7-(7-(2-hydroxypropan-2-yl)-2,3-di-p-tolyl-7,8-dihydropyrido[2,3-b]pyrazin-5(6H)-yl)heptanoic acid;
(R)-7-(7-(2-hydroxypropan-2-yl)-2,3-di-p-tolyl-7,8-dihydropyrido[2,3-b]pyrazin-5(6H)-yl)heptanoic acid;
(S)-7-(7-(2-hydroxypropan-2-yl)-2,3-di-p-tolyl-7,8-dihydropyrido[2,3-b]pyrazin-5(6H)-yl)heptanoic acid;
6-(2,3-Di-p-tolyl-7,8-dihydropyrido[2,3-b]pyrazin-5(6H)-yl)hexanoic acid;
(R)-7-(7-hydroxy-6-oxo-2,3-di-p-tolyl-7,8-dihydropyrido[2,3-b]pyrazin-5(6H)-yl)heptanoic acid;
(S)-7-(7-hydroxy-6-oxo-2,3-di-p-tolyl-7,8-dihydropyrido[2,3-b]pyrazin-5(6H)-yl)heptanoic acid;
(rac or R or S)-7-(7-hydroxy-7-methyl-2,3-di-p-tolyl-7,8-dihydropyrido[2,3-b]pyrazin-5(6H)-yl)heptanoic acid;
(rac or R or S)-7-(8-hydroxy-8-methyl-2,3-di-p-tolyl-7,8-dihydropyrido[2,3-b]pyrazin-5(6H)-yl)heptanoic acid;
(rac or R or S)-7-(7-(dimethylamino)-2,3-di-p-tolyl-7,8-dihydropyrido[2,3-b]pyrazin-5(6H)-yl)heptanoic acid;
7-(3-(4-chlorophenyl)-2-(p-tolyl)-7,8-dihydropyrido[2,3-b]pyrazin-5(6H)-yl)heptanoic acid;
7-(2-(4-chlorophenyl)-3-(p-tolyl)-7,8-dihydropyrido[2,3-b]pyrazin-5(6H)-yl)heptanoic acid;
7-(2,3-bis(4-chlorophenyl)-7,8-dihydropyrido[2,3-b]pyrazin-5(6H)-yl)heptanoic acid;
7-(6-oxo-2,3-di-p-tolyl-7,8-dihydropyrido[2,3-b]pyrazin-5(6H)-yl)heptanoic acid;
7-(2-(4-chlorophenyl)-6-oxo-3-(p-tolyl)-7,8-dihydropyrido[2,3-b]pyrazin-5(6H)-yl)heptanoic acid;
7-(3-(4-chlorophenyl)-6-oxo-2-(p-tolyl)-7,8-dihydropyrido[2,3-b]pyrazin-5(6H)-yl)heptanoic acid;
7-(2,3-bis(4-chlorophenyl)-6-oxo-7,8-dihydropyrido[2,3-b]pyrazin-5(6H)-yl)heptanoic acid;
7-(7-hydroxy-6-oxo-2,3-di-p-tolyl-7,8-dihydropyrido[2,3-b]pyrazin-5(6H)-yl)heptanoic acid;
7-(2-(4-chlorophenyl)-7-hydroxy-6-oxo-3-(p-tolyl)-7,8-dihydropyrido[2,3-b]pyrazin-5(6H)-yl)heptanoic acid;
7-(3-(4-chlorophenyl)-7-hydroxy-6-oxo-2-(p-tolyl)-7,8-dihydropyrido[2,3-b]pyrazin-5(6H)-yl)heptanoic acid;
7-(2,3-bis(4-chlorophenyl)-7-hydroxy-6-oxo-7,8-dihydropyrido[2,3-b]pyrazin-5(6H)-yl)heptanoic acid;
7-(7-hydroxy-2,3-di-p-tolyl-7,8-dihydropyrido[2,3-b]pyrazin-5(6H)-yl)heptanoic acid;
7-(2-(4-chlorophenyl)-7-hydroxy-3-(p-tolyl)-7,8-dihydropyrido[2,3-b]pyrazin-5(6H)-yl)heptanoic acid;
7-(3-(4-chlorophenyl)-7-hydroxy-2-(p-tolyl)-7,8-dihydropyrido[2,3-b]pyrazin-5(6H)-yl)heptanoic acid;
7-(2,3-bis(4-chlorophenyl)-7-hydroxy-7,8-dihydropyrido[2,3-b]pyrazin-5(6H)-yl)heptanoic acid;
7-(8-hydroxy-2,3-di-p-tolyl-7,8-dihydropyrido[2,3-b]pyrazin-5(6H)-yl)heptanoic acid;
7-(2-(4-chlorophenyl)-8-hydroxy-3-(p-tolyl)-7,8-dihydropyrido[2,3-b]pyrazin-5(6H)-yl)heptanoic acid;
7-(3-(4-chlorophenyl)-8-hydroxy-2-(p-tolyl)-7,8-dihydropyrido[2,3-b]pyrazin-5(6H)-yl)heptanoic acid;
7-(2,3-bis(4-chlorophenyl)-8-hydroxy-7,8-dihydropyrido[2,3-b]pyrazin-5(6H)-yl)heptanoic acid;
7-(2,3-di-p-tolyl-7,8-dihydropyrido[2,3-b]pyrazin-5(6H)-yl)-N-(phenylsulfonyl)heptanamide;

7-(2-(4-chlorophenyl)-3-(p-tolyl)-7,8-dihydropyrido[2,3-b]pyrazin-5(6H)-yl)-N-(phenylsulfonyl)heptanamide;
7-(3-(4-chlorophenyl)-2-(p-tolyl)-7,8-dihydropyrido[2,3-b]pyrazin-5(6H)-yl)-N-(phenylsulfonyl)heptanamide;
7-(2,3-bis(4-chlorophenyl)-7,8-dihydropyrido[2,3-b]pyrazin-5(6H)-yl)-N-(phenylsulfonyl)heptanamide;
7-(6-oxo-2,3-di-p-tolyl-7,8-dihydropyrido[2,3-b]pyrazin-5(6H)-yl)-N-(phenylsulfonyl)heptanamide;
7-(2-(4-chlorophenyl)-6-oxo-3-(p-tolyl)-7,8-dihydropyrido[2,3-b]pyrazin-5(6H)-yl)-N-(phenylsulfonyl)heptanamide;
7-(3-(4-chlorophenyl)-6-oxo-2-(p-tolyl)-7,8-dihydropyrido[2,3-b]pyrazin-5(6H)-yl)-N-(phenylsulfonyl)heptanamide;
7-(2,3-bis(4-chlorophenyl)-6-oxo-7,8-dihydropyrido[2,3-b]pyrazin-5(6H)-yl)-N-(phenylsulfonyl)heptanamide;
7-(7-hydroxy-6-oxo-2,3-di-p-tolyl-7,8-dihydropyrido[2,3-b]pyrazin-5(6H)-yl)-N-(phenylsulfonyl)heptanamide;
7-(2-(4-chlorophenyl)-7-hydroxy-6-oxo-3-(p-tolyl)-7,8-dihydropyrido[2,3-b]pyrazin-5(6H)-yl)-N-(phenylsulfonyl)heptanamide;
7-(3-(4-chlorophenyl)-7-hydroxy-6-oxo-2-(p-tolyl)-7,8-dihydropyrido[2,3-b]pyrazin-5(6H)-yl)-N-(phenylsulfonyl)heptanamide;
7-(2,3-bis(4-chlorophenyl)-7-hydroxy-6-oxo-7,8-dihydropyrido[2,3-b]pyrazin-5(6H)-yl)-N-(phenylsulfonyl)heptanamide;
7-(7-hydroxy-2,3-di-p-tolyl-7,8-dihydropyrido[2,3-b]pyrazin-5(6H)-yl)-N-(phenylsulfonyl)heptanamide;
7-(2-(4-chlorophenyl)-7-hydroxy-3-(p-tolyl)-7,8-dihydropyrido[2,3-b]pyrazin-5(6H)-yl)-N-(phenylsulfonyl)heptanamide;
7-(3-(4-chlorophenyl)-7-hydroxy-2-(p-tolyl)-7,8-dihydropyrido[2,3-b]pyrazin-5(6H)-yl)-N-(phenylsulfonyl)heptanamide;
7-(2,3-bis(4-chlorophenyl)-7-hydroxy-7,8-dihydropyrido[2,3-b]pyrazin-5(6H)-yl)-N-(phenylsulfonyl)heptanamide;
7-(8-hydroxy-2,3-di-p-tolyl-7,8-dihydropyrido[2,3-b]pyrazin-5(6H)-yl)-N-(phenylsulfonyl)heptanamide;
7-(2-(4-chlorophenyl)-8-hydroxy-3-(p-tolyl)-7,8-dihydropyrido[2,3-b]pyrazin-5(6H)-yl)-N-(phenylsulfonyl)heptanamide;
7-(3-(4-chlorophenyl)-8-hydroxy-2-(p-tolyl)-7,8-dihydropyrido[2,3-b]pyrazin-5(6H)-yl)-N-(phenylsulfonyl)heptanamide;
7-(2,3-bis(4-chlorophenyl)-8-hydroxy-7,8-dihydropyrido[2,3-b]pyrazin-5(6H)-yl)-N-(phenylsulfonyl)heptanamide;
N-(benzylsulfonyl)-7-(2,3-di-p-tolyl-7,8-dihydropyrido[2,3-b]pyrazin-5(6H)-yl)heptanamide;
N-(benzylsulfonyl)-7-(2,3-bis(4-chlorophenyl)-7,8-dihydropyrido[2,3-b]pyrazin-5(6H)-yl)heptanamide;
N-(benzylsulfonyl)-7-(2-(4-chlorophenyl)-3-(p-tolyl)-7,8-dihydropyrido[2,3-b]pyrazin-5(6H)-yl)heptanamide;
N-(benzylsulfonyl)-7-(3-(4-chlorophenyl)-2-(p-tolyl)-7,8-dihydropyrido[2,3-b]pyrazin-5(6H)-yl)heptanamide;
N-(benzylsulfonyl)-7-(6-oxo-2,3-di-p-tolyl-7,8-dihydropyrido[2,3-b]pyrazin-5(6H)-yl)heptanamide;
N-(benzylsulfonyl)-7-(3-(4-chlorophenyl)-6-oxo-2-(p-tolyl)-7,8-dihydropyrido[2,3-b]pyrazin-5(6H)-yl)heptanamide;
N-(benzylsulfonyl)-7-(3-(4-chlorophenyl)-6-oxo-2-(p-tolyl)-7,8-dihydropyrido[2,3-b]pyrazin-5(6H)-yl)heptanamide;
N-(benzylsulfonyl)-7-(3-(4-chlorophenyl)-6-oxo-2-(p-tolyl)-7,8-dihydropyrido[2,3-b]pyrazin-5(6H)-yl)heptanamide;
N-(benzylsulfonyl)-7-(7-hydroxy-6-oxo-2,3-di-p-tolyl-7,8-dihydropyrido[2,3-b]pyrazin-5(6H)-yl)heptanamide;
N-(benzylsulfonyl)-7-(3-(4-chlorophenyl)-7-hydroxy-6-oxo-2-(p-tolyl)-7,8-dihydropyrido[2,3-b]pyrazin-5(6H)-yl)heptanamide;
N-(benzylsulfonyl)-7-(3-(4-chlorophenyl)-7-hydroxy-6-oxo-2-(p-tolyl)-7,8-dihydropyrido[2,3-b]pyrazin-5(6H)-yl)heptanamide;
N-(benzylsulfonyl)-7-(3-(4-chlorophenyl)-7-hydroxy-6-oxo-2-(p-tolyl)-7,8-dihydropyrido[2,3-b]pyrazin-5(6H)-yl)heptanamide;
N-(benzylsulfonyl)-7-(7-hydroxy-2,3-di-p-tolyl-7,8-dihydropyrido[2,3-b]pyrazin-5(6H)-yl)heptanamide;
N-(benzylsulfonyl)-7-(3-(4-chlorophenyl)-7-hydroxy-2-(p-tolyl)-7,8-dihydropyrido[2,3-b]pyrazin-5(6H)-yl)heptanamide;
N-(benzylsulfonyl)-7-(3-(4-chlorophenyl)-7-hydroxy-2-(p-tolyl)-7,8-dihydropyrido[2,3-b]pyrazin-5(6H)-yl)heptanamide;
N-(benzylsulfonyl)-7-(3-(4-chlorophenyl)-7-hydroxy-2-(p-tolyl)-7,8-dihydropyrido[2,3-b]pyrazin-5(6H)-yl)heptanamide;
N-(benzylsulfonyl)-7-(8-hydroxy-2,3-di-p-tolyl-7,8-dihydropyrido[2,3-b]pyrazin-5(6H)-yl)heptanamide;
N-(benzylsulfonyl)-7-(3-(4-chlorophenyl)-8-hydroxy-2-(p-tolyl)-7,8-dihydropyrido[2,3-b]pyrazin-5(6H)-yl)heptanamide;
N-(benzylsulfonyl)-7-(3-(4-chlorophenyl)-8-hydroxy-2-(p-tolyl)-7,8-dihydropyrido[2,3-b]pyrazin-5(6H)-yl)heptanamide;
N-(benzylsulfonyl)-7-(3-(4-chlorophenyl)-8-hydroxy-2-(p-tolyl)-7,8-dihydropyrido[2,3-b]pyrazin-5(6H)-yl)heptanamide;
7-(2,3-di-p-tolyl-7,8-dihydropyrido[2,3-b]pyrazin-5(6H)-yl)-N-phenylheptanamide;
7-(2-(4-chlorophenyl)-3-(p-tolyl)-7,8-dihydropyrido[2,3-b]pyrazin-5(6H)-yl)-N-phenylheptanamide;
7-(3-(4-chlorophenyl)-2-(p-tolyl)-7,8-dihydropyrido[2,3-b]pyrazin-5(6H)-yl)-N-phenylheptanamide;
7-(2,3-bis(4-chlorophenyl)-7,8-dihydropyrido[2,3-b]pyrazin-5(6H)-yl)-N-phenylheptanamide;
7-(6-oxo-2,3-di-p-tolyl-7,8-dihydropyrido[2,3-b]pyrazin-5(6H)-yl)-N-phenylheptanamide;
7-(2-(4-chlorophenyl)-6-oxo-3-(p-tolyl)-7,8-dihydropyrido[2,3-b]pyrazin-5(6H)-yl)-N-phenylheptanamide;
7-(3-(4-chlorophenyl)-6-oxo-2-(p-tolyl)-7,8-dihydropyrido[2,3-b]pyrazin-5(6H)-yl)-N-phenylheptanamide;
7-(2,3-bis(4-chlorophenyl)-6-oxo-7,8-dihydropyrido[2,3-b]pyrazin-5(6H)-yl)-N-phenylheptanamide;
7-(7-hydroxy-6-oxo-2,3-di-p-tolyl-7,8-dihydropyrido[2,3-b]pyrazin-5(6H)-yl)-N-phenylheptanamide;
7-(2-(4-chlorophenyl)-7-hydroxy-6-oxo-3-(p-tolyl)-7,8-dihydropyrido[2,3-b]pyrazin-5(6H)-yl)-N-phenylheptanamide;
7-(3-(4-chlorophenyl)-7-hydroxy-6-oxo-2-(p-tolyl)-7,8-dihydropyrido[2,3-b]pyrazin-5(6H)-yl)-N-phenylheptanamide;
7-(2,3-bis(4-chlorophenyl)-7-hydroxy-6-oxo-7,8-dihydropyrido[2,3-b]pyrazin-5(6H)-yl)-N-phenylheptanamide;
7-(7-hydroxy-2,3-di-p-tolyl-7,8-dihydropyrido[2,3-b]pyrazin-5(6H)-yl)-N-phenylheptanamide;
7-(2-(4-chlorophenyl)-7-hydroxy-3-(p-tolyl)-7,8-dihydropyrido[2,3-b]pyrazin-5(6H)-yl)-N-phenylheptanamide;
7-(3-(4-chlorophenyl)-7-hydroxy-2-(p-tolyl)-7,8-dihydropyrido[2,3-b]pyrazin-5(6H)-yl)-N-phenylheptanamide;
7-(2,3-bis(4-chlorophenyl)-7-hydroxy-7,8-dihydropyrido[2,3-b]pyrazin-5(6H)-yl)-N-phenylheptanamide;

7-(8-hydroxy-2,3-di-p-tolyl-7,8-dihydropyrido[2,3-b]
pyrazin-5(6H)-yl)-N-phenylheptanamide
7-(2-(4-chlorophenyl)-8-hydroxy-3-(p-tolyl)-7,8-dihydro-
pyrido[2,3-b]pyrazin-5(6H)-yl)-N-phenylheptanamide;
7-(3-(4-chlorophenyl)-8-hydroxy-2-(p-tolyl)-7,8-dihydro-
pyrido[2,3-b]pyrazin-5(6H)-yl)-N-phenylheptanamide;
7-(2,3-bis(4-chlorophenyl)-8-hydroxy-7,8-dihydropyrido[2,
3-b]pyrazin-5(6H)-yl)-N-phenylheptanamide;
N-benzyl-7-(2,3-di-p-tolyl-7,8-dihydropyrido[2,3-b]
pyrazin-5(6H)-yl)heptanamide;
N-benzyl-7-(2-(4-chlorophenyl)-3-(p-tolyl)-7,8-dihydropy-
rido[2,3-b]pyrazin-5(6H)-yl)heptanamide;
N-benzyl-7-(3-(4-chlorophenyl)-2-(p-tolyl)-7,8-dihydropy-
rido[2,3-b]pyrazin-5(6H)-yl)heptanamide;
N-benzyl-7-(2,3-bis(4-chlorophenyl)-7,8-dihydropyrido[2,
3-b]pyrazin-5(6H)-yl)heptanamide;
N-benzyl-7-(6-oxo-2,3-di-p-tolyl-7,8-dihydropyrido[2,3-b]
pyrazin-5(6H)-yl)heptanamide;
N-benzyl-7-(2-(4-chlorophenyl)-6-oxo-3-(p-tolyl)-7,8-dihy-
dropyrido[2,3-b]pyrazin-5(6H)-yl)heptanamide;
N-benzyl-7-(3-(4-chlorophenyl)-6-oxo-2-(p-tolyl)-7,8-dihy-
dropyrido[2,3-b]pyrazin-5(6H)-yl)heptanamide;
N-benzyl-7-(2,3-bis(4-chlorophenyl)-6-oxo-7,8-dihydropy-
rido[2,3-b]pyrazin-5(6H)-yl)heptanamide;
N-benzyl-7-(7-hydroxy-6-oxo-2,3-di-p-tolyl-7,8-dihydro-
pyrido[2,3-b]pyrazin-5(6H)-yl)heptanamide;
N-benzyl-7-(2-(4-chlorophenyl)-7-hydroxy-6-oxo-3-(p-
tolyl)-7,8-dihydropyrido[2,3-b]pyrazin-5(6H)-yl)hep-
tanamide;
N-benzyl-7-(3-(4-chlorophenyl)-7-hydroxy-6-oxo-2-(p-
tolyl)-7,8-dihydropyrido[2,3-b]pyrazin-5(6H)-yl)hep-
tanamide;
N-benzyl-7-(2,3-bis(4-chlorophenyl)-7-hydroxy-6-oxo-7,8-
dihydropyrido[2,3-b]pyrazin-5(6H)-yl)heptanamide;
N-benzyl-7-(7-hydroxy-2,3-di-p-tolyl-7,8-dihydropyrido[2,
3-b]pyrazin-5(6H)-yl)heptanamide;
N-benzyl-7-(2-(4-chlorophenyl)-7-hydroxy-3-(p-tolyl)-7,8-
dihydropyrido[2,3-b]pyrazin-5(6H)-yl)heptanamide;
N-benzyl-7-(3-(4-chlorophenyl)-7-hydroxy-2-(p-tolyl)-7,8-
dihydropyrido[2,3-b]pyrazin-5(6H)-yl)heptanamide;
N-benzyl-7-(2,3-bis(4-chlorophenyl)-7-hydroxy-7,8-dihy-
dropyrido[2,3-b]pyrazin-5(6H)-yl)heptanamide;
N-benzyl-7-(8-hydroxy-2,3-di-p-tolyl-7,8-dihydropyrido[2,
3-b]pyrazin-5(6H)-yl)heptanamide;
N-benzyl-7-(2-(4-chlorophenyl)-8-hydroxy-3-(p-tolyl)-7,8-
dihydropyrido[2,3-b]pyrazin-5(6H)-yl)heptanamide;
N-benzyl-7-(3-(4-chlorophenyl)-8-hydroxy-2-(p-tolyl)-7,8-
dihydropyrido[2,3-b]pyrazin-5(6H)-yl)heptanamide;
N-benzyl-7-(2,3-bis(4-chlorophenyl)-8-hydroxy-7,8-dihy-
dropyrido[2,3-b]pyrazin-5(6H)-yl)heptanamide;
7-(2,3-di-p-tolyl-7,8-dihydropyrido[2,3-b]pyrazin-5(6H)-
yl)-N-(methylsulfonyl)heptanamide;
7-(2-(4-chlorophenyl)-3-(p-tolyl)-7,8-dihydropyrido[2,3-b]
pyrazin-5(6H)-yl)-N-(methylsulfonyl)heptanamide;
7-(3-(4-chlorophenyl)-2-(p-tolyl)-7,8-dihydropyrido[2,3-b]
pyrazin-5(6H)-yl)-N-(methylsulfonyl)heptanamide;
7-(2,3-bis(4-chlorophenyl)-7,8-dihydropyrido[2,3-b]
pyrazin-5(6H)-yl)-N-(methylsulfonyl)heptanamide;
7-(2,3-di-p-tolyl-7,8-dihydropyrido[2,3-b]pyrazin-5(6H)-
yl)-N-(isopropylsulfonyl)heptanamide;
7-(2-(4-chlorophenyl)-3-(p-tolyl)-7,8-dihydropyrido[2,3-b]
pyrazin-5(6H)-yl)-N-(isopropylsulfonyl)heptanamide;
7-(3-(4-chlorophenyl)-2-(p-tolyl)-7,8-dihydropyrido[2,3-b]
pyrazin-5(6H)-yl)-N-(isopropylsulfonyl)heptanamide;
7-(2,3-bis(4-chlorophenyl)-7,8-dihydropyrido[2,3-b]
pyrazin-5(6H)-yl)-N-(isopropylsulfonyl)heptanamide;
7-(2,3-di-p-tolyl-7,8-dihydropyrido[2,3-b]pyrazin-5(6H)-
yl)-N-methylheptanamide;
7-(2-(4-chlorophenyl)-3-(p-tolyl)-7,8-dihydropyrido[2,3-b]
pyrazin-5(6H)-yl)-N-methylheptanamide;
7-(3-(4-chlorophenyl)-2-(p-tolyl)-7,8-dihydropyrido[2,3-b]
pyrazin-5(6H)-yl)-N-methylheptanamide;
7-(2,3-bis(4-chlorophenyl)-7,8-dihydropyrido[2,3-b]
pyrazin-5(6H)-yl)-N-methylheptanamide;
7-(2,3-di-p-tolyl-7,8-dihydropyrido[2,3-b]pyrazin-5(6H)-
yl)-N-isopropylheptanamide;
7-(2-(4-chlorophenyl)-3-(p-tolyl)-7,8-dihydropyrido[2,3-b]
pyrazin-5(6H)-yl)-N-isopropylheptanamide;
7-(3-(4-chlorophenyl)-2-(p-tolyl)-7,8-dihydropyrido[2,3-b]
pyrazin-5(6H)-yl)-N-isopropylheptanamide;
7-(2,3-bis(4-chlorophenyl)-7,8-dihydropyrido[2,3-b]
pyrazin-5(6H)-yl)-N-isopropylheptanamide;
7-(2,3-di-p-tolyl-7,8-dihydropyrido[2,3-b]pyrazin-5(6H)-
yl)-N-hydroxyheptanamide;
7-(2-(4-chlorophenyl)-3-(p-tolyl)-7,8-dihydropyrido[2,3-b]
pyrazin-5(6H)-yl)-N-hydroxyheptanamide;
7-(3-(4-chlorophenyl)-2-(p-tolyl)-7,8-dihydropyrido[2,3-b]
pyrazin-5(6H)-yl)-N-hydroxyheptanamide;
6-(5-methyl-2,3-di-p-tolyl-5,6,7,8-tetrahydropyrido[2,3-b]
pyrazin-6-yl)hexanoic acid;
6-(5-isopropyl-2,3-di-p-tolyl-5,6,7,8-tetrahydropyrido[2,3-
b]pyrazin-6-yl)hexanoic acid;
5-(2,3-di-p-tolyl-5,6,7,8-tetrahydropyrido[2,3-b]pyrazin-6-
yl)pentanoic acid;
5-(5-methyl-2,3-di-p-tolyl-5,6,7,8-tetrahydropyrido[2,3-b]
pyrazin-6-yl)pentanoic acid;
5-(5-isopropyl-2,3-di-p-tolyl-5,6,7,8-tetrahydropyrido[2,3-
b]pyrazin-6-yl)pentanoic acid;
7-(2,3-di-p-tolyl-5,6,7,8-tetrahydropyrido[2,3-b]pyrazin-6-
yl)heptanoic acid;
7-(5-methyl-2-phenyl-3-(p-tolyl)-5,6,7,8-tetrahydropyrido
[2,3-b]pyrazin-6-yl)heptanoic acid;
7-(5-isopropyl-2,3-di-p-tolyl-5,6,7,8-tetrahydropyrido[2,3-
b]pyrazin-6-yl)heptanoic acid;
6-(7-hydroxy-2,3-di-p-tolyl-5,6,7,8-tetrahydropyrido[2,3-b]
pyrazin-6-yl)hexanoic acid;
6-(7-hydroxy-5-methyl-2,3-di-p-tolyl-5,6,7,8-tetrahydropy-
rido[2,3-b]pyrazin-6-yl)hexanoic acid;
6-(7-hydroxy-5-isopropyl-2,3-di-p-tolyl-5,6,7,8-tetrahydro-
pyrido[2,3-b]pyrazin-6-yl)hexanoic acid;
5-(7-hydroxy-2,3-di-p-tolyl-5,6,7,8-tetrahydropyrido[2,3-b]
pyrazin-6-yl)pentanoic acid;
5-(7-hydroxy-5-methyl-2,3-di-p-tolyl-5,6,7,8-tetrahydropy-
rido[2,3-b]pyrazin-6-yl)pentanoic acid;
5-(7-hydroxy-5-isopropyl-2,3-di-p-tolyl-5,6,7,8-tetrahydro-
pyrido[2,3-b]pyrazin-6-yl)pentanoic acid;
7-(7-hydroxy-2,3-di-p-tolyl-5,6,7,8-tetrahydropyrido[2,3-b]
pyrazin-6-yl)heptanoic acid;
7-(7-hydroxy-5-methyl-2-phenyl-3-(p-tolyl)-5,6,7,8-tet-
rahydropyrido[2,3-b]pyrazin-6-yl)heptanoic acid;
7-(7-hydroxy-5-isopropyl-2,3-di-p-tolyl-5,6,7,8-tetrahydro-
pyrido[2,3-b]pyrazin-6-yl)heptanoic acid;
6-(8-hydroxy-2,3-di-p-tolyl-5,6,7,8-tetrahydropyrido[2,3-b]
pyrazin-6-yl)hexanoic acid;
6-(8-hydroxy-5-methyl-2,3-di-p-tolyl-5,6,7,8-tetrahydropy-
rido[2,3-b]pyrazin-6-yl)hexanoic acid;
6-(8-hydroxy-5-isopropyl-2,3-di-p-tolyl-5,6,7,8-tetrahydro-
pyrido[2,3-b]pyrazin-6-yl)hexanoic acid;
5-(8-hydroxy-2,3-di-p-tolyl-5,6,7,8-tetrahydropyrido[2,3-b]
pyrazin-6-yl)pentanoic acid;
5-(8-hydroxy-5-methyl-2,3-di-p-tolyl-5,6,7,8-tetrahydropy-
rido[2,3-b]pyrazin-6-yl)pentanoic acid;

5-(8-hydroxy-5-isopropyl-2,3-di-p-tolyl-5,6,7,8-tetrahydropyrido[2,3-b]pyrazin-6-yl)pentanoic acid;
7-(8-hydroxy-2,3-di-p-tolyl-5,6,7,8-tetrahydropyrido[2,3-b]pyrazin-6-yl)heptanoic acid;
7-(8-hydroxy-5-methyl-2,3-di-p-tolyl-5,6,7,8-tetrahydropyrido[2,3-b]pyrazin-6-yl)heptanoic acid;
7-(8-hydroxy-5-isopropyl-2,3-di-p-tolyl-5,6,7,8-tetrahydropyrido[2,3-b]pyrazin-6-yl)heptanoic acid; and
7-(2,3-bis(4-chlorophenyl)-7,8-dihydropyrido[2,3-b]pyrazin-5(6H)-yl)-N-hydroxyheptanamide; or a pharmaceutically acceptable salt thereof.

In an embodiment of the first aspect, the compound is selected from the group consisting of
(rac)-6-(2,3-di-p-tolyl-5,6,7,8-tetrahydropyrido[2,3-b]pyrazin-6-yl)hexanoic acid or (S)-6-(2,3-di-p-tolyl-5,6,7,8-tetrahydropyrido[2,3-b]pyrazin-6-yl)hexanoic acid;
(R)-6-(2,3-di-p-tolyl-5,6,7,8-tetrahydropyrido[2,3-b]pyrazin-6-yl)hexanoic acid or (S)-6-(2,3-di-p-tolyl-5,6,7,8-tetrahydropyrido[2,3-b]pyrazin-6-yl)hexanoic acid;
(S)-6-(2,3-di-p-tolyl-5,6,7,8-tetrahydropyrido[2,3-b]pyrazin-6-yl)hexanoic acid;
(rac)-7-(7-(2-Hydroxypropan-2-yl)-6-oxo-2,3-di-p-tolyl-7,8-dihydropyrido[2,3-b]pyrazin-5(6H)-yl)heptanoic acid;
(R)-7-(7-(2-hydroxypropan-2-yl)-6-oxo-2,3-di-p-tolyl-7,8-dihydropyrido[2,3-b]pyrazin-5(6H)-yl)heptanoic acid or (S)-7-(7-(2-hydroxypropan-2-yl)-6-oxo-2,3-di-p-tolyl-7,8-dihydropyrido[2,3-b]pyrazin-5(6H)-yl)heptanoic acid;
(S)-7-(7-(2-hydroxypropan-2-yl)-6-oxo-2,3-di-p-tolyl-7,8-dihydropyrido[2,3-b]pyrazin-5(6H)-yl)heptanoic acid or (S)-7-(7-(2-hydroxypropan-2-yl)-6-oxo-2,3-di-p-tolyl-7,8-dihydropyrido[2,3-b]pyrazin-5(6H)-yl)heptanoic acid;
7-(7-Ethyl-2,3-di-p-tolyl-7,8-dihydropyrido[2,3-b]pyrazin-5(6H)-yl)heptanoic acid;
7-(7-Methyl-2-phenyl-3-(p-tolyl)-7,8-dihydropyrido[2,3-b]pyrazin-5(6H)-yl)heptanoic acid;
(rac)-7-(6-Ethyl-2,3-di-p-tolyl-7,8-dihydropyrido[2,3-b]pyrazin-5(6H)-yl)heptanoic acid;
(R)-7-(6-Ethyl-2,3-di-p-tolyl-7,8-dihydropyrido[2,3-b]pyrazin-5(6H)-yl)heptanoic acid;
(S)-7-(6-Ethyl-2,3-di-p-tolyl-7,8-dihydropyrido[2,3-b]pyrazin-5(6H)-yl)heptanoic acid;
7-(6-Methyl-2-phenyl-3-p-tolyl-7,8-dihydropyrido[2,3-b]pyrazin-5(6H)-yl)heptanoic acid;
7-(3-o-Tolyl-2-p-tolyl-7,8-dihydropyrido[3,2-b]pyrazin-5(6H)-yl)heptanoic acid;
7-(2-o-Tolyl-3-p-tolyl-7,8-dihydropyrido[3,2-b]pyrazin-5(6H)-yl)heptanoic acid;
7-(2-(2-Fluorophenyl)-3-p-tolyl-7,8-dihydropyrido[2,3-b]pyrazin-5(6H)-yl)heptanoic acid;
7-(2-(4-Fluorophenyl)-3-p-tolyl-7,8-dihydropyrido[2,3-b]pyrazin-5(6H)-yl)heptanoic acid;
7-(2-(3-Fluorophenyl)-3-p-tolyl-7,8-dihydropyrido[2,3-b]pyrazin-5(6H)-yl)heptanoic acid;
7-(2-(4-Methoxyphenyl)-3-p-tolyl-7,8-dihydropyrido[2,3-b]pyrazin-5(6H)-yl)heptanoic acid;
(rac)-7-(8-Methoxy-2,3-di-p-tolyl-7,8-dihydropyrido[2,3-b]pyrazin-5(6H)-yl)heptanoic acid;
(R)-7-(8-methoxy-2,3-di-p-tolyl-7,8-dihydropyrido[2,3-b]pyrazin-5(6H)-yl)heptanoic acid;
(S)-7-(8-methoxy-2,3-di-p-tolyl-7,8-dihydropyrido[2,3-b]pyrazin-5(6H)-yl)heptanoic acid;
7-(2,3-Bis(2,4-difluorophenyl)-7,8-dihydropyrido[2,3-b]pyrazin-5(6H)-yl)heptanoic acid;
7-(2,3-Bis(6-methylpyridin-3-yl)-7,8-dihydropyrido[2,3-b]pyrazin-5(6H)-yl)heptanoic acid;
7-(2-(6-Methylpyridin-3-yl)-3-p-tolyl-7,8-dihydropyrido[2,3-b]pyrazin-5(6H)-yl)heptanoic acid;
7-(3-(6-Methylpyridin-3-yl)-2-p-tolyl-7,8-dihydropyrido[2,3-b]pyrazin-5(6H)-yl)heptanoic acid;
9-(6-Oxo-2,3-di-p-tolyl-7,8-dihydropyrido[2,3-b]pyrazin-5(6H)-yl)nonanoic acid;
9-(2,3-Di-p-tolyl-7,8-dihydropyrido[2,3-b]pyrazin-5(6H)-yl)nonanoic acid;
(rac)-7-(7-(2-hydroxypropan-2-yl)-2,3-di-p-tolyl-7,8-dihydropyrido[2,3-b]pyrazin-5(6H)-yl)heptanoic acid;
(R)-7-(7-(2-hydroxypropan-2-yl)-2,3-di-p-tolyl-7,8-dihydropyrido[2,3-b]pyrazin-5(6H)-yl)heptanoic acid;
(S)-7-(7-(2-hydroxypropan-2-yl)-2,3-di-p-tolyl-7,8-dihydropyrido[2,3-b]pyrazin-5(6H)-yl)heptanoic acid;
6-(2,3-Di-p-tolyl-7,8-dihydropyrido[2,3-b]pyrazin-5(6H)-yl)hexanoic acid;
(R)-7-(7-hydroxy-6-oxo-2,3-di-p-tolyl-7,8-dihydropyrido[2,3-b]pyrazin-5(6H)-yl)heptanoic acid;
(S)-7-(7-hydroxy-6-oxo-2,3-di-p-tolyl-7,8-dihydropyrido[2,3-b]pyrazin-5(6H)-yl)heptanoic acid;
8-(6-Oxo-2,3-di-p-tolyl-7,8-dihydropyrido[2,3-b]pyrazin-5(6H)-yl)octanoic acid;
7-(2,3-Di-p-tolyl-7,8-dihydropyrido[2,3-b]pyrazin-5(6H)-yl)-N-methoxyheptanamide;
7-(2,3-Di-p-tolyl-7,8-dihydropyrido[2,3-b]pyrazin-5(6H)-yl)-N,N-dimethylheptanamide;
7-(2,3-Di-p-tolyl-7,8-dihydropyrido[2,3-b]pyrazin-5(6H)-yl)-N-hydroxy-N-methylheptanamide;
6-(2,3-Di-p-tolyl-7,8-dihydropyrido[2,3-b]pyrazin-5(6H)-yl)-N-hydroxyhexanamide;
(R)-7-(8-Hydroxy-2,3-di-p-tolyl-7,8-dihydropyrido[3,2-b]pyrazin-5(6H)-yl)-N-(methylsulfonyl)heptanamide;
(S)-7-(8-Hydroxy-2,3-di-p-tolyl-7,8-dihydropyrido[3,2-b]pyrazin-5(6H)-yl)-N-(methylsulfonyl)heptanamide;
(R)—N-(Benzylsulfonyl)-7-(8-hydroxy-2,3-di-p-tolyl-7,8-dihydropyrido[3,2-b]pyrazin-5(6H)-yl)heptanamide;
(S)—N-(Benzylsulfonyl)-7-(8-hydroxy-2,3-di-p-tolyl-7,8-dihydropyrido[3,2-b]pyrazin-5(6H)-yl)heptanamide;
7-(2,3-Di-p-tolyl-7,8-dihydropyrido[2,3-b]pyrazin-5(6H)-yl)-N-(methylsulfonyl)heptanamide;
7-(7-Piperidin-1-yl)-2,3-di-p-tolyl-7,8-dihydropyrido[2,3-b]pyrazin-5(6H)-yl)heptanoic acid;
rac-7-(8-Methoxy-8-methyl-2,3-di-p-tolyl-7,8-dihydropyrido[2,3-b]pyrazin-5(6H)-yl)heptanoic acid;
7-(8-Hydroxy-8-methyl-2,3-di-p-tolyl-7,8-dihydropyrido[2,3-b]pyrazin-5(6H)-yl)heptanoic acid;
rac-7-(2,3-Di-p-tolyl-7,8-dihydropyrido[2,3-b]pyrazin-5(6H)-yl)-3-hydroxyheptanoic acid;
(R)-7-(8-Methoxy-8-methyl-2,3-di-p-tolyl-7,8-dihydropyrido[2,3-b]pyrazin-5(6H)-yl)heptanoic acid;
(S)-7-(8-Methoxy-8-methyl-2,3-di-p-tolyl-7,8-dihydropyrido[2,3-b]pyrazin-5(6H)-yl)heptanoic acid;
(R)-7-(2,3-di-p-tolyl-7,8-dihydropyrido[2,3-b]pyrazin-5(6H)-yl)-3-hydroxyheptanoic acid;
(S)-7-(2,3-di-p-tolyl-7,8-dihydropyrido[2,3-b]pyrazin-5(6H)-yl)-3-hydroxyheptanoic acid;
7-(2,3-Bis(4-chlorophenyl)-6-oxo-7,8-dihydropyrido[2,3-b]pyrazin-5(6H)-yl)heptanoic acid;
7-(2-(4-Chlorophenyl)-6-oxo-3-p-tolyl-7,8-dihydropyrido[2,3-b]pyrazin-5(6H)-yl)heptanoic acid;
7-(3-(4-Chlorophenyl)-6-oxo-2-p-tolyl-7,8-dihydropyrido[2,3-b]pyrazin-5(6H)-yl)heptanoic acid;
N-(Benzylsulfonyl)-7-(2,3-di-p-tolyl-7,8-dihydropyrido[2,3-b]pyrazin-5(6H)-yl)heptanamide;
N-Benzyl-7-(2,3-di-p-tolyl-7,8-dihydro pyrido[2,3-b]pyrazin-5(6H)-yl)heptanamide;
7-(2,3-Di-p-tolyl-7,8-dihydro pyrido[2,3-b]pyrazin-5(6H)-yl)-N-(phenyl sulfonyl) heptanamide;

7-(2,3-Di-p-tolyl-7,8-dihydropyrido[2,3-b]pyrazin-5(6H)-yl)-N-isopropylheptanamide;
7-(2,3-Di-p-tolyl-7,8-dihydropyrido[2,3-b]pyrazin-5(6H)-yl)-N-methylheptanamide;
7-(2,3-Di-p-tolyl-7,8-dihydropyrido[2,3-b]pyrazin-5(6H)-yl)-N-phenylheptanamide;
7-(2,3-Di-p-tolyl-7,8-dihydropyrido[2,3-b]pyrazin-5(6H)-yl)-N-hydroxyheptanamide; and
7-(2,3-Di-p-tolyl-7,8-dihydropyrido[2,3-b]pyrazin-5(6H)-yl)-N-(isopropylsulfonyl)heptanamide;
or a pharmaceutically acceptable salt thereof.

In an embodiment of the first aspect, the compound is selected from the group consisting of
(rac)-6-(2,3-di-p-tolyl-5,6,7,8-tetrahydropyrido[2,3-b]pyrazin-6-yl)hexanoic acid or (S)-6-(2,3-di-p-tolyl-5,6,7,8-tetrahydropyrido[2,3-b]pyrazin-6-yl)hexanoic acid;
(R)-6-(2,3-di-p-tolyl-5,6,7,8-tetrahydropyrido[2,3-b]pyrazin-6-yl)hexanoic acid or (S)-6-(2,3-di-p-tolyl-5,6,7,8-tetrahydropyrido[2,3-b]pyrazin-6-yl)hexanoic acid;
(S)-6-(2,3-di-p-tolyl-5,6,7,8-tetrahydropyrido[2,3-b]pyrazin-6-yl)hexanoic acid;
(rac)-7-(7-(2-Hydroxypropan-2-yl)-6-oxo-2,3-di-p-tolyl-7,8-dihydropyrido[2,3-b]pyrazin-5(6H)-yl)heptanoic acid;
(R)-7-(7-(2-hydroxypropan-2-yl)-6-oxo-2,3-di-p-tolyl-7,8-dihydropyrido[2,3-b]pyrazin-5(6H)-yl)heptanoic acid or (S)-7-(7-(2-hydroxypropan-2-yl)-6-oxo-2,3-di-p-tolyl-7,8-dihydropyrido[2,3-b]pyrazin-5(6H)-yl)heptanoic acid;
(S)-7-(7-(2-hydroxypropan-2-yl)-6-oxo-2,3-di-p-tolyl-7,8-dihydropyrido[2,3-b]pyrazin-5(6H)-yl)heptanoic acid or (S)-7-(7-(2-hydroxypropan-2-yl)-6-oxo-2,3-di-p-tolyl-7,8-dihydropyrido[2,3-b]pyrazin-5(6H)-yl)heptanoic acid;
7-(7-Ethyl-2,3-di-p-tolyl-7,8-dihydropyrido[2,3-b]pyrazin-5(6H)-yl)heptanoic acid;
7-(7-Methyl-2-phenyl-3-(p-tolyl)-7,8-dihydropyrido[2,3-b]pyrazin-5(6H)-yl)heptanoic acid;
(rac)-7-(6-Ethyl-2,3-di-p-tolyl-7,8-dihydropyrido[2,3-b]pyrazin-5(6H)-yl)heptanoic acid;
(R)-7-(6-Ethyl-2,3-di-p-tolyl-7,8-dihydropyrido[2,3-b]pyrazin-5(6H)-yl)heptanoic acid;
(S)-7-(6-Ethyl-2,3-di-p-tolyl-7,8-dihydropyrido[2,3-b]pyrazin-5(6H)-yl)heptanoic acid;
7-(6-Methyl-2-phenyl-3-p-tolyl-7,8-dihydropyrido[2,3-b]pyrazin-5(6H)-yl)heptanoic acid;
7-(3-o-Tolyl-2-p-tolyl-7,8-dihydropyrido[3,2-b]pyrazin-5(6H)-yl)heptanoic acid;
7-(2-o-Tolyl-3-p-tolyl-7,8-dihydropyrido[3,2-b]pyrazin-5(6H)-yl)heptanoic acid;
7-(2-(2-Fluorophenyl)-3-p-tolyl-7,8-dihydropyrido[2,3-b]pyrazin-5(6H)-yl)heptanoic acid;
7-(2-(4-Fluorophenyl)-3-p-tolyl-7,8-dihydropyrido[2,3-b]pyrazin-5(6H)-yl)heptanoic acid;
7-(2-(3-Fluorophenyl)-3-p-tolyl-7,8-dihydropyrido[2,3-b]pyrazin-5(6H)-yl)heptanoic acid;
7-(2-(4-Methoxyphenyl)-3-p-tolyl-7,8-dihydropyrido[2,3-b]pyrazin-5(6H)-yl)heptanoic acid;
(rac)-7-(8-Methoxy-2,3-di-p-tolyl-7,8-dihydropyrido[2,3-b]pyrazin-5(6H)-yl)heptanoic acid;
(R)-7-(8-methoxy-2,3-di-p-tolyl-7,8-dihydropyrido[2,3-b]pyrazin-5(6H)-yl)heptanoic acid;
(S)-7-(8-methoxy-2,3-di-p-tolyl-7,8-dihydropyrido[2,3-b]pyrazin-5(6H)-yl)heptanoic acid;
7-(2,3-Bis(2,4-difluorophenyl)-7,8-dihydropyrido[2,3-b]pyrazin-5(6H)-yl)heptanoic acid;
7-(2,3-Bis(6-methylpyridin-3-yl)-7,8-dihydropyrido[2,3-b]pyrazin-5(6H)-yl)heptanoic acid;
7-(2-(6-Methylpyridin-3-yl)-3-p-tolyl-7,8-dihydropyrido[2,3-b]pyrazin-5(6H)-yl)heptanoic acid;
7-(3-(6-Methylpyridin-3-yl)-2-p-tolyl-7,8-dihydropyrido[2,3-b]pyrazin-5(6H)-yl)heptanoic acid;
9-(6-Oxo-2,3-di-p-tolyl-7,8-dihydropyrido[2,3-b]pyrazin-5(6H)-yl)nonanoic acid;
9-(2,3-Di-p-tolyl-7,8-dihydropyrido[2,3-b]pyrazin-5(6H)-yl)nonanoic acid;
(rac)-7-(7-(2-hydroxypropan-2-yl)-2,3-di-p-tolyl-7,8-dihydropyrido[2,3-b]pyrazin-5(6H)-yl)heptanoic acid;
(R)-7-(7-(2-hydroxypropan-2-yl)-2,3-di-p-tolyl-7,8-dihydropyrido[2,3-b]pyrazin-5(6H)-yl)heptanoic acid;
(S)-7-(7-(2-hydroxypropan-2-yl)-2,3-di-p-tolyl-7,8-dihydropyrido[2,3-b]pyrazin-5(6H)-yl)heptanoic acid;
6-(2,3-Di-p-tolyl-7,8-dihydropyrido[2,3-b]pyrazin-5(6H)-yl)hexanoic acid;
(R)-7-(7-hydroxy-6-oxo-2,3-di-p-tolyl-7,8-dihydropyrido[2,3-b]pyrazin-5(6H)-yl)heptanoic acid; and
(S)-7-(7-hydroxy-6-oxo-2,3-di-p-tolyl-7,8-dihydropyrido[2,3-b]pyrazin-5(6H)-yl)heptanoic acid;
or a pharmaceutically acceptable salt thereof.

In a second aspect, the invention provides a compound, or a pharmaceutically acceptable salt thereof, as defined in the first aspect, for use as a medicine.

Activating the IP receptor has been shown to have a beneficial effect or treat the following diseases or disorders:
PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH); Raynaud's phenomenon, including Raynaud's disease and Raynaud's syndrome; fibrotic diseases, including pulmonary fibrosis, systemic sclerosis/scleroderma, hepatic fibrosis/cirrhosis, renal fibrosis; thrombotic diseases associated with excessive platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy, glaucoma or other disease of the eye with abnormal intraocular pressure, hypertension, preeclampsia, inflammation, prophylaxis against unwanted side effects of COX-1, COX-2 and non-selective COX inhibitors, psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD).

In a further aspect, the invention provides a compound as defined in the first aspect, or a pharmaceutically acceptable salt thereof, for use in the treatment of PAH as described above.

In a further aspect, the invention provides a compound as defined in the first aspect, or a pharmaceutically acceptable salt thereof, for use in the treatment of a disorder selected from the aforementioned diseases and disorders.

In a still further aspect, the present invention provides for the use of a compound as defined in the first aspect, in free or pharmaceutically acceptable salt form, for the manufacture of a medicament for the treatment of pulmonary arterial hypertension. In an embodiment of the present invention, there is provided for the use of a compound as defined in the first aspect, in free or pharmaceutically acceptable salt form, for the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH).

In a further aspect, the present invention provides a method for the prevention or treatment of an IP receptor mediated condition or disease comprising administering an effective amount of at least one compound as defined in the first aspect to a subject in need of such treatment. Such IP receptor mediated conditions or diseases are selected from PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH).

Other IP receptor mediated conditions or diseases are selected from platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy, glaucoma or other disease of the eye with abnormal intraocular pressure, hypertension, inflammation, psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD).

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

As used herein, the term "pharmaceutically acceptable salts" refers to salts that retain the biological effectiveness and properties of the compounds of this invention and which typically are not biologically or otherwise undesirable. In many cases, the compounds as defined in the first aspect are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethanedisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate trifluoroacetate and xinafoate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, 1-hydroxy-2-naphtoic acid and sulfosalicylic acid.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, acetone or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds as defined in the first aspect, including their salts, can also be obtained in the form of their hydrates, or include other solvents used for their crystallization.

Compounds of the invention that contain groups capable of acting as donors and/or acceptors for hydrogen bonds may be capable of forming co-crystals with suitable co-crystal formers. These co-crystals may be prepared from compounds as defined in the first aspect by known co-crystal forming procedures. Such procedures include grinding, heating, co-subliming, co-melting, or contacting in solution compounds as defined in the first aspect with the co-crystal former under crystallization conditions and isolating co-crystals thereby formed. Suitable co-crystal formers include those described in WO 2004/078163. Hence the invention further provides co-crystals comprising a compound as defined in the first aspect.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds as defined in the first aspect into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

Compounds as defined in the first aspect are either obtained in the free form, as a salt thereof, or as prodrug derivatives thereof.

When both a basic group and an acid group are present in the same molecule, the compounds as defined in the first aspect may also form internal salts, e.g., zwitterionic molecules.

The present invention also provides pro-drugs of the compounds as defined in the first aspect that converts in vivo to the compounds as defined in the first aspect. A pro-drug is an active or inactive compound that is modified chemically through in vivo physiological action, such as hydrolysis, metabolism and the like, into a compound of this invention following administration of the prodrug to a subject. The suitability and techniques involved in making and using prodrugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or disubstituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$, $^{13}C$, and $^{14}C$, are present. Such isotopically labeled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound as defined in the first aspect. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds as defined in the first aspect can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds as defined in the first aspect, in free form, may be converted into salt form, and vice versa, in a conventional manner understood by those skilled in the art. The compounds in free or salt form can be obtained in the form of hydrates or solvates containing a solvent used for crystallisation. Compounds as defined in the first aspect can be recovered from reaction mixtures and purified in a conventional manner. Isomers, such as stereoisomers, may be obtained in a conventional manner, e.g., by fractional crystallisation or asymmetric synthesis from correspondingly asymmetrically substituted, e.g., optically active, starting materials.

The compounds as defined in the first aspect or a pharmaceutically acceptable salt thereof can be prepared, e.g., using the reactions and techniques described below and in the Examples. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula I, Ia, II or IIa into another compound of formula I, Ia, II or IIa. Examples of such manipulations are conversion of an ester or a ketone to an alcohol; conversion of an ester to a ketone; interconversions of esters, acids and amides; alkylation, acylation and sulfonylation of alcohols and amines; and many others.

Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry*, 5*th* Edition, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995); and *Comprehensive Organic Synthesis*, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is Greene and Wuts, *Protective Groups in Organic Synthesis*, Wiley and Sons, 4*th* Edition (2006).

Pharmacological Activity

The compounds disclosed herein activate the IP receptor and are useful in the treatment of several diseases and disorders, and in the amelioration of symptoms thereof. Without limitation, these include the following:

Pulmonary Arterial Hypertension (PAH)

PAH has a multifactorial pathobiology. Vasoconstriction, remodeling of the pulmonary vessel wall, and thrombosis contribute to increased pulmonary vascular resistance in PAH (Humbert et al, J. Am. Coll. Cardiol., 2004, 43:13S-24S.). The compounds as defined in the first aspect disclosed herein are useful in the treatment of pulmonary arterial hypertension (PAH) and symptoms thereof. PAH shall be understood to encompass the following forms of pulmonary arterial hypertension described in the 2003 World Health Organization (WHO) clinical classification of pulmonary arterial hypertension: idiopathic PAH (BPAH); familial PAH (FPAH); PAH associated with other conditions (APAH), such as PAH associated with collagen vascular disease, PAH associated with congenital systemic-to-pulmonary shunts, PAH associated with portal hypertension, PAH associated with HTV infection, PAH associated with drugs or toxins, or PAH associated with Other; and PAH associated with significant venous or capillary involvement. Idiopathic PAH refers to PAH of undetermined cause. Familial PAH refers to PAH for which hereditary transmission is suspected or documented. PAH associated with collagen vascular disease shall be understood to encompass PAH associated with scleroderma, PAH associated with CREST (calcinosis cutis, Raynaud's phenomenon, esophageal dysfunction, sclerodactyly, and telangiectasias) syndrome, PAH associated with systemic lupus erythematosus (SLE), PAH associated with rheumatoid arthritis, PAH associated with Takayasu's arteritis, PAH associated with polymyositis, and PAH associated with dermatomyositis. PAH associated with congenital systerruc-to-pulmonary shunts shall be understood to encompass PAH associated with atrial septic defect (ASD), PAH associated with ventricular septic defect (VSD) and PAH associated with patent ductus arteriosus.

PAH associated with drugs or toxins shall be understood to encompass PAH associated with ingestion of aminorex, PAH associated with ingestion of a fenfluramine compound (e.g., PAH associated with ingestion of fenfluramine or PAH associated with ingestion of dexfenfluramine), PAH associated with ingestion of certain toxic oils (e g, PAH associated with ingestion of rapeseed oil), PAH associated with ingestion of pyrrolizidine alkaloids (e.g, PAH associated with ingestion of bush tea) and PAH associated with ingestion of monocrotaline. PAH associated with Other shall be understood to encompass PAH associated with a thyroid disorder, PAH associated with glycogen storage disease, PAH associated with Gaucher disease, PAH associated with hereditary hemorrhagic telangiectasia, PAH associated with a hemoglobinopathy, PAH associated with a myeloproliferative disorder, and PAH associated with splenectomy. PAH associated with significant venous or capillary involvement shall be understood to encompass PAH associated with pulmonary veno-occlusive disease (PVOD) and PAH associated with pulmonary capillary hemangiomatosis (PCH). (See, e.g, Simonneau et al, J. Am. Coll. Cardiol., 2004, 43:5S-12S; McGoon et al., Chest, 2004, 126:14S-34S; Rabinovitch, Annu. Rev. Pathol. Mech. Dis., 2007, 2:369-399; McLaughlin et al, Circulation, 2006, 114:1417-1431; Strauss et al, Clin. Chest. Med., 2007, 28:127-142; Taichman et al., Clin. Chest. Med., 2007, 28:1-22.).

Evidence for the association of PAH with scleroderma and the beneficial effect of an agonist of the IP receptor on PAH is given by Badesch et al (Badesch et al, Ann. Intern. Med., 2000, 132:425-434). Evidence for the association of PAH with the collagen vascular diseases mixed connective tissue disease (MCTD), systemic lupus erythematosus (SLE), Sjogren's syndrome and CREST syndrome and the beneficial effect of an agonist of the IP receptor on PAH is given by Humbert et al. (Eur. Respir. J., 1999, 13:1351-1356). Evidence for the association of PAH with CREST syndrome and the beneficial effect of an agonist of the IP receptor on PAH is given by Miwa et al. (Int. Heart J., 2007, 48:417-422). Evidence for the association of PAH with SLE and the beneficial effect of an agonist of the IP receptor on PAH is given by Robbins et al (Chest, 2000, 117:14-18). Evidence for the association of PAH with HIV infection and the beneficial of an agonist of the IP receptor on PAH is given by Aguilar et al. (Am. J. Respir. Crit. Care Med., 2000, 162:1846-1850). Evidence for the association of PAH with congenital heart defects (including ASD, VSD and patent ductus arteriosus) and the beneficial effect of an agonist of the IP receptor on PAH is given by Rosenzweig et al. (Circulation, 1999, 99:1858-1865).

Evidence for the association of PAH with fenfluramine and with dexfenfluramine, anorexigens, is given by Archer et al. (Am. J. Respir. Crit. Care Med., 1998, 158: 1061-1067). Evidence for the association of PAH with hereditary hemorrhagic telangiectasia is given by McGoon et al. (Chest, 2004, 126:14-34). Evidence for the association of PAH with splenectomy is given by Hoeper et al. (Ann. Intern. Med., 1999, 130:506-509). Evidence for the association of PAH with portal hypertension and the beneficial effect of an agonist of the IP receptor on PAH is given by Hoeper et al. (Eur. Respir. J., 2005, 25:502-508).

Symptoms of PAH include dyspnea, angina, syncope and edema (McLaughlin et al., Circulation, 2006, 114:1417-1431). The compounds as defined in the first aspect disclosed herein are useful in the treatment of symptoms of PAH.

Antiplatelet Therapies (Conditions Related to Platelet Aggregation)

Antiplatelet agents (antiplatelets) are prescribed for a variety of conditions. For example, in coronary artery disease they are used to help prevent myocardial infarction or stroke in patients who are at risk of developing obstructive blood clots (e.g., coronary thrombosis).

In a myocardial infarction, the heart muscle does not receive enough oxygen-rich blood as a result of a blockage in the coronary blood vessels. If taken while an attack is in progress or immediately afterward (preferably within 30 min), antiplatelets can reduce the damage to the heart.

A transient ischemic attack ("TIA" or "mini-stroke") is a brief interruption of oxygen flow to the brain due to decreased blood flow through arteries, usually due to an obstructing blood clot. Antiplatelet drugs have been found to be effective in preventing TIAs. Angina is a temporary and often recurring chest pain, pressure or discomfort caused by inadequate oxygen-rich blood flow (ischemia) to some parts of the heart. In patients with angina, antiplatelet therapy can reduce the effects of angina and the risk of myocardial infarction.

Stroke is an event in which the brain does not receive enough oxygen-rich blood, usually due to blockage of a cerebral blood vessel by a blood clot. In high-risk patients, taking antiplatelets regularly has been found to prevent the formation of blood clots that cause first or second strokes. Angioplasty is a catheter based technique used to open arteries obstructed by a blood clot. Whether or not stenting is performed immediately after this procedure to keep the artery open, antiplatelets can reduce the risk of forming additional blood clots following the procedure(s).

Coronary bypass surgery is a surgical procedure in which an artery or vein is taken from elsewhere in the body and grafted to a blocked coronary artery, rerouting blood around the blockage and through the newly attached vessel. After the procedure, antiplatelets can reduce the risk of secondary blood clots.

Atrial fibrillation is the most common type of sustained irregular heart rhythm (arrhythmia). Atrial fibrillation affects about two million Americans every year. In atrial fibrillation, the atria (the heart's upper chambers) rapidly fire electrical signals that cause them to quiver rather than contract normally. The result is an abnormally fast and highly irregular heartbeat. When given after an episode of atrial fibrillation, antiplatelets can reduce the risk of blood clots forming in the heart and traveling to the brain (embolism).

There is evidence that an IP receptor agonist will inhibit platelet aggregation and thus be a potential treatment as an antiplatelet therapy (see, e.g., Moncada et al., Lancet, 1977, 1: 18-20). It has been shown that genetic deficiency of the IP receptor in mice leads to an increased propensity towards thrombosis (Murata et al, Nature, 1997, 388:678-682).

IP receptor agonists can be used to treat, for example, claudication or peripheral artery disease as well as cardiovascular complications, arterial thrombosis, atherosclerosis, vasoconstriction caused by serotonin, ischemia-reperfusion injury, and restenosis of arteries following angioplasty or stent placement. (See, e.g., Fetalvero et al, Prostaglandins Other Lipid Mediat., 2007, 82:109-118; Arehart et al, Curr. Med. Chem., 2007, 14:2161-2169; Davi et al, N. Engl. J. Med., 2007, 357:2482-2494; Fetalvero et al, Am. J. Physiol. Heart. Circ. Physiol., 2006, 290:H1337-H1346; Murata et al, Nature, 1997, 388:678-682; Wang et al, Proc. Natl. Acad. Sci. USA, 2006, 103:14507-14512; Xiao et al, Circulation, 2001, 104:2210-2215; McCormick et al, Biochem. Soc. Trans., 2007, 35:910-911; Arehart et al, Circ. Res., 2008, Mar. 6.).

IP receptor agonists can also be used alone or in combination with thrombolytic therapy, for example, tissue-type plasminogen activator (t-PA), to provide cardioprotection following MI or postischemic myocardial dysfunction or protection from ischemic injury during percutaneous coronary intervention, and the like, including complications resulting therefrom. IP receptor agonists can also be used in antiplatelet therapies in combination with, for example, alpha-tocopherol (vitamin E), echistatin (a disintegrin) or, in states of hypercoagulability, heparin. (See, e.g., Chan., J. Nutr., 1998, 128: 1593-1596; Mardla et al, Platelets, 2004, 15:319-324; Bernabei et al, Ann. Thorac. Surg., 1995, 59:149-153; Gainza et al, J. Nephrol., 2006, 19:648-655.)

The IP receptor agonists disclosed herein provide beneficial improvement in microcirculation to patients in need of antiplatelet therapy by antagonizing the vasoconstrictive products of the aggregating platelets in, for example and not limited to the indications described above.

Accordingly, in some embodiments, the present invention provides methods for reducing platelet aggregation in a patient in need thereof, comprising administering to the patient a composition comprising an IP receptor agonist disclosed herein. In further embodiments, the present invention provides methods for treating coronary artery disease, myocardial infarction, transient ischemic attack, angina, stroke, atrial fibrillation, or a symptom of any of the foregoing in a patient in need of the treatment, comprising administering to the patient a composition comprising an IP receptor agonist disclosed herein.

In further embodiments, the present invention provides methods for reducing risk of blood clot formation in an angioplasty or coronary bypass surgery patient, or a patient suffering from atrial fibrillation, comprising administering to the patient a composition comprising an IP receptor agonist disclosed herein at a time where such risk exists.

Atherosclerosis

Atherosclerosis is a complex disease characterized by inflammation, lipid accumulation, cell death and fibrosis. It is the leading cause of mortality in many countries, including the United States. Atherosclerosis, as the term is used herein, shall be understood to encompass disorders of large and medium-sized arteries that result in the progressive accumulation within the intima of smooth muscle cells and lipids.

It has been shown that an agonist of the IP receptor can confer protection from atherosclerosis, such as from atherothrombosis (Arehart et al, Curr. Med. Chem., 2007, 14:2161-2169; Stitham et al, Prostaglandins Other Lipid Mediat., 2007, 82:95-108; Fries et al, Hematology Am. Soc. Hematol. Educ. Program, 2005, :445-451; Egan et al, Science, 2004, 306:1954-1957; Kobayashi et al, J. Clin. Invest, 2004, 114: 784-794; Arehart et al, Circ. Res., 2008, Mar. 6). It has been shown that defective IP receptor signaling appears to accelerate atherothrombosis in humans, i e that an agonist of the IP receptor can confer protection from atherothrombosis in humans (Arehart et al, Circ. Res., 2008, Mar. 6.)

The compounds as defined in the first aspect disclosed herein are useful in the treatment of atherosclerosis, and the treatment of the symptoms thereof. Accordingly, in some embodiments, the present invention provides methods for treating atherosclerosis in a patient in need of the treatment, comprising administering to the patient a composition comprising an IP receptor agonist disclosed herein. In further embodiments, methods are provided for treating a symptom of atherosclerosis in a patient in need of the treatment, comprising administering to the patient a composition comprising an IP receptor agonist disclosed herein.

Asthma

Asthma is a lymphocyte-mediated inflammatory airway disorder characterised by airway eosinophilia, increased mucus production by goblet cells, and structural remodeling of the airway wall. The prevalence of asthma has dramatically increased worldwide in recent decades. It has been shown that genetic deficiency of the IP receptor in mice augments allergic airway inflammation (Takahashi et al, Br J Pharmacol, 2002, 137:315-322). It has been shown that an agonist of the IP receptor can suppress not only the development of asthma when given during the sensitization phase, but also the cardinal features of experimental asthma when given during the challenge phase (Idzko et al, J. Clin. Invest., 2007, 117:464-72, Nagao et al, Am. J. Respir. Cell Mol. Biol., 2003, 29:314-320), at least in part through markedly interfering with the function of antigen-presenting dendnuc cells within the airways (Idzko et al., J. Clin. Invest., 2007, 117:464-472; Zhou et al, J. Immunol., 2007, 178:702-710; Jaffar et al., J. Immunol., 2007, 179:6193-6203; Jozefowski et al, Int. Immunopharmacol., 2003, 3:865-878). These cells are crucial for both the initiation and the maintenance phases of allergic asthma, as depletion of airway dendritic cells during secondary challenge in sensitized mice abolished all characteristic features of asthma, an effect that could be completely restored by adoptive transfer of wild-type dendritic cells (van Rijt et al., J. Exp. Med., 2005, 201:981-991). It has also been shown that an agonist of the IP receptor can inhibit proinflammatory cytokine secretion by human alveolar macrophages (Raychaudhuri et al., J. Biol. Chem., 2002, 277:33344-33348). The compounds as defined in the first aspect disclosed herein are useful in the treatment of asthma, and the treatment of the symptoms thereof. Accordingly, in some embodiments, the present invention provides methods for treating asthma in a patient in need of the treatment, comprising administering to the patient a composition comprising IP receptor agonist disclosed herein.

In further embodiments, methods are provided for treating a symptom of asthma in a patient in need of the treatment, comprising administering to the patient a composition comprising IP receptor agonist disclosed herein.

Chronic Obstructive Pulmonary Disease

Activation of the IP-receptor may also be beneficial in chronic obstructive pulmonary disease (COPD). Taprostene, an IP-receptor agonist, suppressed the generation of the CD8+ T cell chemoattractants CXCL9 and CXCL10 from human airway epithelial cells in vitro. (Ayer, L. M., S. M. Wilson, S. L. Traves, D. Proud, M. A. Giembycz. 2008. J. Pharmacol. Exp. Ther. 324: 815-826.) Beraprost, an IP-receptor agonist, protected rats against the development of experimental cigarette smoke-induced emphysema, possibly by means of a concerted inhibitory action on alveolar epithelial cell apoptosis, oxidative burden, matrix metalloproteinase expression, and proinflammatory cytokine generation. (Chen, Y, M. Hanaoka, P. Chen, Y. Droma, N. F. Voelkel, K. Kubo. 2009. *Am. J. Physiol.* 296: L648-L656.)

In further embodiments, methods are provided for treating COPD in a patient in need of the treatment, comprising administering to the patient a composition comprising IP receptor agonist disclosed herein.

Hyperglycemia

Although hyperglycemia is the major cause for the pathogenesis of diabetic complications such as diabetic peripheral neuropathy (DPN), diabetic nephropathy (DN) and diabetic retinopathy (DR), enhanced vasoconstriction and platelet aggregation in diabetic patients has also been implicated to play a role in disease progression (Cameron et al., Naunyn Schmiedebergs Arch. Pharmacol., 2003, 367:607-614). Agonists of the IP receptor promote vasodilation and inhibit platelet aggregation. Improving microvascular blood flow is able to benefit diabetic complications (Cameron, Diabetologia, 2001, 44:1973-1988).

It has been shown that an agonist of the IP receptor can prevent and reverse motor and sensory peripheral nerve conduction abnormalities in streptozotocin-diabetic rats (Cotter et al., Naunyn Schmiedebergs Arch. Pharmacol., 1993, 347: 534-540). Further evidence for the beneficial effect of an agonist of the IP receptor in the treatment of diabetic peripheral neuropathy is given by Hotta et al. (Diabetes, 1996, 45:361-366), Ueno et al. (Jpn. J. Pharmacol., 1996, 70:177-182), Ueno et al. (Life Sci., 1996, 59:PL1O5-PL110), Hotta et al. (Prostaglandins, 1995, 49:339-349), Shindo et al. (Prostaglandins, 1991, 41:85-96), Okuda et al. (Prostaglandins, 1996, 52:375-384), and Koike et al. (FASEB J., 2003, 17:779-781).

Evidence for the beneficial effect of an agonist of the IP receptor in the treatment of diabetic nephropathy is given by Owada et al. (Nephron, 2002, 92:788-796) and Yamashita et al. (Diabetes Res. Clin. Pract., 2002, 57:149-161). Evidence for the beneficial effect of an agonist of the IP receptor in the treatment of diabetic retinopathy is given by Yamagishi et al. (Mol. Med., 2002, 8:546-550), Burnette et al. (Exp. Eye Res., 2006, 83: 1359-1365), and Hotta et al. (Diabetes, 1996, 45:361-366). It has been shown that an agonist of the IP receptor can reduce increased tumor necrosis factor-[alpha] (TNF-[alpha]) levels in diabetic patients, implying that an agonist of the IP receptor may contribute to the prevention of progression in diabetic complications (Fujiwara et al, Exp. Clin. Endocrinol. Diabetes, 2004, 112:390-394).

Evidence that topical administration of an agonist of the IP receptor can result in a decrease in intraocular pressure (IOP) in rabbits and dogs and thereby have beneficial effect in the treatment of glaucoma is given by Hoyng et al (Hoyng et al, Invest. Ophthalmol. Vis. Sci., 1987, 28:470-476).

Agonists of the IP receptor have been shown to have activity for regulation of vascular tone, for vasodilation, and for amelioration of pulmonary hypertension (see, e.g., Strauss et al, Clin Chest Med, 2007, 28:127-142; Driscoll et al, Expert Opin. Pharmacother., 2008, 9:65-81).

Evidence for a beneficial effect of an agonist of the IP receptor in the treatment of hypertension is given by Yamada et al. (Peptides, 2008, 29:412-418). Evidence that an agonist of the IP receptor can protect against cerebral ischemia is given by Dogan et al. (Gen. Pharmacol., 1996, 27:1163-1166) and Fang et al (J. Cereb. Blood Flow Metab., 2006, 26:491-501).

Anti-Inflammation

Anti-inflammation agents are prescribed for a variety of conditions. For example, in an inflammatory disease they are used to interfere with and thereby reduce an underlying deleterious.

There is evidence that an IP receptor agonist can inhibit inflammation and thus be a potential treatment as an anti-inflammation therapy. It has been shown that an agonist of the IP receptor can inhibit pro-inflammatory cytokine and chemokine (interleukin-12 (IL-12), tumor necrosis factor-[alpha] (TNF-[alpha]), DL-I([alpha], EL-6, macrophage inflammatory protein-1 alpha (MIP-I([alpha]), monocyte chemoattractant protein-1 (MCP-I)) production and T cell stimulatory function of dendritic cells (Jozefowski et al, Int. Immunopharmacol., 2003, 865-878; Zhou et al, J. Immunol., 2007, 178:702-710; Nagao et al, Am. J. Respir. Cell Mol. Biol., 2003, 29:314-320; Idzko et al, J. Clin. Invest., 2007, 117:464-472). It has been shown that an agonist of the IP receptor can inhibit pro-inflammatory cytokine (TNF-[alpha], IL-1/3, EL-6, granulocyte macrophage stimulating factor (GM-CSF)) production by macrophages (Raychaudhuri et al, J. Biol. Chem., 2002, 277:33344-33348; Czeslick et al, Eur. J. Clin. Invest., 2003, 33:1013-1017; Di Renzo et al, Prostaglandin Leukot. Essent. Fatty Acids, 2005, 73:405-410; Shinomiya et al, Biochem. Pharmacol., 2001, 61:1153-1160). It has been shown that an agonist of the IP receptor can stimulate anti-inflammatory cytokine (DL-IO) production by dendritic cells (Jozefowski et al, Int. Immunopharmacol., 2003, 865-878; Zhou et al, J. Immunol., 2007, 178:702-710). It has been shown that an agonist of the IP receptor can stimulate anti-inflammatory cytokine (DL-10) production by macrophages (Shinomiya et al, Biochem. Pharmacol., 2001, 61: 1153-1160). It has been shown that an agonist of the IP receptor can inhibit a chemokine (CCL 17)-induced chemotaxis of leukocytes (CD4<+>Th2 T cells) (Jaffar et al, J. Immunol., 2007, 179:6193-6203). It has been shown that an agonist of the IP receptor can confer protection from atherosclerosis, such as from atherothrombosis (Arehart et al, Curr. Med. Chem., 2007, 14:2161-2169; Stitham et al, Prostaglandins Other Lipid Mediat., 2007, 82:95-108; Fries et al, Hematology Am. Soc. Hematol. Educ. Program, 2005, :445-451; Egan et al, Science, 2004, 306:1954-1957; Kobayashi et al, J. Clin. Invest., 2004, 114:784-794; Arehart et al, Circ. Res., 2008, Mar. 6). It has been shown that an agonist of the IP receptor can attenuate asthma (Idzko et al, J. Clin. Invest., 2007, 117:464-472; Jaffar et al, J. Immunol., 2007, 179:6193-6203; Nagao et al, Am. J. Respir. Cell. Mol. Biol., 2003, 29:314-320). It has been shown that an agonist of the IP receptor can decrease TNF-[alpha] production in type 2 diabetes patients (Fujiwara et al, Exp. Clin. Endocrinol. Diabetes, 2004, 112:390-394; Goya et al, Metabolism, 2003, 52: 192-198). It has been shown that an agonist of the IP receptor can inhibit ischemia-reperfusion injury (Xiao et al, Circulation, 2001, 104:2210-2215). It has been shown that an agonist of the IP receptor can inhibit restenosis (Cheng et al, Science, 2002, 296:539-541). It has been shown that an agonist of the IP receptor can attenuate pulmonary vascular injury and shock in a rat model of septic shock (Harada et al, Shock, 2008, Feb. 21). It has been shown that an agonist of the IP receptor can reduce the serum levels of TNF-[alpha] in vivo in patients with rheumatoid arthritis, and this is associated with improvement in the clinical course of the disease (Gao et al, Rheumatol. Int., 2002, 22:45-51; Boehme et al, Rheumatol. Int., 2006, 26:340-347).

The compounds as defined in the first aspect disclosed herein provide beneficial reduction of inflammation. The compounds as defined in the first aspect disclosed herein provide beneficial reduction of a deleterious inflammatory response associated with an inflammatory disease. Accordingly, in some embodiments, the present invention provides methods for reducing inflammation in a patient in need thereof, comprising administering to the patient a composition comprising an IP receptor agonist disclosed herein. In some embodiments, the present invention provides methods for decreasing IL-12, TNF-[alpha], IL-I[alpha], IL-IjS, BL-6, MIP-la or MCP-I production in a patient in need thereof, comprising administering to the patient a composition comprising an IP receptor agonist disclosed herein. In some embodiments, the present invention provides methods for decreasing TNF-[alpha] production in a patient in need thereof, comprising administering to the patient a composition comprising an IP receptor agonist disclosed herein. In some embodiments, the present invention provides methods for increasing EL-IO production in a patient in need thereof, comprising administering to the patient a composition comprising an IP receptor agonist disclosed herein. In some embodiments, the present invention provides methods for reducing a deleterious inflammatory response associated with an inflammatory disease in a patient in need thereof, comprising administering to the patient a composition comprising an IP receptor agonist disclosed herein. In some embodiments, the present invention provides methods for treating an inflammatory disease or a symptom thereof in a patient in need of the treatment comprising administering to the patient a composition comprising an IP receptor agonist disclosed herein. In some embodiments, the present invention provides methods for treating an inflammatory disease or a symptom thereof in a patient in need of the treatment comprising administering to the patient a composition comprising an IP receptor agonist disclosed herein. In some embodiments, the present invention provides methods for treating an inflammatory disease or a symptom thereof in a patient in need of the treatment comprising administering to the patient a composition comprising an IP receptor agonist disclosed herein, wherein the inflammatory disease is selected from the group consisting of psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, diabetes (including type 1 diabetes and type 2 diabetes), sepsis, chronic obstructive pulmonary disease (COPD), and asthma.

Fibrosis

PGI2 signaling has been shown to play a beneficial role in fibrotic diseases of various organs, including kidney, heart, lung, skin, pancreas and liver, as well as in systemic sclerosis and associated pathologies. It has been shown that an agonist of the IP receptor can ameliorate cardiac fibrosis (Chan E C et al (2010) *J Mol Cell Cardiol*. April 18; Hirata Y et al (2009) *Biomed Pharmacother.* 63(10):781-6; Kaneshige T et al (2007) *J Vet Med Sci*. 69(12):1271-6). It has been shown that an agonist of the IP receptor can attenuate renal fibrosis (Takenaka M et al (2009) Prostaglandins Leukot Essent Fatty Acids. 80(5-6):263-7). It has been shown that an agonist of the IP receptor can protect against pulmonary fibrosis in a bleomycin model (Zhu Y et al (2010) *Respir Res.* 20; 11(1): 34). It has been shown that an agonist of the IP receptor can suppress the production of connective tissue growth factor, a key mediator of fibrosis, in scleroderma patients (Stratton R et al (2001) *J Clin Invest*. 108(2):241-50). It has been shown that an agonist of the IP receptor can reduce the incidence of digital ulcerations in patients with systemic sclerosis M. Vayssairat (1999) *J Rheumatol* 26:2173-2178. It has been shown that an agonist of the IP receptor can reduce fingertip necrosis in infants with refractory Renaud's phenomenon (Shouval D S et al (2008) *Clin Exp Rheumatol*. 26(3 Suppl 49):5105-7). It has been shown that an agonist of the IP receptor can reduce markers of endothelial activation in patients with systemic sclerosis (Rehberger P et al (2009) *Acta Derm Venereol.* 89(3):245-9.). It has been shown that an agonist of the IP receptor can reduce severity, frequency, and duration of Raynaud's attacks in patients with systemic sclerosis (Torlay et al (1991) *Ann Rheum Dis* 50, 800-804). It has been shown that an agonist of the IP receptor can improve portal hemodynamics in patients with systemic sclerosis and Raynaud's phenomenon (Zardi et al (2006) *In Vivo* 20(3):377-80). It has been shown that an agonist of the IP receptor can inhibit the progression of pancreatic fibrosis in obese Zucker rats (Sato et al (2010) *Diabetes* 59(4):1092-100).

The IP receptor agonists disclosed herein provide beneficial anti-fibrotic effects to patients suffering from fibrosis of the kidney, heart, lung, skin, pancreas and liver which can be idiopathic or secondary to chronic inflammation and systemic sclerosis, for example, and are not limited to the indications described above.

In addition, there is substantial evidence that an agonist of the IP receptor can improve kidney function in acute and chronic renal failure. It has been shown that an agonist of the IP receptor can restore kidney function in endotoxemia-related acute renal failure (Johannes T et al (2009) *Crit Care Med.* 37(4):1423-32). It has been shown that an agonist of the IP receptor can improve renal function in a model of renal ischemia/reperfusion injury Sahsivar M O et al (2009) *Shock* 32(5):498-502). It has been shown that an agonist of the IP receptor can prevent contrast agent-induced nephropathy in patients with renal dysfunction undergoing cardiac surgery (Spargias K et al (2009) *Circulation* 3; 120(18):1793-9.) It has been shown that an agonist of the IP receptor can improve renal function, reduce inflammation and sclerotic changes of the kidney in a model for diabetic nephropathy Watanabe M et al (2009) Am J Nephrol. 2009; 30(1):1-11).

The IP receptor agonists disclosed herein provide beneficial improvement of renal function in patients with acute and chronic kidney injury and nephropathies secondary to dye-contrast agents, ischemia-reperfusion injury, systemic inflammation and diabetes for example, and are not limited to the indications described above.

There is considerable evidence for a causal role of Prostacyclin deficiency in the development of preeclampsia (Mills J L et al (1999) *JAMA* 282: 356-362; Walsh S W (2004) *Prostaglandins Leukot Essent Fatty Acids* 70: 223-232). The administration of an agonist of the IP receptor has been shown to lower blood pressure in a rat model of preeclampsia (Zlatnik M G et al (1999) *Am J Obstet Gynecol.* 180(5):1191-5).

The IP receptor agonists disclosed herein provide beneficial improvement of hemodynamics in patients with preeclampsia.

The IP receptor agonist disclosed herein may provide beneficial treatment of cystic fibrosis.

The IP receptor agonists disclosed herein may provide chemoprevention. Chemoprevention is the practice of using of drugs, vitamins, or nutritional supplements to reduce the risk of developing, or having a recurrence of cancer. Oral iloprost (Ventavis), an analogue of prostacyclin, shows promise as a chemopreventive agent for lung cancer. Data supporting IP receptor agonist chemoprevention was presented by Paul Bunn Jr. MD, who is the executive Director of the International Association for the Study of Lung Cancer at the American Association for Cancer Research 102nd Annual Meeting showed that it significantly improved endobronchial dysplasia in former smokers.

PGI2 agonist, including the compounds as defined in the first aspect, are also useful as co-therapeutic agents for use in combination with second agents, such as organic nitrates and NO-donors, such as sodium nitroprusside, nitroglycerin, isosorbide mononitrate, isosorbide dinitrate, molsidomine or SIN-1, and inhalational NO; compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, especially PDE 5 inhibitors such as sildenafil, vardenafil and tadalafil; NO-independent, but haem-dependent stimulators of guanylate cyclase, such as in particular the compounds described in WO 00/06568, WO 00/06569, WO 02/42301 and WO 03/095451; NO- and haem-independent activators of guanylate cyclase, such as in particular the compounds described in WO 01/19355, WO 01/19776, WO 01/19778, WO 01/19780, WO 02/070462 and WO 02/070510; compounds which inhibit human neutrophilic elastase, such as sivelestat or DX-890 (Reltran); compounds inhibiting the signal transduction cascade, such as tyrosine kinase and/or serine/threonine kinase inhibitors, in particular imatinib, gefitinib, erlotinib, sorafenib and sunitinib; compounds influencing the energy metabolism of the heart, for example and preferably etomoxir, dichloroacetate, ranolazine or trimetazidine; antithrombotic agents, for example and preferably from the group comprising platelet aggregation inhibitors, anticoagulants or profibrinolytic substances; active substances for lowering blood pressure, for example and preferably from the group comprising calcium antagonists, angiotensin II antagonists, ACE inhibitors, endothelin antagonists, renin inhibitors, aldosterone synthase inhibitors, alpha receptor blockers, beta receptor blockers, mineralocorticoid receptor antagonists, Rho-kinase inhibitors and diuretics; and/or active substances that modify lipid metabolism, for example and preferably from the group comprising thyroid receptor agonists, inhibitors of cholesterol synthesis, for example and preferably HMG-CoA-reductase inhibitors or inhibitors of squalene synthesis, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists, particularly in the treatment of PAH or diseases and disorders such as those mentioned hereinbefore, e.g., as potentiators of therapeutic activity of such drugs or as a means of reducing required dosaging or potential side effects of such drugs.

In particular, an embodiment of this invention is a pharmaceutical combination comprising the compounds as defined in the first aspect or a pharmaceutically acceptable salt thereof and a second agent wherein the second agent is a PDEV inhibitor or neutral endopeptidase inhibitor.

The compounds as defined in the first aspect or a pharmaceutically acceptable salt thereof may be mixed with a second agent in a fixed pharmaceutical composition or it may be administered separately, before, simultaneously with or after the other drug substance.

Accordingly, the invention includes as a further aspect a combination of an IP receptor activity with osmotic agents (hypertonic saline, dextran, mannitol, Xylitol), ENaC blockers, an anti-inflammatory, bronchodilatory, antihistamine, anti-tussive, antibiotic and/or DNase drug substance, wherein the IP receptor agonist and the further drug substance may be in the same or different pharmaceutical composition.

Suitable antibiotics include macrolide antibiotics, e.g., tobramycin (TOBI™). Suitable DNase drug substances include dornase alfa (Pulmozyme™), a highly-purified solution of recombinant human deoxyribonuclease I (rhDNase), which selectively cleaves DNA. Dornase alfa is used to treat cystic fibrosis.

Other useful combinations of IP receptor agonist with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H-benzo-cyclohepten-8-yl]carbonyl]amino]phenyl]-methyl] tetrahydro-N,N-dimethyl-2H-pyran-4-aminium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, for example corticosteroids. Suitable steroids include budesonide, beclamethasone (e.g. dipropionate), butixocort (e.g. propionate), CHF5188, ciclesonide, dexamethasone, flunisolide, fluticasone (e.g. propionate or furoate), GSK-685698, GSK-870086, LAS40369, methyl prednisolone, mometasone (e.g. furoate), prednisolone, rofleponide, and triamcinolone (e.g. acetonide). In certain preferred embodiments the steroid is long-acting corticosteroids such as budesonide, ciclesonide, fluticasone or mometasone.

Suitable second active ingredients include $\beta_2$-agonists. Suitable $\beta_2$-agonists include arformoterol (e.g. tartrate), albuterol/salbutamol (e.g. racemate or single enantiomer such as the R-enantiomer, or salt thereof especially sulfate), AZD3199, bambuterol, BI-171800, bitolterol (e.g. mesylate), carmoterol, clenbuterol, etanterol, fenoterol (e.g. racemate or single enantiomer such as the R-enantiomer, or salt thereof especially hydrobromide), flerbuterol, formoterol (e.g. racemate or single diastereomer such as the R,R-diastereomer, or salt thereof especially fumarate or fumarate dihydrate), GSK-159802, GSK-597901, GSK-678007, indacaterol (e.g. racemate or single enantiomer such as the R-enantiomer, or salt thereof especially maleate, acetate or xinafoate), LAS100977, metaproterenol, milveterol (e.g. hydrochloride), naminterol, olodaterol (e.g. racemate or single enantiomer such as the R-enantiomer, or salt thereof especially hydrochloride), PF-610355, pirbuterol (e.g. acetate), procaterol, reproterol, salmefamol, salmeterol (e.g. racemate or single enantiomer such as the R-enantiomer, or salt thereof especially xinafoate), terbutaline (e.g. sulphate) and vilanterol (or a salt thereof especially trifenatate. In certain preferred embodiments the $\beta_2$-agonist is an ultra-long-acting $\beta_2$-agonist such as indacaterol, or potentially carmoterol, LAS-100977, milveterol, olodaterol, PF-610355 or vilanterol. A preferred embodiment one of the second active ingredients is indacaterol (i.e. (R)-5-[2-(5,6-diethyl-indan-2-ylamino)-1-hydroxyethyl]-8-hydroxy-1H-quinolin-2-one) or a salt thereof. This is a $\beta_2$-adrenoceptor agonist that has an especially long duration of action (i.e. over 24 hours) and a short onset of action (i.e. about 10 minutes). This compound is prepared by the processes described in international patent applications WO 2000/75114 and WO 2005/123684. It is capable of forming acid addition salts, particularly pharmaceutically acceptable acid addition salts. A preferred salt of (R)-5-[2-(5,6-diethyl-indan-2-ylamino)-1-hydroxyethyl]-8-hydroxy-1H-quinolin-2-one is the maleate salt. Another preferred salt is (R)-5-[2-(5,6-diethyl-indan-2-ylamino)-1-hydroxyethyl]-8-hydroxy-1H-quinolin-2-one acetate. Another preferred salt is (R)-5-[2-(5,6-diethyl-indan-2-ylamino)-1-hydroxyethyl]-8-hydroxy-1H-quinolin-2-one xinafoate.

Suitable bronchodilatory drugs include anticholinergic or antimuscarinic agents, such as aclidinium (e.g. bromide), BEA-2108 (e.g. bromide), BEA-2180 (e.g. bromide), CHF-5407, darifenacin (e.g. bromide), darotropium (e.g. bromide), glycopyrrolate (e.g. racemate or single enantiomer, or salt thereof especially bromide), dexpirronium (e.g. bromide), iGSK-202405, GSK-203423, GSK-573719, GSK-656398, ipratropium (e.g. bromide), LAS35201, LAS186368, otilonium (e.g. bromide), oxitropium (e.g. bromide), oxybutynin, PF-3715455, PF-3635659, pirenzepine, revatropate (e.g. hydrobromide), solifenacin (e.g. succinate), SVT-40776, TD-4208, terodiline, tiotropium (e.g. bromide), tolterodine (e.g. tartrate), and trospium (e.g. chloride). In certain preferred embodiments the muscarinic antagonists is long-acting muscarinic antagonist such as darotropium bromide, glycopyrrolate or tiotropium bromide.

Suitable dual anti-inflammatory and bronchodilatory drugs include dual beta-2 adrenoceptor agonist/muscarinic antagonists such as GSK-961081 (e.g. succinate). and those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

Accordingly, the invention includes as a further aspect a combination of IP receptor agonist with agents that inhibit ALK5 and/or ALK4 phosphorylation of Smad2 and Smad3.

Accordingly, the invention includes as a further aspect a combination of IP receptor agonist with second agents that are Rho-kinase inhibitors.

Accordingly, the invention includes as a further aspect a combination of IP receptor agonist with second agents that are tryptophan hydroxylase 1 (TPH1) inhibitors.

Accordingly, the invention includes as a further aspect a combination of IP receptor agonist with second agents that are multi-kinase inhibitors, such as imatinib mysilate, Gleevec. Imatinib functions as a specific inhibitor of a number of tyrosine kinase enzymes. It occupies the TK active site, leading to a decrease in activity. TK enzymes in the body include the insulin receptor. Imatinib is specific for the TK domain in the Abelson proto-oncogene, c-kit and PDGF-R (platelet-derived growth factor receptor).

In an embodiment of this invention, the IP receptor agonist of this invention are dosed in combination with a second active agent selected from phosphodiesterase V inhibitors, neutral endopeptidase 1 inhibitors, THP1 inhibitors, multi-kinase inhibitors, endothelin antagonist, diuretic, aldosteron receptor blocker, and endothelin receptor blocker.

In an embodiment of this invention, the IP receptor agonist of this invention are dosed in combination with a second active agent selected from phosphodiesterase V inhibitors, neutral endopeptidase 1 inhibitors, THP1 inhibitors, and multi-kinase inhibitors, such as PDGFR or c-Kit.

In another aspect the invention provides a compound as defined in the first aspect, in free form or in the form of a pharmaceutically acceptable salt, for use in the manufacture of a medicament for the treatment of a condition responsive to IP receptor agonist activity, particularly in PAH.

The agents of the invention may be administered by any appropriate route, e.g. orally, e.g., in the form of a tablet or capsule; parenterally, e.g., intravenously; by inhalation, e.g., in the treatment of an obstructive airways disease; intranasally, e.g., in the treatment of allergic rhinitis; topically to the skin; or rectally. In a further aspect, the invention also provides a pharmaceutical composition comprising a compound as defined in the first aspect, in free form or in the form of a pharmaceutically acceptable salt, optionally together with a pharmaceutically acceptable diluent or carrier therefor. The composition may contain a co-therapeutic agent, such as an anti-inflammatory, broncho-dilatory, antihistamine or anti-tussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations.

When the composition comprises an aerosol formulation, it preferably contains, e.g., a hydro-fluoro-alkane (HFA) propellant, such as HFA134a or HFA227 or a mixture of these, and may contain one or more co-solvents known in the art, such as ethanol (up to 20% by weight), and/or one or more surfactants, such as oleic acid or sorbitan trioleate, and/or one or more bulking agents, such as lactose. When the composition comprises a dry powder formulation, it preferably contains, e.g., a compound as defined in the first aspect or a pharmaceutically acceptable salt thereof having a particle diameter up to 10 microns, optionally together with a diluent or carrier, such as lactose, of the desired particle size distribution and a compound that helps to protect against product performance deterioration due to moisture, e.g., magnesium stearate. When the composition comprises a nebulised formulation, it preferably contains, e.g., a compound as defined in the first aspect or a pharmaceutically acceptable salt thereof either dissolved, or suspended, in a vehicle containing water, a co-solvent, such as ethanol or propylene glycol and a stabilizer, which may be a surfactant.

Further aspects of the invention include:
(a) a compound as defined in the first aspect or a pharmaceutically acceptable salt thereof in inhalable form, e.g., in an aerosol or other atomisable composition or in inhalable particulate, e.g., micronised form;
(b) an inhalable medicament comprising a compound as defined in the first aspect or a pharmaceutically acceptable salt thereof in inhalable form;
(c) a pharmaceutical product comprising a compound of formula (I) in inhalable form in association with an inhalation device; and
(d) an inhalation device containing a compound as defined in the first aspect or a pharmaceutically acceptable salt thereof in inhalable form.

Dosages of compounds as defined in the first aspect or a pharmaceutically acceptable salt thereof employed in practicing the present invention will of course vary depending, e.g., on the particular condition to be treated, the effect desired and the mode of administration. In general, suitable daily dosages for administration by inhalation are of the order of 0.005-10 mg, while for oral administration suitable daily doses are of the order of 0.05-100 mg.

Pharmaceutical Use and Assay

Compounds of and their pharmaceutically acceptable salts, hereinafter referred to alternatively as "agents of the invention", are useful as pharmaceuticals. In particular, the compounds are suitable IP receptor agonist and may be tested in the following assays.

Activity of compounds at the IP receptor (IP receptor) is assessed by measuring cAMP accumulation in CHO cells stably expressing the IP receptor (CHO-IP) using the Perkin Elmer AlphaScreen assay. This technology measures the endogenous production of cAMP, in a non-radioactive luminescence proximity homogenous assay. A biological reaction occurs between streptavidin coated donor beads, biotinylated cAMP and anti-cAMP acceptor beads, bringing the donor and acceptor beads close enough together so that upon excitation a fluorescence signal is produced. On production of endogenous cAMP, competition between the biotinylated cAMP and cellular-derived cAMP causes a reduction in the fluorescent signal. The reduction in signal is proportional to the amount of cAMP being produced, thus it is possible to quantify the amount of cAMP being produced on stimulation with agonist.

Test and reference compounds are prepared at 100× [final] in 100% DMSO, and diluted 1:3 using a Biomek Fx (Beckman Coulter). This is followed by an intermediate dilution to give 5× [final] in assay buffer (HBSS containing 5 mM HEPES, 0.1% (w/v) BSA). 5 µL of 5× [final] test compounds, reference compounds and buffer/DMSO control are then transferred to a 384-well white OptiPlate, containing 20 µL CHO-IP cell suspension (15,000 cells/well, prepared from frozen), and plate is incubated at room temperature for 1 hour. A cAMP standard curve is constructed for each experiment (concentration range of 10000 nM to 0.001 nM, in assay buffer) and 25 µL of each concentration added to the last two columns of the assay plate. The incubation is terminated by the addition of lysis buffer ($dH_2O$; 0.3% (v $v^{-1}$) Tween-20) containing 20 units $mL^{-1}$ streptavidin coated donor beads and biotinylated cAMP (pre-incubated for 30 minutes) and 20 units $mL^{-1}$ anti-cAMP acceptor beads, which are added to the lysis buffer just before addition to the assay plate. The assay plate is then incubated at room temperature in the dark, for 60 minutes with gentle shaking, and read on the Envision plate reader (Perkin Elmer).

The raw data of the reference compounds, test compounds and controls are converted into cAMP concentrations, using the cAMP standard curve, in Graph Pad Prism (Graph Pad Software Inc). $EC_{50}$ as well as maximal values of the agonist curves are determined using a 4-parameter logistic equation. The % maximum response values of all test compounds are determined using the top of the treprostinil concentration-response curve.

Compounds of the Examples, herein below, generally have $EC_{50}$ values in the data measurements described above below 5 µM. Table 1 provides a list of representative compounds with their $EC_{50}$ value.

TABLE 1

| Example | $EC_{50}/\mu M$ |
|---|---|
| 1(i) | 0.0009 |
| 1(ii) | 0.0009 |
| 1.1 | 0.0003 |
| 1.1(i) | 0.0003 |
| 1.1(ii) | 0.0006 |
| 1.2 | 0.0019 |
| 2.1 | 0.0004 |
| 2.2 | 0.0001 |
| 2.3(i) | 0.0048 |
| 2.3(ii) | 0.0003 |
| 2.4 | 0.0024 |
| 2.5 | 0.0039 |
| 2.6 | 0.0006 |
| 2.7 | 0.0003 |
| 2.8 | 0.0004 |
| 2.9 | 0.0001 |
| 2.10 | 0.0004 |
| 3.1 | 0.0008 |
| 3.2 | 0.0136 |
| 3.3 | 0.0023 |
| 4 | 0.0007 |
| 5 | 0.0117 |
| 6 | 0.0002 |
| 7 | 0.0002 |
| 7.1 | 0.0023 |
| 7.2 | 0.0012 |
| 7.3 | 0.0003 |
| 8 | 0.0070 |
| 9.1 | 0.0006 |
| 9.2(i) | 0.0127 |
| 10 | 0.0003 |
| 11(i) | 0.0003 |
| 11(ii) | 0.0005 |
| 12 | 0.0059 |
| 12.1 | 0.0402 |
| 12.2 | 0.0064 |
| 12.3 | 0.0450 |
| 12.4 | 0.0121 |
| 12.5 | 0.0407 |
| 12.6 | 0.0047 |
| 12.7 | 0.0759 |
| 12.8 | 0.0080 |
| 12.9 | 0.0004 |
| 12.10 | 0.0556 |
| 13.1 | 0.0286 |
| 13.2 | 0.51 |
| 13.3 | 0.0662 |
| 13.4 | 0.0007 |
| 13.5 | 0.005 |
| 14 | 0.0027 |
| 15 | 0.0003 |
| 15a | 0.0011 |
| 15b | 0.0036 |
| 16 | 0.0004 |
| 17 | 0.0018 |
| 17a | 0.0036 |
| 17b | 0.0018 |

Preparation of the Exemplified Compounds:

The exemplified compounds may be prepared as described below or according to the preparation procedures disclosed in PCT patent application PCT/EP2011/062028 (WO 2012/007539).

The invention is illustrated by the following Examples.

General Conditions:

Mass spectra were acquired on LC-MS, SFC-MS, or GC-MS systems using electrospray, chemical and electron impact ionization methods from a range of instruments of the following configurations: Agilent 1100 HPLC systems with an Agilent 6110 Mass Spectrometer, or Micromass Platform Mass Spectrometer or Thermo LTQ Mass Spectrometer; a Waters Acquity UPLC system with SQD Mass Spectrometer, a Waters FractionLynx HPLC system with 3100 Mass Spectrometer, a Waters UPC2 system with TQD Mass Spectrometer or a Waters Prep100 SFC-MS system with SQD2 Mass Spectrometer. [M+H]+ refers to protonated molecular ion of the chemical species. Some [M+H]+ are a mass unit higher than expected due to saturation of the Mass Spec signal response. Due to this, mass unit resolution was lost and the reporting of the result via centroid mode led to the carbon-13 isotope being reported rather than the carbon-12 isotope.

NMR spectra were run on Bruker AVANCE 400 MHz or 500 MHz NMR spectrometers using ICON-NMR, under TopSpin program control. Spectra were measured at 298K, unless indicated otherwise, and were referenced relative to the solvent resonance.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. If not defined, the terms have their generally accepted meanings.

Abbreviations:
AcOH acetic acid
br broad
d doublet
DCM dichloromethane
DCE 1,2-dichloroethane
DEAD Diethyl azodicarboxylate
DIPEA Diisopropylethylamine
DMF N,N-dimethylformamide
DMSO dimethylsulfoxide
Grubbs (II) Catalyst benzylidene[1,3-bis(2,4,6-trimethylphenyl)-2-imidazolidinylidene]dichloro(tricyclohexylphosphine)ruthenium
EDCI 1-ethyl-3-(3'-dimethylaminopropyl) carbodiimide
$Et_2O$ diethyl ether
EtOAc ethyl acetate
EtOH ethanol
h hour(s)
HPLC high pressure liquid chromatography
LCMS liquid chromatography and mass spectrometry
MeOH methanol
MeCN acetonitrile
MS mass spectrometry
m multiplet
min minutes
ml milliliter(s)
m/z mass to charge ratio
$NaBH(OAc)_3$ sodium triacetoxyborohydride
NMR nuclear magnetic resonance
ppm parts per million
PS polymer supported
Rt retention time
RT room temperature
s singlet
sat. saturated
SCX-2 strong cation exchange (e.g. Isolute® SCX-2 columns from Biotage)
t triplet
TBME methyl-tert-butyl ether
THF tetrahydrofuran Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

If not indicated otherwise, the analytical conditions are as follows:

HPLC Conditions: (%=percent by volume)

Method A:

Agilent 1100 & 1200 series; Column—Zorbax XDB—C18 5µ, 150×4.6 mm; gradient: A—0.01% TFA in water/B—acetonitrile:methanol (1:1); 0-1 min 70A-30B; 1-6 min 30A-100B; 6-10 min 0A-30B; 10-12 min 70A-30B; flow 1.0 ml/min; column temperature 40° C.

Method B:

Agilent 1100 & 1200 series; Column—Zorbax XDB—C18 5µ, 150×4.6 mm; gradient: A—0.01% TFA in water/B—acetonitrile:methanol (1:1); 0-1 min 95A-05B; 1-6 min 95A-100B; 6-10 min 0A-05B; 10-12 min 95A-05B; flow 1.0 ml/min; column temperature 40° C.

Method-C

Agilent 1100 & 1200 series; Column—Zorbax XDB—C18 5µ, 250×4.6 mm; isocratic—[98:02::A:B]; A—5 mM Ammonium Acetate/B—methanol; Flow—0.8 ml/min; column temperature 40° C.

Method D

Agilent 1100 & 1200 series; Column—Zorbax XDB—C18 5µ, 150×4.6 mm; gradient: A—5 mM Ammonium Acetate/B—acetonitrile; 0-1 min 70A-30B; 1-6 min 30A-100B; 6-10 min 0A-30B; 10-12 min 70A-30B; Flow-1.0 ml/min; column temperature 40° C.

Method E

Agilent 1100 & 1200 series; Column—Zorbax XDB—C18 5µ, 150×4.6 mm; gradient: A—0.01% TFA in water/B—acetonitrile:methanol (1:1); 0-1 min 70A-30B; 1-2 min 30A-100B; 2-8 min 0A-100B; 8-10 min 0A-30B; 10-12 min 70A-30B flow 1.0 ml/min; column temperature 40° C.

Method F

Agilent 1100 & 1200 series; Column—Zorbax XDB—C18 5µ, 150×4.6 mm; gradient: A—5 mM Ammonium Acetate/B—acetonitrile; 0-1 min 70A-30B; 1-2 min 30A-100B; 2-8 min 0A-100B; 8-10 min 0A-30B; 10-12 min 70A-30B flow 1.0 ml/min; column temperature 40° C.

LCMS Conditions:

Method G:
Agilent 1100 series; LC-MSD; column Mercury MS Synergi 2μ, 20×4.0 mm; gradient: A—0.1% formic acid in water/B—acetonitrile; 0-0.5 min 70A-30B; 1.5-2.4 min 5A-95B; 2.5-3.0 min 70A-30B; flow 2.0 ml/min; column temperature 30° C.

Method H:
Agilent 1100 series; LC-MSD; column Mercury MS Synergi 2μ, 20×4.0 mm; gradient: A—0.1% formic acid in water/B—acetonitrile; 0-0.5 min 30A-70B; 1.5-2.4 min 100B-0A; 2.5-3.0 min 30A-70B; flow 2.0 ml/min; column temperature 30° C.

Method I:
API 2000 LC-MS/MS/MS; column Mercury MS Synergi 2μ, 20×4.0 mm; gradient: A—0.1% formic acid in water/B—acetonitrile; 0-0.5 min 70A-30B; 1.5-2.4 min 5A-95B; 2.5-3.0 min 70A-30B; flow 2.0 ml/min; column temperature 30° C.

Method J
Column Zorbax Eclipse XDB-C18 4.6×50 mm, 1.8 μm
Column Temperature 35° C.
Eluents A: $H_2O$+0.1% TFA, B: acetonitrile+0.1% TFA
Flow Rate 1 ml/min
Gradient 5-100% MeCN (6 min), 100 MeCN (1.5 min), 100-5% MeCN (0.5 min)

Method 2minLC_v003
Column Waters BEH C18 50×2.1 mm, 1.7 μm
Column Temperature 50° C.
Eluents A: $H_2O$, B: acetonitrile, both containing 0.1% TFA
Flow Rate 0.8 ml/min
Gradient 0.20 min 5% B; 5% to 95% B in 1.30 min, 0.25 min 95% B Method 2minLowpH
Column: Waters Acquity CSH 1.7 μm, 2.1×50 mm
Temperature: 50° C.
Mobile Phase: A: Water+0.1% Formic Acid B: Acetonitrile+0.1% Formic Acid
Flow rate: 1.0 mL/min
Gradient: 0.0 min 5% B, 0.2-1.3 min 5-98% B, 1.3-1.55 min 98% B, 1.55-1.6 min 98-5% B Method 2minLowpHv01:
Column: Waters Acquity CSH 1.7 μm, 2.1×50 mm
Temperature: 50° C.
Mobile Phase: A: Water+0.1% Formic Acid B: Acetonitrile+0.1% Formic Acid
Flow rate: 1.0 mL/min
Gradient: 0.0 min 5% B, 0.2-1.55 min 5-98% B, 1.55-1.75 min 98% B, 1.75-1.8 min 98-5% B Method 2minLowpH30:
Column: Waters Acquity CSH 1.7 μm, 2.1×50 mm
Temperature: 50° C.
Mobile Phase: A: Water+0.1% Formic Acid B: Acetonitrile+0.1% Formic Acid
Flow rate: 1.0 mL/min
Gradient: 0.0 min 30% B, 0.2-1.3 min 30-98% B, 1.3-1.55 min 98% B, 1.55-1.6 min 98-30% B Method 10minLowpH
Column: Waters Acquity CSH 1.7 μm, 2.1×100 mm
Temperature: 50° C.
Mobile Phase: A: Water+0.1% Formic Acid B: Acetonitrile+0.1% Formic Acid
Flow rate: 0.7 mL/min
Gradient: 0.0 min 2% B, 0.5-8.0 min 2-98% B, 8.0-9.0 min 98% B, 9.0-9.1 min 98-2% B

EXAMPLES 1(I) AND 1(II)

(R) and (S) Enantiomers of 6-(2,3-di-p-tolyl-5,6,7,8-tetrahydropyrido[2,3-b]pyrazin-6-yl)hexanoic acid

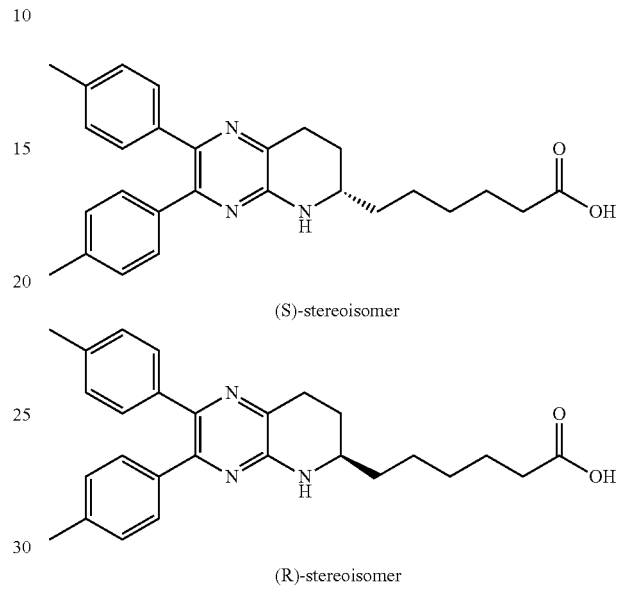

(S)-stereoisomer (R)-stereoisomer

Step 1: Tert-butyl 2,3-di-p-tolyl-7,8-dihydropyrido[2,3-b]pyrazine-5(6H)-carboxylate Di-tert-butyl dicarbonate (5.52 ml, 23.78 mmol) in THF (100 ml) was treated with 2,3-di-p-tolyl-5,6,7,8-tetrahydropyrido[2,3-b]pyrazine (Intermediate B) (5 g, 15.85 mmol) followed by 4-dimethylaminopyridine (0.194 g, 1.585 mmol). The suspension was stirred at room temperature for two days and then stirred at reflux for 4 hours. The solution was cooled to room temperature and concentrated under reduced pressure. The crude solid was purified via recrystallisation from EtOAc (15 ml). The resultant solid was filtered and washed with 1:3 EtOAc:iso-hexane (~40 ml) to afford the titled compound:

LCMS Rt 1.41 mins; MS m/z 416.5 [M+H]$^+$, Method 2minLowpH.

Step 2: Tert-butyl 6-allyl-2,3-di-p-tolyl-7,8-dihydropyrido[2,3-b]pyrazine-5(6H)-carboxylate Tert-butyl 2,3-di-p-tolyl-7,8-dihydropyrido[2,3-b]pyrazine-5(6H)-carboxylate (step 1) (500 mg, 1.203 mmol) in Et$_2$O (10 ml) degassed with N$_2$ was treated with 1,2-di(dimethylamino) ethane (0.400 ml, 2.65 mmol). The mixture was cooled to −70° C. and treated with sec-butyllithium (1.4M in cyclohexane, 0.945 ml, 1.324 mmol) dropwise, maintaining the temperature at −70° C. After stirring at −70° C. for 2 hours allyl bromide (0.115 ml, 1.324 mmol) was added and the mixture was allowed to warm to room temperature and stirred for 16 hours. The resulting mixture was added dropwise to water (100 ml) and extracted with DCM (×3). The combined organic extracts were concentrated under reduced pressure and purification of the crude product by chromatography on silica eluting with 0-10% EtOAc in iso-hexane afforded the titled compound as a cream coloured solid;

LC-MS Rt=1.51 mins; [M+H]$^+$456.5, Method 2min-LowpH.

Step 3: tert-Butyl 6-(6-ethoxy-6-oxohex-2-enyl)-2,3-di-p-tolyl-7,8-dihydropyrido[2,3-b]pyrazine-5(6H)-carboxylate Tert-butyl 6-allyl-2,3-di-p-tolyl-7,8-dihydropyrido[2,3-b]pyrazine-5(6H)-carboxylate (step 2)(97 mg, 0.213 mmol) in DCM (3 ml) degassed with $N_2$ was treated with ethyl pent-4-enoate (0.036 ml, 0.255 mmol), copper(I) iodide (4.05 mg, 0.021 mmol) and Grubbs (II) catalyst (9.04 mg, 10.65 µmol). After stirring at 40° C. for 4 hours, the mixture was concentrated under reduced pressure and purification by chromatography on silica eluting with 0-10% EtOAc in iso-hexane afforded the titled compound as a brown oil;

LCMS Rt 1.53 mins; MS m/z 556.5 [M+H]$^+$, Method 2minLowpH.

Step 4: Tert-butyl 6-(6-ethoxy-6-oxohexyl)-2,3-di-p-tolyl-7,8-dihydropyrido[2,3-b]pyrazine-5(6H)-carboxylate tert-Butyl 6-(6-ethoxy-6-oxohex-2-enyl)-2,3-di-p-tolyl-7,8-dihydropyrido[2,3-b]pyrazine-5(6H)-carboxylate (step 3) (88 mg, 0.158 mmol) in EtOH (3 ml) was degassed with $N_2$ and treated with 10% Pd(C) (1.685 mg, 0.016 mmol). The resulting black suspension was stirred at room temperature under an atmosphere of hydrogen for 16 hours. The resulting mixture was filtered through a pre-packed 2.5 g Celite® column eluting with EtOH. The filtrate concentrated under reduced pressure to afford the titled compound as a yellow oil:

LCMS Rt 1.52 mins; MS m/z 558.7 [M+H]$^+$, Method 2minLowpH.

Step 5: ((R) and (S) Enantiomers of 6-(2,3-di-p-tolyl-5,6,7,8-tetrahydropyrido[2,3-b]pyrazin-6-yl)hexanoic acid Tert-butyl 6-(6-ethoxy-6-oxohexyl)-2,3-di-p-tolyl-7,8-dihydropyrido[2,3-b]pyrazine-5(6H)-carboxylate (step 4) (83 mg, 0.149 mmol) in EtOH (2 ml) was treated with 2M NaOH (0.223 ml, 0.446 mmol) and stirred at RT for 16 hours. MeOH (1 ml) and 2M HCl (0.372 ml, 0.744 mmol) were added and stirring continued at RT for 16 hours. The solvent was removed under reduced pressure and the residue was dissolved in water (30 ml). The mixture was extracted with DCM (×3) and the combined organic extracts were concentrated under reduced pressure. The crude product was dissolved in EtOH (1 ml) and treated with 2M NaOH (0.223 ml, 0.446 mmol). After stirring at RT overnight, the mixture was diluted with water (30 ml) and the pH was adjusted to pH1 using 1 M HCl. The aqueous portion was extracted with DCM (×3) and the combined organic extracts were concentrated under reduced pressure to afford an enantiomeric mixture.

Purification of the mixture by preparative LCMS (40%-80% gradient low pH) followed by chiral separation using Supercritical Fluid Chromatography afforded the individual enantiomers:

Method Details:
Column: Chiralcel AD-H 250×10 mm, 5 um @ 35 deg C.
Mobile phase: 50% isopropanol/50% CO2
Flow: 10 ml/min
Detection: UV @ 220 nm

EXAMPLE 1(I)

First eluted peak; Rt=2.31 mins Enantiomer 1: (R)-6-(2,3-di-p-tolyl-5,6,7,8-tetrahydropyrido[2,3-b]pyrazin-6-yl)hexanoic acid or (S)-6-(2,3-di-p-tolyl-5,6,7,8-tetrahydropyrido[2,3-b]pyrazin-6-yl)hexanoic acid LCMS Rt 1.22 mins; MS m/z 431.6 [M+H]$^+$, Method 2minLowpH $^1$H NMR (400 MHz, DMSO-d6) δ 11.87 (1H, br s), 7.08 (2H, m), 7.03 (2H, m), 7.00-6.91 (5H, br m), 3.25 (2H, br m), 2.75 (1H, br m), 2.19 (3H, s), 2.17 (3H, s), 2.12 (2H, t), 1.94-1.78 (2H, br m), 1.72-1.63 (1H, br m), 1.49-1.31 (5H, br m), 1.30-1.20 (2H, br m).

EXAMPLE 1(II)

Second eluted peak; Rt=4.85 mins Enantiomer 2: (R)-6-(2,3-di-p-tolyl-5,6,7,8-tetrahydropyrido[2,3-b]pyrazin-6-yl)hexanoic acid or (S)-6-(2,3-di-p-tolyl-5,6,7,8-tetrahydropyrido[2,3-b]pyrazin-6-yl)hexanoic acid LCMS Rt 1.23 mins; MS m/z 431.4 [M+H]$^+$, Method 2minLowpH $^1$H NMR (400 MHz, DMSO-d6) δ 11.98 (1H, br s), 7.18 (2H, m), 7.13 (2H, m), 7.10-7.00 (5H, br m), 3.35 (2H, m), 2.85 (1H, m), 2.28 (3H, s), 2.26 (3H, s), 2.21 (2H, t), 2.04-1.88 (2H, br m), 1.82-1.72 (1H, br m), 1.59-1.40 (5H, br m), 1.39-1.30 (2H, br m).

EXAMPLE 1.1, 1.1(I) AND 1.1(II)

Racemate and Enantiomers 1 and 2 of 7-(7-(2-Hydroxypropan-2-yl)-6-oxo-2,3-di-p-tolyl-7,8-dihydropyrido[2,3-b]pyrazin-5(6H)-yl)heptanoic acid

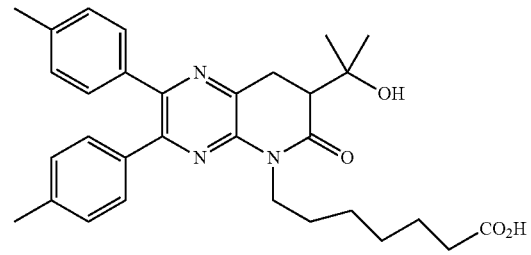 [SMILES: Cc1ccc(-c2nc3c(nc2-c2ccc(C)cc2)N(CCCCCCC(=O)O)C(=O)C(C(C)(C)O)C3)cc1]

Step 1: Ethyl 7-(6-oxo-2,3-di-p-tolyl-7,8-dihydropyrido[2,3-b]pyrazin-5(6H)-yl)heptanoate A yellow solution of 2,3-di-p-tolyl-7,8-dihydropyrido[2,3-b]pyrazin-6(5H)-one ((prepared according to the preparation procedures disclosed in PCT patent application PCT/EP2011/062028, Example 12.1 step 1) (2.0 g, 6.07 mmol) and ethyl 7-bromoheptanoate (2.88 g, 12.14 mmol) in DMF (40 ml) under a nitrogen atmosphere was treated with potassium carbonate (4.20 g, 30.4 mmol) and the resulting suspension was stirred at room temperature for 23 hours. The mixture was diluted with water and extracted with EtOAc (×2). The extracts were washed with water (×2) and brine, dried (MgSO$_4$) and evaporated under reduced pressure to afford a yellow oil. The crude material was diluted with ether (50 ml) and washed with water (2×20 ml), brine, dried (MgSO$_4$) and concentrated under reduced pressure. Purification by chromatography on silica eluting with 0-100% EtOAc in isohexane afforded the titled compound;

LCMS; Rt 1.42 mins MS m/z 486 [M+H]$^+$; Method 2min-LowpH

Step 2: 7-(6-Oxo-2,3-di-p-tolyl-7,8-dihydropyrido[2,3-b]pyrazin-5(6H)-yl)heptanoic acid A solution of ethyl 7-(6-oxo-2,3-di-p-tolyl-7,8-dihydropyrido[2,3-b]pyrazin-5(6H)-yl)heptanoate (step 1) (2.0 g, 4.12 mmol) in MeOH (40 ml) was treated with 1M sodium hydroxide (12.36 ml, 12.36 mmol) and the resulting solution was stirred at 50° C. for 1 hour. The solution was allowed to cool to room temperature and concentrated under reduced pressure. The residue was diluted with water, acidified (pH ~2 with 1N HCl) and the resulting suspension was extracted with DCM (×3). The combined organic extracts were dried (MgSO$_4$) and evaporated under reduced pressure to afford the titled compound as a white solid;

LCMS; Rt 1.27 mins MS m/z 458 [M+H]$^+$; Method 2min-LowpH

Step 3: 7-(7-(2-Hydroxypropan-2-yl)-6-oxo-2,3-di-p-tolyl-7,8-dihydropyrido[2,3-b]pyrazin-5(6H)-yl) heptanoic acid A cooled (−78° C.) solution of 7-(6-oxo-2,3-di-p-tolyl-7,8-dihydropyrido[2,3-b]pyrazin-5(6H)-yl)heptanoic acid (step 2) (100 mg, 0.219 mmol) in THF (5 ml) under a nitrogen atmosphere was treated dropwise with lithium bis trimethylsilylamide (1M in THF, 0.546 ml, 0.546 mmol). The mixture was stirred at −78° C. for 10 minutes and treated with acetone (0.100 ml, 0.546 mmol) in THF (2 ml) maintaining the internal temperature below −65° C. Once addition was complete, the reaction was quenched with sat. NH$_4$Cl (aq). The organic portion was separated and the aqueous was extracted with ethyl acetate (×2). The combined organic extracts were concentrated under reduced pressure and the crude product was purified by chromatography on silica eluting with 0-10% MeOH in DCM to afford the titled compound;

EXAMPLE 1.1 rac-7-(7-(2-Hydroxypropan-2-yl)-6-oxo-2,3-di-p-tolyl-7,8-dihydropyrido[2,3-b]pyrazin-5(6H)-yl) heptanoic acid LCMS; Rt 1.27 mins MS m/z 516 [M+H]$^+$; Method 2min-LowpH $^1$H NMR (Chloroform-d) δ 7.33 (2H, m), 7.36 (2H, m), 7.13 (4H, m), 4.32-4.23 (1H, m), 4.16-4.06 (1H, m), 3.32 (1H, m), 3.09-2.99 (1H, m), 2.92 (1H, m), 2.37 (3H, s), 2.37 (3H, s), 2.33 (2H, t), 1.79-1.71 (2H, m), 1.69-1.63 (2H, m), 1.46-1.40 (7H, m), 1.38 (3H, s)

The racemate was separated under the following conditions to afford the individual enantiomers:
Method Details:
Column: Phenomenex LUX C2 250×10 mm, 5 um (2 columns in series)
Mobile phase: 45% methanol/55% CO2
Flow: 10 ml/min
Column temperature: 35 deg C.
Detection: UV @ 220 nm
System: Berger Minigram SFC2
Sample Concentration: 100 mg in 2 ml EtOH

EXAMPLE 1.1(I)

Enantiomer 1: (R)-7-(7-(2-hydroxypropan-2-yl)-6-oxo-2,3-di-p-tolyl-7,8-dihydropyrido[2,3-b]pyrazin-5(6H)-yl)heptanoic acid or (S)-7-(7-(2-hydroxypropan-2-yl)-6-oxo-2,3-di-p-tolyl-7,8-dihydropyrido[2,3-b]pyrazin-5(6H)-yl)heptanoic acid SFC Retention Time: 7.39 mins 1H NMR (400 MHz, Chloroform-d) δ 7.34 (4H, m), 7.13 (4H, m), 4.26 (1H, s), 4.12 (1H, s), 3.34 (1H, s), 3.06 (1H, s), 2.91 (1H, s), 2.37 (3H, s), 2.37 (3H, s), 2.33 (2H, t), 1.74 (2, m), 1.66 (2H, br m), 1.47-1.40 (7H, m), 1.39 (3H, s)

LCMS; Rt 6.14 mins MS m/z 516 [M+H]$^+$; Method 10min-LowpH

EXAMPLE 1.1(II)

Enantiomer 2: (R)-7-(7-(2-hydroxypropan-2-yl)-6-oxo-2,3-di-p-tolyl-7,8-dihydropyrido[2,3-b]pyrazin-5(6H)-yl)heptanoic acid or (S)-7-(7-(2-hydroxypropan-2-yl)-6-oxo-2,3-di-p-tolyl-7,8-dihydropyrido[2,3-b]pyrazin-5(6H)-yl)heptanoic acid SFC Retention Time: 8.77 mins LCMS; Rt 6.14 mins MS m/z 516 [M+H]$^+$; Method10minLowpH

EXAMPLE 1.2

8-(6-Oxo-2,3-di-p-tolyl-7,8-dihydropyrido[2,3-b]pyrazin-5(6H)-yl)octanoic acid

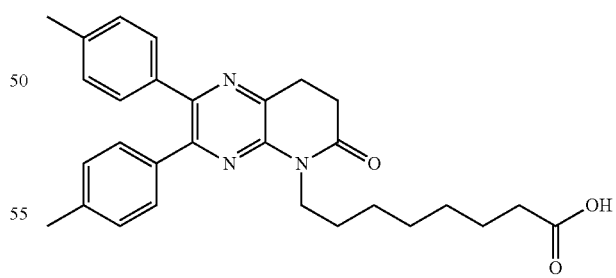

The titled compound was prepared from 2,3-di-p-tolyl-7,8-dihydropyrido[2,3-b]pyrazin-6(5H)-one ((prepared according to the preparation procedures disclosed in PCT patent application PCT/EP2011/062028, Example 12.1 step 1) and ethyl 8-bromooctanoate analogously to Example 1.1 steps 1 and 2;

LCMS: Rt 1.44 mins MS m/z 472.3 [M+H]+: Method 2minLowpHv01

EXAMPLE 2.1

7-(7-Ethyl-2,3-di-p-tolyl-7,8-dihydropyrido[2,3-b]pyrazin-5(6H)-yl)heptanoic acid

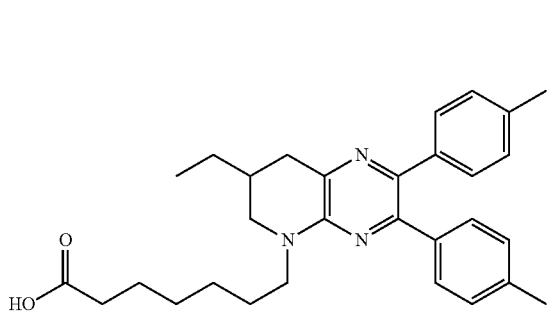 [SMILES: CCC1Cc2nc(-c3ccc(C)cc3)c(-c3ccc(C)cc3)nc2N(CCCCCCC(=O)O)C1]

Step 1: Ethyl 7-(7-ethyl-2,3-di-p-tolyl-7,8-dihydropyrido[2,3-b]pyrazin-5(6H)-yl)heptanoate To a mixture comprising 7-ethyl-2,3-di-p-tolyl-5,6,7,8-tetrahydropyrido[2,3-b]pyrazine (Intermediate D)(0.1 g, 0.291 mmol) in 1,2-dichloroethane (2 ml) was added molecular sieves followed by ethyl 7-oxoheptanoate (0.15 g, 0.874 mmol). The mixture was stirred for 10 minutes and treated with $NaBH(OAc)_3$. After stirring at RT overnight, the reaction mixture was passed through Celite® (filter material) and partitioned between EtOAc and water. The organic layer was washed with saturated brine solution, dried over anhydrous sodium sulphate and concentrated under vacuum to afford the titled compound;

MS m/z 500 $[M+H]^+$;

Step 2: 7-(7-Ethyl-2,3-di-p-tolyl-7,8-dihydropyrido[2,3-b]pyrazin-5(6H)-yl)heptanoic acid A (0° C.) cooled solution of ethyl 7-(7-ethyl-2,3-di-p-tolyl-7,8-dihydropyrido[2,3-b]pyrazin-5(6H)-yl)heptanoate (0.22 g, 0.44 mmol) in $THF:H_2O$ (4:1, 5 ml) was treated with $LiOH.H_2O$ (0.072 g, 1.76 mmol) and stirred at RT overnight. A further 2 equivalents of $LiOH.H_2O$ was added and the reaction mixture was heated to 50° C. for 4 hours. The solvent was removed under reduced pressure and the aqueous layer was acidified to pH 3 and partitioned between water and ethyl acetate. The organic layer was washed with saturated brine solution, dried over anhydrous sodium sulphate and concentrated under vacuum. The crude material was purified by chromatography on silica eluting with 10% EtOAc in hexane followed by preparative HPLC (MeCN in water eluent) to afford the titled compound;

LCMS; Rt 1.43 mins MS m/z 472.1 $[M+H]^+$; Method 2minLowpH

EXAMPLE 2.2

7-(7-Methyl-2-phenyl-3-(p-tolyl)-7,8-dihydropyrido[2,3-b]pyrazin-5(6H)-yl)heptanoic acid

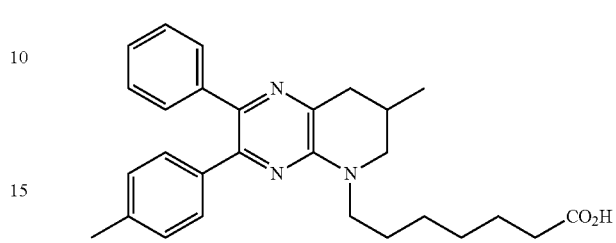

The titled compound was prepared analogously to Example 2.1 by replacing 7-ethyl-2,3-di-p-tolyl-5,6,7,8-tetrahydropyrido[2,3-b]pyrazine (Intermediate D) with 7-methyl-2-phenyl-3-(p-tolyl)-5,6,7,8-tetrahydropyrido[2,3-b]pyrazine (Intermediate CA);

LCMS; Rt 1.36 mins MS m/z 445.5 $[M+H]^+$; Method 2minLowpH

EXAMPLE 2.3(I) AND 2.3(II)

Racemate and Enantiomers 1 and 2 of 7-(6-Ethyl-2,3-di-p-tolyl-7,8-dihydropyrido[2,3-b]pyrazin-5(6H)-yl)heptanoic acid

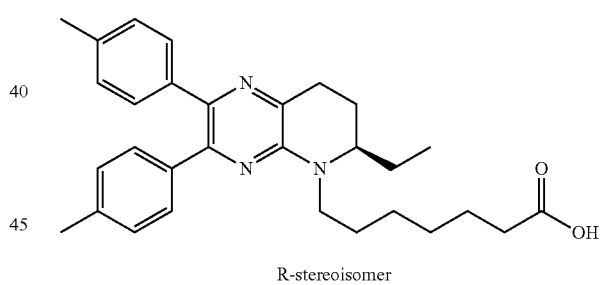

R-stereoisomer

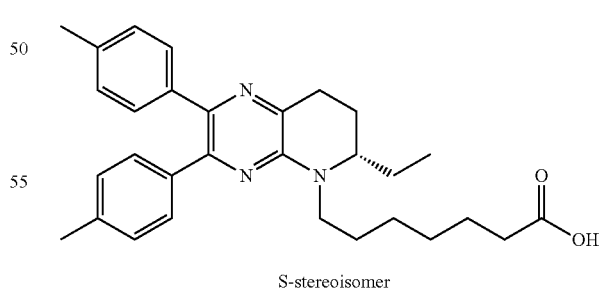

S-stereoisomer

The titled compound was prepared analogously to Example 2.1 by replacing 7-ethyl-2,3-di-p-tolyl-5,6,7,8-tetrahydropyrido[2,3-b]pyrazine (Intermediate D) with 6-ethyl-2,3-di-p-tolyl-5,6,7,8-tetrahydropyrido[2,3-b]pyrazine (Intermediate DA). The racemate was separated under the following conditions to afford the individual enantiomers:

Chiral Prep HPLC
Column: Chiralpak AD-H
Flow rate: 15 ml/min
Eluent: 95: 5 Hexane:0.1% TFA in EtOH

EXAMPLE 2.3(I)

Enantiomer 1: (R)-7-(6-Ethyl-2,3-di-p-tolyl-7,8-dihydropyrido[2,3-b]pyrazin-5(6H)-yl)heptanoic acid or (S)-7-(6-Ethyl-2,3-di-p-tolyl-7,8-dihydropyrido[2,3-b]pyrazin-5(6H)-yl)heptanoic acid Chiral HPLC Retention Time of compound: 7.6 min; LC-MS MS m/z 472 [M+H]$^+$;

EXAMPLE 2.3(II)

Enantiomer 2: (R)-7-(6-Ethyl-2,3-di-p-tolyl-7,8-dihydropyrido[2,3-b]pyrazin-5(6H)-yl)heptanoic acid or (S)-7-(6-Ethyl-2,3-di-p-tolyl-7,8-dihydropyrido[2,3-b]pyrazin-5(6H)-yl)heptanoic acid Chiral HPLC Retention Time of compound: 17.85 min; LC-MS MS m/z 472 [M+H]$^+$;

EXAMPLE 2.4

7-(6-Methyl-2-phenyl-3-p-tolyl-7,8-dihydropyrido[2,3-b]pyrazin-5(6H)-yl)heptanoic acid

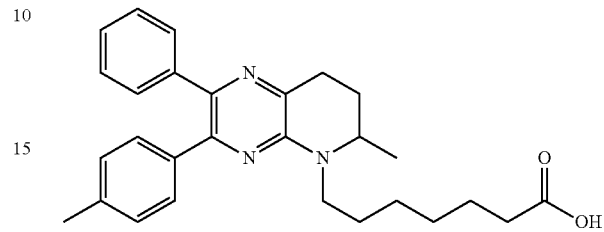

The titled compound was prepared analogously to Example 2.1 by replacing 7-ethyl-2,3-di-p-tolyl-5,6,7,8-tetrahydropyrido[2,3-b]pyrazine (Intermediate D) with 6-methyl-2-phenyl-3-(p-tolyl)-5,6,7,8-tetrahydropyrido[2,3-b]pyrazine (Intermediate CB);
LCMS; Rt 1.936 mins MS m/z 443.9[M+H]$^+$; Method G.

EXAMPLES 2.5 TO 2.10

The compounds of the following tabulated examples were prepared analogously to Example 2.1 from the appropriate starting materials, preparations of which are described hereinafter.

| Ex. | Structure | Name | [M + H]$^+$/NMR |
|---|---|---|---|
| 2.5 | 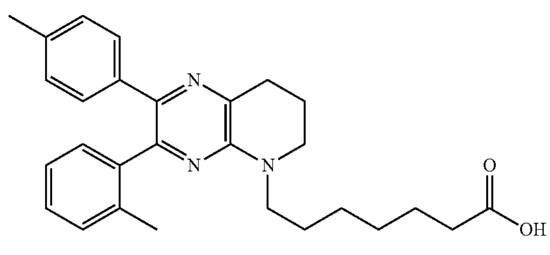 [SMILES: Cc1ccc(-c2nc3c(nc2-c2ccccc2C)N(CCCCCCC(=O)O)CCC3)cc1] | 7-(3-o-Tolyl-2-p-tolyl-7,8-dihydropyrido[3,2-b]pyrazin-5(6H)-yl)heptanoic acid | Rt 1.91 mins; MS m/z 444[M + H]$^+$, Method G |
| 2.6 | 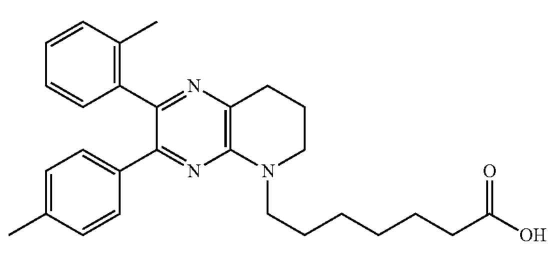 [SMILES: Cc1ccc(-c2nc3c(nc2-c2ccccc2C)CCCN3CCCCCCC(=O)O)cc1] | 7-(2-o-Tolyl-3-p-tolyl-7,8-dihydropyrido[3,2-b]pyrazin-5(6H)-yl)heptanoic acid | Rt 1.87 mins; MS m/z 444 [M + H]$^+$, Method G<br>$^1$H NMR (400 MHz, CDCl$_3$) δ 7.30 (2H, t), 7.24-7.20 (3H, m), 7.13 (1H, d), 7.03 (2H, d), 3.77 (2H, br m), 3.56 (2H, br t), 3.25 (2H, br t), 2.25-2.31 (5H, m), 2.14 (2H, br m), 1.91 (3H, s), 1.73 (2H, br m), 1.60 (2H, br m), 1.45-1.35 (4H, br m) |

| Ex. | Structure | Name | [M + H]⁺/NMR |
|---|---|---|---|
| 2.7 | 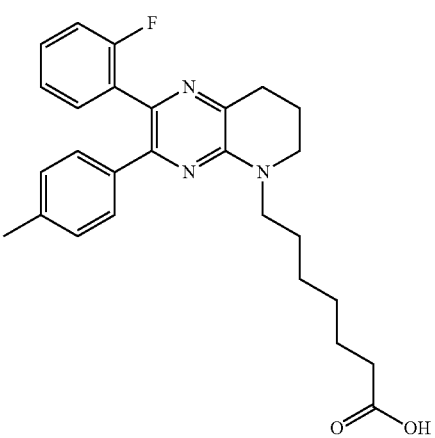 [SMILES: Cc1ccc(-c2nc3c(nc2-c2ccccc2F)CCCN3CCCCCCC(=O)O)cc1] | 7-(2-(2-Fluorophenyl)-3-p-tolyl-7,8-dihydropyrido[2,3-b]pyrazin-5(6H)-yl)heptanoic acid | Rt 1.84 mins; MS m/z 448 [M + H]⁺, Method I ¹H NMR (400 MHz, CDCl₃) δ 7.42-7.32 (2H, m), 7.24 (2H, d), 7.15 (1H, t), 7.01 (2H, d), 6.98 (1H, t), 3.74 (2H, t), 3.54 (2H, t), 3.21 (2H, t), 2.36 (3H, s), 2.29 (2H, t), 2.13 (2H, br m), 1.70 (2H, br m), 1.59 (2H, br m), 1.45-1.35 (4H, br m) |
| 2.8 | 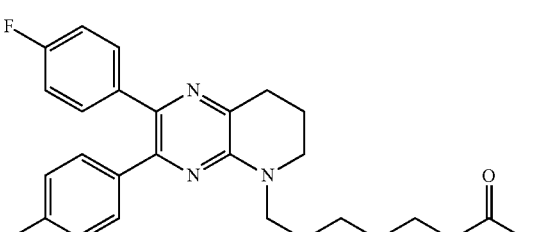 | 7-(2-(4-Fluorophenyl)-3-p-tolyl-7,8-dihydropyrido[2,3-b]pyrazin-5(6H)-yl)heptanoic acid | Rt 1.90 mins; MS m/z 448 [M + H]⁺, Method I ¹H NMR (400 MHz, CDCl₃) δ 7.30 (2H, dd), 7.23 (2H, d), 7.08 (2H, d), 6.99 (2H, t), 3.74 (2H, t), 3.54 (2H, t), 3.21 (2H, t), 2.34 (3H, s), 2.28 (2H, t), 2.13 (2H, m), 1.70 (2H, m), 1.59 (2H, m), 1.45-1.35 (4H, br m) |
| 2.9 | 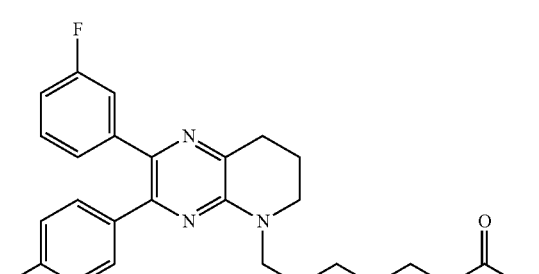 | 7-(2-(3-Fluorophenyl)-3-p-tolyl-7,8-dihydropyrido[2,3-b]pyrazin-5(6H)-yl)heptanoic acid | Rt 1.93 mins; MS m/z 448 [M + H]⁺, Method G ¹H NMR (400 MHz, CDCl₃) δ 7.28-7.21 (3H, m), 7.15-7.06 (3H, m), 7.01 (2H, t), 3.73 (2H, t), 3.54 (2H, t), 3.20 (2H, t), 2.34 (3H, s), 2.29 (2H, t), 2.13 (2H, m), 1.70 (2H, m), 1.60 (2H, m), 1.45-1.35 (4H, br m) |
| 2.10 | 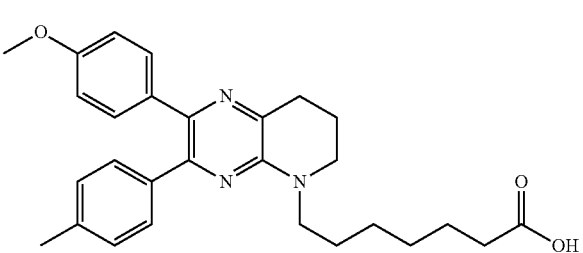 [SMILES: COc1ccc(-c2nc3c(nc2-c2ccc(C)cc2)N(CCCCCCC(=O)O)CCC3)cc1] | 7-(2-(4-Methoxyphenyl)-3-p-tolyl-7,8-dihydropyrido[2,3-b]pyrazin-5(6H)-yl)heptanoic acid | Rt 1.58 mins; MS m/z 460 [M + H]⁺, Method I ¹H NMR (400 MHz, CDCl₃) δ 7.30 (2H, d), 7.25 (2H, d), 7.04 (2H, d), 6.77 (2H, d), 3.78 (3H, s), 3.64 (2H, t), 3.44 (2H, t), 2.99 (2H, t), 2.32 (3H, s), 2.29 (2H, t), 2.07 (2H, m), 1.70-1.58 (4H, m), 1.45-1.35 (4H, br m) |

EXAMPLE 3.1 rac-7-(8-Methoxy-2,3-di-p-tolyl-7,8-dihydropyrido[2,3-b]pyrazin-5(6H)-yl)heptanoic acid

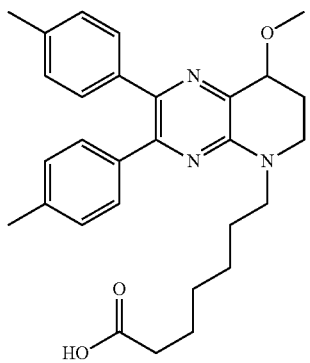

Step 1: rac-Methyl 7-(8-methoxy-2,3-di-p-tolyl-7,8-dihydropyrido[2,3-b]pyrazin-5(6H)-yl)heptanoate To a solution of rac-2,3-di-p-tolyl-5,6,7,8-tetrahydropyrido[2,3-b]pyrazin-8-yl acetate ((prepared according to the preparation procedures disclosed in PCT patent application PCT/EP2011/062028, Intermediate HF) (209 mg, 0.560 mmol) in DCE (dry) (10 ml) was added ethyl 7-oxoheptanoate (289 mg, 1.679 mmol) followed by sodium triacetoxyborohydride (356 mg, 1.679 mmol). The mixture was left to stir overnight at room temperature under an atmosphere of nitrogen. The resulting mixture was diluted with water (20 ml) and extracted with EtOAc (3×20 ml). The combined organic extracts were dried over MgSO$_4$, filtered and concentrated under reduced pressure. The crude product was passed through an Isolute® SCX-2 SPE cartridge and was loaded onto a primed (with MeOH 20 ml) SCX-2 cartridge. The methanolic ammonia fractions were concentrated under reduced pressure to afford the titled compound as a mixture with rac-ethyl 7-(8-acetoxy-2,3-di-p-tolyl-7,8-dihydropyrido[2,3-b]pyrazin-5(6H)-yl)heptanoate; The mixture was used in the next step without further purification;

LCMS; Rt 1.46 mins MS m/z 530.5 [M+H]$^+$; Method 2minLowpH

Step 2: rac-7-(8-Methoxy-2,3-di-p-tolyl-7,8-dihydropyrido[2,3-b]pyrazin-5(6H)-yl)heptanoic acid To a solution of step 1 (201 mg, 0.379 mmol) in EtOH (10 ml) was added 2M NaOH (aq) (0.759 ml, 1.518 mmol) and the suspension was stirred at room temperature overnight under an atmosphere of nitrogen. Ethyl acetate (20 ml) was added to the suspension followed by 2M HCl (aq) (~3 ml) to adjust the pH to pH5-6. The mixture was washed with water (~20 ml) and the organic portion was separated, dried over MgSO$_4$ and concentrated under reduced pressure to give a yellow oil/solid. The solid was purified by chromatography on silica eluting with 0-50% EtOAc in iso-hexane to afford the titled compound (first eluted peak) and rac-7-(8-hydroxy-2,3-d i-p-tolyl-7,8-dihydropyrido[2,3-b]pyrazin-5(6H)-yl)heptanoic acid LCMS; Rt 1.36 mins MS m/z 474.2 [M+H]$^+$; Method 2minLowpH

EXAMPLES 3.2 AND 3.3

Enantiomers 1 and 2 of 7-(8-Methoxy-2,3-di-p-tolyl-7,8-dihydropyrido[2,3-b]pyrazin-5(6H)-yl)heptanoic acid

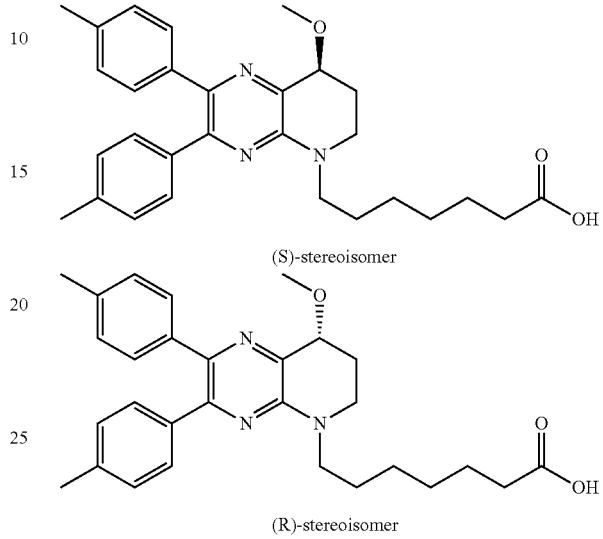

Chiral separation of rac-7-(8-methoxy-2,3-di-p-tolyl-7,8-dihydropyrido[2,3-b]pyrazin-5(6H)-yl)heptanoic acid (Example 3.1) using Supercritical Fluid Chromatography afforded the individual enantiomers.

Method Details:
Column: Phenomenex LUX C2 250×10 mm, 5 um @ 35° C.
Mobile phase: 40% Methanol/60% CO$_2$
Flow: 10 ml/min
Detection: UV @ 220 nm
System: Berger Minigram SFC2

EXAMPLE 3.2

First eluted peak: Enantiomer 1: (R)-7-(8-methoxy-2,3-di-p-tolyl-7,8-dihydropyrido[2,3-b]pyrazin-5(6H)-yl)heptanoic acid or (S)-7-(8-methoxy-2,3-di-p-tolyl-7,8-dihydropyrido[2,3-b]pyrazin-5(6H)-yl)heptanoic acid LCMS; Rt 1.35 mins MS m/z 474.4 [M+H]$^+$; Method 2minLowpH
SFC Retention Time: 3.50 min.

EXAMPLE 3.3

Second eluted peak: Enantiomer 2: (R)-7-(8-methoxy-2,3-di-p-tolyl-7,8-dihydropyrido[2,3-b]pyrazin-5(6H)-yl)heptanoic acid or (S)-7-(8-methoxy-2,3-di-p-tolyl-7,8-dihydropyrido[2,3-b]pyrazin-5(6H)-yl)heptanoic acid LCMS; Rt 1.35 mins MS m/z 474.4 [M+H]$^+$; Method 2minLowpH
SFC Retention Time: 4.40 min

EXAMPLE 4

7-(2,3-Bis(2,4-difluorophenyl)-7,8-dihydropyrido[2,3-b]pyrazin-5(6H)-yl)heptanoic acid

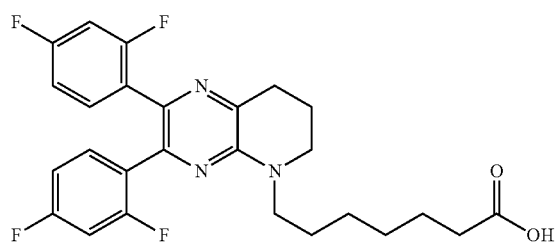 [SMILES: O=C(O)CCCCCCN1CCCc2nc(-c3ccc(F)cc3F)c(-c3ccc(F)cc3F)nc21]

Step 1: Ethyl 7-(2,3-bis(2,4-difluorophenyl)-7,8-dihydropyrido[2,3-b]pyrazin-5(6H)-yl)heptanoate A mixture comprising 2,3-bis(2,4-difluorophenyl)-5,6,7,8-tetrahydropyrido[2,3-b]pyrazine (Intermediate CC) (310 mg, 0.863 mmol) in 1,2-dichloroethane (10 ml) was added to ethyl 7-oxoheptanoate (446 mg, 2.59 mmol) and stirred at RT for 15 mins. Sodium triacetoxyborohydride (914 mg, 4.31 mmol) was added and stirring continued at RT for 3 days. The mixture was heated to 60° C. for 3 h and allowed to cool to RT. The resulting mixture was applied to a pre-wet (iso-hexane) Isolute® cartridge (silica) and eluted with 20-33% EtOAc in iso-hexane to afford the titled compound;

LCMS: Rt 1.48 mins MS m/z 516/517 [M+H]$^+$; Method 2minLC_v003

Step 2: 7-(2,3-Bis(2,4-difluorophenyl)-7,8-dihydropyrido[2,3-b]pyrazin-5(6H)-yl)heptanoic acid Ethyl 7-(2,3-bis(2,4-difluorophenyl)-7,8-dihydropyrido[2,3-b]pyrazin-5(6H)-yl)heptanoate (step 1) (480 mg, 0.931 mmol) in THF (2.5 ml) was treated with LiOH (178 mg, 7.45 mmol) followed by water (2.5 ml) and stirred vigorously for 3 days. The mixture was acidified to pH4/5 using 5M HCl and extracted with DCM. The combined organic extracts were dried (sodium sulphate), filtered and concentrated under reduced pressure. Purification was carried out on silica eluting with 20-25% TBME in DCM. The resulting product was further purified under the following conditions to afford the titled compound;

Sample Concentration: 340 mg in MeOH
Column: Phenomenex LUX C2 250×10 mm, 5 um
Mobile phase: 20% methanol/80% CO$_2$
Flow: 10 ml/min
Detection: UV @ 220 nm
System: SFC2

1H NMR (400 MHz, MeOD-d4) δ 7.28-7.40 (2 H, m), 6.88-6.96 (2 H, m), 6.78-6.85 (2 H, m), 3.65 (2 H, t, J=7.20 Hz), 3.55 (2 H, t, J=5.31 Hz), 2.98 (2 H, t, J=6.32 Hz), 2.23 (2 H, t, J=7.45 Hz), 2.08-2.15 (2 H, m), 1.65-1.74 (2 H, m), 1.55-1.63 (2 H, m), 1.33-1.45 (4 H, m)

LCMS: Rt 4.92 mins MS m/z 488 [M+H]+: Method 10minLC_v003

EXAMPLE 5

7-(2,3-Bis(6-methylpyridin-3-yl)-7,8-dihydropyrido[2,3-b]pyrazin-5(6H)-yl)heptanoic acid

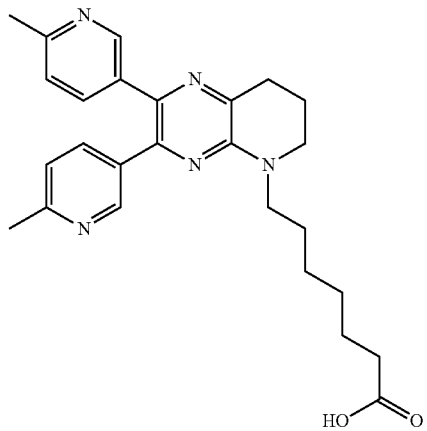

Step 1: Ethyl 7-(3-chloro-2-(6-methylpyridin-3-yl)-7,8-dihydropyrido[2,3-b]pyrazin-5(6H)-yl)heptanoate and Ethyl 7-(2,3-bis(6-methylpyridin-3-yl)-7,8-dihydropyrido[2,3-b]pyrazin-5(6H)-yl)heptanoate A mixture of ethyl 7-(2-bromo-3-chloro-7,8-dihydropyrido[2,3-b]pyrazin-5(6H)-yl)heptanoate (Intermediate EB) (150 mg, 0.371 mmol), 2-methyl-5-(4,4,5,5-tetramethyl-1,3,2-dioxaborolan-2-yl)pyridine (97 mg, 0.445 mmol) and potassium carbonate (154 mg, 1.112 mmol) were combined in a microwave vial. Dioxane (2 ml) was added and the flask was sealed and deoxygenated by evacuation/N$_2$ purge (×3). Pd(Ph$_3$P)$_4$ (42.8 mg, 0.037 mmol) was added, the mixture was de-oxygenated by evacuation/N$_2$ purge (×3) and heated at 150° C. for 3 hours using microwave radiation. The mixture was diluted with water and extracted with EtOAc (×2). The extracts were washed with brine, dried (MgSO$_4$) and evaporated under reduced pressure to give a brown residue. The residue was purified by chromatography on silica eluting with 20-100% EtOAc in iso-hexane followed by 10% MeOH in DCM to afford ethyl 7-(3-chloro-2-(6-methylpyridin-3-yl)-7,8-dihydropyrido[2,3-b]pyrazin-5(6H)-yl)heptanoate:

LC-MS Rt=1.06 mins; [M+H]+417, Method 2minLC_v003.

Further purification was carried out by loading the mixture onto an Isolute® SCX-2 cartridge and eluting with MeOH followed by 2M NH$_3$ in MeOH. The methanolic ammonia fractions were concentrated under reduced pressure and further purified by chromatography on silica eluting with 50-100% EtOAc in iso-hexane to afford ethyl 7-(2,3-bis(6-methylpyridin-3-yl)-7,8-dihydropyrido[2,3-b]pyrazin-5(6H)-yl)heptanoate;

LC-MS Rt 0.87 mins; MS m/z 474 [M+H]$^+$, Method 2min-LowpH.

Step 2: 7-(2,3-Bis(6-methylpyridin-3-yl)-7,8-dihydropyrido[2,3-b]pyrazin-5(6H)-yl)heptanoic acid A solution of ethyl 7-(2,3-bis(6-methylpyridin-3-yl)-7,8-dihydropyrido[2,3-b]pyrazin-5(6H)-yl)heptanoate (step 1)(16 mg, 0.034 mmol) in MeOH (2 ml) was treated with sodium hydroxide 1M (0.101 ml, 0.101 mmol) and the resulting solution was stirred at 25° C. for 68 hours. The solution was concentrated under vacuum and the residue was diluted with water and washed with EtOAc (×2). The aqueous was acidified (pH ~4 with 1N HCl) and extracted with DCM (×3). The extracts were dried (MgSO$_4$) and evaporated under vacuum to afford the titled compound;

LC-MS Rt 2.72 mins; MS m/z 446 [M+H]$^+$, Method 10minLowpH.

EXAMPLE 6

7-(2-(6-Methyl pyridin-3-yl)-3-p-tolyl-7,8-dihydropyrido[2,3-b]pyrazin-5(6H)-yl)heptanoic acid

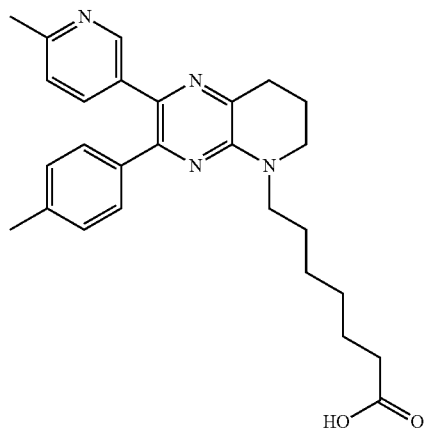 [SMILES: Cc1ccc(-c2nc3c(nc2-c2ccc(C)nc2)CCCN3CCCCCCC(=O)O)cc1]

Step 1: Ethyl 7-(2-(6-methylpyridin-3-yl)-3-p-tolyl-7,8-dihydropyrido[2,3-b]pyrazin-5(6H)-yl)heptanoate A mixture of ethyl 7-(3-chloro-2-(6-methylpyridin-3-yl)-7,8-dihydropyrido[2,3-b]pyrazin-5(6H)-yl) heptanoate (Example 5, step 1) (86 mg, 0.206 mmol), p-tolylboronic acid (56.1 mg, 0.413 mmol) and 2M sodium carbonate (0.309 ml, 0.619 mmol) were combined in a microwave vial. Dioxane (2 ml) was added and the flask was sealed and deoxygenated by evacuation/N$_2$ purge (×3). Pd(Ph$_3$P)$_4$ (47.7 mg, 0.041 mmol) was added and the mixture was de-oxygenated by evacuation/N$_2$ purge (×3) and heated at 150° C. for 3 hours using microwave radiation. The mixture was diluted with water and extracted with EtOAc (×2). The combined organic extracts were washed with brine, dried (MgSO$_4$) and evaporated under reduced pressure to a give a brown gum. The crude product was loaded onto an Isolute® SCX-2 cartridge and eluting with MeOH followed by 2M NH$_3$ in MeOH. The methanolic ammonia fractions were concentrated under reduced pressure and further purification by chromatography on silica eluting with 0-100% EtOAc in iso-hexane afforded the titled compound;

LC-MS Rt 1.08 mins; MS m/z 473[M+H]$^+$, Method 2min-LowpH.

Step 2: 7-(2-(6-Methylpyridin-3-yl)-3-p-tolyl-7,8-dihydropyrido[2,3-b]pyrazin-5(6H)-yl)heptanoic acid The titled compound was prepared from ethyl 7-(2-(6-methylpyridin-3-yl)-3-p-tolyl-7,8-dihydropyrido[2,3-b] pyrazin-5(6H)-yl)heptanoate (step 1) analogously to 7-(2,3-bis(6-methylpyridin-3-yl)-7,8-dihydropyrido[2,3-b]pyrazin-5(6H)-yl)heptanoic acid (Example 5, step 2);

LCMS Rt 0.90 mins; MS m/z 445 [M+H]$^+$, Method 2min-LowpH.

EXAMPLE 7

7-(3-(6-Methyl pyridin-3-yl)-2-p-tolyl-7,8-dihydropyrido[2,3-b]pyrazin-5(6H)-yl)heptanoic acid

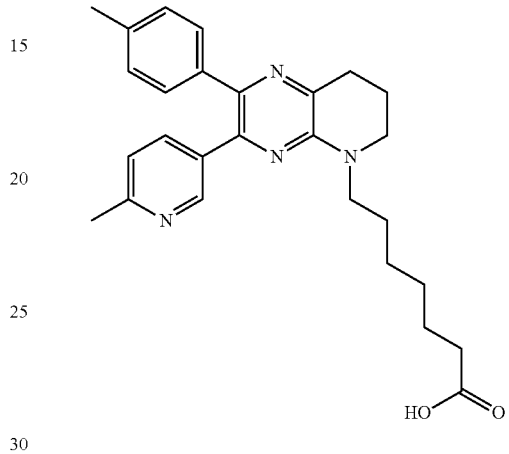

Step 1: Ethyl 7-(3-chloro-2-p-tolyl-7,8-dihydropyrido[2,3-b]pyrazin-5(6H)-yl)heptanoate A mixture of ethyl 7-(2-bromo-3-chloro-7,8-dihydropyrido[2,3-b]pyrazin-5(6H)-yl)heptanoate (Intermediate EB) (200 mg, 0.494 mmol), p-tolylboronic acid (Aldrich) (73.9 mg, 0.544 mmol) and potassium carbonate (205 mg, 1.482 mmol) were combined in a microwave vial. Dioxane (2 ml) was added and the flask was sealed and deoxygenated by evacuation/N$_2$ purge (×3). Pd(Ph$_3$P)$_4$ (57.1 mg, 0.049 mmol) was added and the mixture was de-oxygenated by evacuation/N$_2$ purge (×3) and heated at 150° C. for 3 hours using microwave radiation. The mixture was diluted with water and extracted with EtOAc (×2). The extracts were washed with brine, dried (MgSO$_4$) and evaporated under reduced pressure. The residue was purified by chromatography on silica eluting with 20-100% EtOAc in iso-hexane followed by 10% MeOH in DCM to elute the bis product. Further purification by chromatography on silica eluting with 0-70% EtOAc in iso-hexane afforded a mixture of the titled compound (mono adduct) and the bis adduct (2:1 ratio).

Step 2: Ethyl 7-(3-(6-methylpyridin-3-yl)-2-p-tolyl-7,8-dihydropyrido[2,3-b]pyrazin-5(6H)-yl)heptanoate A mixture of step 1 (70 mg), 2-methyl-5-(4,4,5,5-tetramethyl-1,3,2-dioxaborolan-2-yl)pyridine (73.7 mg, 0.337 mmol) and 2M sodium carbonate (0.252 ml, 0.505 mmol) were combined in a microwave vial. Dioxane (2 ml) was added and the flask was sealed and deoxygenated by evacuation/N$_2$ purge (×3). Pd(Ph$_3$P)$_4$ (38.9 mg, 0.034 mmol) was added and the mixture was de-oxygenated by evacuation/N$_2$ purge (×3) and heated at 150° C. for 3 hours using microwave radiation. The mixture was diluted with water and extracted with EtOAc (×2). The combined organic extracts were washed with brine, dried (MgSO$_4$) and evaporated under reduced pressure to a give a brown gum. The crude product was loaded onto an Isolute® SCX-2 cartridge and eluting with MeOH followed by 2M NH$_3$ in MeOH. The methanolic ammonia fractions were concentrated under reduced pressure and further purification by chromatography on silica eluting with 0-100% EtOAc in iso-hexane to afford the titled compound;

LCMS Rt 1.14 mins; MS m/z 473 [M+H]$^+$, Method 2min-LowpH.

Step 3: 7-(3-(6-Methylpyridin-3-yl)-2-p-tolyl-7,8-dihydropyrido[2,3-b]pyrazin-5(6H)-yl)heptanoic acid The titled compound was prepared from ethyl 7-(3-(6-methylpyridin-3-yl)-2-p-tolyl-7,8-dihydropyrido[2,3-b]pyrazin-5(6H)-yl)heptanoate (step 2) analogously to 7-(2,3-bis(6-methylpyridin-3-yl)-7,8-dihydropyrido[2,3-b]pyrazin-5(6H)-yl)heptanoic acid (Example 5, step 2);

LCMS Rt 0.97 mins; MS m/z 445 [M+H]$^+$, Method 2min-LowpH.

$^1$H NMR (400 MHz, MeOD-d4) δ 8.35 (1 H, d, J 1.9 Hz), 7.73 (1 H, dd, J=8.1 & 2.2 Hz), 7.22-7.10 (5 H, m), 3.70 (2 H, t, J 7.3 Hz), 3.55 (2 H, t, J 5.6 Hz), 2.99 (2 H, t, J), 2.51 (3 H, s), 2.35 (3H, s), 2.25-2.20 (2 H, m), 2.15-2.06 (2 H, m), 1.79-1.66 (2H, m), 1.64-1.1.52 (2H, m), 1.49-1.35 (4H, m).

The compounds of the following tabulated examples were prepared analogously to Example 7 from ethyl 7-(2-bromo-3-chloro-6-oxo-7,8-dihydropyrido[2,3-b]pyrazin-5(6H)-yl) heptanoate (Intermediate EA/EB, step 1) and the appropriate boronic acid.

EXAMPLE 8

9-(6-Oxo-2,3-di-p-tolyl-7,8-dihydropyrido[2,3-b]pyrazin-5(6H)-yl)nonanoic acid

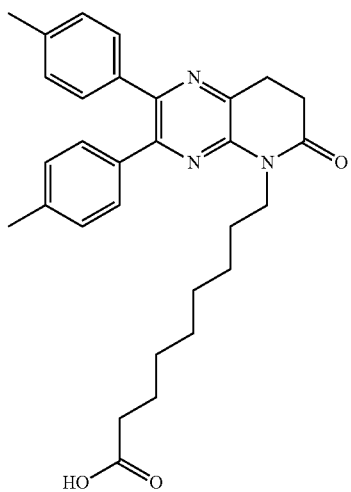

Step 1: Ethyl 9-(6-oxo-2,3-di-p-tolyl-7,8-dihydropyrido[2,3-b]pyrazin-5(6H)-yl)nonanoate A solution of 2,3-di-p-tolyl-7,8-dihydropyrido[2,3-b]pyrazin-6(5H)-one ((prepared according to the preparation

| Ex. | Structure | Name | [M + H]$^+$/NMR |
|---|---|---|---|
| 7.1 | 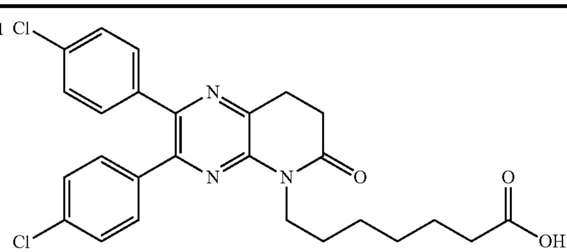 | 7-(2,3-Bis(4-chlorophenyl)-6-oxo-7,8-dihydropyrido[2,3-b]pyrazin-5(6H)-yl)heptanoic acid | LCMS: Rt 1.32 mins MS m/z 498.3/500.2: Method 2 minLowpH |
| 7.2 | 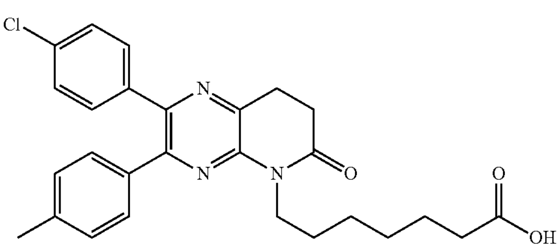 [SMILES: Cc1ccc(-c2nc3c(nc2-c2ccc(Cl)cc2)CCC(=O)N3CCCCCCC(=O)O)cc1] | 7-(2-(4-Chlorophenyl)-6-oxo-3-p-tolyl-7,8-dihydropyrido[2,3-b]pyrazin-5(6H)-yl)heptanoic acid | LCMS: Rt 1.47 mins MS m/z 478.3 [M + H]+ Method 2 minLowpHv01 |
| 7.3 | | 7-(3-(4-Chlorophenyl)-6-oxo-2-p-tolyl-7,8-dihydropyrido[2,3-b]pyrazin-5(6H)-yl)heptanoic acid | LCMS: Rt 1.43 mins MS m/z 478.5 [M + H]+: Method 2 minLowpHv01 | procedures disclosed in PCT patent application PCT/EP2011/062028, Example 12.1 step 1) (500 mg, 1.518 mmol) and potassium carbonate (1049 mg, 7.59 mmol) in DMF (15 ml) under $N_2$ was treated with ethyl 9-bromononanoate (805 mg, 3.04 mmol) and stirred at RT overnight. A further portion of ethyl 9-bromononanoate (805 mg, 3.04 mmol) was added and stirring continued at RT for 3 days. The mixture was diluted with water and extracted with EtOAc. The combined organic extracts were washed with brine (×3), dried ($MgSO_4$) and the solvent was removed under reduced pressure to afford the titled compound as a yellow oil;

LCMS; Rt 1.49 mins MS m/z 514 [M+H]$^+$; Method 2min-LC_v003.

Step 2: 9-(6-Oxo-2,3-di-p-tolyl-7,8-dihydropyrido[2,3-b]pyrazin-5(6H)-yl)nonanoic acid A solution of ethyl 9-(6-oxo-2,3-di-p-tolyl-7,8-dihydropyrido[2,3-b]pyrazin-5(6H)-yl)nonanoate (step 1)(392.5 mg, 0.764 mmol) in MeOH (10 ml) was treated with 1M NaOH (2.292 ml, 2.292 mmol) and stirred at RT overnight. The mixture was concentrated under reduced pressure to remove MeOH and acidified using 1M HCl. The resulting mixture was extracted with DCM and the organic extracts were concentrated under reduced pressure to afford the titled compound;

LCMS; Rt 1.34 mins MS m/z 486.6 [M+H]$^+$; Method 2minLowpH.

$^1$H NMR (400 MHz, DMSO-d6) δ 11.96 (1H, s), 7.31-7.23 (4H, m), 7.16-7.11 (4H, m), 4.02 (2H, m), 3.14 (2H, m), 2.86 (2H, m), 2.31 (3H, s), 2.31 (3H, s), 2.16 (2H, t), 1.62 (2H, br m), 1.45 (2H, m), 1.34-1.18 (8H, br m)

EXAMPLE 9.1

9-(2,3-Di-p-tolyl-7,8-dihydropyrido[2,3-b]pyrazin-5(6H)-yl)nonanoic acid

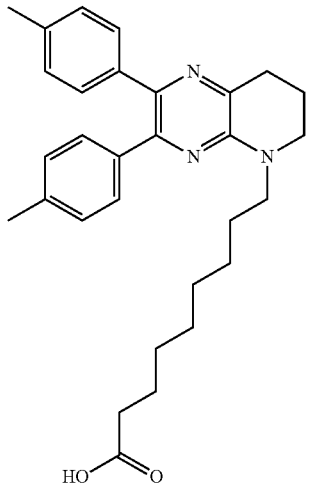 [SMILES: Cc1ccc(-c2nc3c(nc2-c2ccc(C)cc2)N(CCCCCCCCC(=O)O)CCC3)cc1]

9-(6-Oxo-2,3-di-p-tolyl-7,8-dihydropyrido[2,3-b]pyrazin-5(6H)-yl)nonanoic acid (Example 8) (200 mg, 0.412 mmol) in THF (10 ml) was stirred under $N_2$ for 10 mins. Lithium pyrrolidinoborohydride (1M in THF) (2.059 ml, 2.059 mmol) was added carefully and the resulting mixture was stirred at RT for 1.5 hours. The reaction was quenched with 1M HCl and the mixture was concentrated under reduced pressure. The resulting mixture was extracted with DCM and the organic extracts were passed through a phase separating column. The organics were concentrated under reduced pressure and purification of the crude product by chromatography on silica eluting with 0-100% EtOAc in iso-hexane afforded the titled compound;

$^1$H NMR (400 MHz, DMSO-d6) δ 12.02 (1H, br s), 7.21 (2H, m), 7.13 (2H, m), 7.09-7.00 (4H, br m), 3.57 (2H, m), 3.44 (2H, m), 2.88 (2H, m), 2.28 (3H, s), 2.26 (3H, s), 2.15 (2H, t), 2.00 (2H, br m), 1.59 (2H, br m), 1.45 (2H, br m), 1.33-1.16 (8H, br m)

EXAMPLE 9.2(I) AND 9.2(II)

Racemate and enantiomers of 7-(7-(2-hydroxypropan-2-yl)-2,3-di-p-tolyl-7,8-dihydropyrido[2,3-b]pyrazin-5(6H)-yl)heptanoic acid

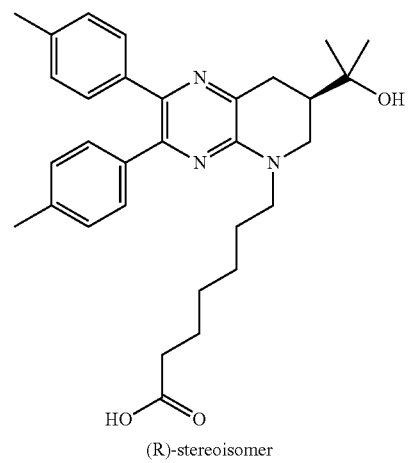
(R)-stereoisomer

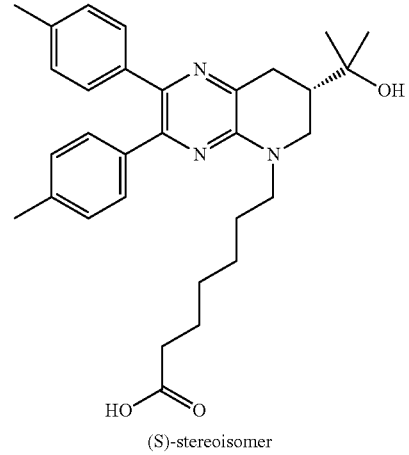
(S)-stereoisomer

The titled compound was prepared from Example 1.1 analogously to Example 9.1. The racemate was separated under the following conditions to afford the individual enantiomers:

Column: Chiralpak AD-H, 250×10 mm, 5 um @ 35 deg C.
Mobile phase: 35% isopropanol/65% CO2
Flow: 10 ml/min
Detection: UV @ 220 nm
System: Berger Minigram SFC1 system 1
Sample Concentration: 14 mg/ml

EXAMPLE 9.2(I)

Enantiomer 1: (R)-7-(7-(2-hydroxypropan-2-yl)-2,3-di-p-tolyl-7,8-dihydropyrido[2,3-b]pyrazin-5(6H)-yl) heptanoic acid or (S)-7-(7-(2-hydroxypropan-2-yl)-2,3-di-p-tolyl-7,8-dihydropyrido[2,3-b]pyrazin-5(6H)-yl)heptanoic acid SFC Retention Time: 3.03 mins $^1$H NMR (400 MHz, CHLOROFORM-d) δ 7.33 (2H, m), 7.24 (2H, m), 7.06 (4H, m), 3.76-3.60 (2H, m), 3.60-3.53 (1H, m), 3.36 (1H, m), 3.17-3.07 (1H, m), 2.83 (1H, m), 2.36-2.29 (8H, m), 2.19-2.09 (1H, m), 1.68 (4H, m), 1.48-1.40 (4H, m), 1.39 (3H, s), 1.31 (3H, s)

LCMS; Rt 6.15 mins MS m/z 502 [M+H]$^+$; Method 10min-LowpH

EXAMPLE 9.2(II)

Enantiomer 2: (R)-7-(7-(2-hydroxypropan-2-yl)-2,3-di-p-tolyl-7,8-dihydropyrido[2,3-b]pyrazin-5(6H)-yl) heptanoic acid or (S)-7-(7-(2-hydroxypropan-2-yl)-2,3-di-p-tolyl-7,8-dihydropyrido[2,3-b]pyrazin-5(6H)-yl)heptanoic acid SFC Retention Time: 6.45 mins
LCMS; Rt 6.15 mins MS m/z 502 [M+H]$^+$; Method 10min-LowpH

EXAMPLE 10

6-(2,3-Di-p-tolyl-7,8-dihydropyrido[2,3-b]pyrazin-5(6H)-yl)hexanoic acid

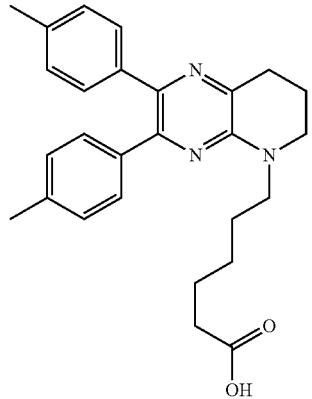 [SMILES: Cc1ccc(-c2nc3c(nc2-c2ccc(C)cc2)N(CCCCCC(=O)O)CCC3)cc1]

Step 1: Ethyl 6-(2,3-di-p-tolyl-7,8-dihydropyrido[2,3-b]pyrazin-5(6H)-yl)hexanoate A solution of 2,3-di-p-tolyl-5,6,7,8-tetrahydropyrido[2,3-b]pyrazine (Intermediate B) (2.0 g, 6.34 mmol) and ethyl 6-oxohexanoate (Intermediate A) (2.508 g, 12.68 mmol) in 1,2-dichloroethane (50 ml) was treated with sodium triacetoxyborohydride (3.36 g, 15.85 mmol) and the resultant suspension was stirred at room temperature overnight. The solution was treated with sat.NaHCO$_3$ and extracted with DCM (×3). The organic extracts were dried (MgSO$_4$) and evaporated under reduced pressure. The residue was loaded onto an Isolute® SCX-2 cartridge and eluted with MeOH followed by 2M NH$_3$ in MeOH. The methanolic ammonia fractions were concentrated under reduced pressure and further purified by chromatography on silica eluting with 10-50% EtOAc in iso-hexane to afford the titled compound;

LCMS; Rt 1.44 mins MS m/z 458.4 [M+H]$^+$; Method 2minLowpH.

Step 2: 6-(2,3-Di-p-tolyl-7,8-dihydropyrido[2,3-b]pyrazin-5(6H)-yl)hexanoic acid A solution of ethyl 6-(2,3-di-p-tolyl-7,8-dihydropyrido[2,3-b]pyrazin-5(6H)-yl)hexanoate (step 1)(2.8 g, 6.12 mmol) in MeOH (50 ml) was treated with 1M sodium hydroxide (9.18 ml, 18.36 mmol) and the resulting white suspension was heated at 50° C. for 2 hours. The mixture was allowed to cool to room temperature and concentrated under reduced pressure. The residue was diluted with water, acidified (pH 4, 2N HCl) and extracted with DCM (×3). The combined organic extracts were dried (MgSO$_4$) and concentrated under reduced pressure to afford an oil which crystallized to yield the titled compound as an off-white solid;

$^1$H NMR (400 MHz, CDCl$_3$-d) δ 7.30-7.35 (2 H, m) 7.21-7.28 (2 H, m) 7.02-7.08 (4 H, m) 3.57-3.75 (2 H, m) 3.42-3.48 (2 H, m) 2.98-3.04 (2 H, m) 2.30-2.38 (8 H, m) 2.05-2.13 (2 H, m) 1.65-1.77 (4 H, m) 1.38-1.47 (2 H, m)

LCMS; Rt 6.24 mins MS m/z 430 [M+H]$^+$; Method 10min-LowpH.

EXAMPLE 11(I) AND 11(II)

Enantiomers of 7-(7-hydroxy-6-oxo-2,3-di-p-tolyl-7,8-dihydropyrido[2,3-b]pyrazin-5(6H)-yl)heptanoic acid

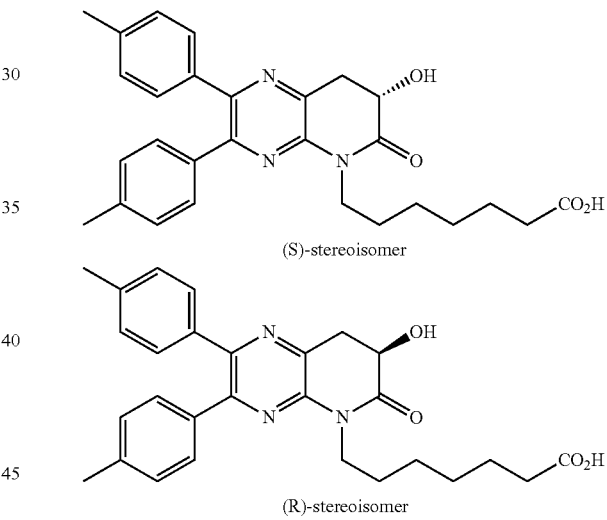

7-(7-Hydroxy-6-oxo-2,3-di-p-tolyl-7,8-dihydropyrido[2,3-b]pyrazin-5(6H)-yl)heptanoic acid ((prepared according to the preparation procedures disclosed in PCT patent application PCT/EP2011/062028, Example 16.1) was separated using SFC under the following conditions to afford the individual enantiomers:

Column: Chiralcel OJ-H 250×10 mm, 5 µm (2 columns in series)
Mobile phase: 15% MeOH+0.1% TFA/85% CO$_2$
Flow: 10 ml/min
Detection: UV @ 220 nm

EXAMPLE 11.1(I)

Enantiomer 1: (R)-7-(7-hydroxy-6-oxo-2,3-di-p-tolyl-7,8-dihydropyrido[2,3-b]pyrazin-5(6H)-yl) heptanoic acid or (S)-7-(7-hydroxy-6-oxo-2,3-di-p-tolyl-7,8-dihydropyrido[2,3-b]pyrazin-5(6H)-yl) heptanoic acid SFC Retention Time: 15.85 mins

EXAMPLE 11.1(II)

Enantiomer 2: (R)-7-(7-hydroxy-6-oxo-2,3-di-p-tolyl-7,8-dihydropyrido[2,3-b]pyrazin-5(6H)-yl)heptanoic acid or (S)-7-(7-hydroxy-6-oxo-2,3-di-p-tolyl-7,8-dihydropyrido[2,3-b]pyrazin-5(6H)-yl)heptanoic acid SFC Retention Time: 17.81 mins
1H NMR (400 MHz, MeOD-d4) δ 7.33-7.23 (4H, m), 7.15-7.07 (4H, m), 4.58-4.51 (1H, m), 4.25-4.19 (1H, m), 4.17-4.11, (1H, m), 3.46-3.39, (1H, m), 3.25-3.16 (1H, m), 2.34 (6H, s), 2.26-2.19 (2H, m), 1.76-1.72 (2H, m), 1.61-1.54 (2H, m), 1.48-1.36 (4H, m).

EXAMPLE 12

N-(Benzylsulfonyl)-7-(2,3-di-p-tolyl-7,8-dihydropyrido[2,3-b]pyrazin-5(6H)-yl)heptanamide

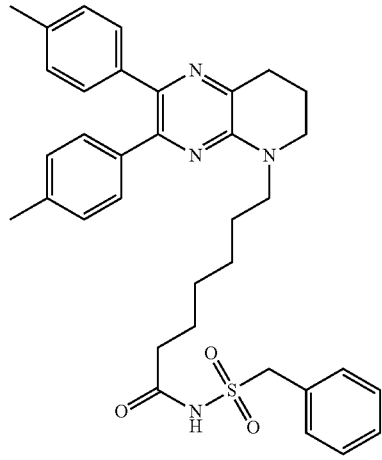 [SMILES: Cc1ccc(-c2nc3c(nc2-c2ccc(C)cc2)N(CCCCCCC(=O)NS(=O)(=O)Cc2ccccc2)CCC3)cc1]

A mixture comprising 7-(2,3-di-p-tolyl-7,8-dihydropyrido[2,3-b]pyrazin-5(6H)-yl)heptanoic acid [prepared according to the preparation procedures disclosed in PCT patent application PCT/EP2011/062028, Example 4.3] (100 mg, 0.225 mmol) in dry DCM (5 ml) at RT, under nitrogen, was treated with DMF (1.746 μl, 0.023 mmol) followed by oxalyl chloride (0.022 ml, 0.248 mmol). After stirring at RT for 2 hours, DIPEA (0.157 ml, 0.902 mmol) was added followed by phenylmethane sulfonamide (154 mg, 0.902 mmol). The resulting mixture was stirred at RT for 2 hours and subsequently added to water (30 ml). The mixture was extracted with DCM (×3) and the combined organic extracts were passed through a phase separating column. The organic solvent was removed under reduced pressure and purification of the crude residue by chromatography on silica eluting with 0-40% EtOAc in iso-hexane afforded an orange solid. The solid was dissolved in a minimal volume of EtOAc and treated with an excess of iso-hexane. The resulting suspension was filtered and the solid rinsed with iso-hexane (×3) the afford the titled compound;

LCMS: Rt 1.39 mins MS m/z 597.4 [M+H]+ Method 2minLowpH

The compounds of the following tabulated examples were prepared analogously to Example 12 from the appropriate starting materials, preparations of which are described hereinafter.

| Ex. | Structure | Name | [M + H]+/NMR |
|---|---|---|---|
| 12.1 | 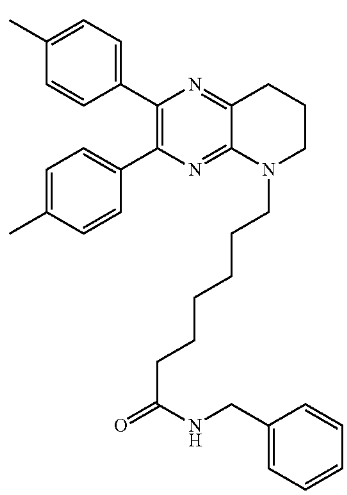 [SMILES: Cc1ccc(-c2nc3c(nc2-c2ccc(C)cc2)N(CCCCCCC(=O)NCc2ccccc2)CCC3)cc1] | N-Benzyl-7-(2,3-di-p-tolyl-7,8-dihydro-pyrido[2,3-b]pyrazin-5(6H)-yl)heptanamide | LCMS: Rt 1.40 mins; MS m/z 533.5 [M + H]+, Method 2 minLowpH |

| Ex. | Structure | Name | [M + H]⁺/NMR |
|---|---|---|---|
| 12.2 | 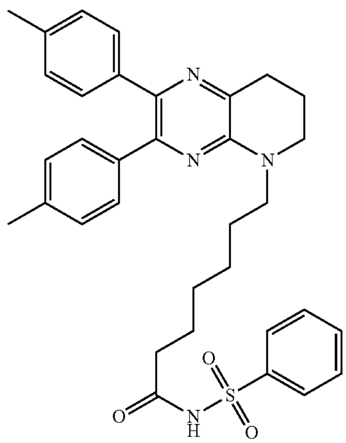 [SMILES: Cc1ccc(-c2nc3c(nc2-c2ccc(C)cc2)N(CCCCCCC(=O)NS(=O)(=O)c2ccccc2)CCC3)cc1] | 7-(2,3-Di-p-tolyl-7,8-dihydropyrido[2,3-b]pyrazin-5(6H)-yl)-N-(phenylsulfonyl)heptanamide | LCMS: Rt 1.36 mins MS m/z 583.6 [M + H]+: Method 2 minLowpH |
| 12.3 | 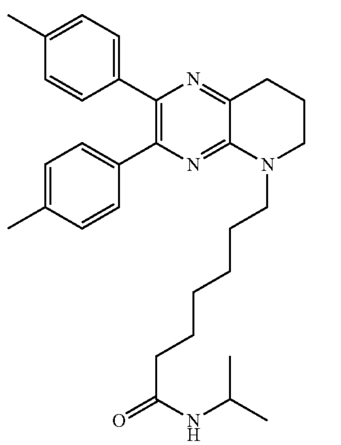 [SMILES: Cc1ccc(-c2nc3c(nc2-c2ccc(C)cc2)N(CCCCCCC(=O)NC(C)C)CCC3)cc1] | 7-(2,3-Di-p-tolyl-7,8-dihydropyrido[2,3-b]pyrazin-5(6H)-yl)-N-isopropylheptanamide | LCMS: Rt 1.35 mins MS m/z 485.6 [M + H]+: Method 2 minLowpH |
| 12.4 | 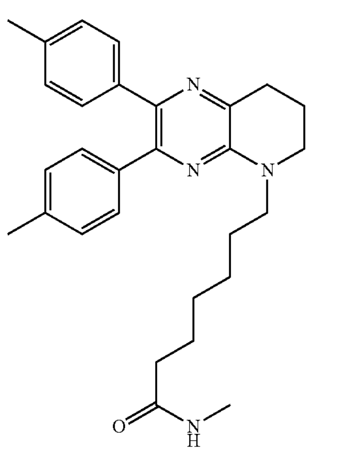 [SMILES: CNC(=O)CCCCCCN1CCCc2nc(-c3ccc(C)cc3)c(-c3ccc(C)cc3)nc21] | 7-(2,3-Di-p-tolyl-7,8-dihydropyrido[2,3-b]pyrazin-5(6H)-yl)-N-methylheptanamide | LCMS: Rt 1.28 mins MS m/z 457.0/458.4 [M + H]+: Method 2 minLowpH |

| Ex. | Structure | Name | [M + H]+/NMR |
|---|---|---|---|
| 12.5 | 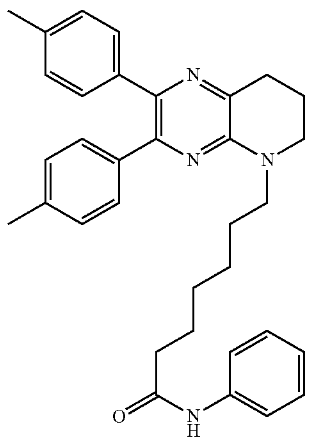 [SMILES: Cc1ccc(-c2nc3c(nc2-c2ccc(C)cc2)N(CCCCCCC(=O)Nc2ccccc2)CCC3)cc1] | 7-(2,3-Di-p-tolyl-7,8-dihydropyrido[2,3-b]pyrazin-5(6H)-yl)-N-phenylheptanamide | LCMS: Rt 1.43 mins MS m/z 519.5 [M + H]+: Method 2 minLowpH |
| 12.6 | 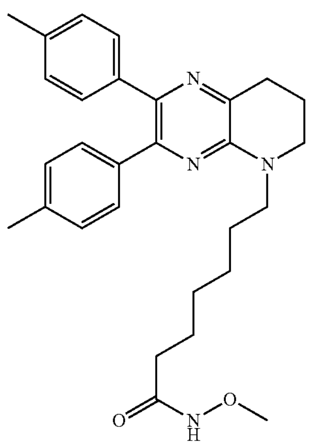 [SMILES: CONC(=O)CCCCCCN1CCCc2nc(-c3ccc(C)cc3)c(-c3ccc(C)cc3)nc21] | 7-(2,3-Di-p-tolyl-7,8-dihydropyrido[2,3-b]pyrazin-5(6H)-yl)-N-methoxyheptanamide | LCMS: Rt 1.41 mins MS m/z 473.7 [M + H]+: Method 2 minLowpHv01 |
| 12.7 | 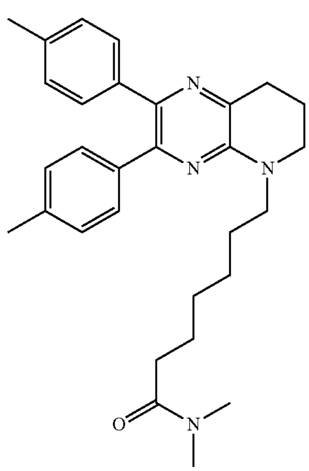 [SMILES: Cc1ccc(-c2nc3c(nc2-c2ccc(C)cc2)N(CCCCCCC(=O)N(C)C)CCC3)cc1] | 7-(2,3-Di-p-tolyl-7,8-dihydropyrido[2,3-b]pyrazin-5(6H)-yl)-N,N-dimethylheptanamide | LCMS: Rt 1.50 mins MS m/z 471.7 [M + H]+: Method 2 minLowpHv01 |

-continued

| Ex. | Structure | Name | [M + H]⁺/NMR |
|---|---|---|---|
| 12.8 | 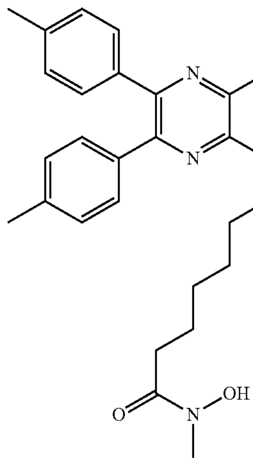 | 7-(2,3-Di-p-tolyl-7,8-dihydropyrido[2,3-b]pyrazin-5(6H)-yl)-N-hydroxy-N-methylheptanamide | LCMS: Rt 1.43 mins MS m/z 474.3 [M + H]+: Method 2 minLowpHv01 |
| 12.9 | 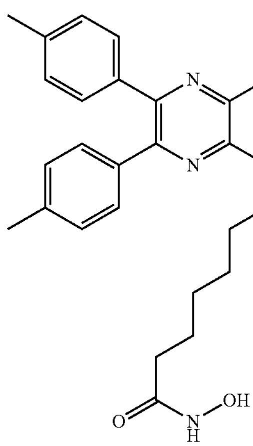 | 7-(2,3-Di-p-tolyl-7,8-dihydropyrido[2,3-b]pyrazin-5(6H)-yl)-N-hydroxyheptanamide | LCMS: Rt 1.34 mins MS m/z 459.4 [M + H]+: Method 2 minLowpHv01 |
| 12.10 | 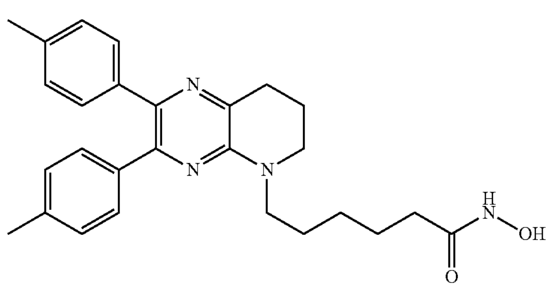 [SMILES: Cc1ccc(-c2nc3c(nc2-c2ccc(C)cc2)N(CCCCCC(=O)NO)CCC3)cc1] | 6-(2,3-Di-p-tolyl-7,8-dihydropyrido[2,3-b]pyrazin-5(6H)-yl)-N-hydroxyhexanamide | LCMS: Rt 1.28 mins MS m/z 446.6 [M + H]+ Method 2 minLowpHv01 |

EXAMPLE 13.1

(R or S)-7-(8-Hydroxy-2,3-di-p-tolyl-7,8-dihydropyrido[3,2-b]pyrazin-5(6H)-yl)-N-(methylsulfonyl)heptanamide

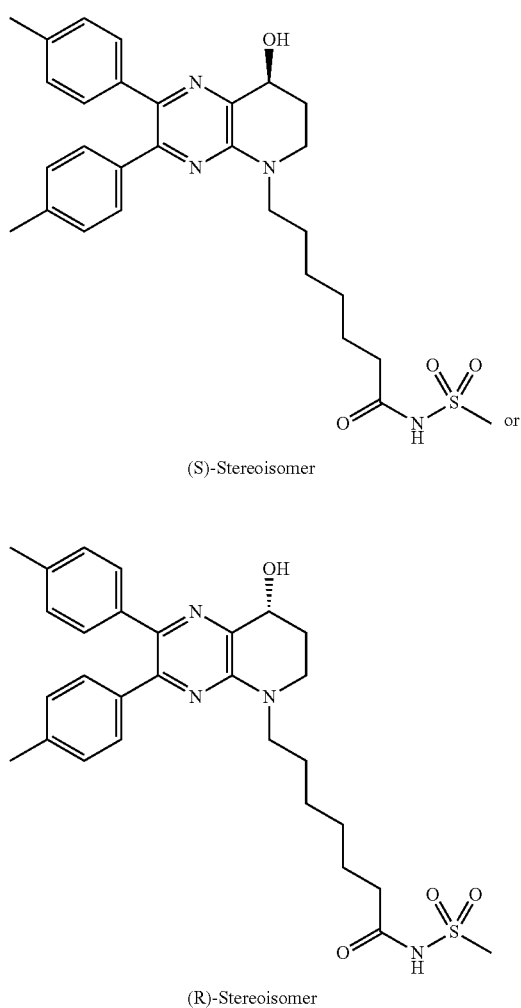

(S)-Stereoisomer or (R)-Stereoisomer

A suspension of polymer supported carbodiimide (1.36 mmol/g, 60 mg, 0.082 mmol) in DCM (dry) at RT (2 ml) under nitrogen was treated with (R or S)-7-(8-Hydroxy-2,3-di-p-tolyl-7,8-dihydropyrido[2,3-b]pyrazin-5(6H)-yl)heptanoic acid ([prepared according to the preparation procedures disclosed in PCT patent application PCT/EP2011/062028 Example 9.8a)(25 mg, 0.054 mmol), methanesulfonamide (5.17 mg, 0.054 mmol) followed by DMAP (6.65 mg, 0.054 mmol). The resulting orange suspension was stirred at RT overnight under an atmosphere of nitrogen. The reaction mixture was diluted with DCM (20 ml) and washed with 10% aqueous citric acid solution (20 ml×2), passing the organic portion through a phase separating column. The organic filtrate was concentrated under reduced pressure. Purification of the crude material by chromatography on silica eluting with EtOAc/iso-hexane followed by further purification by SFC (Chiralpak AD 250×10 mm; 30% IPA) afforded the titled compound;

LC-MS: Rt 1.35 mins; MS m/z [M+H]+537.3, Method 2minLowpHv01.

EXAMPLE 13.2

(R or S)—N-(Benzylsulfonyl)-7-(8-hydroxy-2,3-di-p-tolyl-7,8-dihydropyrido[3,2-b]pyrazin-5(6H)-yl)heptanamide and

EXAMPLE 13.3

(R or S)—N-(Benzylsulfonyl)-7-(8-hydroxy-2,3-di-p-tolyl-7,8-dihydropyrido[3,2-b]pyrazin-5(6H)-yl)heptanamide

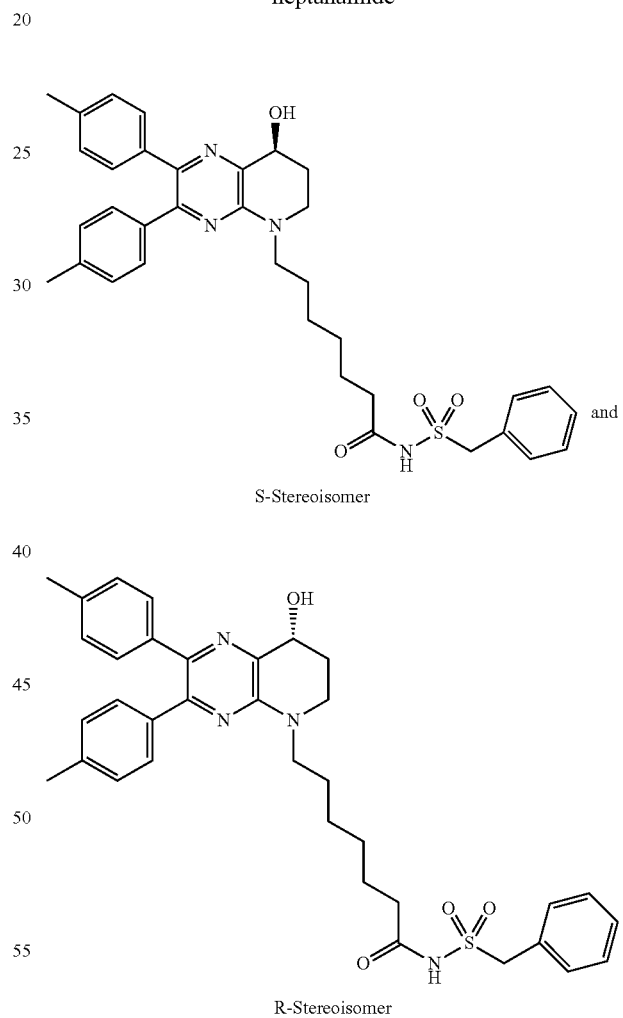

S-Stereoisomer and

R-Stereoisomer

The titled compounds were prepared analogously to Example 13.1 from rac-7-(8-Hydroxy-2,3-di-p-tolyl-7,8-dihydropyrido[2,3-b]pyrazin-5(6H)-yl)heptanoic acid ([prepared according to the preparation procedures disclosed in PCT patent application PCT/EP2011/Example 9.8) and phenylmethansulfonamide . Chiral separation of the racemic mixture using Supercritical Fluid Chromatography afforded the individual enantiomers:

Method Details:
  Column: Chiralpak AD-H 250×10 mm, 5 um@35 deg C.
  Mobile phase: 45% Iisopropanol/55% $CO_2$
  Flow: 10 ml/min
  Detection: UV @ 220 nm
  System: Berger Minigram SFC2

EXAMPLE 13.2

First eluted peak: (R)—N-(benzylsulfonyl)-7-(8-hydroxy-2,3-di-p-tolyl-7,8-dihydropyrido[3,2-b]pyrazin-5(6H)-yl)heptanamide or (S)—N-(benzylsulfonyl)-7-(8-hydroxy-2,3-di-p-tolyl-7,8-dihydropyrido[3,2-b]pyrazin-5(6H)-yl)heptanamide SFC Retention Time=4.13 mins
LC-MS: Rt=1.47 mins; [M+H]+613.4, Method 2minLowpHv01

EXAMPLE 13.3

Second eluted peak: (R)—N-(benzylsulfonyl)-7-(8-hydroxy-2,3-di-p-tolyl-7,8-dihydropyrido[3,2-b]pyrazin-5(6H)-yl)heptanamide or (S)—N-(benzylsulfonyl)-7-(8-hydroxy-2,3-di-p-tolyl-7,8-dihydropyrido[3,2-b]pyrazin-5(6H)-yl)heptanamide SFC Retention Time=5.70 mins
LC-MS: Rt=1.48 mins; [M+H]+613.4, Method 2minLowpHv01

The compounds of the following tabulated examples were prepared analogously to Example 13.1 from the appropriate starting materials, 7-(2,3-di-p-tolyl-7,8-dihydropyrido[2,3-b]pyrazin-5(6H)-yl)heptanoic acid, [prepared according to the preparation procedures disclosed in PCT patent application PCT/EP2011/062028, Example 4.31

| Ex. | Structure | Name | [M + H]+/NMR |
|---|---|---|---|
| 13.4 | 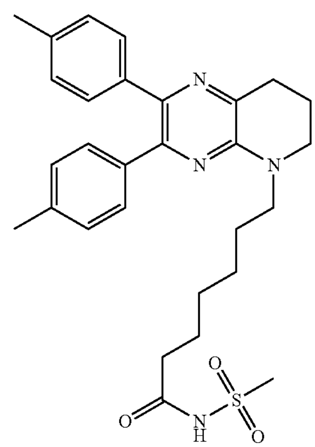 [SMILES: Cc1ccc(-c2nc3c(nc2-c2ccc(C)cc2)N(CCCCCCC(=O)NS(C)(=O)=O)CCC3)cc1] | 7-(2,3-Di-p-tolyl-7,8-dihydropyrido[2,3-b]pyrazin-5(6H)-yl)-N-(methylsulfonyl)heptanamide | LCMS: Rt 1.43 mins MS m/z 521.6 [M + H]+: Method 2 minLowpHv01 |
| 13.5 | 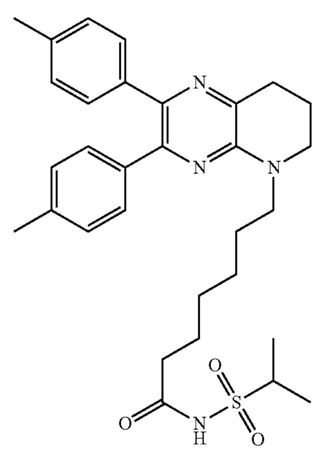 [SMILES: Cc1ccc(-c2nc3c(nc2-c2ccc(C)cc2)N(CCCCCCC(=O)NS(=O)(=O)C(C)C)CCC3)cc1] | 7-(2,3-Di-p-tolyl-7,8-dihydropyrido[2,3-b]pyrazin-5(6H)-yl)-N-(isopropylsulfonyl)heptanamide | LCMS: Rt 1.50 mins MS m/z 549.9/550.6 [M + H]+: Method 2 minLowpHv01 |

EXAMPLE 14

7-(7-Piperidin-1-yl)-2,3-di-p-tolyl-7,8-dihydropyrido[2,3-b]pyrazin-5(6H)-yl)heptanoic acid

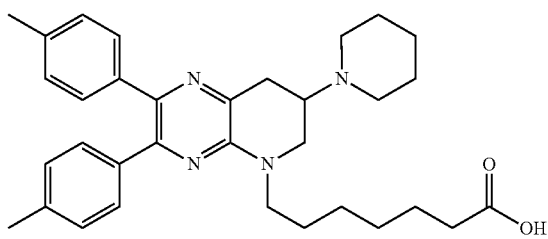 [SMILES: Cc1ccc(-c2nc3c(nc2-c2ccc(C)cc2)N(CCCCCCC(=O)O)CC(N2CCCCC2)C3)cc1]

Step 1: tert-Butyl 2,3-di-p-tolylpyrido[2,3-b]pyrazine-5(6H)-carboxylate 2,3-Di-p-tolylpyrido[2,3-b]pyrazine (Intermediate B, step 1) (2 g, 6.42 mmol) was dissolved in THF (15 ml). The mixture was degassed by bubbling nitrogen through for 5 mins and 1M LiAlH$_4$ in THF (3.21 ml, 3.21 mmol) was added dropwise at 5° C. (ice-bath) over ~3 minutes. Boc$_2$O (2.98 ml, 12.85 mmol) was added in DCM (15 ml) in a single portion and the reaction mixture stirred at RT overnight. A further portion of BOC$_2$O (1.4 g, 6.42 mmol) was added and the mixture was warmed to 40° C. for 3 hours. Aqueous potassium sodium tartrate tetrahydrate "Rochelle's salt" [CAS 6381-59-5] (~10 ml; 10% by wt) was added followed by DCM (20 ml) and the mixture was stirred vigorously for 10 min. The organic phase was separated, washed with aq. Rochelle's salt (30 ml), NaHCO$_3$, dried over MgSO$_4$, filtered and concentrated under reduced pressure to yield a viscous yellow oil. The oil was loaded onto a 120 g silica column (primed with iso-hexane) using DCM and eluted with TBME/iso-hexane gradient (0-40%). The product fractions were concentrated under reduced pressure the afford the titled compound;
LC-MS: Rt=1.35 mins; MS m/z 414.3 [M+H]+; Method 2minLowpH30

Step 2: tert-Butyl 7,8-dihydroxy-2,3-di-p-tolyl-7,8-dihydropyrido[2,3-b]pyrazine-5(6H)-carboxylate To a solution of tributylmethylammonium chloride (7.27 g, 30.8 mmol) in DCM (50 ml) was added potassium permanganate (4.87 g, 30.8 mmol) portionwise over 10 minutes at room temperature. On completion the reaction mixture was allowed to stir under an atmosphere of nitrogen for 30 minutes and then cooled down to 0° C. tert-Butyl 2,3-di-p-tolylpyrido[2,3-b]pyrazine-5(6H)-carboxylate (step 1)(7.5 g, 18.14 mmol) in DCM (50 ml) was added dropwise and the mixture was stirred at 4° C. for 10 minutes. To this mixture was added a solution of sodium bisulfite (11.32 g, 109 mmol) in water (50 ml) keeping the temperature below 10° C. The suspension was filtered through coarse Celite® (filter material) and washed through with DCM (200 ml). The organic layer was separated and the aqueous layer washed with DCM (50 ml). The combined organic portions were dried over MgSO$_4$, filtered and evaporated to dryness. The residue was purified by flash chromatography using a 125 g silica column eluting with 0-10% MeOH in DCM. The product fractions were combined and evaporated to dryness. The resulting oil was dissolved in EtOAc (approx. 15 ml). The resulting suspension was diluted with iso-hexane/EtOAc (2:1, 20 ml) and filtered to afford the titled compound as a pale yellow solid;
LC-MS: Rt. 1.22 mins; MS m/z 448.5 [M+H]+; Method 2minLowpH

Step 3: tert-Butyl 2-thioxo-7,8-di-p-tolyl-3a,4-dihydro-[1,3]dioxolo[4',5':4,5]pyrido[2,3-b]pyrazine-5(9bH)-carboxylate tert-Butyl 7,8-di hydroxy-2,3-d i-p-tolyl-7,8-dihydropyrido[2,3-b]pyrazine-5(6H)-carboxylate (step 2) (1.28 g, 2.86 mmol) was dissolved in tetrahydrofuran (50 ml). 1,1'-Thiocarbonyl diimidazole (1.019 g, 5.72 mmol) was added and the solution heated at reflux for 3 h. The reaction mixture was cooled to room temperature and evaporated to dryness. Water and DCM (300 ml) were added. The organic layer was separated and evaporated to dryness. Ethyl acetate (5 ml) was added to the dark residue and the resulting solid filtered off. The solid was washed twice with EtOAc (5 ml) to afford the titled compound;
LC-MS: Rt=1.35 mins; Method 2minLowpH

Step 4: tert-Butyl 7-hydroxy-2,3-di-p-tolyl-7,8-dihydropyrido[2,3-b]pyrazine-5(6H)-carboxylate A suspension of tert-butyl 2-thioxo-7,8-di-p-tolyl-3a,4-dihydro-[1,3]dioxolo[4$^1$,5$^1$:4,5]pyrido[2,3-b]pyrazine-5(9bH)-carboxylate (step 3)(14 g, 28.6 mmol) in toluene (400 ml) was treated with tributyltin hydride (16.65 g, 57.2 mmol) and heated at reflux for 2 h. A further portion of tributyltin hydride (10 g) was added and refluxing continued for 6 h. The reaction mixture was left stirring over night at room temperature. The reaction mixture was evaporated to dryness and the iso-hexane (250 ml) was added to the residue. The suspension was stirred for 30 minutes at room temperature and then filtered. The solid was washed with iso-hexane (3×50 ml) to afford the titled compound;
LC-MS: Rt 1.25 mins; MS m/z 432.5[M+H]+; Method 2minLowpH

Step 5: tert-Butyl-7-acetoxy-2,3-di-p-tolyl-7,8-dihydropyrido[2,3-b]pyrazine-5(6H)-carboxylate A solution of tert-butyl 7-hydroxy-2,3-di-p-tolyl-7,8-dihydropyrido[2,3-b]pyrazine-5(6H)-carboxylate (step 4) (500 mg, 1.159 mmol) in pyridine (3 ml) was treated slowly with acetic anhydride (0.219 ml, 2.317 mmol) and the resulting yellow solution was stirred at room temperature overnight. The reaction mixture was evaporated to dryness and purification of the crude material by chromatography on silica eluting with 0-60% EtOAc in iso-hexane afforded the titled compound;
LC-MS: Rt 1.21 mins; MS m/z 474.5 [M+H]+; Method 2minlowpH30

Step 6: tert-Butyl 7-(piperidin-1-yl)-2,3-di-p-tolyl-7,8-dihydropyrido[2,3-b]pyrazine-5(6H)-carboxylate tert-Butyl-7-acetoxy-2,3-di-p-tolyl-7,8-dihydropyrido[2,3-b]pyrazine-5(6H)-carboxylate (step 5)(210 mg, 0.443 mmol) was treated with piperidine (4380 µl, 44.3 mmol). The resulting pale yellow suspension was sonicated and then stirred at room temperature overnight. The resulting solution was added to water (100 ml) and extracted with DCM (×3), passing the organic extracts through a phase separating column. The filtrate was concentrated under reduced pressure and purification of the crude material by chromatography on silica eluting with 0-40% EtOAc in iso-hexane afforded the titled compound;
LCMS: Rt 1.05 mins MS m/z 499.7 [M+H]+; Method 2minLowpHv01

Step 7: 7-(Piperidin-1-yl)-2,3-di-p-tolyl-5,6,7,8-tetrahydropyrido[2,3-b]pyrazine A solution of tert-butyl 7-(piperidin-1-yl)-2,3-di-p-tolyl-7,8-dihydropyrido[2,3-b]pyrazine-5(6H)-carboxylate (step 6)

(90 mg, 0.180 mmol) in DCM (1 ml) was treated with TFA (0.501 mL, 6.50 mmol) and stirred at room temperature for 3 hours. The resulting mixture was diluted with DCM (3 ml) and washed with a saturated solution of sodium hydrogen carbonate. The organic portion was passed through a phase separating column and the solvent removed under reduced pressure to afford the titled compound;

LCMS: Rt 0.89 mins MS m/z 400.5 [M+H]+; Method 2minLowpHv01

Step 8: Ethyl 7-(7-(piperidin-1-yl)-2,3-di-p-tolyl-7,8-dihydropyrido[2,3-b]pyrazin-5(6H)-yl)heptanoate A solution of 7-(piperidin-1-yl)-2,3-di-p-tolyl-5,6,7,8-tetrahydropyrido[2,3-b]pyrazine (step 7) (62 mg, 0.156 mmol) in DCE (5 ml) under nitrogen, was treated with ethyl 7-oxoheptanoate (53.6 mg, 0.311 mmol) and stirred at room temperature for 15 minutes. Sodium triacetoxyborohydride (132 mg, 0.622 mmol) was added and the resulting mixture was stirred at room temperature overnight. The reaction mixture was diluted with DCM (20 ml) and washed with water. The organic portion was passed through a phase separating column and concentrated under reduced pressure. Purification of the crude material by chromatography on silica eluting with 0-100% EtOAc in iso-hexane afforded the titled compound;

LCMS: Rt 1.14 mins MS m/z 555.8 [M+H]+: Method 2minLowpHv01

Step 9: 7-(7-(Piperidin-1-yl)-2,3-di-p-tolyl-7,8-dihydropyrido[2,3-b]pyrazin-5(6H)-yl)heptanoic acid A solution of ethyl 7-(7-(piperidin-1-yl)-2,3-di-p-tolyl-7,8-dihydropyrido[2,3-b]pyrazin-5(6H)-yl)heptanoate (step 8) (39 mg, 0.070 mmol) in EtOH (1 ml) was treated with 2M NaOH (0.105 mL, 0.211 mmol) and stirred at room temperature overnight. The resulting mixture was added to water (30 ml) and the pH was adjusted to pH4 by addition of 10% aqueous citric acid solution. The aqueous portion was extracted with DCM (×3) and the combined extracts were passed through a phase separating column. The solvent was removed under reduced pressure to afford the titled compound;

LCMS: Rt 1.03 mins MS m/z 527.8 [M+H]+ Method 2minLowpHv01

EXAMPLE 15 rac-7-(8-Methoxy-8-methyl-2,3-di-p-tolyl-7,8-dihydropyrido[2,3-b]pyrazin-5(6H)-yl)heptanoic acid

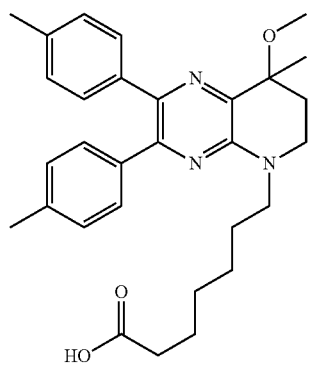

Step 1: Ethyl 7-(8-hydroxy-8-methyl-2,3-di-p-tolyl-7,8-dihydropyrido[3,2-b]pyrazin-5(6H)-yl)heptanoate compound with ethyl 7-(8-methoxy-8-methyl-2,3-di-p-tolyl-7,8-dihydropyrido[3,2-b]pyrazin-5(6H)-yl)heptanoate To a solution of 8-methyl-2,3-di-p-tolyl-5,6,7,8-tetrahydropyrido[2,3-b]pyrazin-8-ol (Intermediate G)(240 mg, 0.695 mmol) in DCE (10 ml) was added ethyl 7-oxoheptanoate (359 mg, 2.084 mmol) followed by sodium triacetoxyborohydride (442 mg, 2.084 mmol) and the resulting mixture was left to stir overnight at room temperature under an atmosphere of nitrogen. The reaction mixture was diluted with water and extracted with EtOAc (2×20 ml). The combined organic extracts were dried over MgSO$_4$, filtered and concentrated under reduced pressure to give a brown oil. The oil was purified by chromatography on silica eluting with EtOAc in iso-hexane to afford ethyl 7-(8-hydroxy-8-methyl-2,3-di-p-tolyl-7,8-dihydropyrido[3,2-b]pyrazin-5(6H)-yl) heptanoate (Intermediate 15.1). This compound was passed through a 5 g Isolute® SCX-2 SPE cartridge (primed with MeOH—20 ml) and washing with MeOH (30 ml). The product was eluted with 2M NH$_3$ in MeOH (20 ml). The basic eluent was concentrated under reduced pressure to afford a 1:2 mixture of ethyl 7-(8-hydroxy-8-methyl-2,3-di-p-tolyl-7,8-dihydropyrido[3,2-b]pyrazin-5(6H)-yl)heptanoate compound: ethyl 7-(8-methoxy-8-methyl-2,3-d i-p-tolyl-7,8-dihydropyrido[3,2-b]pyrazin-5(6H)-yl)heptanoate;

LCMS: Rt 1.53 mins; MS m/z 502.1 [M+H]$^+$, Method 2minLowpH (hydroxy product)

The material was used in the next step without further purification.

Step 2: rac-7-(8-Methoxy-8-methyl-2,3-di-p-tolyl-7,8-dihydropyrido[2,3-b]pyrazin-5(6H)-yl)heptanoic acid To a solution of the mixture of compounds from step 1 (120 mg) in Ethanol (5 ml) was added 2M NaOH (aq) (0.478 ml, 0.956 mmol) and the suspension was stirred under an atmosphere of nitrogen at room temperature overnight. The resulting suspension was treated ethyl acetate (20 ml) followed by 2M HCl (aq) (~3 ml) until pH 5-6 was reached. The resulting mixture was washed with water (~20 ml). The organic layer was separated and dried over MgSO$_4$, filtered and concentrated under reduced pressure to give a yellow oil/solid. Purification of the solid by chromatography on silica eluting with EtOAc in iso-hexane afforded the titled compound;

LCMS: Rt 1.44 mins; MS m/z 488.7 [M+H]$^+$, Method 2minLowpH.

EXAMPLE 15A (R or S)-7-(8-Methoxy-8-methyl-2,3-di-p-tolyl-7,8-dihydropyrido[2,3-b]pyrazin-5(6H)-yl)heptanoic acid and

EXAMPLE 15B (R or S)-7-(8-Methoxy-8-methyl-2,3-di-p-tolyl-7,8-dihydropyrido[2,3-b]pyrazin-5(6H)-yl)heptanoic acid

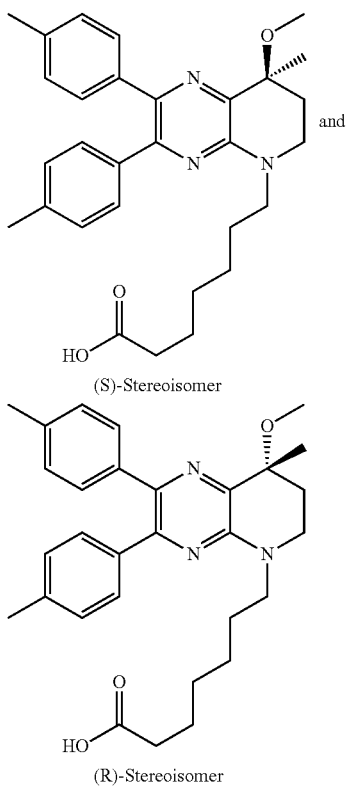

rac-7-(8-Methoxy-8-methyl-2,3-di-p-tolyl-7,8-dihydropyrido[2,3-b]pyrazin-5(6H)-yl)heptanoic acid (Example 15) was separated under the following conditions to afford the individual enantiomers:
Column: Chiralpak AD-H, 250×10 mm, 5 um @ 35 deg C.
Mobile phase: 20% Isopropanol/80% CO2
Flow: 10 ml/min
Detection: UV @ 220 nm
Instrument: Berger Minigram SFC1

EXAMPLE 15A

First eluted peak: (R)-7-(8-Methoxy-8-methyl-2,3-di-p-tolyl-7,8-dihydropyrido[2,3-b]pyrazin-5(6H)-yl) heptanoic acid or (S)-7-(8-Methoxy-8-methyl-2,3-di-p-tolyl-7,8-dihydropyrido[2,3-b]pyrazin-5(6H)-yl) heptanoic acid SFC Retention Time=6.35 mins
LCMS: Rt 1.62 mins; MS m/z 488.3 [M+H]$^+$, Method 2minLowpHv01

EXAMPLE 15B

Second eluted peak: (R)-7-(8-Methoxy-8-methyl-2,3-di-p-tolyl-7,8-dihydropyrido[2,3-b]pyrazin-5(6H)-yl)heptanoic acid or (S)-7-(8-Methoxy-8-methyl-2,3-di-p-tolyl-7,8-dihydropyrido[2,3-b]pyrazin-5(6H)-yl) heptanoic acid SFC Retention Time=9.01 mins
LCMS: Rt 1.62 mins; MS m/z 488.3 [M+H]$^+$, Method 2minLowpHv01

EXAMPLE 16

7-(8-Hydroxy-8-methyl-2,3-di-p-tolyl-7,8-dihydropyrido[2,3-b]pyrazin-5(6H)-yl)heptanoic acid

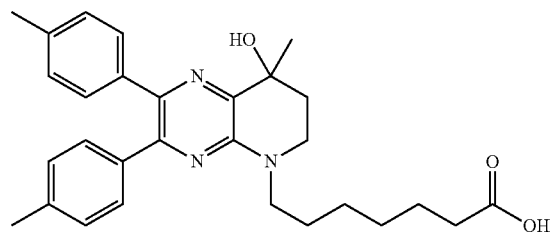 [SMILES: Cc1ccc(-c2nc3c(nc2-c2ccc(C)cc2)C(C)(O)CCN3CCCCCCC(=O)O)cc1]

Step 1: Ethyl 7-(8-hydroxy-8-methyl-2,3-di-p-tolyl-7,8-dihydropyrido[2,3-b]pyrazin-5(6H)-yl)heptanoate

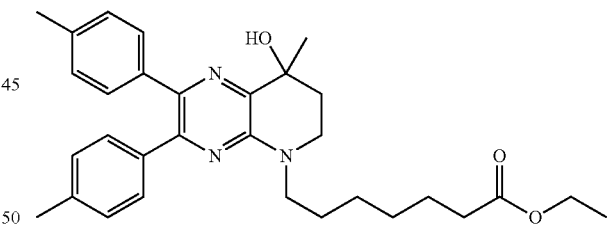

To a solution of 8-methyl-2,3-di-p-tolyl-5,6,7,8-tetrahydropyrido[2,3-b]pyrazin-8-ol (Intermediate G) (290 mg, 0.840 mmol) in DCE (10 ml) was added ethyl 7-oxoheptanoate (434 mg, 2.52 mmol) followed by sodium triacetoxyborohydride (534 mg, 2.52 mmol). The reaction mixture was left to stir overnight at room temperature under an atmosphere of nitrogen and then water was added (20 ml). The product was extracted with EtOAc (2×20 ml) and the combined organic extracts were dried over MgSO4, filtered and concentrated under reduced pressure to give a crude brown oil. Purification of the crude product by C18 reverse phase chromatography eluting with water/acetonitrile afforded the title compound;

LCMS: Rt 1.67 mins; MS m/z 502.1 [M+H]$^+$; Method 2minLowpHv01

Step 2: 7-(8-Hydroxy-8-methyl-2,3-di-p-tolyl-7,8-dihydropyrido[2,3-b]pyrazin-5(6H)-yl)heptanoic acid To a solution of ethyl 7-(8-hydroxy-8-methyl-2,3-di-p-tolyl-7,8-dihydropyrido[3,2-b]pyrazin-5(6H)-yl)heptanoate (step 1) (10 mg, 0.020 mmol) in EtOH (1 ml) was added 2M NaOH (aq) (0.040 ml, 0.080 mmol). The reaction mixture was stirred at RT overnight under an atmosphere of nitrogen. A further portion of 2M NaOH (aq) (0.040 ml, 0.080 mmol) was added and stirring continued overnight. The resulting mixture was treated with 2M HCl (aq) to adjust the pH to pH5. The organic solvent was removed under reduced pressure and the mixture was diluted with water (10 ml) and extracted with ethyl acetate (2×10 ml). The combined extracts were dried over MgSO4, filtered and concentrated under reduced pressure. The crude product was purified by chromatography on silica eluting with iso-hexane/EtOAc to afford the titled compound;

LCMS: Rt 1.51 mins; MS m/z 475.5 [M+H]+, Method 2minLowpHv01.

EXAMPLE 17 rac-7-(2,3-Di-p-tolyl-7,8-dihydropyrido[2,3-b]pyrazin-5(6H)-yl)-3-hydroxyheptanoic acid

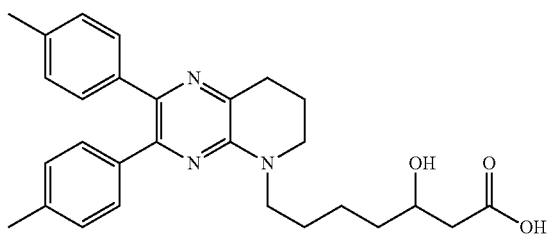 [SMILES: Cc1ccc(-c2nc3c(nc2-c2ccc(C)cc2)N(CCCCC(O)CC(=O)O)CCC3)cc1]

Step 1: 3-Bromo-5-(4-(2,3-di-p-tolyl-7,8-dihydropyrido[2,3-b]pyrazin-5(6H)-yl)butyl)-4,5-dihydroisoxazole A mixture comprising 5-(hex-5-enyl)-2,3-di-p-tolyl-5,6,7,8-tetrahydropyrido[2,3-b]pyrazine (Intermediate H) (3.98 g, 10 mmol) and potassium hydrogen carbonate (5.01 g, 50.0 mmol) in EtOAc (50 ml) was treated dropwise with dibromoformaldoxime (6.08 g, 30.0 mmol) in EtOAc (50 ml) over 2 hours. The mixture was stirred at room temperature overnight and then filtered. The filtrate was washed with 1H HCl, water, brine and dried by passing through a phase separator. The solvent was removed under reduced pressure to afford the titled compound which was used without further purification.

Step 2: 5-(4-(2,3-Di-p-tolyl-7,8-dihydropyrido[2,3-b]pyrazin-5(6H)-yl)butyl)-3-methoxy-4,5-dihydroisoxazole A solution of 3-bromo-5-(4-(2,3-di-p-tolyl-7,8-dihydropyrido[2,3-b]pyrazin-5(6H)-yl)butyl)-4,5-dihydroisoxazole (step 1) (5195 mg, 10 mmol) in MeOH (5 ml) was treated with NaOMe (10 ml of 30% solution by weight) and heated at reflux for 2 hours. After cooling to RT, the reaction was quenched with water (100 ml) and the aqueous portion was extracted with EtOAc. The combined organic extracts were washed with brine, dried by passing through a phase separator and were concentrated under reduced pressure. The crude product was purified by chromatography on silica eluting with 0-60% EtOAc in iso-hexane to afford the titled compound as an orange oil;

LCMS: Rt 1.5 mins; MS m/z 471.4 [M+H]+; Method 2minLowpHv01

Step 3: Methyl 7-(2,3-di-p-tolyl-7,8-dihydropyrido[2,3-b]pyrazin-5(6H)-yl)-3-hydroxyheptanoate A solution of 5-(4-(2,3-di-p-tolyl-7,8-dihydropyrido[2,3-b]pyrazin-5(6H)-yl)butyl)-3-methoxy-4,5-dihydroisoxazole (step 2) (94 mg, 0.2 mmol) in MeOH (3 ml) and water (0.2 ml) was treated with boric acid (37.1 mg, 0.600 mmol) followed by Mo(CO)6 (37.0 mg, 0.140 mmol). The resulting mixture was heated at overnight. After cooling to RT, the mixture was concentrated under reduced pressure and diluted with DCM. The organic portion was washed with water and dried by passing through a phase separating column. The solvent was removed under reduced pressure and purification of the crude product by chromatography on silica eluting with 0-60% EtOAc in iso-hexane afforded the titled compound;

LCMS: Rt 1.43 mins; MS m/z 474.7 [M+H]+; Method 2minLowpHv01

Step 4: rac-7-(2,3-Di-p-tolyl-7,8-dihydropyrido[2,3-b]pyrazin-5(6H)-yl)-3-hydroxyheptanoic acid A solution of methyl 7-(2,3-di-p-tolyl-7,8-dihydropyrido[2,3-b]pyrazin-5(6H)-yl)-3-hydroxy heptanoate (step 3)(43 mg, 0.091 mmol) in EtOH (908 μL) was treated with sodium hydroxide (136 μL, 0.272 mmol) and stirred at room temperature for 1 hour. The resulting mixture was diluted with water (2 ml) and acidified to pH 2. The mixture was extracted with EtOAc and the combined organic extracts were washed with brine, dried by passing through a phase separator and concentrated under reduced pressure to give an oil. The oil was purified by flash column chromatography using the ISCO combiflash Rf, eluting with 0-50% EtOAc (containing 10% MeOH) in iso-hexane on a 4 g silca cartridge. The product fractions were combined and the solvent removed under reduced pressure to yield the titled compound as a colourless oil;

LCMS: Rt 1.32 mins; MS m/z 460.3 [M+H]+; Method 2minLowpHv01

EXAMPLE 17A (R or S)-7-(2,3-d i-p-tolyl-7,8-dihydropyrido[2,3-b]pyrazin-5(6H)-yl)-3-hydroxyheptanoic acid and

EXAMPLE 17B (R or S)-7-(2,3-di-p-tolyl-7,8-dihydropyrido[2,3-b]pyrazin-5(6H)-yl)-3-hydroxyheptanoic acid

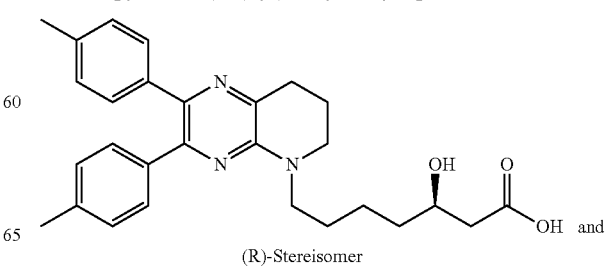

(R)-Stereisomer and

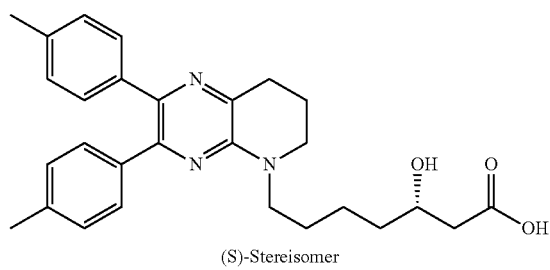

(S)-Stereisomer rac-7-(2,3-Di-p-tolyl-7,8-dihydropyrido[2,3-b]pyrazin-5(6H)-yl)-3-hydroxyheptanoic acid (Example 17) was separated under the following conditions to afford the individual enantiomers:

Column: Chiralpak OJ-H, 250×10 mm, 5 um @ 35 deg C.
Mobile phase: 15% MeOH+v/v 0.1% TFA/75% $CO_2$
Flow: 10 ml/min
Detection: UV @ 220 nm
Instrument: Berger Minigram SFC1

EXAMPLE 17A

First Eluted Peak: (R)-7-(2,3-Di-p-tolyl-7,8-dihydropyrido[2,3-b]pyrazin-5(6H)-yl)-3-hydroxyheptanoic acid or (S)-7-(2,3-Di-p-tolyl-7,8-dihydropyrido[2,3-b]pyrazin-5(6H)-yl)-3-hydroxyheptanoic acid SFC Retention Time=9.18 mins
LCMS: Rt 1.33 mins; MS m/z 460.6 [M+H]+; Method 2minLowpHv01

EXAMPLE 17B

Second Eluted Peak: (R)-7-(2,3-Di-p-tolyl-7,8-dihydropyrido[2,3-b]pyrazin-5(6H)-yl)-3-hydroxyheptanoic acid or (S)-7-(2,3-Di-p-tolyl-7,8-dihydropyrido[2,3-b]pyrazin-5(6H)-yl)-3-hydroxyheptanoic acid SFC Retention Time=11.15 mins
LCMS: Rt 1.36 mins; MS m/z 460.7 [M+H]+; Method 2minLowpHv01

Preparation of Intermediates

Intermediate A

Ethyl 6-oxohexanoate

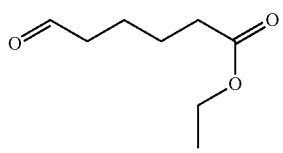

KBr (0.111 g, 0.936 mmol) in water (30 ml) was treated with sodium bicarbonate (4.72 g, 56.2 mmol). The solution was cooled (ice-bath) and treated with a solution of (2,2,6,6-tetramethyl piperidin-1-yl)oxidanyl (0.029 g, 0.187 mmol) in DCM (30 ml) followed by sodium hypochlorite (1.387 ml, 22.47 mmol) and ethyl 6-hydroxyhexaonate (3 g, 18.73 mmol). The reaction mixture was partitioned between EtOAc and water and the organic portion was separated, dried ($MgSO_4$) and concentrated under reduced pressure to afford the titled compound Intermediate B 2,3-Di-p-tolyl-5,6,7,8-tetrahydropyrido[2,3-b]pyrazine

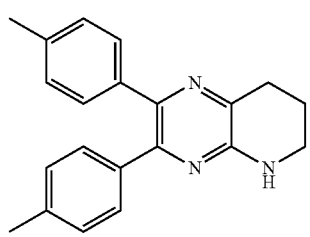 [SMILES: Cc1ccc(-c2nc3c(nc2-c2ccc(C)cc2)NCCC3)cc1]

Step 1: 2,3-Di-p-tolylpyrido[2,3-b]pyrazine

A solution of 1,2-di-p-tolylethane-1,2-dione (commercially available)(175 g, 733 mmol) and pyridine-2,3-diamine (80 g, 733 mmol) in EtOH (1609 ml) and AcOH (179 ml) was heated to reflux (bath at 85° C.) for 1.5 h. The mixture was allowed to cool and concentrated in vacuo. The crude material was dissolved in DCM (500 ml) and filtered through silica to remove baseline impurities. The silica was washed with EtOAc (2 L). The combined filtrate layers were concentrated in vacuo to give a brown solid. The material was triturated in 1:1 TBME/heptane (300 ml). The solid was removed by filtration and washed with 1:1 TBME/heptane (200 ml) before drying at RT over 2 days to afford the titled compound as an AcOH salt (1 eq).

HPLC (Agilent 1200), Rt 5.37 min, Method J.

Step 2: 2,3-Di-p-tolyl-5,6,7,8-tetrahydropyrido[2,3-b]pyrazine

A solution of 2,3-di-p-tolylpyrido[2,3-b]pyrazine (step 1)(181 g, 487 mmol) in EtOH/THF (1:2, 2100 ml) was treated with 10% palladium on carbon (30 g, 28.8 mmol) and the reaction mixture was placed under 0.1 bar of hydrogen at RT. After 2 days and 4 days respectively, additional batches of 10% palladium on carbon (10 g, 9.6 mmol, twice) were added along with $Et_3N$ (85 ml, 706 mmol, twice). After 7 days in total, the reaction mixture was filtered through Hyflo (filter material) and washed through with THF (2.5 L in portions). The filtrate was concentrated in vacuo to give a green/yellow solid. The solid was triturated with 1:1 TBME/heptane (500 ml) and filtered. The solid was washed with 1:1 TBME/heptane (200 ml) to give a pale yellow solid which was dried overnight to afford the titled compound;

HPLC (Agilent 1200), Rt 4.73 min, Method J.

Intermediate C

3-Phenyl-2-p-tolyl-5,6,7,8-tetrahydropyrido[2,3-b]pyrazine

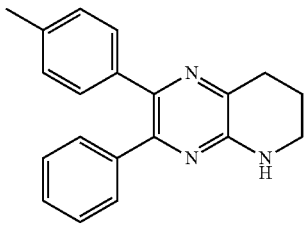 [SMILES: Cc1ccc(-c2nc3c(nc2-c2ccccc2)NCCC3)cc1]

Step 1: Pyrido[3,2-b]pyrazine-2,3(1H,4H)-dione

A stirred suspension of 2,3-diaminopyridine (75 g, 687 mmol) in diethyl oxalate (291 ml, 2131 mmol) under $N_2$ was heated to 120° C. After 1 h, the ethanol was distilled off the reaction mixture and the temperature was elevated to 160° C. for a further 2 hours. The reaction mixture was allowed to cool to RT and diluted with diethyl ether (200 ml). The resulting suspension was stirred for 1 hour and the solid was isolated by filtration and dried in a vacuum oven. The solid was suspended in ethanol (500 ml) and sonicated for 1 hour. The suspension was filtered and dried (vacuum oven overnight) to afford the titled compound;

LCMS: Rt 0.29 mins MS m/z 164 [M+H]$^+$; Method 2minLC_v003

Step 2: 2,3-Dichloropyrido[3,2-b]pyrazine $POCl_3$ (57.1 ml, 613 mmol) was added to pyrido[3,2-b]pyrazine-2,3(1H,4H)-dione (step 1) (20 g, 123 mmol) and the suspension was heated at 110° C. for 8 hours. After cooling to RT, the reaction mixture was added dropwise to stirred water at RT, cooling with ice, if necessary. The aqueous phase was basified by addition of a cooled solution of sat. $NaHCO_3$ (~4 L). The aqueous portion was extracted with EtOAc (2×2.5 L) and the combined organic extracts were dried over $MgSO_4$ and concentrated in vacuo to afford a solid. The crude product was purified by chromatography on silica eluting with 5%-70% EtOAc in iso-hexane to afford the titled compound as a yellow solid;

LCMS: Rt 0.53 mins MS m/z 200 [M+H]$^+$; Method 2minLC_30_v003

Step 3: 2-Chloro-3-phenylpyrido[2,3-b]pyrazine 2,3-Dichloropyrido[2,3-b]pyrazine (step 2) (500 mg, 2.5 mmol) in dry dioxane (10 ml), under nitrogen was treated with phenylboronic acid (305 mg, 2.5 mmol), potassium carbonate (691 mg, 5 mmol) in water (0.5 ml) and tetrakis(triphenylphosphine)palladium(0) (144 mg, 0.125 mmol). The resulting mixture was heated using microwave radiation at 100° C. for 1 hour. After cooling to RT, the mixture was diluted with water (100 ml) and extracted with DCM (×3). The combined organic extracts were washed with brine, dried over $MgSO_4$ and filtered. The solvent was removed in vacuo and the crude product was purified by chromatography on silica eluting with 0-30% EtOAc in iso-hexane to afford the titled compound as a solid;

LCMS: Rt 1.03 mins MS m/z 242/244 [M+H]$^+$; Method 2minLC_v003

Step 4: 3-Phenyl-2-p-tolylpyrido[2,3-b]pyrazine

2-Chloro-3-phenylpyrido[2,3-b]pyrazine (step 3) (175 mg, 0.724 mmol) in dry dioxane (4 ml) under nitrogen was treated with p-tolylboronic acid (108 mg, 0.797 mmol), potassium carbonate (200 mg, 1.448 mmol) in water (0.5 ml) and tetrakis(triphenylphosphine)palladium(0) (41.8 mg, 0.036 mmol). The resulting mixture was heated using microwave radiation at 150° C. for 1 hour. After cooling to RT, the mixture was diluted with water (100 ml) and extracted with DCM (×3). The combined organic extracts were washed with brine, dried over $MgSO_4$ and filtered. The solvent was removed in vacuo and the crude product was purified by chromatography on silica eluting with 0-30% EtOAc in iso-hexane to afford the titled compound as a yellow solid;

LCMS; Rt 1.19 mins MS m/z 298 [M+H]+; Method 2minLC_v003

Step 5: 3-Phenyl-2-p-tolyl-5,6,7,8-tetrahydropyrido[2,3-b]pyrazine

3-Phenyl-2-p-tolylpyrido[2,3-b]pyrazine (step 4) (179 mg, 0.602 mmol) under nitrogen in dry MeOH (5 ml) was treated with ammonium formate (190 mg, 3.01 mmol) and 10% palladium on carbon (64.1 mg, 0.060 mmol). The resulting mixture was heated at reflux for 16 hours. After cooling to RT, the mixture was filtered through Celite® (filter material) and the catalyst was washed with MeOH and MeOH/DCM (1:1). The filtrate was concentrated in vacuo and dissolved in DCM (50 ml). The solution was washed with water (×2) and brine (×1). The resulting organic portion was passed through a phase separating column and concentrated in vacuo to afford the titled compound;

LCMS; Rt 1.08 mins MS m/z 303 [M+H]$^+$ Method 2minLC_v003

Intermediate CA

7-Methyl-2-phenyl-3-(p-tolyl)-5,6,7,8-tetrahydropyrido[2,3-b]pyrazine

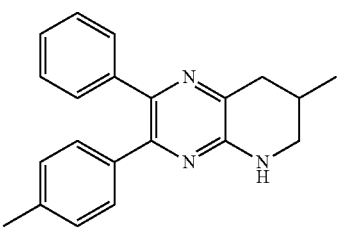

The titled compound was prepared analogously to Intermediate C by replacing 2,3-diaminopyridine (step 1) with 5-methylpyridine-2,3-diamine (commercially available) and by using the appropriate boronic acids in step 3 and 4;
LCMS; Rt 1.73 mins MS m/z 316 [M+H]+ Method I Intermediate CB 6-Methyl-2-phenyl-3-(p-tolyl)-5,6,7,8-tetrahydropyrido[2,3-b]pyrazine

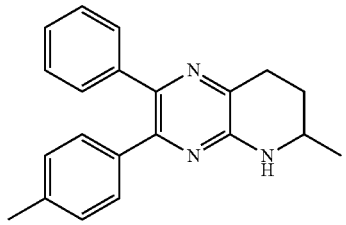

The titled compound was prepared analogously to Intermediate C by replacing 2,3-diaminopyridine (step 1) with 6-methylpyridine-2,3-diamine (commercially available) and by using the appropriate boronic acids in step 3 and 4;
LCMS; Rt 1.766 mins MS m/z 316 [M+H]+ Method G Intermediate CC 2,3-Bis(2,4-difluorophenyl)-5,6,7,8-tetrahydropyrido[2,3-b]pyrazine

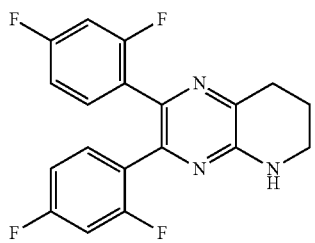 [SMILES: Fc1ccc(-c2nc3c(nc2-c2ccc(F)cc2F)NCCC3)c(F)c1]

The titled compound was prepared analogously to Intermediate C by using the appropriate boronic acids in step 3 and 4;
$^1$H NMR (400 MHz, MeOD-d$_4$) δ 7.43-7.23 (m, 2 H), 7.02-6.89 (m, 2 H), 6.87-6.78 (m, 2H), 3.55-3.44 (m, 2 H), 3.05-2.92 (m, 2 H), 2.15-2.05 (m, 2 H)

Intermediates CD-CI

The following intermediates were prepared analogously to Intermediate C by using the appropriate boronic acids in step 3 and 4;

| Int. | Structure | Name | Data |
|---|---|---|---|
| CD | 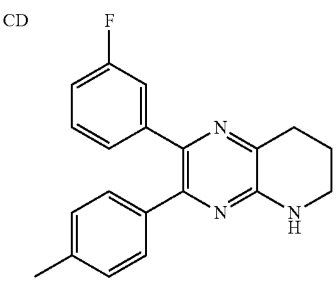 | 2-(3-Fluorophenyl)-3-(p-tolyl)-5,6,7,8-tetrahydropyrido[2,3-b]pyrazine | LCMS; Rt 1.68 mins MS m/z 320.1 [M + H]+ Method I |
| CE | 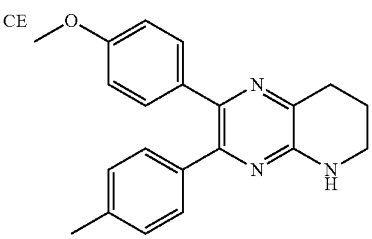 | 2-(4-Methoxyphenyl)-3-(p-tolyl)-5,6,7,8-tetrahydropyrido[2,3-b]pyrazine | |
| CF | 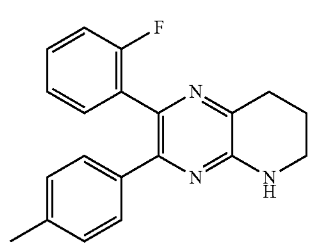 | 2-(2-Fluorophenyl)-3-(p-tolyl)-5,6,7,8-tetrahydropyrido[2,3-b]pyrazine | LCMS; Rt 1.607 mins MS m/z 319.9 [M + H]+ Method G |

-continued

| Int. | Structure | Name | Data |
|---|---|---|---|
| CG | 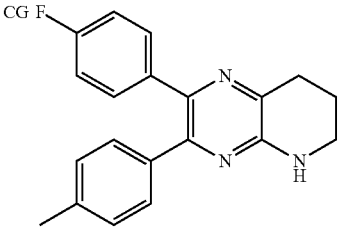 | 2-(4-Fluorophenyl)-3-(p-tolyl)-5,6,7,8-tetrahydropyrido[2,3-b]pyrazine | LCMS; Rt 1.691 mins MS m/z 319.9 [M + H]+ Method G |
| CH | 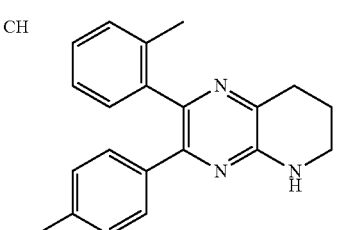 | 2-(o-Tolyl)-3-(p-tolyl)-5,6,7,8-tetrahydropyrido[2,3-b]pyrazine | LCMS; Rt 1.629 mins MS m/z 315.9 [M + H]+ Method G |
| CI | 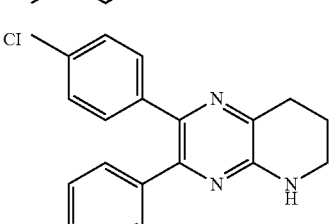 | 3-(o-Tolyl)-2-(p-tolyl)-5,6,7,8-tetrahydropyrido[2,3-b]pyrazine | LCMS; Rt 1.69 mins MS m/z 316.2 [M + H]+ Method I |

Intermediate D

7-Ethyl-2,3-di-p-tolyl-5,6,7,8-tetrahydropyrido[2,3-b]pyrazine

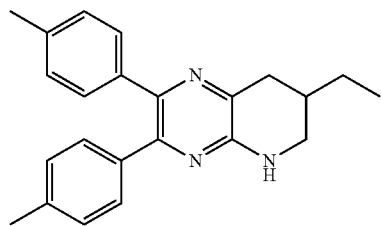 [SMILES: CCC1CNc2nc(-c3ccc(C)cc3)c(-c3ccc(C)cc3)nc2C1]

Step 1: 7-Chloro-2,3-di-p-tolylpyrido[2,3-b]pyrazine

A mixture comprising 5-chloropyridine-2,3-diamine (1 g, 6.9 mmol) and 1,2-di-p-tolylethane-1,2-dione (1.6 g, 6.9 mmol) in EtOH (15 ml) under argon was stirred at 70° C. overnight. The mixture was heated for a further 8 hours and the solvent was removed under reduced pressure. The resulting crude material was purified by chromatography on silica eluting with 5% EtOAc in hexane to afford the titled compound;
LCMS; Rt 1.98 mins MS m/z 346 [M+H]+ Method I Step 2: 7-Ethyl-2,3-di-p-tolylpyrido[2,3-b]pyrazine A mixture comprising 7-chloro-2,3-di-p-tolylpyrido[2,3-b]pyrazine (step 1) (2.5 g, 7.24 mmol), ethyl boronic acid (0.748 g, 10.14 mmol) and K$_2$CO$_3$ (2.9 g, 21.73 mmol) was degassed with argon and treated with Pd(PPh$_3$)$_4$(0.418 g, 0.362 mmol). The resulting mixture was flushed with argon and heated at 100° C. for 12 h and heating continued overnight. The reaction mixture was diluted with water and extracted with ethyl acetate. The organic layer was dried over anhydrous sodium sulphate and concentrated under vacuum. Purification of the crude product by chromatography on silica eluting with 10% EtOAc in hexane afforded the titled compound;
LCMS; Rt 1.95 mins MS m/z 340 [M+H]+ Method I Step 3: 7-Ethyl-2,3-di-p-tolyl-5,6,7,8-tetrahydropyrido[2,3-b]pyrazine 7-Ethyl-2,3-di-p-tolylpyrido[2,3-b]pyrazine (2 g, 5.89 mmol) in EtOH (5 ml) was treated with Pd/C (0.2 g) and placed under an atmosphere of hydrogen. After stirring overnight the mixture was treated with a catalytic quantity of NaHCO$_3$ and stirring continued under hydrogen overnight. The mixture was passed through Celite® (filter material) and the solvent was removed under reduced pressure. Purification of the crude product by chromatography on silica eluting with 5% EtOAc in hexane afforded the titled compound;
LCMS; Rt 1.925 mins MS m/z 344 [M+H]+ Method G Intermediate DA 6-Ethyl-2,3-di-p-tolyl-5,6,7,8-tetrahydropyrido[2,3-b]pyrazine

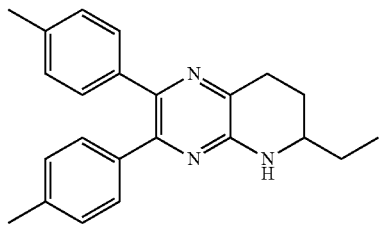 [SMILES: CCC1CCc2nc(-c3ccc(C)cc3)c(-c3ccc(C)cc3)nc2N1]

The titled compound was prepared analogously to Intermediate D by replacing 5-chloropyridine-2,3-diamine with 6-chloropyridine-2,3-diamine;

LCMS; Rt 1.937 mins MS m/z 343.9 [M+H]+ Method G

Intermediate EA and EB 7-(2-Bromo-3-chloro-7,8-dihydropyrido[2,3-b]pyrazin-5(6H)-yl)heptan-1-ol (Intermediate EA) and Ethyl 7-(2-bromo-3-chloro-7,8-dihydropyrido[2,3-b]pyrazin-5(6H)-yl)heptanoate (Intermediate EB)

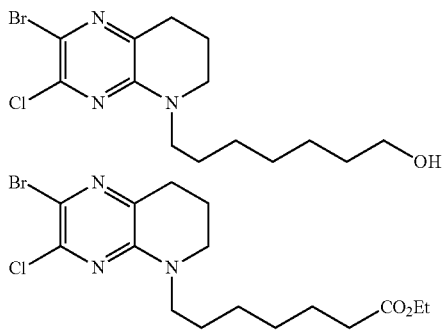

Step 1: Ethyl 7-(2-bromo-3-chloro-6-oxo-7,8-dihydropyrido[2,3-b]pyrazin-5(6H)-yl)heptanoate A solution of 2-bromo-3-chloro-7,8-dihydro-5H-pyrido[2,3-b]pyrazin-6-one (prepared according to the preparation procedures disclosed in PCT patent application PCT/EP2011/062028, Intermediate J) (3.9 g, 14.86 mmol) and ethyl 7-bromoheptanoate (7.05 g, 29.7 mmol) in DMF (75 ml) under a nitrogen atmosphere was treated with potassium carbonate (10.27 g, 74.3 mmol) and the resulting solution was stirred at room temperature for 4 days. The mixture was diluted with water and extracted with EtOAc (×2). The extracts were washed with water and brine, dried (MgSO$_4$) and evaporated under vacuum. The crude product was purified by chromatography on silica eluting with 0-60% EtOAc in iso-hexane to afford the titled compound;

LCMS: Rt 3.71 mins; [M+H]$^+$418/420, Method 10minLC_v003.

Step 2: 7-(2-Bromo-3-chloro-7,8-dihydropyrido[2,3-b]pyrazin-5(6H)-yl)heptan-1-ol and Ethyl 7-(2-bromo-3-chloro-7,8-dihydropyrido[2,3-b]pyrazin-5(6H)-yl)heptanoate A cooled (0° C.) solution of ethyl 7-(2-bromo-3-chloro-6-oxo-7,8-dihydropyrido[2,3-b]pyrazin-5(6H)-yl)heptanoate (step 1)(1.0 g, 2.388 mmol) in THF (10 ml) under a nitrogen atmosphere was treated with borane-methyl sulfide complex over 30 mins. The resulting mixture was stirred at 0° C. for 2 h 30 minutes and stored in a fridge overnight. The mixture was cooled in an ice bath and cautiously treated with MeOH (5 ml). The yellow solution was stirred at 0° C. for 1 hour and concentrated under reduced pressure. The crude material was purified by chromatography on silica eluting with 0-100% EtOAc in iso-hexane to afford ethyl 7-(2-bromo-3-chloro-7,8-dihydropyrido[2,3-b]pyrazin-5(6H)-yl)heptanoate LCMS Rt 1.10 mins; MS m/z 362/364 [M+H]$^+$, Method 2minLC_v003 and 7-(2-bromo-3-chloro-7,8-dihydropyrido[2,3-b]pyrazin-5(6H)-yl)heptan-1-ol;

LCMS: Rt 1.46 mins; MS m/z 404/406 [M+H]$^+$, Method 2minLC_v003

Intermediate F tert-Butyl 8-bromo-2,3-di-p-tolyl-7,8-dihydropyrido[2,3-b]pyrazine-5(6H)-carboxylate

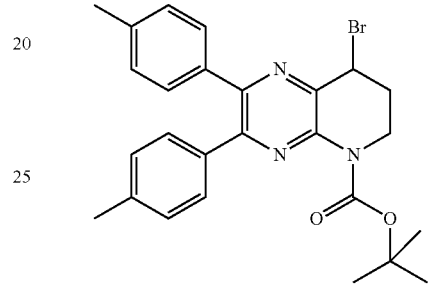

The titled compound was prepared from 2,3-di-p-tolyl-5,6,7,8-tetrahydropyrido[2,3-b]pyrazine (Intermediate B) analogously to tert-butyl 8-bromo-2,3-diphenyl-7,8-dihydropyrido[2,3-b]pyrazine-5(6H)-carboxylate (prepared according to the preparation procedures disclosed in PCT patent application PCT/EP2011/062028, Intermediate H);

Intermediate FA 2,3-Di-p-tolyl-5,6,7,8-tetrahydropyrido[2,3-b]pyrazin-8-yl acetate

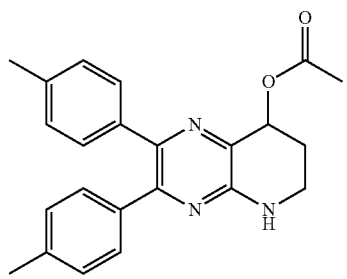 [SMILES: CC(=O)OC1CCNc2nc(-c3ccc(C)cc3)c(-c3ccc(C)cc3)nc21]

The titled compound was prepared from tert-butyl 8-bromo-2,3-di-p-tolyl-7,8-dihydropyrido[2,3-b]pyrazine-5(6H)-carboxylate (Intermediate F) analogously to 2,3-diphenyl-5,6,7,8-tetrahydropyrido[2,3-b]pyrazin-8-yl acetate (prepared according to the preparation procedures disclosed in PCT patent application PCT/EP2011/062028, Intermediate HA);

LCMS Rt 1.21 mins; MS m/z 374.3 [M+H]$^+$, Method 2minLowpH.

Intermediate G

8-Methyl-2,3-di-p-tolyl-5,6,7,8-tetrahydropyrido[2,3-b]pyrazin-8-ol

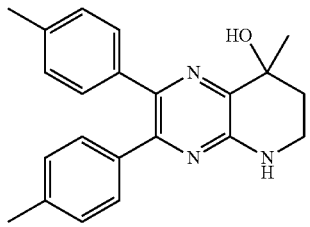 [SMILES: Cc1ccc(-c2nc3c(nc2-c2ccc(C)cc2)C(C)(O)CCN3)cc1]

Step 1: tert-Butyl 8-hydroxy-2,3-di-p-tolyl-7,8-dihydropyrido[2,3-b]pyrazine-5(6H)-carboxylate To a solution of tert-butyl 8-bromo-2,3-di-p-tolyl-7,8-dihydropyrido[2,3-b]pyrazine-5(6H)-carboxylate (Intermediate F) (5.95 g, 12.03 mmol) in chloroform (360 ml) was added silver acetate (5.02 g, 30.1 mmol). The reaction mixture was stirred at room temperature for 1 hour under an atmosphere of nitrogen and then filtered through Celite® (filter material) washing through with DCM. The filtrate was concentrated under reduced pressure and purification by chromatography on silica eluting with EtOAc in iso-hexane afforded the titled compound and tert-butyl 8-acetoxy-2,3-di-p-tolyl-7,8-dihydropyrido[2,3-b]pyrazine-5(6H)-carboxylate as a by-product;

LCMS: Rt 1.29 mins; MS m/z 432.3 [M+H]$^+$, Method 2minLowpH.

Step 2: tert-Butyl 8-oxo-2,3-di-p-tolyl-7,8-dihydropyrido[2,3-b]pyrazine-5(6H)-carboxylate To a stirred solution of oxalyl chloride (0.085 ml, 0.973 mmol) in DCM (20 ml) at −78° C. under nitrogen was added a dropwise solution of DMSO (0.168 ml, 2.373 mmol) in DCM (10 ml). After stirring at −78° C. for two hours, a solution of tert-butyl 8-hydroxy-2,3-di-p-tolyl-7,8-dihydropyrido[2,3-b]pyrazine-5(6H)-carboxylate (step 1) (200 mg, 0.463 mmol) in DCM (5 ml) was added dropwise and the mixture was left to stir for 15 minutes at −78° C. under an atmosphere of nitrogen. Triethylamine (0.331 ml, 2.373 mmol) was added and after 5 minutes the reaction mixture allowed to warm to 18° C. under an atmosphere of nitrogen overnight. The reaction mixture was diluted with DCM (30 ml) and was sequentially washed with 2M NaOH (30 ml), water (30 ml) and brine (30 ml). The organic layer was separated and dried using a hydrophobic frit and the solvent evaporated to afford the titled compound as a yellow solid;

LCMS: Rt 1.30 mins; MS m/z 430.4 [M+H]$^+$, Method 2minLowpH.

Step 3: tert-Butyl 8-hydroxy-8-methyl-2,3-di-p-tolyl-7,8-dihydropyrido[2,3-b]pyrazine-5(6H)-carboxylate To a solution of tert-butyl 8-oxo-2,3-di-p-tolyl-7,8-dihydropyrido[2,3-b]pyrazine-5(6H)-carboxylate (step 2) (591 mg, 1.376 mmol) in THF (20 ml) at 0° C. was added 1M MeMgBr in THF (5.50 ml, 5.50 mmol). The mixture was left to stir at 0° C. for 30 mins under an atmosphere of nitrogen and then warmed to room temperature. After 1.5 hours, the reaction mixture was poured into a saturated ammonium chloride solution (30 ml). The product was extracted with ethyl acetate (2×30 ml) and the combined organic extracts were dried over MgSO$_4$, filtered and concentrated under reduced pressure to give the crude product as an oil. Purification of the oil by chromatography on silica eluting with EtOAc in iso-hexane afforded the titled compound;

LCMS: Rt 1.34 mins; MS m/z 446.6 [M+H]$^+$, Method 2minLowpH.

Step 4: 8-Methyl-2,3-di-p-tolyl-5,6,7,8-tetrahydropyrido[2,3-b]pyrazin-8-ol A solution of tert-butyl 8-hydroxy-8-methyl-2,3-di-p-tolyl-7,8-dihydropyrido[2,3-b]pyrazine-5(6H)-carboxylate (step 3) (310 mg, 0.696 mmol) in 4M HCl in dioxane (2 ml, 8.00 mmol) was stirred at room temperature for 30 mins. The reaction mixture was concentrated under reduced pressure and the residue partitioned between saturated aqueous sodium bicarbonate and DCM. The organic portion was separated and the aqueous portion extracted with DCM (30 ml). The combined organic layers concentrated under reduced pressure to afford the titled compound;

LCMS: Rt 1.14 mins; MS m/z 346.6 [M+H]$^+$, Method 2minLowpH.

Intermediate H

5-(Hex-5-enyl)-2,3-dip-tolyl-5,6,7,8-tetrahydropyrido[2,3-b]pyrazine

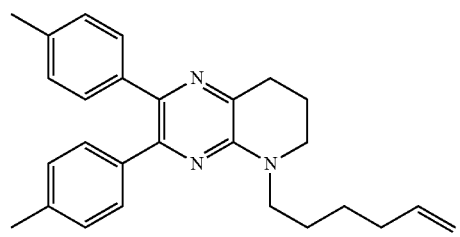 [SMILES: C=CCCCCN1CCCc2nc(-c3ccc(C)cc3)c(-c3ccc(C)cc3)nc21]

Step 1: Hex-5-enal

Anhydrous dichloromethane (20 ml) was cooled in a dry-ice/acetone bath and oxalyl chloride (5.47 mL, 62.5 mmol) was added by syringe. To this mixture was added DMSO (4.44 mL, 62.5 mmol) in DCM (30 ml). After gas evolution ceased the mixture was stirred for 5 minutes after which time hex-5-en-1-ol (3.00 mL, 25 mmol) was added. After a further 5 minutes triethylamine (17.42 mL, 125 mmol) was added and stirring continued for 15 minutes. The mixture was allowed to come to room temperature and a white solid precipitated. The mixture was washed with HCl (0.5M), saturated NaHCO$_3$ and brine. The organic portion was dried by passing them through a phase separator and used as a solution of the title compound in DCM in the subsequent step without further purification

Step 2: 5-(Hex-5-enyl)-2,3-dip-tolyl-5,6,7,8-tetrahydropyrido[2,3-b]pyrazine Hex-5-enal (step 1) (solution in DCM, 25 mmol) was treated with 2,3-di-p-tolyl-5,6,7,8-tetrahydropyrido[2,3-b]

pyrazine (Intermediate B) (3.94 g, 12.5 mmol). After stirring at room temp under nitrogen for 30 mins, sodium triacetoxyborohydride (3.18 g, 15.00 mmol) was added and stirring continued at room temperature overnight. Water (100 ml) was added to the reaction mixture. Once effervescence had ceased the organic portion was separated and dried by passing through a phase separating column. The solvent was removed under reduced pressure and the resulting brown oil was purified by flash column chromatography on silica eluting with 0-100% EtOAc in iso-hexane on a 80 g silca cartridge. The combined fractions were allowed to stand at room temperature for 2 days. The resulting suspension was collected by filtration and dried in a vacuum oven. The crude material was purified by chromatography on silica eluting with 0-50% EtOAc in iso-hexane to afford the title compound;

Prophetic Compounds

The following compounds may be prepared according to methods as described herein or as disclosed in PCT patent application PCT/EP2011/062028 (WO 2012/007539).

| Structure | Name |
|---|---|
| 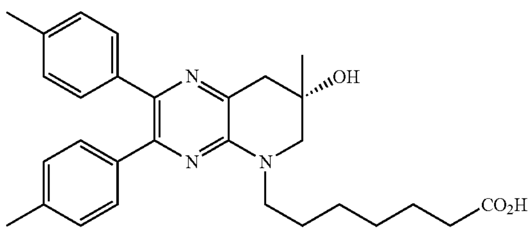 [SMILES: Cc1ccc(-c2nc3c(nc2-c2ccc(C)cc2)N(CCCCCCC(=O)O)C[C@@](C)(O)C3)cc1] | (rac or R or S)-7-(7-hydroxy-7-methyl-2,3-di-p-tolyl-7,8-dihydropyrido[2,3-b]pyrazin-5(6H)-yl)heptanoic acid |
| 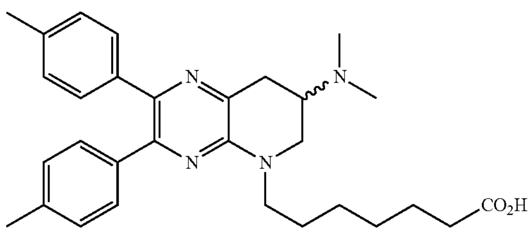 [SMILES: Cc1ccc(-c2nc3c(nc2-c2ccc(C)cc2)N(CCCCCCC(=O)O)CC(N(C)C)C3)cc1] | (rac or R or S)-7-(7-(dimethylamino)-2,3-di-p-tolyl-7,8-dihydropyrido[2,3-b]pyrazin-5(6H)-yl)heptanoic acid |
| 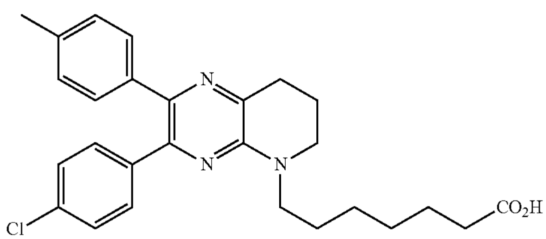 [SMILES: Cc1ccc(-c2nc3c(nc2-c2ccc(Cl)cc2)N(CCCCCCC(=O)O)CCC3)cc1] | 7-(3-(4-chlorophenyl)-2-(p-tolyl)-7,8-dihydropyrido[2,3-b]pyrazin-5(6H)-yl)heptanoic acid |
| 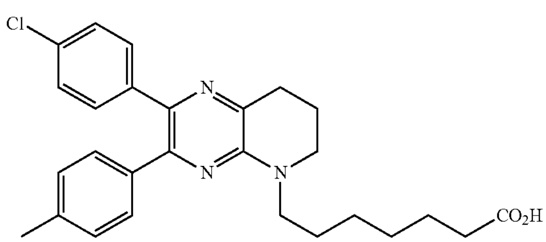 [SMILES: Cc1ccc(-c2nc3c(nc2-c2ccc(Cl)cc2)CCCN3CCCCCCC(=O)O)cc1] | 7-(2-(4-chlorophenyl)-3-(p-tolyl)-7,8-dihydropyrido[2,3-b]pyrazin-5(6H)-yl)heptanoic acid |
| 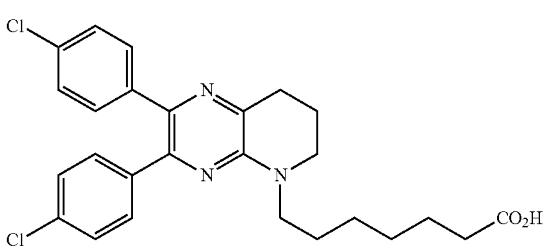 [SMILES: O=C(O)CCCCCCN1CCCc2nc(-c3ccc(Cl)cc3)c(-c3ccc(Cl)cc3)nc21] | 7-(2,3-bis(4-chlorophenyl)-7,8-dihydropyrido[2,3-b]pyrazin-5(6H)-yl)heptanoic acid |

| Structure | Name |
|---|---|
| 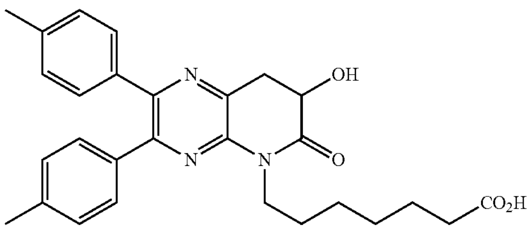 [SMILES: Cc1ccc(-c2nc3c(nc2-c2ccc(C)cc2)N(CCCCCCC(=O)O)C(=O)C(O)C3)cc1] | 7-(7-hydroxy-6-oxo-2,3-di-p-tolyl-7,8-dihydropyrido[2,3-b]pyrazin-5(6H)-yl)heptanoic acid |
| 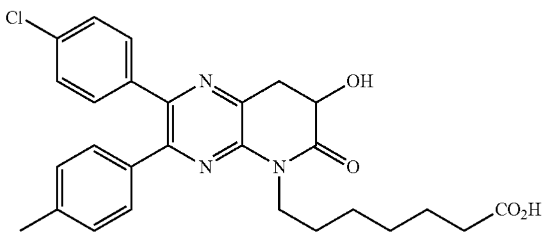 [SMILES: Cc1ccc(-c2nc3c(nc2-c2ccc(Cl)cc2)CC(O)C(=O)N3CCCCCCC(=O)O)cc1] | 7-(2-(4-chlorophenyl)-7-hydroxy-6-oxo-3-(p-tolyl)-7,8-dihydropyrido[2,3-b]pyrazin-5(6H)-yl)heptanoic acid |
| 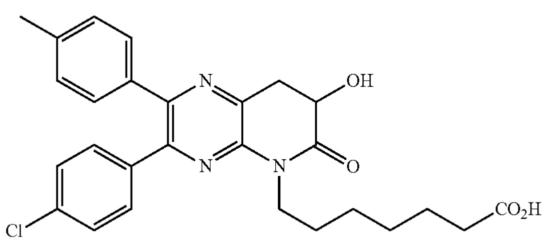 [SMILES: Cc1ccc(-c2nc3c(nc2-c2ccc(Cl)cc2)N(CCCCCCC(=O)O)C(=O)C(O)C3)cc1] | 7-(3-(4-chlorophenyl)-7-hydroxy-6-oxo-2-(p-tolyl)-7,8-dihydropyrido[2,3-b]pyrazin-5(6H)-yl)heptanoic acid |
| 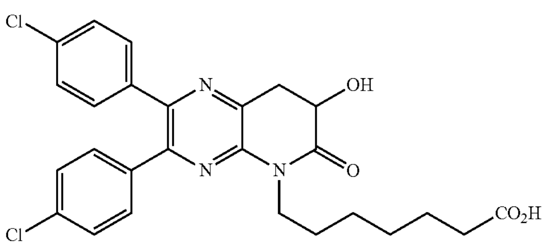 [SMILES: O=C(O)CCCCCCN1C(=O)C(O)Cc2nc(-c3ccc(Cl)cc3)c(-c3ccc(Cl)cc3)nc21] | 7-(2,3-bis(4-chlorophenyl)-7-hydroxy-6-oxo-7,8-dihydropyrido[2,3-b]pyrazin-5(6H)-yl)heptanoic acid |
| 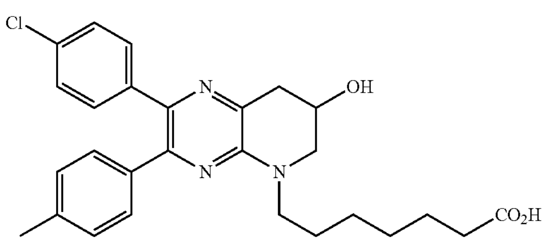 [SMILES: Cc1ccc(-c2nc3c(nc2-c2ccc(Cl)cc2)CC(O)CN3CCCCCCC(=O)O)cc1] | 7-(2-(4-chlorophenyl)-7-hydroxy-3-(p-tolyl)-7,8-dihydropyrido[2,3-b]pyrazin-5(6H)-yl)heptanoic acid |
| 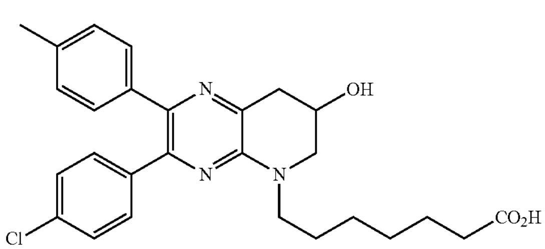 [SMILES: Cc1ccc(-c2nc3c(nc2-c2ccc(Cl)cc2)N(CCCCCCC(=O)O)CC(O)C3)cc1] | 7-(3-(4-chlorophenyl)-7-hydroxy-2-(p-tolyl)-7,8-dihydropyrido[2,3-b]pyrazin-5(6H)-yl)heptanoic acid |

| Structure | Name |
|---|---|
| 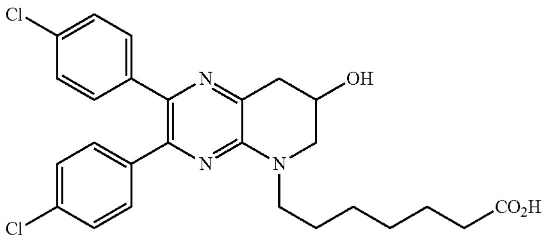 [SMILES: O=C(O)CCCCCCN1CC(O)Cc2nc(-c3ccc(Cl)cc3)c(-c3ccc(Cl)cc3)nc21] | 7-(2,3-bis(4-chlorophenyl)-7-hydroxy-7,8-dihydropyrido[2,3-b]pyrazin-5(6H)-yl)heptanoic acid |
| 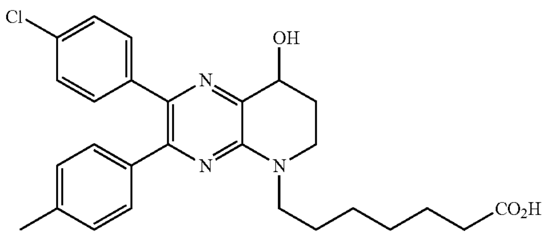 [SMILES: Cc1ccc(-c2nc3c(nc2-c2ccc(Cl)cc2)C(O)CCN3CCCCCCC(=O)O)cc1] | 7-(2-(4-chlorophenyl)-8-hydroxy-3-(p-tolyl)-7,8-dihydropyrido[2,3-b]pyrazin-5(6H)-yl)heptanoic acid |
| 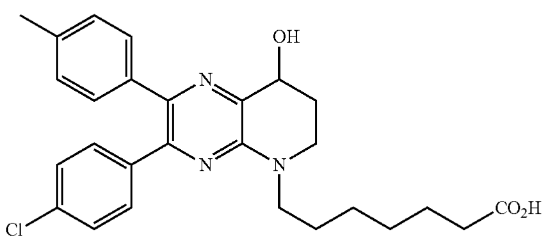 [SMILES: Cc1ccc(-c2nc3c(nc2-c2ccc(Cl)cc2)N(CCCCCCC(=O)O)CCC3O)cc1] | 7-(3-(4-chlorophenyl)-8-hydroxy-2-(p-tolyl)-7,8-dihydropyrido[2,3-b]pyrazin-5(6H)-yl)heptanoic acid |
| 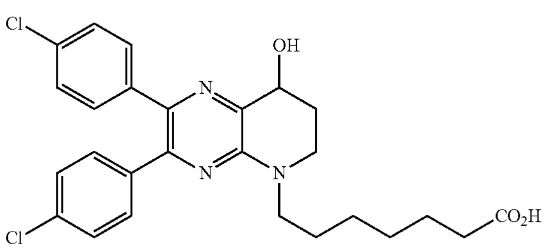 [SMILES: O=C(O)CCCCCCN1CCC(O)c2nc(-c3ccc(Cl)cc3)c(-c3ccc(Cl)cc3)nc21] | 7-(2,3-bis(4-chlorophenyl)-8-hydroxy-7,8-dihydropyrido[2,3-b]pyrazin-5(6H)-yl)heptanoic acid |
| 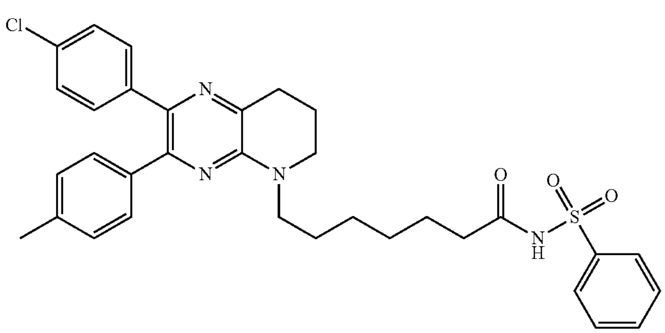 [SMILES: Cc1ccc(-c2nc3c(nc2-c2ccc(Cl)cc2)CCCN3CCCCCCC(=O)NS(=O)(=O)c2ccccc2)cc1] | 7-(2-(4-chlorophenyl)-3-(p-tolyl)-7,8-dihydropyrido[2,3-b]pyrazin-5(6H)-yl)-N-(phenylsulfonyl)heptanamide |

| Structure | Name |
|---|---|
| 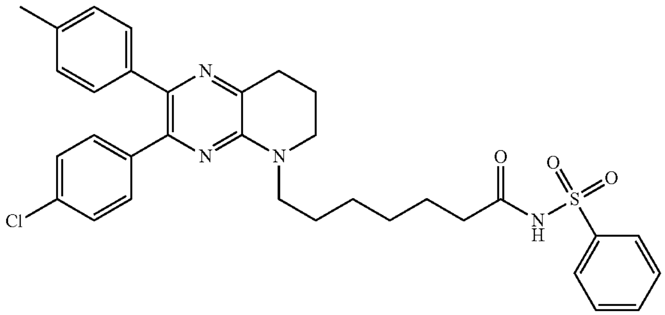 [SMILES: Cc1ccc(-c2nc3c(nc2-c2ccc(Cl)cc2)N(CCCCCCC(=O)NS(=O)(=O)c2ccccc2)CCC3)cc1] | 7-(3-(4-chlorophenyl)-2-(p-tolyl)-7,8-dihydropyrido[2,3-b]pyrazin-5(6H)-yl)-N-(phenylsulfonyl)heptanamide |
| 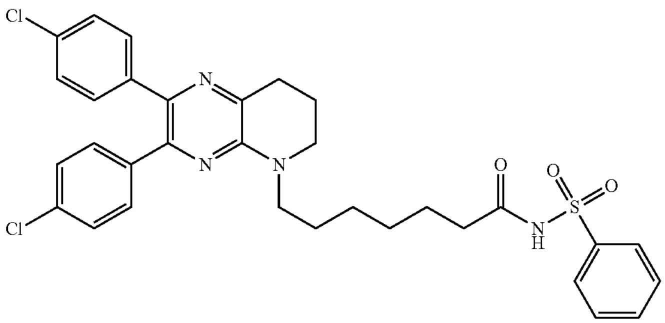 [SMILES: O=C(CCCCCCN1CCCc2nc(-c3ccc(Cl)cc3)c(-c3ccc(Cl)cc3)nc21)NS(=O)(=O)c1ccccc1] | 7-(2,3-bis(4-chlorophenyl)-7,8-dihydropyrido[2,3-b]pyrazin-5(6H)-yl)-N-(phenylsulfonyl)heptanamide |
| 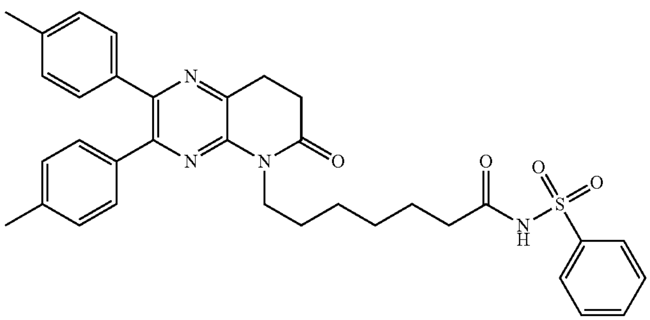 [SMILES: Cc1ccc(-c2nc3c(nc2-c2ccc(C)cc2)N(CCCCCCC(=O)NS(=O)(=O)c2ccccc2)C(=O)CC3)cc1] | 7-(6-oxo-2,3-di-p-tolyl-7,8-dihydropyrido[2,3-b]pyrazin-5(6H)-yl)-N-(phenylsulfonyl)heptanamide |
| 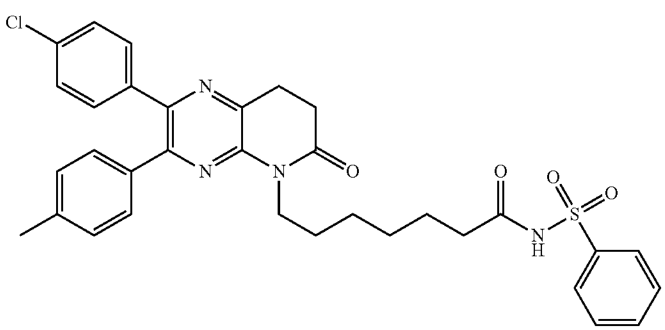 [SMILES: Cc1ccc(-c2nc3c(nc2-c2ccc(Cl)cc2)CCC(=O)N3CCCCCCC(=O)NS(=O)(=O)c2ccccc2)cc1] | 7-(2-(4-chlorophenyl)-6-oxo-3-(p-tolyl)-7,8-dihydropyrido[2,3-b]pyrazin-5(6H)-yl)-N-(phenylsulfonyl)heptanamide |
| 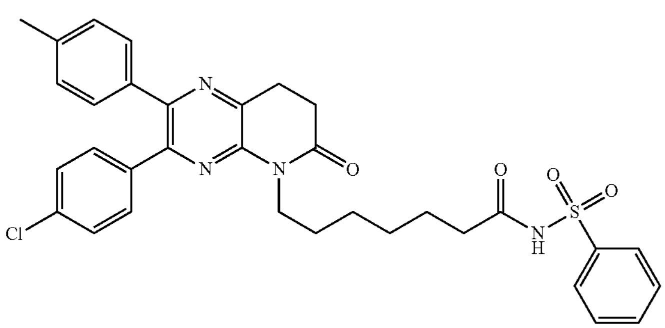 [SMILES: Cc1ccc(-c2nc3c(nc2-c2ccc(Cl)cc2)N(CCCCCCC(=O)NS(=O)(=O)c2ccccc2)C(=O)CC3)cc1] | 7-(3-(4-chlorophenyl)-6-oxo-2-(p-tolyl)-7,8-dihydropyrido[2,3-b]pyrazin-5(6H)-yl)-N-(phenylsulfonyl)heptanamide |

| Structure | Name |
|---|---|
| 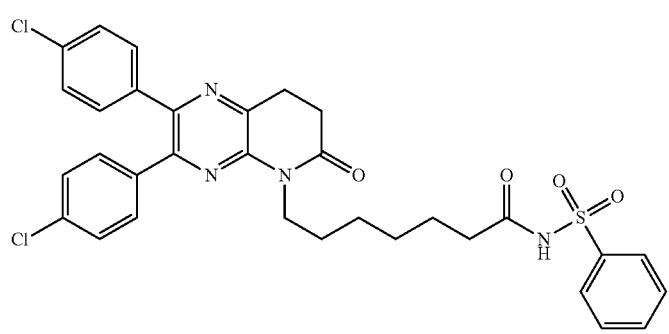 [SMILES: O=C(CCCCCCN1C(=O)CCc2nc(-c3ccc(Cl)cc3)c(-c3ccc(Cl)cc3)nc21)NS(=O)(=O)c1ccccc1] | 7-(2,3-bis(4-chlorophenyl)-6-oxo-7,8-dihydropyrido[2,3-b]pyrazin-5(6H)-yl)-N-(phenylsulfonyl)heptanamide |
| 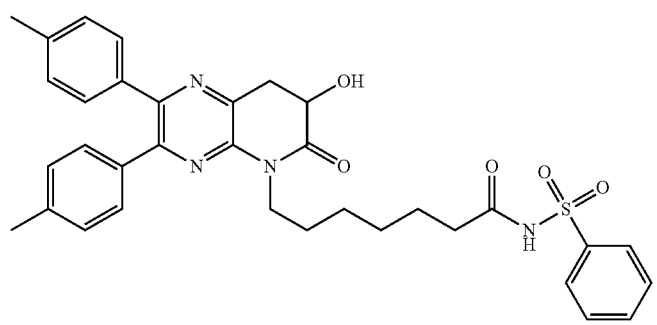 [SMILES: Cc1ccc(-c2nc3c(nc2-c2ccc(C)cc2)N(CCCCCCC(=O)NS(=O)(=O)c2ccccc2)C(=O)C(O)C3)cc1] | 7-(7-hydroxy-6-oxo-2,3-di-p-tolyl-7,8-dihydropyrido[2,3-b]pyrazin-5(6H)-yl)-N-(phenylsulfonyl)heptanamide |
| 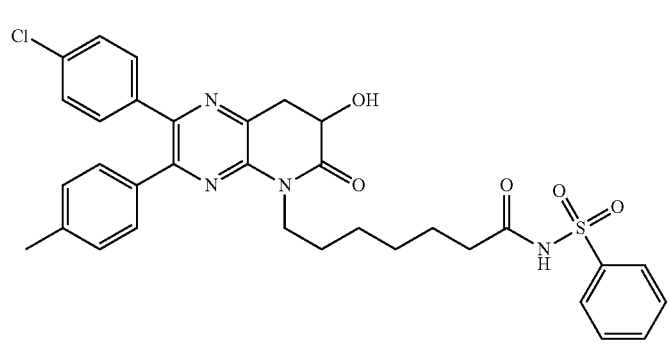 [SMILES: Cc1ccc(-c2nc3c(nc2-c2ccc(Cl)cc2)CC(O)C(=O)N3CCCCCCC(=O)NS(=O)(=O)c2ccccc2)cc1] | 7-(2-(4-chlorophenyl)-7-hydroxy-6-oxo-3-(p-tolyl)-7,8-dihydropyrido[2,3-b]pyrazin-5(6H)-yl)-N-(phenylsulfonyl)heptanamide |
| 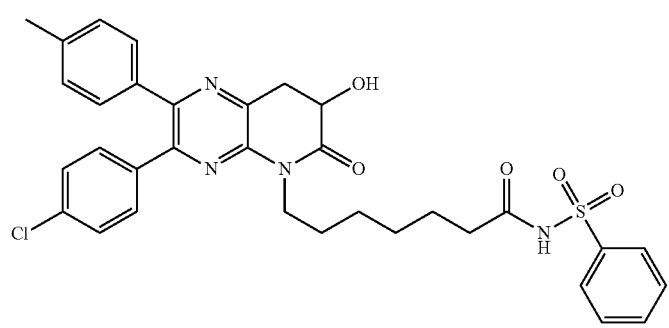 [SMILES: Cc1ccc(-c2nc3c(nc2-c2ccc(Cl)cc2)N(CCCCCCC(=O)NS(=O)(=O)c2ccccc2)C(=O)C(O)C3)cc1] | 7-(3-(4-chlorophenyl)-7-hydroxy-6-oxo-2-(p-tolyl)-7,8-dihydropyrido[2,3-b]pyrazin-5(6H)-yl)-N-(phenylsulfonyl)heptanamide |

-continued

| Structure | Name |
|---|---|
| 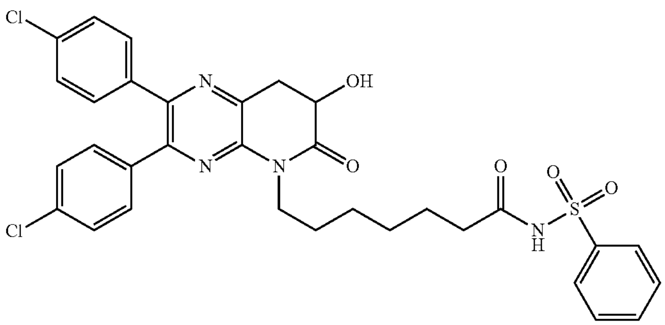 [SMILES: O=C(CCCCCCN1C(=O)C(O)Cc2nc(-c3ccc(Cl)cc3)c(-c3ccc(Cl)cc3)nc21)NS(=O)(=O)c1ccccc1] | 7-(2,3-bis(4-chlorophenyl)-7-hydroxy-6-oxo-7,8-dihydropyrido[2,3-b]pyrazin-5(6H)-yl)-N-(phenylsulfonyl)heptanamide |
| 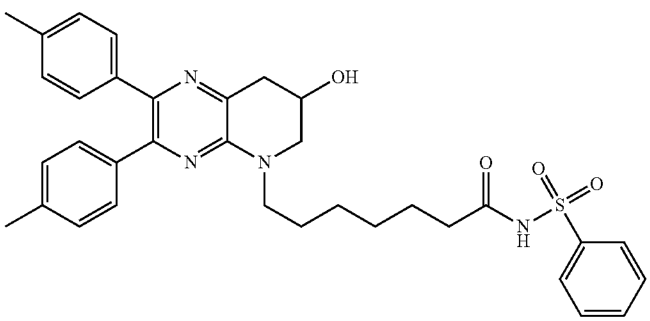 [SMILES: Cc1ccc(-c2nc3c(nc2-c2ccc(C)cc2)N(CCCCCCC(=O)NS(=O)(=O)c2ccccc2)CC(O)C3)cc1] | 7-(7-hydroxy-2,3-di-p-tolyl-7,8-dihydropyrido[2,3-b]pyrazin-5(6H)-yl)-N-(phenylsulfonyl)heptanamide |
| 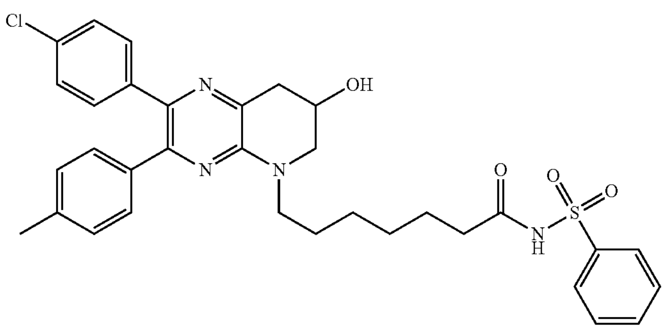 | 7-(2-(4-chlorophenyl)-7-hydroxy-3-(p-tolyl)-7,8-dihydropyrido[2,3-b]pyrazin-5(6H)-yl)-N-(phenylsulfonyl)heptanamide |
| 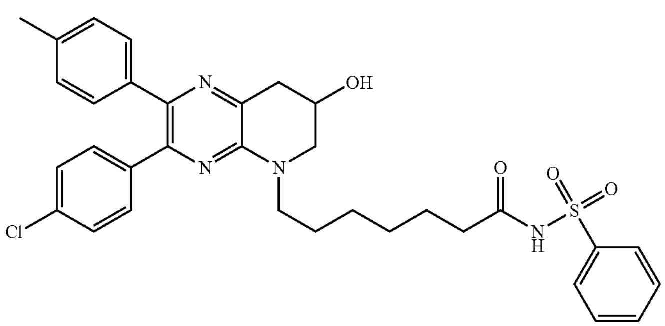 [SMILES: Cc1ccc(-c2nc3c(nc2-c2ccc(Cl)cc2)N(CCCCCCC(=O)NS(=O)(=O)c2ccccc2)CC(O)C3)cc1] | 7-(3-(4-chlorophenyl)-7-hydroxy-2-(p-tolyl)-7,8-dihydropyrido[2,3-b]pyrazin-5(6H)-yl)-N-(phenylsulfonyl)heptanamide |
| 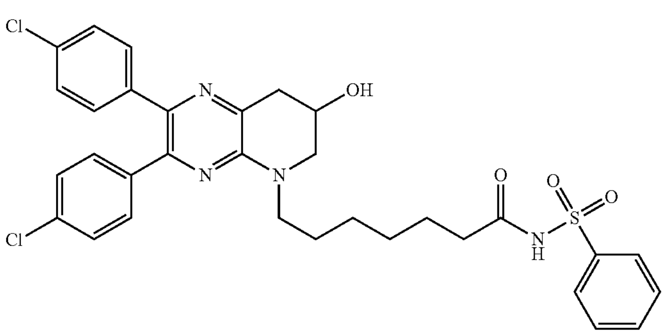 [SMILES: O=C(CCCCCCN1CC(O)Cc2nc(-c3ccc(Cl)cc3)c(-c3ccc(Cl)cc3)nc21)NS(=O)(=O)c1ccccc1] | 7-(2,3-bis(4-chlorophenyl)-7-hydroxy-7,8-dihydropyrido[2,3-b]pyrazin-5(6H)-yl)-N-(phenylsulfonyl)heptanamide |

| Structure | Name |
|---|---|
| 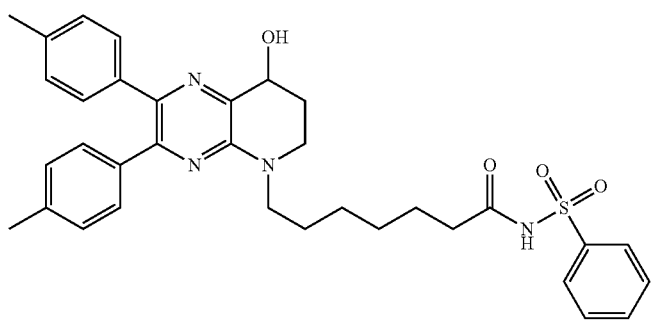 [SMILES: Cc1ccc(-c2nc3c(nc2-c2ccc(C)cc2)N(CCCCCCC(=O)NS(=O)(=O)c2ccccc2)CCC3O)cc1] | 7-(8-hydroxy-2,3-di-p-tolyl-7,8-dihydropyrido[2,3-b]pyrazin-5(6H)-yl)-N-(phenylsulfonyl)heptanamide |
| 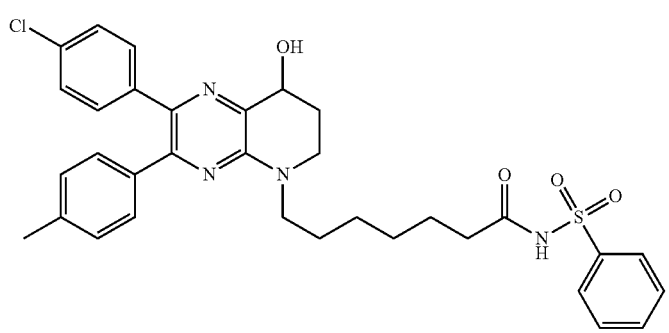 [SMILES: Cc1ccc(-c2nc3c(nc2-c2ccc(Cl)cc2)C(O)CCN3CCCCCCC(=O)NS(=O)(=O)c2ccccc2)cc1] | 7-(2-(4-chlorophenyl)-8-hydroxy-3-(p-tolyl)-7,8-dihydropyrido[2,3-b]pyrazin-5(6H)-yl)-N-(phenylsulfonyl)heptanamide |
| 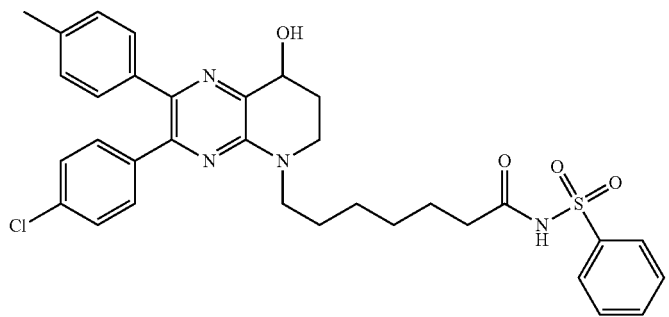 [SMILES: Cc1ccc(-c2nc3c(nc2-c2ccc(Cl)cc2)N(CCCCCCC(=O)NS(=O)(=O)c2ccccc2)CCC3O)cc1] | 7-(3-(4-chlorophenyl)-8-hydroxy-2-(p-tolyl)-7,8-dihydropyrido[2,3-b]pyrazin-5(6H)-yl)-N-(phenylsulfonyl)heptanamide |
| 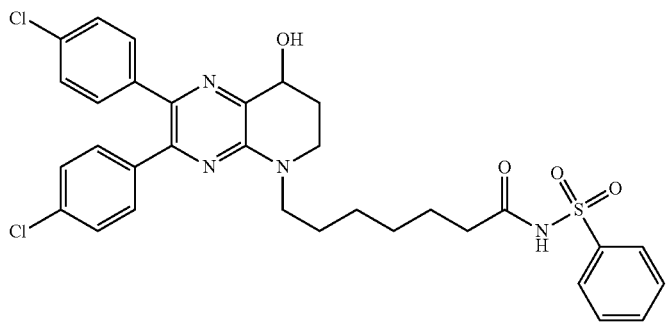 [SMILES: O=C(CCCCCCN1CCC(O)c2nc(-c3ccc(Cl)cc3)c(-c3ccc(Cl)cc3)nc21)NS(=O)(=O)c1ccccc1] | 7-(2,3-bis(4-chlorophenyl)-8-hydroxy-7,8-dihydropyrido[2,3-b]pyrazin-5(6H)-yl)-N-(phenylsulfonyl)heptanamide |
| 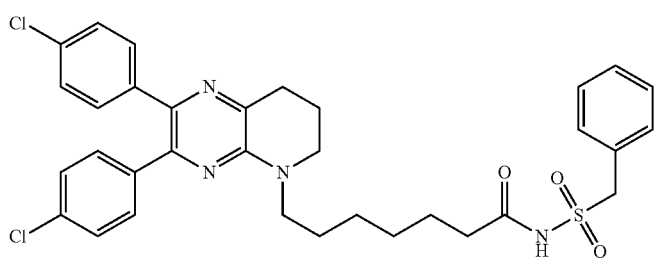 [SMILES: O=C(CCCCCCN1CCCc2nc(-c3ccc(Cl)cc3)c(-c3ccc(Cl)cc3)nc21)NS(=O)(=O)Cc1ccccc1] | N-(benzylsulfonyl)-7-(2,3-bis(4-chlorophenyl)-7,8-dihydropyrido[2,3-b]pyrazin-5(6H)-yl)heptanamide |

| Structure | Name |
|---|---|
| 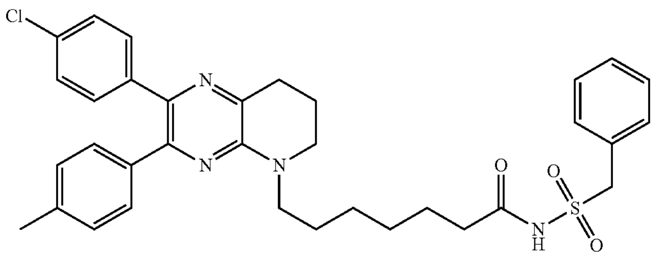 [SMILES: Cc1ccc(-c2nc3c(nc2-c2ccc(Cl)cc2)CCCN3CCCCCCC(=O)NS(=O)(=O)Cc2ccccc2)cc1] | N-(benzylsulfonyl)-7-(2-(4-chlorophenyl)-3-(p-tolyl)-7,8-dihydropyrido[2,3-b]pyrazin-5(6H)-yl)heptanamide |
| 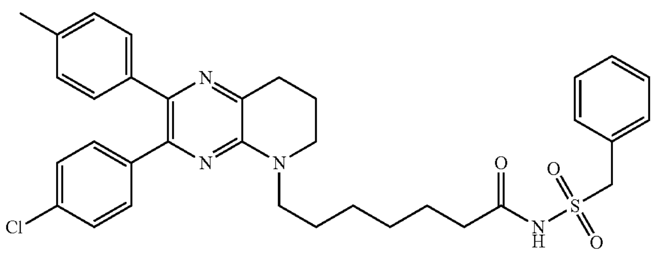 [SMILES: Cc1ccc(-c2nc3c(nc2-c2ccc(Cl)cc2)N(CCCCCCC(=O)NS(=O)(=O)Cc2ccccc2)CCC3)cc1] | N-(benzylsulfonyl)-7-(3-(4-chlorophenyl)-2-(p-tolyl)-7,8-dihydropyrido[2,3-b]pyrazin-5(6H)-yl)heptanamide |
| 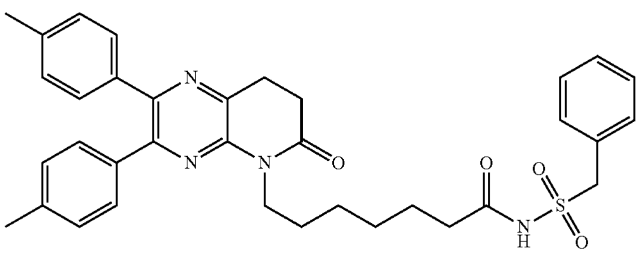 [SMILES: Cc1ccc(-c2nc3c(nc2-c2ccc(C)cc2)N(CCCCCCC(=O)NS(=O)(=O)Cc2ccccc2)C(=O)CC3)cc1] | N-(benzylsulfonyl)-7-(6-oxo-2,3-di-p-tolyl-7,8-dihydropyrido[2,3-b]pyrazin-5(6H)-yl)heptanamide |
| 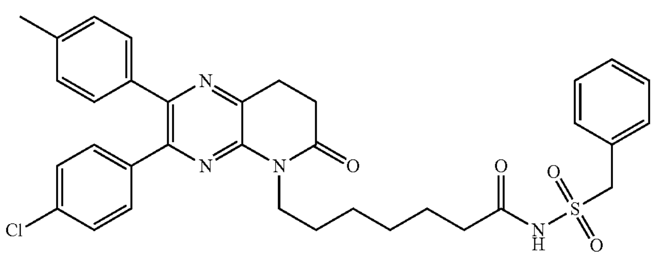 [SMILES: Cc1ccc(-c2nc3c(nc2-c2ccc(Cl)cc2)N(CCCCCCC(=O)NS(=O)(=O)Cc2ccccc2)C(=O)CC3)cc1] | N-(benzylsulfonyl)-7-(3-(4-chlorophenyl)-6-oxo-2-(p-tolyl)-7,8-dihydropyrido[2,3-b]pyrazin-5(6H)-yl)heptanamide |
| 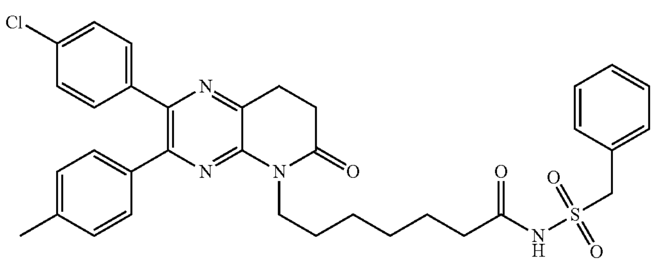 [SMILES: Cc1ccc(-c2nc3c(nc2-c2ccc(Cl)cc2)CCC(=O)N3CCCCCCC(=O)NS(=O)(=O)Cc2ccccc2)cc1] | N-(benzylsulfonyl)-7-(2-(4-chlorophenyl)-6-oxo-3-(p-tolyl)-7,8-dihydropyrido[2,3-b]pyrazin-5(6H)-yl)heptanamide |
| 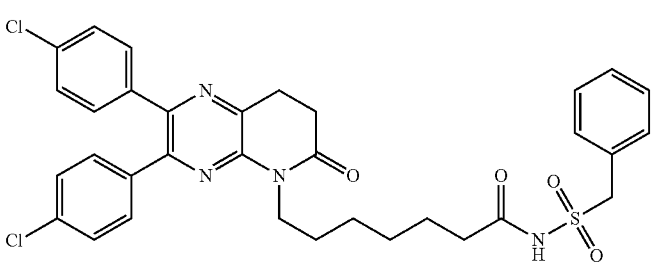 [SMILES: O=C(CCCCCCN1C(=O)CCc2nc(-c3ccc(Cl)cc3)c(-c3ccc(Cl)cc3)nc21)NS(=O)(=O)Cc1ccccc1] | N-(benzylsulfonyl)-7-(2,3-bis(4-chlorophenyl)-6-oxo-7,8-dihydropyrido[2,3-b]pyrazin-5(6H)-yl)heptanamide |

| Structure | Name |
|---|---|
| 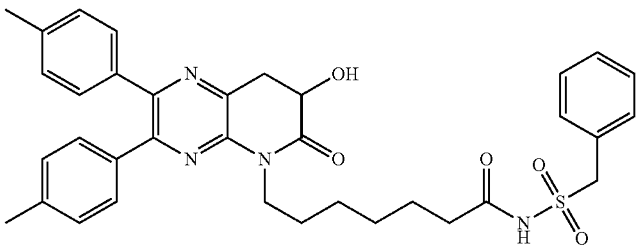 [SMILES: Cc1ccc(-c2nc3c(nc2-c2ccc(C)cc2)N(CCCCCCC(=O)NS(=O)(=O)Cc2ccccc2)C(=O)C(O)C3)cc1] | N-(benzylsulfonyl)-7-(7-hydroxy-6-oxo-2,3-di-p-tolyl-7,8-dihydropyrido[2,3-b]pyrazin-5(6H)-yl)heptanamide |
| 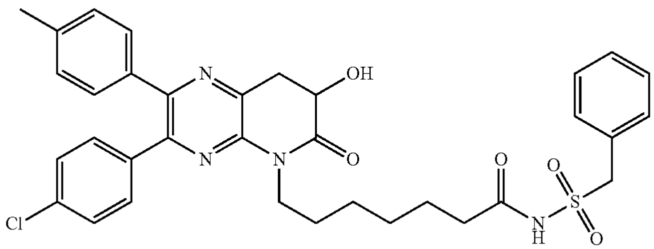 [SMILES: Cc1ccc(-c2nc3c(nc2-c2ccc(Cl)cc2)N(CCCCCCC(=O)NS(=O)(=O)Cc2ccccc2)C(=O)C(O)C3)cc1] | N-(benzylsulfonyl)-7-(3-(4-chlorophenyl)-7-hydroxy-6-oxo-2-(p-tolyl)-7,8-dihydropyrido[2,3-b]pyrazin-5(6H)-yl)heptanamide |
| 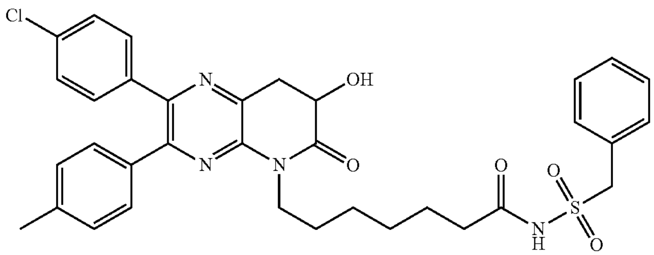 [SMILES: Cc1ccc(-c2nc3c(nc2-c2ccc(Cl)cc2)CC(O)C(=O)N3CCCCCCC(=O)NS(=O)(=O)Cc2ccccc2)cc1] | N-(benzylsulfonyl)-7-(2-(4-chlorophenyl)-7-hydroxy-6-oxo-3-(p-tolyl)-7,8-dihydropyrido[2,3-b]pyrazin-5(6H)-yl)heptanamide |
| 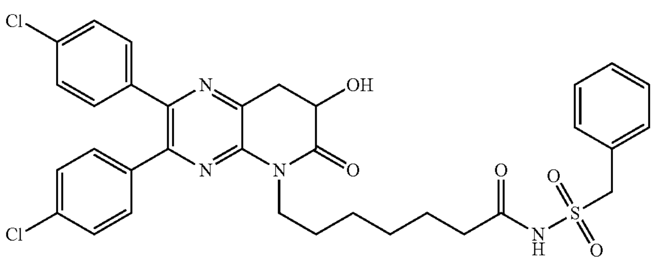 [SMILES: O=C(CCCCCCN1C(=O)C(O)Cc2nc(-c3ccc(Cl)cc3)c(-c3ccc(Cl)cc3)nc21)NS(=O)(=O)Cc1ccccc1] | N-(benzylsulfonyl)-7-(2,3-bis(4-chlorophenyl)-7-hydroxy-6-oxo-7,8-dihydropyrido[2,3-b]pyrazin-5(6H)-yl)heptanamide |
| 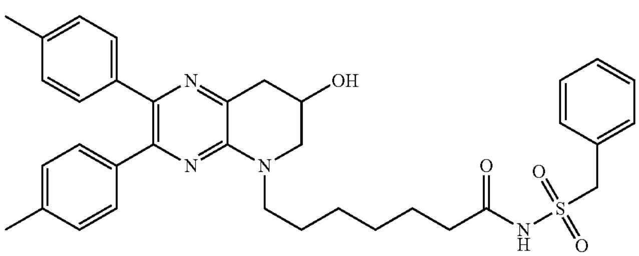 [SMILES: Cc1ccc(-c2nc3c(nc2-c2ccc(C)cc2)N(CCCCCCC(=O)NS(=O)(=O)Cc2ccccc2)CC(O)C3)cc1] | N-(benzylsulfonyl)-7-(7-hydroxy-2,3-di-p-tolyl-7,8-dihydropyrido[2,3-b]pyrazin-5(6H)-yl)heptanamide |
| 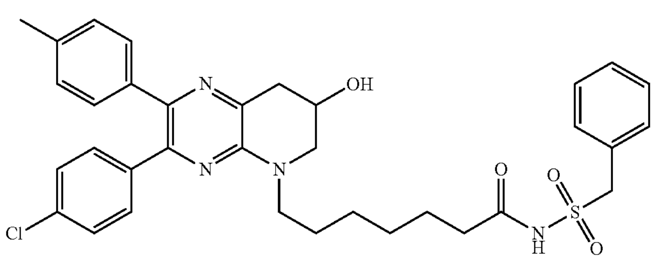 [SMILES: Cc1ccc(-c2nc3c(nc2-c2ccc(Cl)cc2)N(CCCCCCC(=O)NS(=O)(=O)Cc2ccccc2)CC(O)C3)cc1] | N-(benzylsulfonyl)-7-(3-(4-chlorophenyl)-7-hydroxy-2-(p-tolyl)-7,8-dihydropyrido[2,3-b]pyrazin-5(6H)-yl)heptanamide |

| Structure | Name |
|---|---|
| 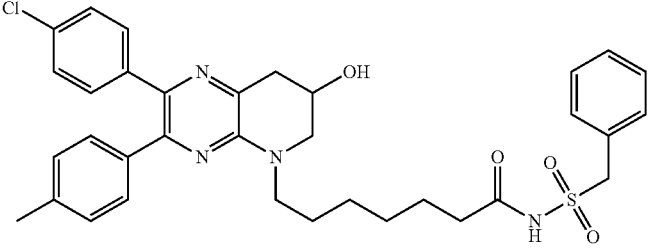 [SMILES: Cc1ccc(-c2nc3c(nc2-c2ccc(Cl)cc2)CC(O)CN3CCCCCCC(=O)NS(=O)(=O)Cc2ccccc2)cc1] | N-(benzylsulfonyl)-7-(2-(4-chlorophenyl)-7-hydroxy-3-(p-tolyl)-7,8-dihydropyrido[2,3-b]pyrazin-5(6H)-yl)heptanamide |
| 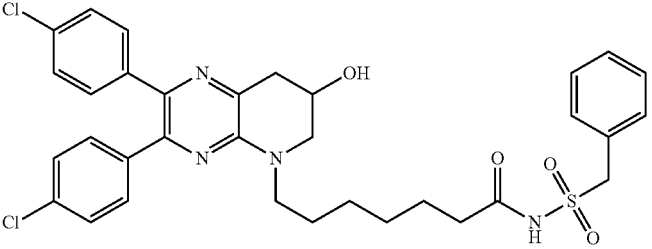 | N-(benzylsulfonyl)-7-(2,3-bis(4-chlorophenyl)-7-hydroxy-7,8-dihydropyrido[2,3-b]pyrazin-5(6H)-yl)heptanamide |
| 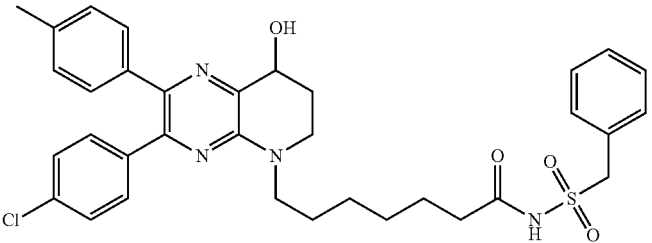 [SMILES: Cc1ccc(-c2nc3c(nc2-c2ccc(Cl)cc2)N(CCCCCCC(=O)NS(=O)(=O)Cc2ccccc2)CCC3O)cc1] | N-(benzylsulfonyl)-7-(3-(4-chlorophenyl)-8-hydroxy-2-(p-tolyl)-7,8-dihydropyrido[2,3-b]pyrazin-5(6H)-yl)heptanamide |
| 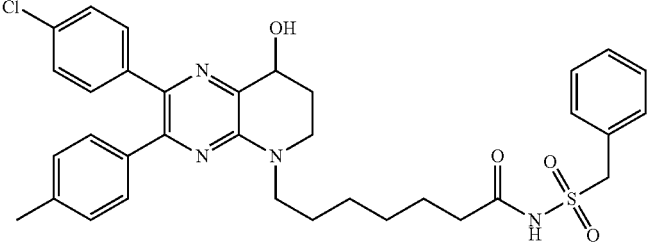 [SMILES: Cc1ccc(-c2nc3c(nc2-c2ccc(Cl)cc2)C(O)CCN3CCCCCCC(=O)NS(=O)(=O)Cc2ccccc2)cc1] | N-(benzylsulfonyl)-7-(2-(4-chloropheny)-8-hydroxy-3-(p-tolyl)-7,8-dihydropyrido[2,3-b]pyrazin-5(6H)-yl)heptanamide |
| 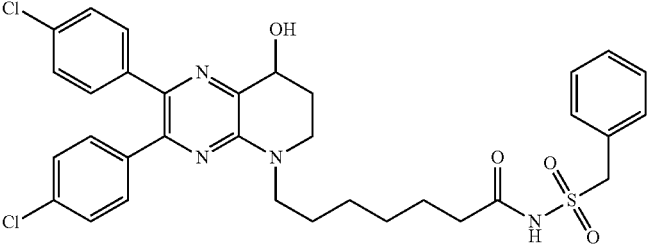 [SMILES: O=C(CCCCCCN1CCC(O)c2nc(-c3ccc(Cl)cc3)c(-c3ccc(Cl)cc3)nc21)NS(=O)(=O)Cc1ccccc1] | N-(benzylsulfonyl)-7-(2,3-bis(4-chlorophenyl)-8-hydroxy-7,8-dihydropyrido[2,3-b]pyrazin-5(6H)-yl)heptanamide |
| 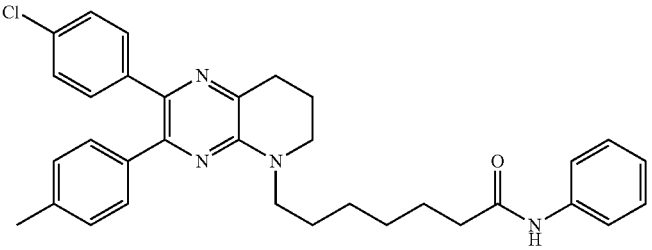 | 7-(2-(4-chlorophenyl)-3-(p-tolyl)-7,8-dihydropyrido[2,3-b]pyrazin-5(6H)-yl)-N-phenylheptanamide |

| Structure | Name |
|---|---|
| 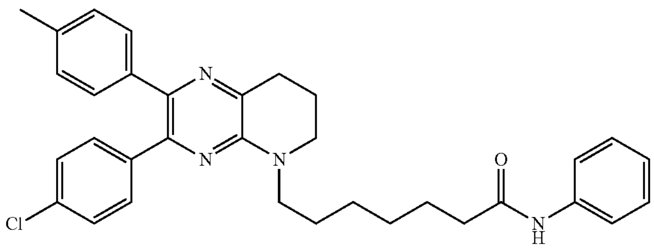 | 7-(3-(4-chlorophenyl)-2-(p-tolyl)-7,8-dihydropyrido[2,3-b]pyrazin-5(6H)-yl)-N-phenylheptanamide |
| 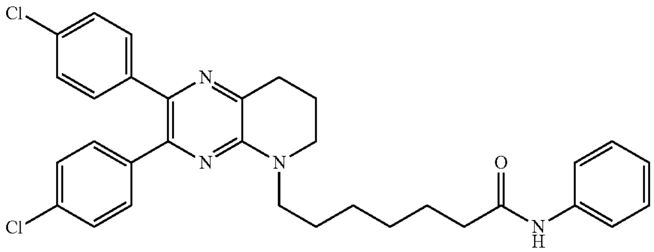 [SMILES: Cc1ccc(-c2nc3c(nc2-c2ccc(Cl)cc2)CCCN3CCCCCCC(=O)Nc2ccccc2)cc1] | 7-(2,3-bis(4-chlorophenyl)-7,8-dihydropyrido[2,3-b]pyrazin-5(6H)-yl)-N-phenylheptanamide |
| 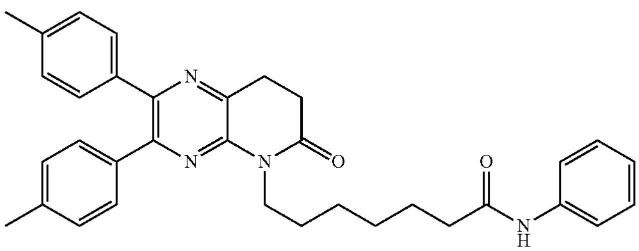 [SMILES: Cc1ccc(-c2nc3c(nc2-c2ccc(C)cc2)N(CCCCCCC(=O)Nc2ccccc2)C(=O)CC3)cc1] | 7-(6-oxo-2,3-di-p-tolyl-7,8-dihydropyrido[2,3-b]pyrazin-5(6H)-yl)-N-phenylheptanamide |
| 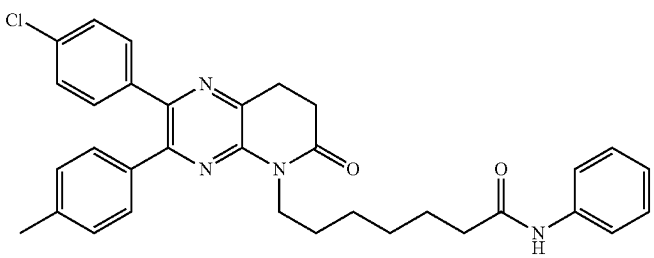 [SMILES: Cc1ccc(-c2nc3c(nc2-c2ccc(Cl)cc2)CCC(=O)N3CCCCCCC(=O)Nc2ccccc2)cc1] | 7-(2-(4-chlorophenyl)-6-oxo-3-(p-tolyl)-7,8-dihydropyrido[2,3-b]pyrazin-5(6H)-yl)-N-phenylheptanamide |
| 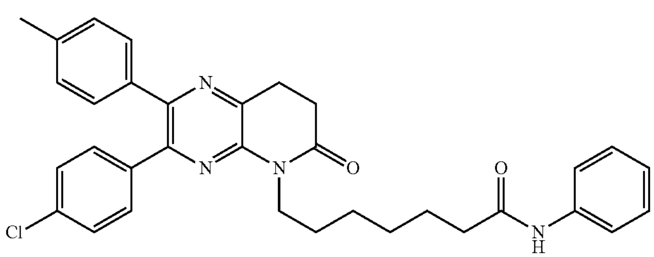 [SMILES: Cc1ccc(-c2nc3c(nc2-c2ccc(Cl)cc2)N(CCCCCCC(=O)Nc2ccccc2)C(=O)CC3)cc1] | 7-(3-(4-chlorophenyl)-6-oxo-2-(p-tolyl)-7,8-dihydropyrido[2,3-b]pyrazin-5(6H)-yl)-N-phenylheptanamide |
| 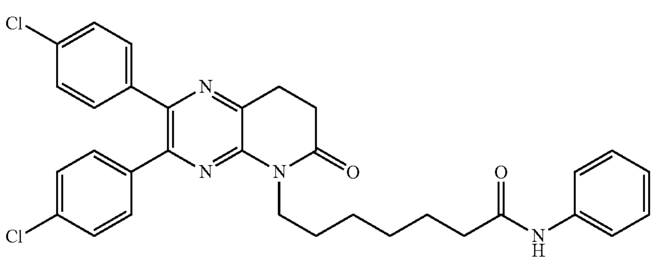 | 7-(2,3-bis(4-chlorophenyl)-6-oxo-7,8-dihydropyrido[2,3-b]pyrazin-5(6H)-yl)-N-phenylheptanamide |

| Structure | Name |
|---|---|
| 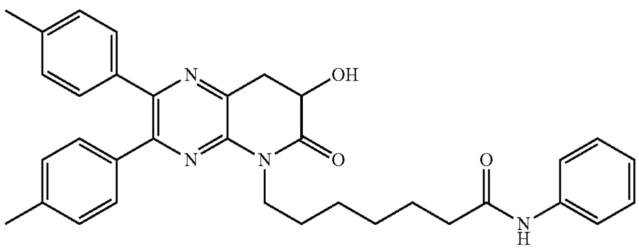 [SMILES: Cc1ccc(-c2nc3c(nc2-c2ccc(C)cc2)N(CCCCCCC(=O)Nc2ccccc2)C(=O)C(O)C3)cc1] | 7-(7-hydroxy-6-oxo-2,3-di-p-tolyl-7,8-dihydropyrido[2,3-b]pyrazin-5(6H)-yl)-N-phenylheptanamide |
| 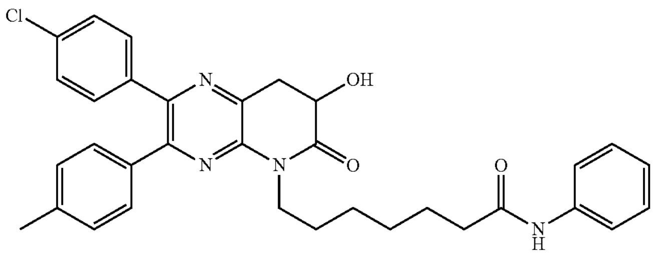 [SMILES: Cc1ccc(-c2nc3c(nc2-c2ccc(Cl)cc2)CC(O)C(=O)N3CCCCCCC(=O)Nc2ccccc2)cc1] | 7-(2-(4-chlorophenyl)-7-hydroxy-6-oxo-3-(p-tolyl)-7,8-dihydropyrido[2,3-b]pyrazin-5(6H)-yl)-N-phenylheptanamide |
| 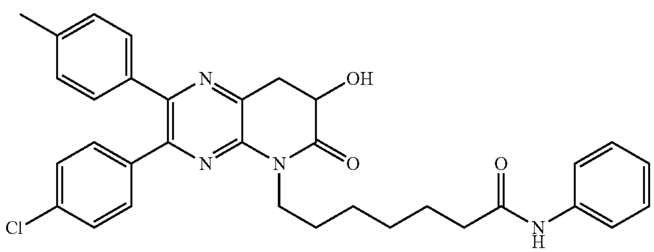 [SMILES: Cc1ccc(-c2nc3c(nc2-c2ccc(Cl)cc2)N(CCCCCCC(=O)Nc2ccccc2)C(=O)C(O)C3)cc1] | 7-(3-(4-chlorophenyl)-7-hydroxy-6-oxo-2-(p-tolyl)-7,8-dihydropyrido[2,3-b]pyrazin-5(6H)-yl)-N-phenylheptanamide |
| 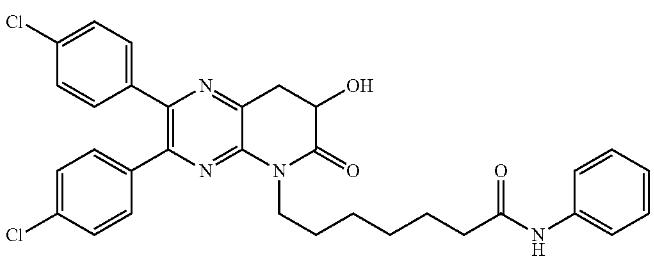 [SMILES: O=C(CCCCCCN1C(=O)C(O)Cc2nc(-c3ccc(Cl)cc3)c(-c3ccc(Cl)cc3)nc21)Nc1ccccc1] | 7-(2,3-bis(4-chlorophenyl)-7-hydroxy-6-oxo-7,8-dihydropyrido[2,3-b]pyrazin-5(6H)-yl)-N-phenylheptanamide |
| 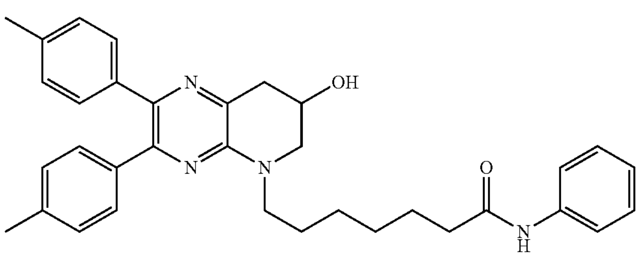 [SMILES: Cc1ccc(-c2nc3c(nc2-c2ccc(C)cc2)N(CCCCCCC(=O)Nc2ccccc2)CC(O)C3)cc1] | 7-(7-hydroxy-2,3-di-p-tolyl-7,8-dihydropyrido[2,3-b]pyrazin-5(6H)-yl)-N-phenylheptanamide |
| 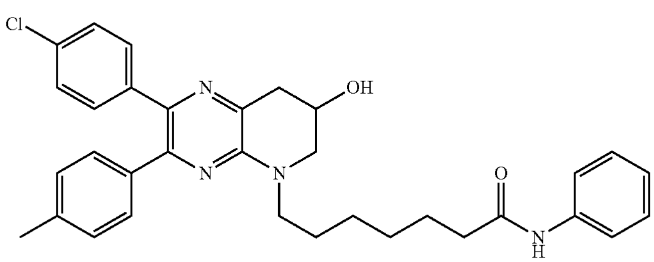 [SMILES: Cc1ccc(-c2nc3c(nc2-c2ccc(Cl)cc2)CC(O)CN3CCCCCCC(=O)Nc2ccccc2)cc1] | 7-(2-(4-chlorophenyl)-7-hydroxy-3-(p-tolyl)-7,8-dihydropyrido[2,3-b]pyrazin-5(6H)-yl)-N-phenylheptanamide |

| Structure | Name |
|---|---|
| 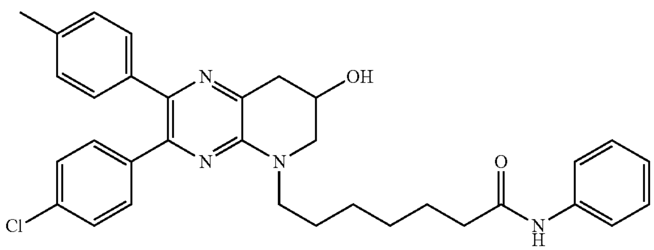 [SMILES: Cc1ccc(-c2nc3c(nc2-c2ccc(Cl)cc2)N(CCCCCCC(=O)Nc2ccccc2)CC(O)C3)cc1] | 7-(3-(4-chlorophenyl)-7-hydroxy-2-(p-tolyl)-7,8-dihydropyrido[2,3-b]pyrazin-5(6H)-yl)-N-phenylheptanamide |
| 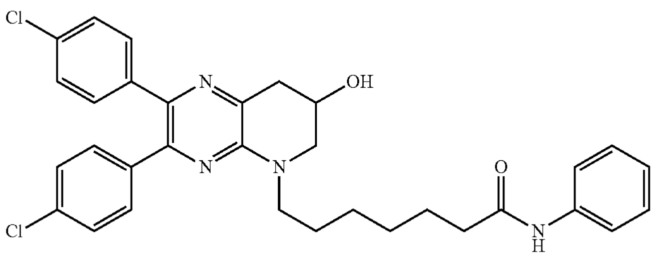 [SMILES: O=C(CCCCCCN1CC(O)Cc2nc(-c3ccc(Cl)cc3)c(-c3ccc(Cl)cc3)nc21)Nc1ccccc1] | 7-(2,3-bis(4-chlorophenyl)-7-hydroxy-7,8-dihydropyrido[2,3-b]pyrazin-5(6H)-yl)-N-phenylheptanamide |
| 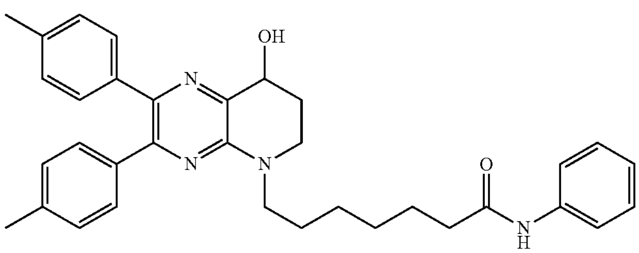 [SMILES: Cc1ccc(-c2nc3c(nc2-c2ccc(C)cc2)N(CCCCCCC(=O)Nc2ccccc2)CCC3O)cc1] | 7-(8-hydroxy-2,3-di-p-tolyl-7,8-dihydropyrido[2,3-b]pyrazin-5(6H)-yl)-N-phenylheptanamide |
| 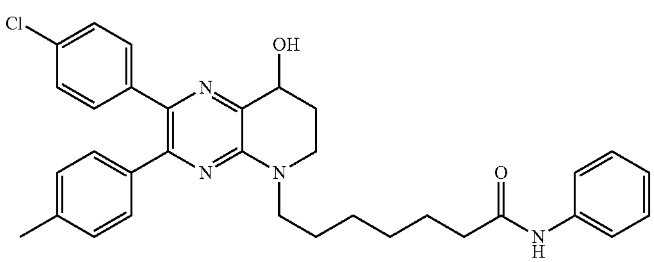 | 7-(2-(4-chlorophenyl)-8-hydroxy-3-(p-tolyl)-7,8-dihydropyrido[2,3-b]pyrazin-5(6H)-yl)-N-phenylheptanamide |
| 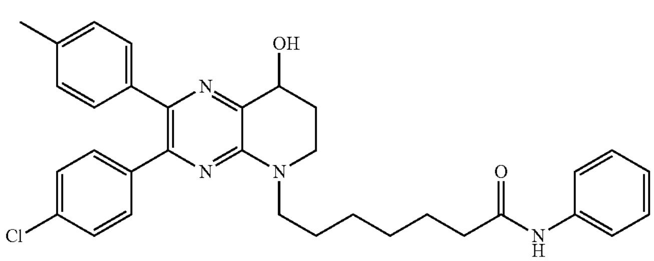 [SMILES: Cc1ccc(-c2nc3c(nc2-c2ccc(Cl)cc2)N(CCCCCCC(=O)Nc2ccccc2)CCC3O)cc1] | 7-(3-(4-chlorophenyl)-8-hydroxy-2-(p-tolyl)-7,8-dihydropyrido[2,3-b]pyrazin-5(6H)-yl)-N-phenylheptanamide |
| 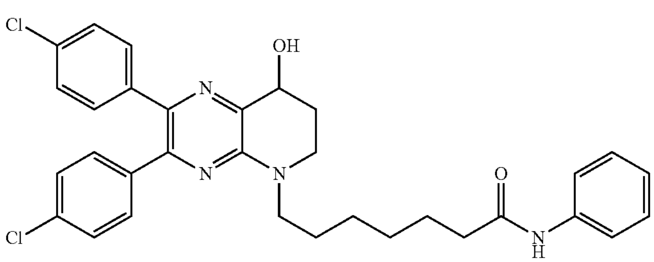 [SMILES: O=C(CCCCCCN1CCC(O)c2nc(-c3ccc(Cl)cc3)c(-c3ccc(Cl)cc3)nc21)Nc1ccccc1] | 7-(2,3-bis(4-chlorophenyl)-8-hydroxy-7,8-dihydropyrido[2,3-b]pyrazin-5(6H)-yl)-N-phenylheptanamide |

| Structure | Name |
|---|---|
| 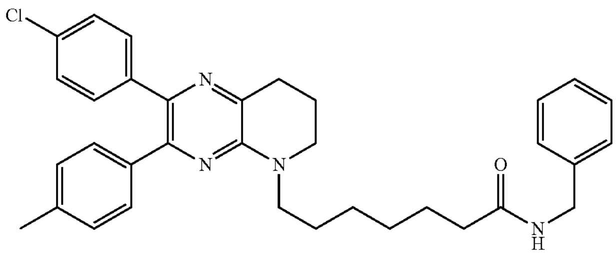 [SMILES: Cc1ccc(-c2nc3c(nc2-c2ccc(Cl)cc2)CCCN3CCCCCCC(=O)NCc2ccccc2)cc1] | N-benzyl-7-(2-(4-chlorophenyl)-3-(p-tolyl)-7,8-dihydropyrido[2,3-b]pyrazin-5(6H)-yl)heptanamide |
| 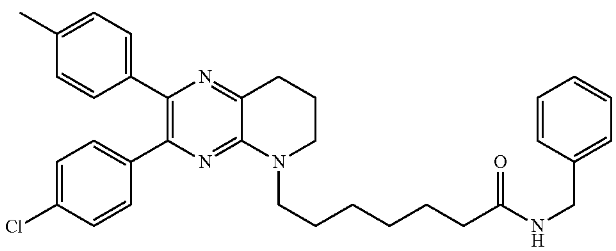 [SMILES: Cc1ccc(-c2nc3c(nc2-c2ccc(Cl)cc2)N(CCCCCCC(=O)NCc2ccccc2)CCC3)cc1] | N-benzyl-7-(3-(4-chlorophenyl)-2-(p-tolyl)-7,8-dihydropyrido[2,3-b]pyrazin-5(6H)-yl)heptanamide |
| 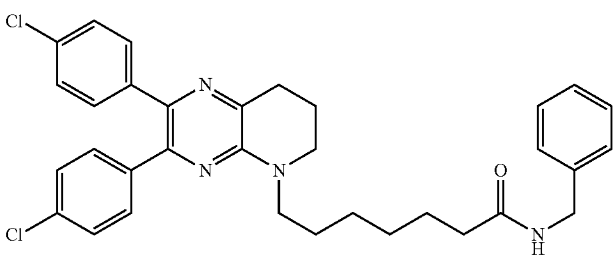 | N-benzyl-7-(2,3-bis(4-chlorophenyl)-7,8-dihydropyrido[2,3-b]pyrazin-5(6H)-yl)heptanamide |
| 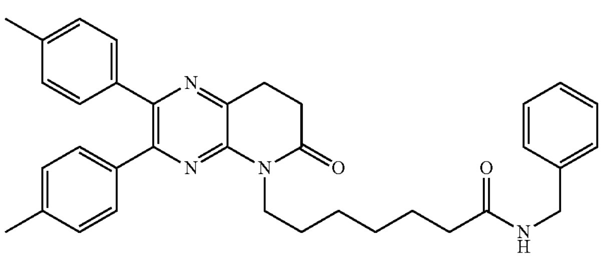 [SMILES: Cc1ccc(-c2nc3c(nc2-c2ccc(C)cc2)N(CCCCCCC(=O)NCc2ccccc2)C(=O)CC3)cc1] | N-benzyl-7-(6-oxo-2,3-di-p-tolyl-7,8-dihydropyrido[2,3-b]pyrazin-5(6H)-yl)heptanamide |
| 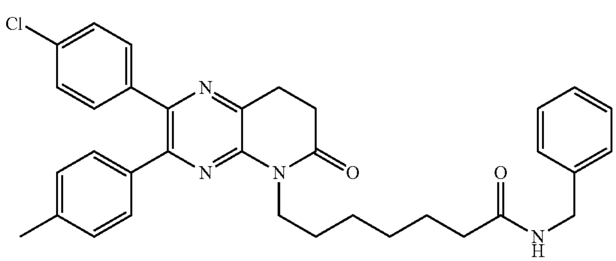 [SMILES: Cc1ccc(-c2nc3c(nc2-c2ccc(Cl)cc2)CCC(=O)N3CCCCCCC(=O)NCc2ccccc2)cc1] | N-benzyl-7-(2-(4-chlorophenyl)-6-oxo-3-(p-tolyl)-7,8-dihydropyrido[2,3-b]pyrazin-5(6H)-yl)heptanamide |
| 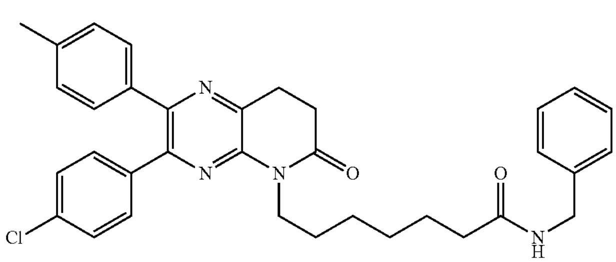 [SMILES: Cc1ccc(-c2nc3c(nc2-c2ccc(Cl)cc2)N(CCCCCCC(=O)NCc2ccccc2)C(=O)CC3)cc1] | N-benzyl-7-(3-(4-chlorophenyl)-6-oxo-2-(p-tolyl)-7,8-dihydropyrido[2,3-b]pyrazin-5(6H)-yl)heptanamide |

| Structure | Name |
|---|---|
| 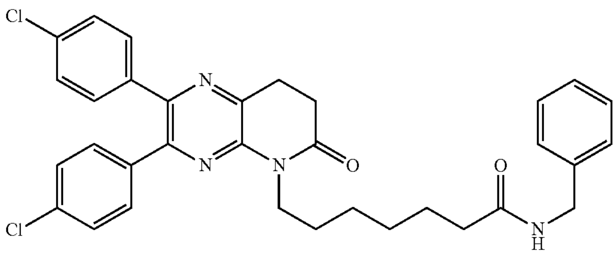 [SMILES: O=C(CCCCCCN1C(=O)CCc2nc(-c3ccc(Cl)cc3)c(-c3ccc(Cl)cc3)nc21)NCc1ccccc1] | N-benzyl-7-(2,3-bis(4-chlorophenyl)-6-oxo-7,8-dihydropyrido[2,3-b]pyrazin-5(6H)-yl)heptanamide |
| 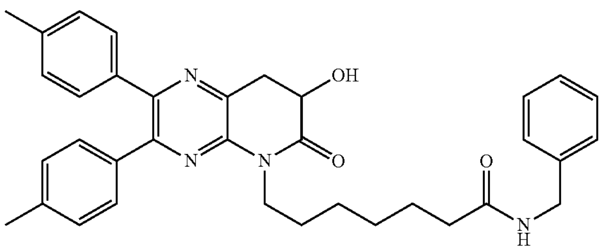 [SMILES: Cc1ccc(-c2nc3c(nc2-c2ccc(C)cc2)N(CCCCCCC(=O)NCc2ccccc2)C(=O)C(O)C3)cc1] | N-benzyl-7-(7-hydroxy-6-oxo-2,3-di-p-tolyl-7,8-dihydropyrido[2,3-b]pyrazin-5(6H)-yl)heptanamide |
| 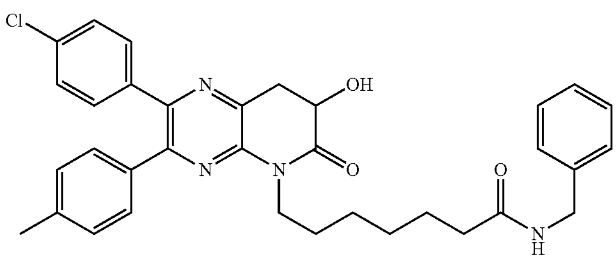 [SMILES: Cc1ccc(-c2nc3c(nc2-c2ccc(Cl)cc2)CC(O)C(=O)N3CCCCCCC(=O)NCc2ccccc2)cc1] | N-benzyl-7-(2-(4-chlorophenyl)-7-hydroxy-6-oxo-3-(p-tolyl)-7,8-dihydropyrido[2,3-b]pyrazin-5(6H)-yl)heptanamide |
| 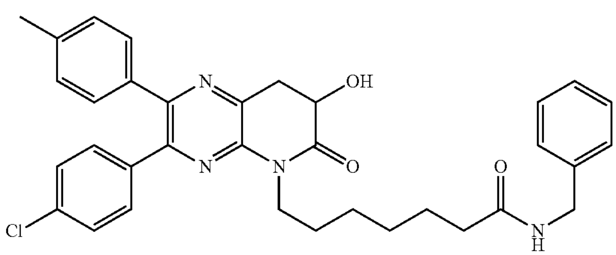 [SMILES: Cc1ccc(-c2nc3c(nc2-c2ccc(Cl)cc2)N(CCCCCCC(=O)NCc2ccccc2)C(=O)C(O)C3)cc1] | N-benzyl-7-(3-(4-chlorophenyl)-7-hydroxy-6-oxo-2-(p-tolyl)-7,8-dihydropyrido[2,3-b]pyrazin-5(6H)-yl)heptanamide |
| 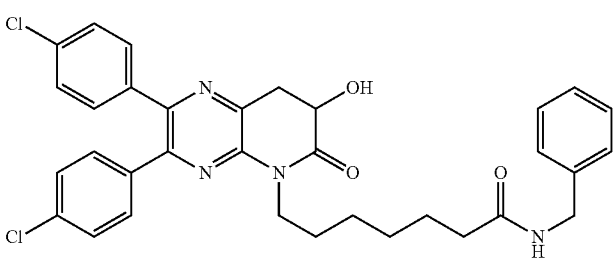 [SMILES: O=C(CCCCCCN1C(=O)C(O)Cc2nc(-c3ccc(Cl)cc3)c(-c3ccc(Cl)cc3)nc21)NCc1ccccc1] | N-benzyl-7-(2,3-bis(4-chlorophenyl)-7-hydroxy-6-oxo-7,8-dihydropyrido[2,3-b]pyrazin-5(6H)-yl)heptanamide |
| 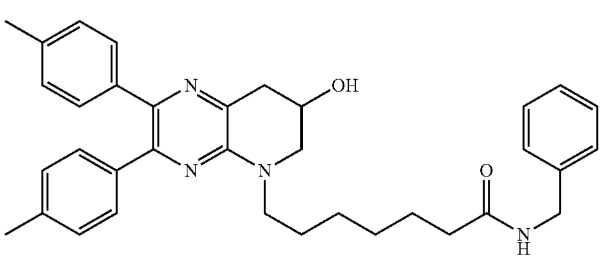 [SMILES: Cc1ccc(-c2nc3c(nc2-c2ccc(C)cc2)N(CCCCCCC(=O)NCc2ccccc2)CC(O)C3)cc1] | N-benzyl-7-(7-hydroxy-2,3-di-p-tolyl-7,8-dihydropyrido[2,3-b]pyrazin-5(6H)-yl)heptanamide |

| Structure | Name |
|---|---|
| 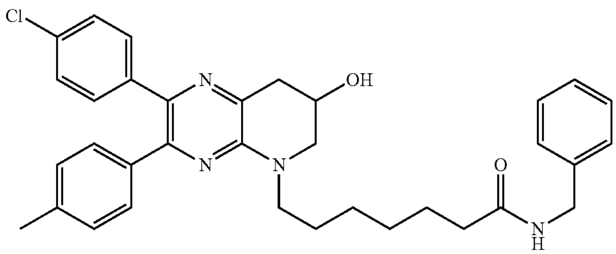 [SMILES: Cc1ccc(-c2nc3c(nc2-c2ccc(Cl)cc2)CC(O)CN3CCCCCCC(=O)NCc2ccccc2)cc1] | N-benzyl-7-(2-(4-chlorophenyl)-7-hydroxy-3-(p-tolyl)-7,8-dihydropyrido[2,3-b]pyrazin-5(6H)-yl)heptanamide |
| 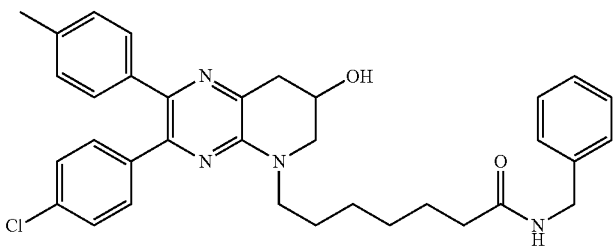 [SMILES: Cc1ccc(-c2nc3c(nc2-c2ccc(Cl)cc2)N(CCCCCCC(=O)NCc2ccccc2)CC(O)C3)cc1] | N-benzyl-7-(3-(4-chlorophenyl)-7-hydroxy-2-(p-tolyl)-7,8-dihydropyrido[2,3-b]pyrazin-5(6H)-yl)heptanamide |
| 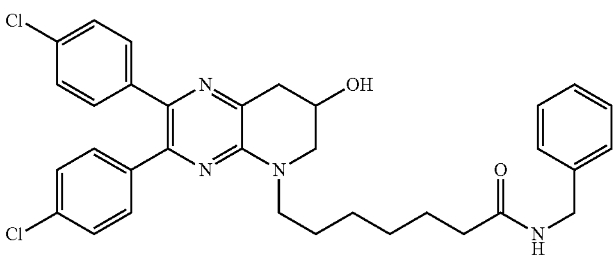 [SMILES: O=C(CCCCCCN1CC(O)Cc2nc(-c3ccc(Cl)cc3)c(-c3ccc(Cl)cc3)nc21)NCc1ccccc1] | N-benzyl-7-(2,3-bis(4-chlorophenyl)-7-hydroxy-7,8-dihydropyrido[2,3-b]pyrazin-5(6H)-yl)heptanamide |
| 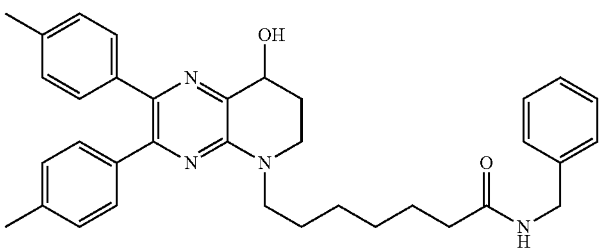 [SMILES: Cc1ccc(-c2nc3c(nc2-c2ccc(C)cc2)N(CCCCCCC(=O)NCc2ccccc2)CCC3O)cc1] | N-benzyl-7-(8-hydroxy-2,3-di-p-tolyl-7,8-dihydropyrido[2,3-b]pyrazin-5(6H)-yl)heptanamide |
| 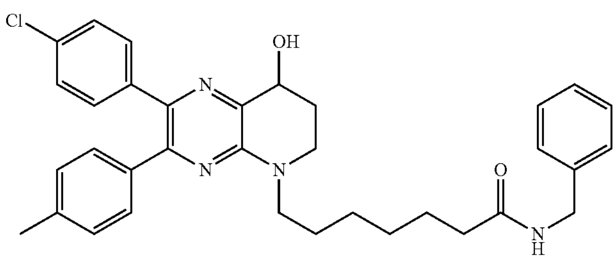 [SMILES: Cc1ccc(-c2nc3c(nc2-c2ccc(Cl)cc2)C(O)CCN3CCCCCCC(=O)NCc2ccccc2)cc1] | N-benzyl-7-(2-(4-chlorophenyl)-8-hydroxy-3-(p-tolyl)-7,8-dihydropyrido[2,3-b]pyrazin-5(6H)-yl)heptanamide |
| 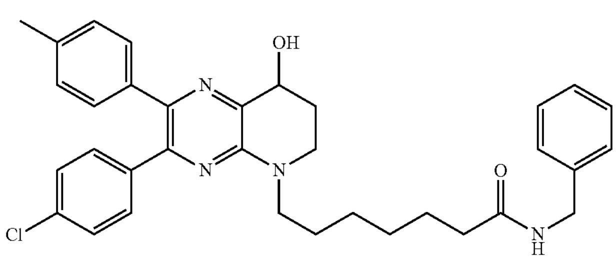 [SMILES: Cc1ccc(-c2nc3c(nc2-c2ccc(Cl)cc2)N(CCCCCCC(=O)NCc2ccccc2)CCC3O)cc1] | N-benzyl-7-(3-(4-chlorophenyl)-8-hydroxy-2-(p-tolyl)-7,8-dihydropyrido[2,3-b]pyrazin-5(6H)-yl)heptanamide |

-continued

| Structure | Name |
|---|---|
| 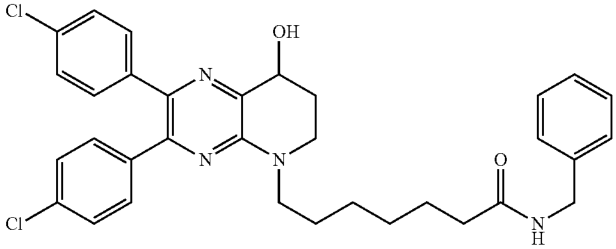 | N-benzyl-7-(2,3-bis(4-chlorophenyl)-8-hydroxy-7,8-dihydropyrido[2,3-b]pyrazin-5(6H)-yl)heptanamide |
| 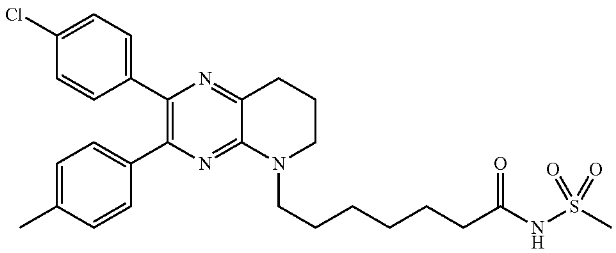 [SMILES: Cc1ccc(-c2nc3c(nc2-c2ccc(Cl)cc2)CCCN3CCCCCCC(=O)NS(C)(=O)=O)cc1] | 7-(2-(4-chlorophenyl)-3-(p-tolyl)-7,8-dihydropyrido[2,3-b]pyrazin-5(6H)-yl)-N-(methylsulfonyl)heptanamide |
| 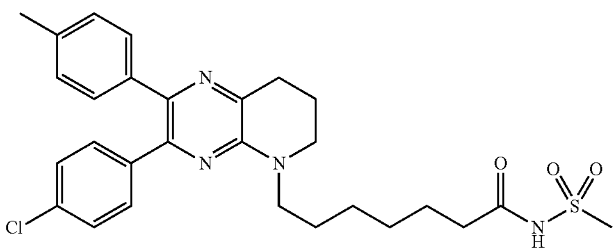 | 7-(3-(4-chlorophenyl)-2-(p-tolyl)-7,8-dihydropyrido[2,3-b]pyrazin-5(6H)-yl)-N-(methylsulfonyl)heptanamide |
| 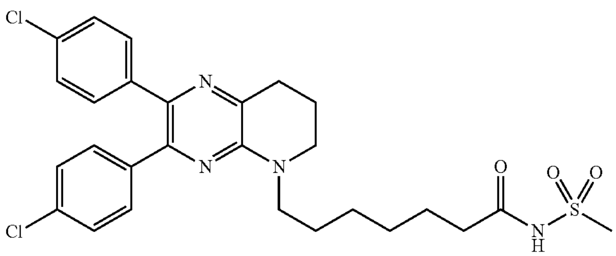 [SMILES: CS(=O)(=O)NC(=O)CCCCCCN1CCCc2nc(-c3ccc(Cl)cc3)c(-c3ccc(Cl)cc3)nc21] | 7-(2,3-bis(4-chlorophenyl)-7,8-dihydropyrido[2,3-b]pyrazin-5(6H)-yl)-N-(methylsulfonyl)heptanamide |
| 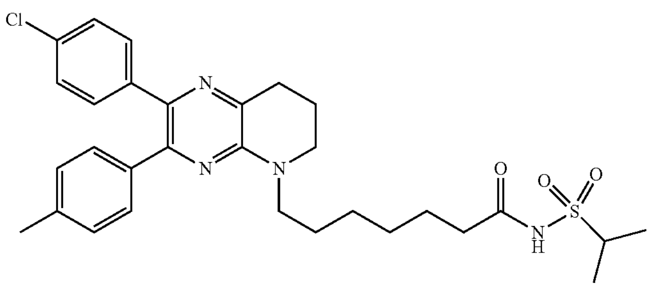 [SMILES: Cc1ccc(-c2nc3c(nc2-c2ccc(Cl)cc2)CCCN3CCCCCCC(=O)NS(=O)(=O)C(C)C)cc1] | 7-(2-(4-chlorophenyl)-3-(p-tolyl)-7,8-dihydropyrido[2,3-b]pyrazin-5(6H)-yl)-N-(isopropylsulfonyl)heptanamide |
| 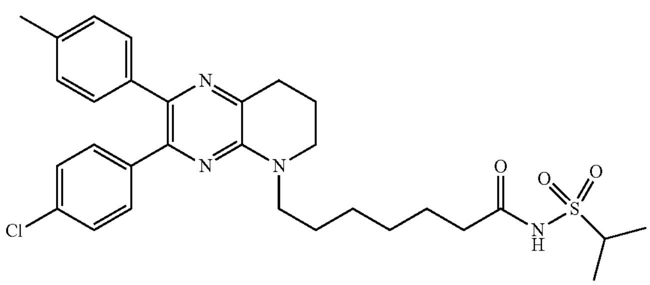 [SMILES: Cc1ccc(-c2nc3c(nc2-c2ccc(Cl)cc2)N(CCCCCCC(=O)NS(=O)(=O)C(C)C)CCC3)cc1] | 7-(3-(4-chlorophenyl)-2-(p-tolyl)-7,8-dihydropyrido[2,3-b]pyrazin-5(6H)-yl)-N-(isopropylsulfonyl)heptanamide |

| Structure | Name |
|---|---|
| 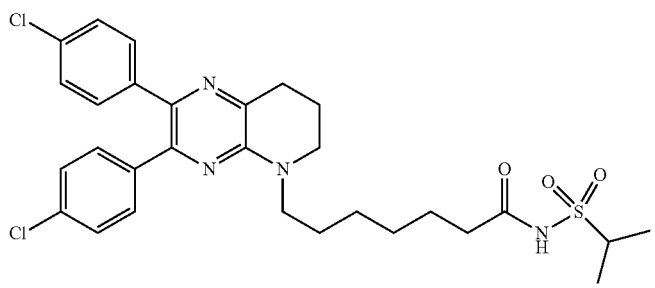 [SMILES: CC(C)S(=O)(=O)NC(=O)CCCCCCN1CCCc2nc(-c3ccc(Cl)cc3)c(-c3ccc(Cl)cc3)nc21] | 7-(2,3-bis(4-chlorophenyl) 7,8-dihydropyrido[2,3-b]pyrazin-5(6H)-yl)-N-(isopropylsulfonyl)heptanamide |
| 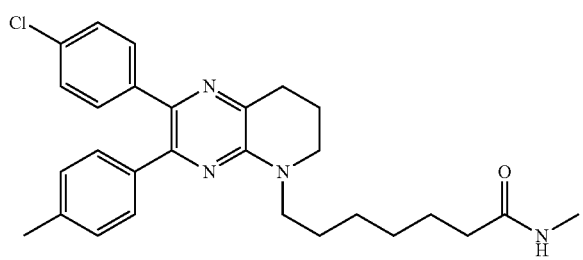 [SMILES: CNC(=O)CCCCCCN1CCCc2nc(-c3ccc(Cl)cc3)c(-c3ccc(C)cc3)nc21] | 7-(2-(4-chlorophenyl)-3-(p-tolyl)-7,8-dihydropyrido[2,3-b]pyrazin-5(6H)-yl)-N-methylheptanamide |
| 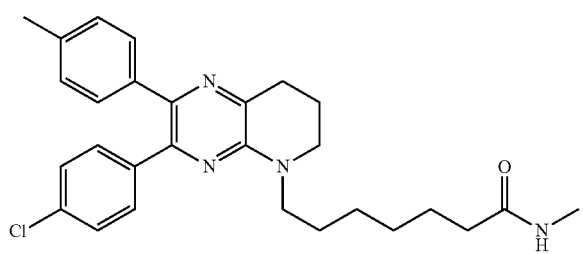 | 7-(3-(4-chlorophenyl)-2-(p-tolyl)-7,8-dihydropyrido[2,3-b]pyrazin-5(6H)-yl)-N-methylheptanamide |
| 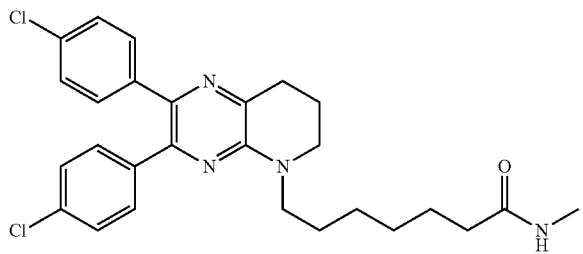 [SMILES: CNC(=O)CCCCCCN1CCCc2nc(-c3ccc(Cl)cc3)c(-c3ccc(Cl)cc3)nc21] | 7-(2,3-bis(4-chlorophenyl)-7,8-dihydropyrido[2,3-b]pyrazin-5(6H)-yl)-N-methylheptanamide |
| 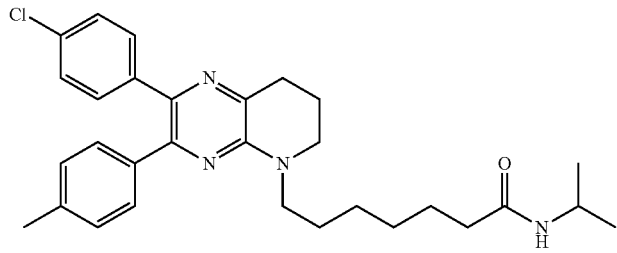 [SMILES: Cc1ccc(-c2nc3c(nc2-c2ccc(Cl)cc2)CCCN3CCCCCCC(=O)NC(C)C)cc1] | 7-(2-(4-chlorophenyl)-3-(p-tolyl)-7,8-dihydropyrido[2,3-b]pyrazin-5(6H)-yl)-N-isopropylheptanamide |
| 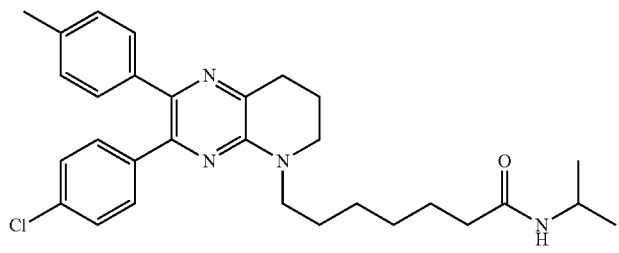 [SMILES: Cc1ccc(-c2nc3c(nc2-c2ccc(Cl)cc2)N(CCCCCCC(=O)NC(C)C)CCC3)cc1] | 7-(3-(4-chlorophenyl)-2-(p-tolyl)-7,8-dihydropyrido[2,3-b]pyrazin-5(6H)-yl)-N-isopropylheptanamide |

| Structure | Name |
|---|---|
| 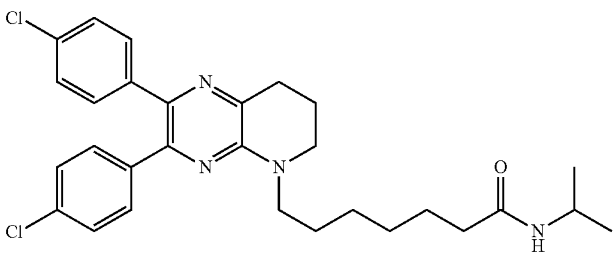 [SMILES: CC(C)NC(=O)CCCCCCN1CCCc2nc(-c3ccc(Cl)cc3)c(-c3ccc(Cl)cc3)nc21] | 7-(2,3-bis(4-chlorophenyl)-7,8-dihydropyrido[2,3-b]pyrazin-5(6H)-yl)-N-isopropylheptanamide |
| 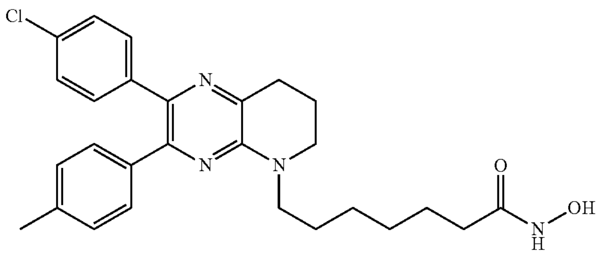 [SMILES: Cc1ccc(-c2nc3c(nc2-c2ccc(Cl)cc2)CCCN3CCCCCCC(=O)NO)cc1] | 7-(2-(4-chlorophenyl)-3-(p-tolyl)-7,8-dihydropyrido[2,3-b]pyrazin-5(6H)-yl)-N-hydroxyheptanamide |
| 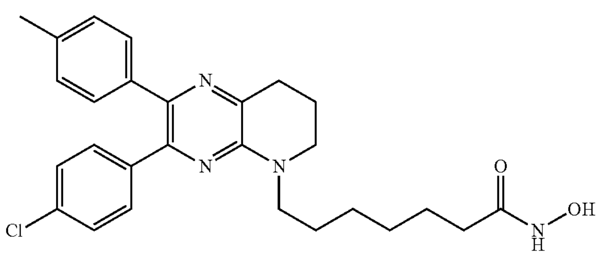 [SMILES: Cc1ccc(-c2nc3c(nc2-c2ccc(Cl)cc2)N(CCCCCCC(=O)NO)CCC3)cc1] | 7-(3-(4-chlorophenyl)-2-(p-tolyl)-7,8-dihydropyrido[2,3-b]pyrazin-5(6H)-yl)-N-hydroxyheptanamide |
| 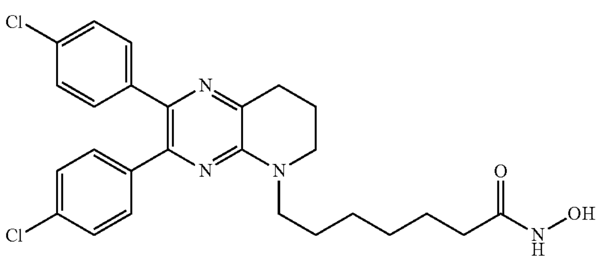 [SMILES: O=C(CCCCCCN1CCCc2nc(-c3ccc(Cl)cc3)c(-c3ccc(Cl)cc3)nc21)NO] | 7-(2,3-bis(4-chlorophenyl)-7,8-dihydropyrido[2,3-b]pyrazin-5(6H)-yl)-N-hydroxyheptanamide |
| 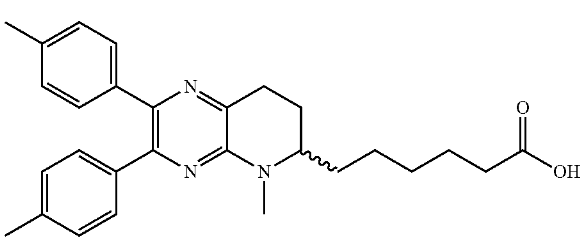 [SMILES: Cc1ccc(-c2nc3c(nc2-c2ccc(C)cc2)N(C)C(CCCCCC(=O)O)CC3)cc1] | 6-(5-methyl-2,3-di-p-tolyl-5,6,7,8-tetrahydropyrido[2,3-b]pyrazin-6-yl)hexanoic acid |
| 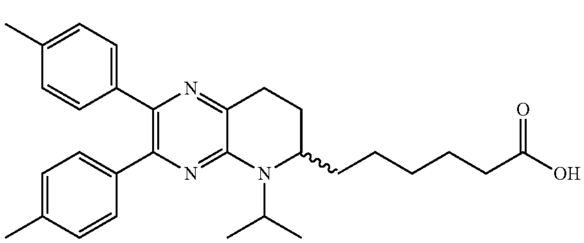 [SMILES: Cc1ccc(-c2nc3c(nc2-c2ccc(C)cc2)N(C(C)C)C(CCCCCC(=O)O)CC3)cc1] | 6-(5-isopropyl-2,3-di-p-tolyl-5,6,7,8-tetrahydropyrido[2,3-b]pyrazin-6-yl)hexanoic acid |

-continued

| Structure | Name |
|---|---|
| 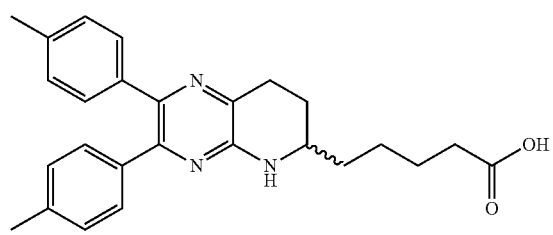 | 5-(2,3-di-p-tolyl-5,6,7,8-tetrahydropyrido[2,3-b]pyrazin-6-yl)pentanoic acid |
| 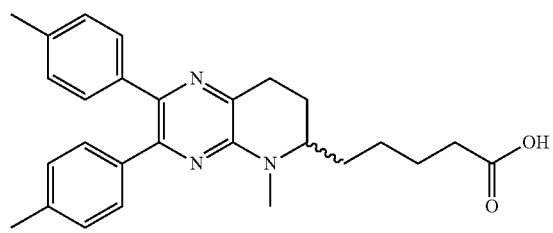 [SMILES: Cc1ccc(-c2nc3c(nc2-c2ccc(C)cc2)N(C)C(CCCCC(=O)O)CC3)cc1] | 5-(5-methyl-2,3-di-p-tolyl-5,6,7,8-tetrahydropyrido[2,3-b]pyrazin-6-yl)pentanoic acid |
| 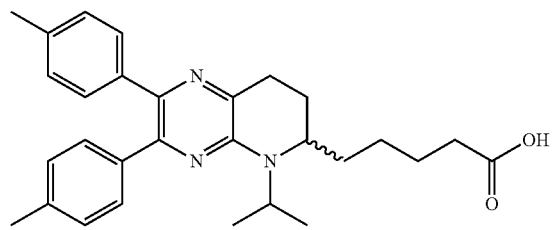 [SMILES: Cc1ccc(-c2nc3c(nc2-c2ccc(C)cc2)N(C(C)C)C(CCCCC(=O)O)CC3)cc1] | 5-(5-isopropyl-2,3-di-p-tolyl-5,6,7,8-tetrahydropyrido[2,3-b]pyrazin-6-yl)pentanoic acid |
| 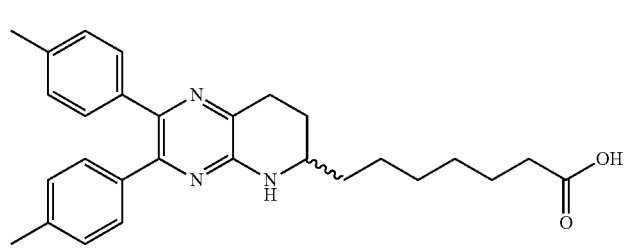 [SMILES: Cc1ccc(-c2nc3c(nc2-c2ccc(C)cc2)NC(CCCCCCC(=O)O)CC3)cc1] | 7-(2,3-di-p-tolyl-5,6,7,8-tetrahydropyrido[2,3-b]pyrazin-6-yl)heptanoic acid |
| 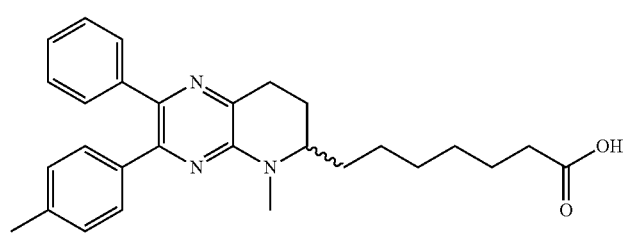 [SMILES: Cc1ccc(-c2nc3c(nc2-c2ccccc2)CCC(CCCCCCC(=O)O)N3C)cc1] | 7-(5-methyl-2-phenyl-3-(p-tolyl)-5,6,7,8-tetrahydropyrido[2,3-b]pyrazin-6-yl)heptanoic acid |
| 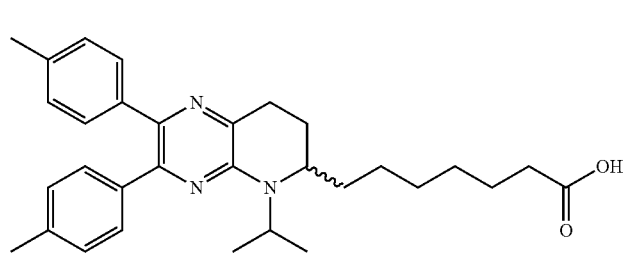 [SMILES: Cc1ccc(-c2nc3c(nc2-c2ccc(C)cc2)N(C(C)C)C(CCCCCCC(=O)O)CC3)cc1] | 7-(5-isopropyl-2,3-di-p-tolyl-5,6,7,8-tetrahydropyrido[2,3-b]pyrazin-6-yl)heptanoic acid |

| Structure | Name |
|---|---|
| 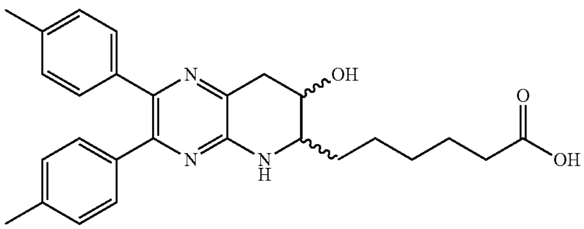 [SMILES: Cc1ccc(-c2nc3c(nc2-c2ccc(C)cc2)NC(CCCCCC(=O)O)C(O)C3)cc1] | 6-(7-hydroxy-2,3-di-p-tolyl-5,6,7,8-tetrahydropyrido[2,3-b]pyrazin-6-yl)hexanoic acid |
| 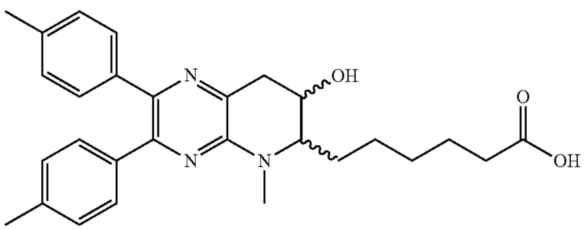 [SMILES: Cc1ccc(-c2nc3c(nc2-c2ccc(C)cc2)N(C)C(CCCCCC(=O)O)C(O)C3)cc1] | 6-(7-hydroxy-5-methyl-2,3-di-p-tolyl-5,6,7,8-tetrahydropyrido[2,3-b]pyrazin-6-yl)hexanoic acid |
| 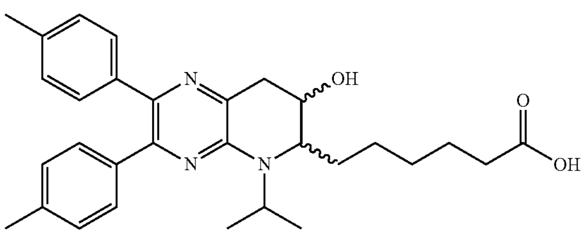 [SMILES: Cc1ccc(-c2nc3c(nc2-c2ccc(C)cc2)N(C(C)C)C(CCCCCC(=O)O)C(O)C3)cc1] | 6-(7-hydroxy-5-isopropyl-2,3-di-p-tolyl-5,6,7,8-tetrahydropyrido[2,3-b]pyrazin-6-yl)hexanoic acid |
| 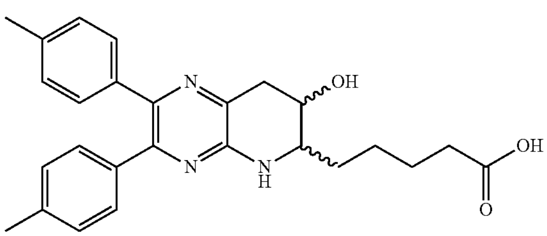 [SMILES: Cc1ccc(-c2nc3c(nc2-c2ccc(C)cc2)NC(CCCCC(=O)O)C(O)C3)cc1] | 5-(7-hydroxy-2,3-di-p-tolyl-5,6,7,8-tetrahydropyrido[2,3-b]pyrazin-6-yl)pentanoic acid |
| 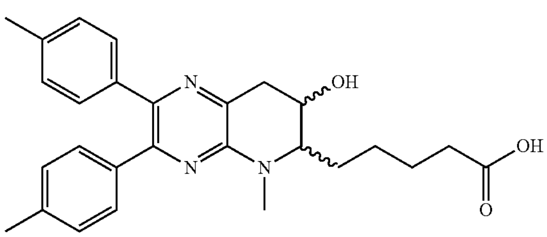 [SMILES: Cc1ccc(-c2nc3c(nc2-c2ccc(C)cc2)N(C)C(CCCCC(=O)O)C(O)C3)cc1] | 5-(7-hydroxy-5-methyl-2,3-di-p-tolyl-5,6,7,8-tetrahydropyrido[2,3-b]pyrazin-6-yl)pentanoic acid |
| 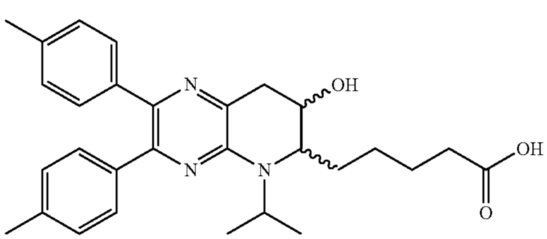 [SMILES: Cc1ccc(-c2nc3c(nc2-c2ccc(C)cc2)N(C(C)C)C(CCCCC(=O)O)C(O)C3)cc1] | 5-(7-hydroxy-5-isopropyl-2,3-di-p-tolyl-5,6,7,8-tetrahydropyrido[2,3-b]pyrazin-6-yl)pentanoic acid |

| Structure | Name |
|---|---|
| 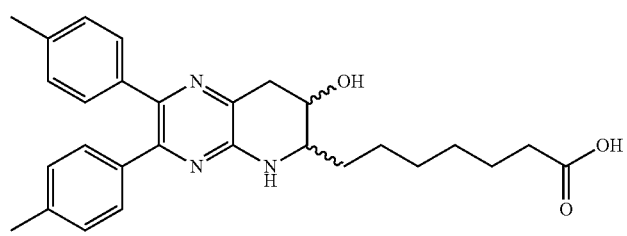 [SMILES: Cc1ccc(-c2nc3c(nc2-c2ccc(C)cc2)NC(CCCCCCC(=O)O)C(O)C3)cc1] | 7-(7-hydroxy-2,3-di-p-tolyl-5,6,7,8-tetrahydropyrido[2,3-b]pyrazin-6-yl)heptanoic acid |
| 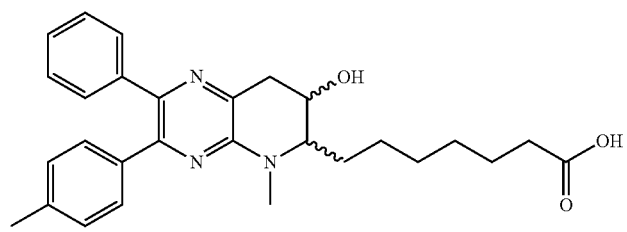 [SMILES: Cc1ccc(-c2nc3c(nc2-c2ccccc2)CC(O)C(CCCCCCC(=O)O)N3C)cc1] | 7-(7-hydroxy-5-methyl-2-phenyl-3-(p-tolyl)-5,6,7,8-tetrahydropyrido[2,3-b]pyrazin-6-yl)heptanoic acid |
| 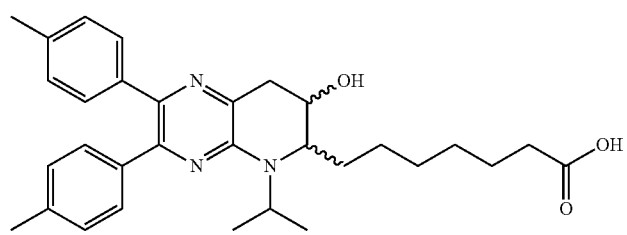 [SMILES: Cc1ccc(-c2nc3c(nc2-c2ccc(C)cc2)N(C(C)C)C(CCCCCCC(=O)O)C(O)C3)cc1] | 7-(7-hydroxy-5-isopropyl-2,3-di-p-tolyl-5,6,7,8-tetrahydropyrido[2,3-b]pyrazin-6-yl)heptanoic acid |
| 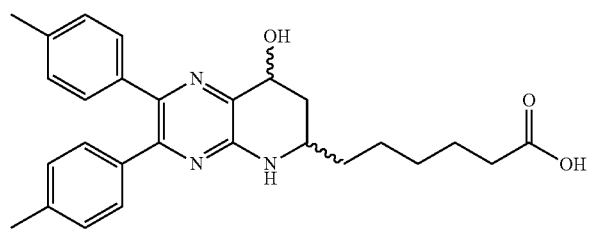 | 6-(8-hydroxy-2,3-di-p-tolyl-5,6,7,8-tetrahydropyrido[2,3-b]pyrazin-6-yl)hexanoic acid |
| 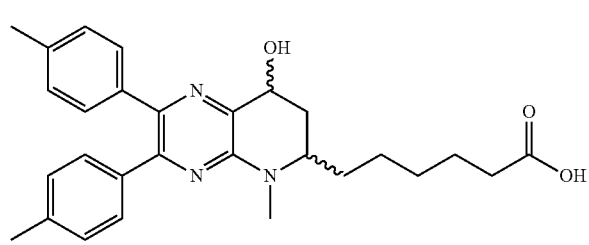 [SMILES: Cc1ccc(-c2nc3c(nc2-c2ccc(C)cc2)N(C)C(CCCCCC(=O)O)CC3O)cc1] | 6-(8-hydroxy-5-methyl-2,3-di-p-tolyl-5,6,7,8-tetrahydropyrido[2,3-b]pyrazin-6-yl)hexanoic acid |
| 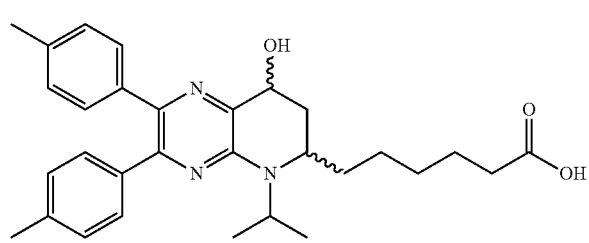 [SMILES: Cc1ccc(-c2nc3c(nc2-c2ccc(C)cc2)N(C(C)C)C(CCCCCC(=O)O)CC3O)cc1] | 6-(8-hydroxy-5-isopropyl-2,3-di-p-tolyl-5,6,7,8-tetrahydropyrido[2,3-b]pyrazin-6-yl)hexanoic acid |

| Structure | Name |
|---|---|
| 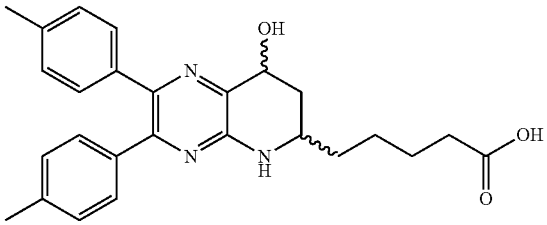 [SMILES: Cc1ccc(-c2nc3c(nc2-c2ccc(C)cc2)C(O)CC(CCCCC(=O)O)N3)cc1] | 5-(8-hydroxy-2,3-di-p-tolyl-5,6,7,8-tetrahydropyrido[2,3-b]pyrazin-6-yl)pentanoic acid |
| 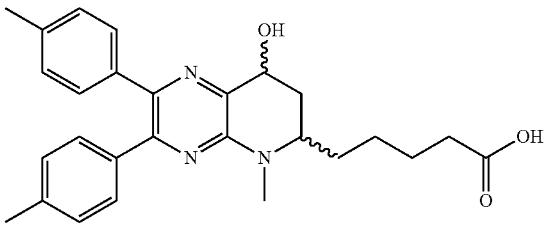 [SMILES: Cc1ccc(-c2nc3c(nc2-c2ccc(C)cc2)N(C)C(CCCCC(=O)O)CC3O)cc1] | 5-(8-hydroxy-5-methyl-2,3-di-p-tolyl-5,6,7,8-tetrahydropyrido[2,3-b]pyrazin-6-yl)pentanoic acid |
| 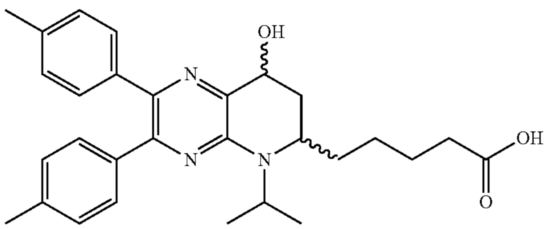 [SMILES: Cc1ccc(-c2nc3c(nc2-c2ccc(C)cc2)N(C(C)C)C(CCCCC(=O)O)CC3O)cc1] | 5-(8-hydroxy-5-isopropyl-2,3-di-p-tolyl-5,6,7,8-tetrahydropyrido[2,3-b]pyrazin-6-yl)pentanoic acid |
| 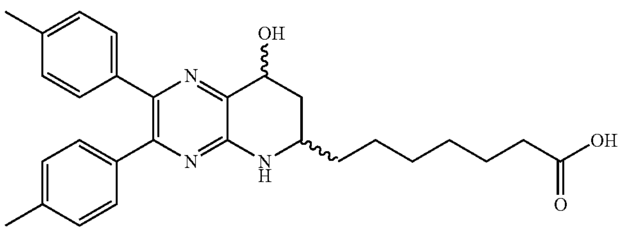 | 7-(8-hydroxy-2,3-di-p-tolyl-5,6,7,8-tetrahydropyrido[2,3-b]pyrazin-6-yl)heptanoic acid |
| 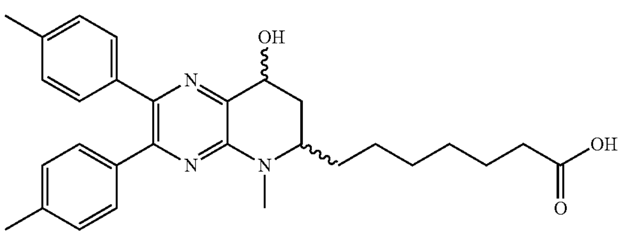 [SMILES: Cc1ccc(-c2nc3c(nc2-c2ccc(C)cc2)N(C)C(CCCCCCC(=O)O)CC3O)cc1] | 7-(8-hydroxy-5-methyl-2,3-di-p-tolyl-5,6,7,8-tetrahydropyrido[2,3-b]pyrazin-6-yl)heptanoic acid |
| 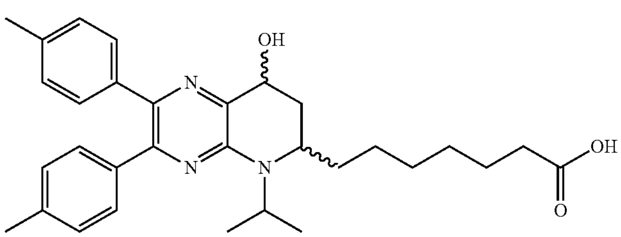 [SMILES: Cc1ccc(-c2nc3c(nc2-c2ccc(C)cc2)N(C(C)C)C(CCCCCCC(=O)O)CC3O)cc1] | 7-(8-hydroxy-5-isopropyl-2,3-di-p-tolyl-5,6,7,8-tetrahydropyrido[2,3-b]pyrazin-6-yl)heptanoic acid |

The invention claimed is:
1. A compound selected from the group consisting of
(rac)-6-(2,3-di-p-tolyl-5,6,7,8-tetrahydropyrido[2,3-b]pyrazin-6-yl)hexanoic acid;
(S)-6-(2,3-di-p-tolyl-5,6,7,8-tetrahydropyrido[2,3-b]pyrazin-6-yl)hexanoic acid;
(R)-6-(2,3-di-p-tolyl-5,6,7,8-tetrahydropyrido[2,3-b]pyrazin-6-yl)hexanoic acid
(rac)-7-(7-(2-Hydroxypropan-2-yl)-6-oxo-2,3-di-p-tolyl-7,8-dihydropyrido[2,3-b]pyrazin-5(6H)-yl)heptanoic acid;
(R)-7-(7-(2-hydroxypropan-2-yl)-6-oxo-2,3-di-p-tolyl-7,8-dihydropyrido[2,3-b]pyrazin-5(6H)-yl)heptanoic acid;
(S)-7-(7-(2-hydroxypropan-2-yl)-6-oxo-2,3-di-p-tolyl-7,8-dihydropyrido[2,3-b]pyrazin-5(6H)-yl)heptanoic acid;
7-(7-Ethyl-2,3-di-p-tolyl-7,8-dihydropyrido[2,3-b]pyrazin-5(6H)-yl)heptanoic acid;
7-(7-Methyl-2-phenyl-3-(p-tolyl)-7,8-dihydropyrido[2,3-b]pyrazin-5(6H)-yl)heptanoic acid;
(rac)-7-(6-Ethyl-2,3-di-p-tolyl-7,8-dihydropyrido[2,3-b]pyrazin-5(6H)-yl)heptanoic acid;
(R)-7-(6-Ethyl-2,3-di-p-tolyl-7,8-dihydropyrido[2,3-b]pyrazin-5(6H)-yl)heptanoic acid;
(S)-7-(6-Ethyl-2,3-di-p-tolyl-7,8-dihydropyrido[2,3-b]pyrazin-5(6H)-yl)heptanoic acid;
7-(6-Methyl-2-phenyl-3-p-tolyl-7,8-dihydropyrido[2,3-b]pyrazin-5(6H)-yl)heptanoic acid;
7-(3-o-Tolyl-2-p-tolyl-7,8-dihydropyrido[3,2-b]pyrazin-5(6H)-yl)heptanoic acid;
7-(2-o-Tolyl-3-p-tolyl-7,8-dihydropyrido[3,2-b]pyrazin-5(6H)-yl)heptanoic acid;
7-(2-(2-Fluorophenyl)-3-p-tolyl-7,8-dihydropyrido[2,3-b]pyrazin-5(6H)-yl)heptanoic acid;
7-(2-(4-Fluorophenyl)-3-p-tolyl-7,8-dihydropyrido[2,3-b]pyrazin-5(6H)-yl)heptanoic acid;
7-(2-(3-Fluorophenyl)-3-p-tolyl-7,8-dihydropyrido[2,3-b]pyrazin-5(6H)-yl)heptanoic acid;
7-(2-(4-Methoxyphenyl)-3-p-tolyl-7,8-dihydropyrido[2,3-b]pyrazin-5(6H)-yl)heptanoic acid;
(rac)-7-(8-Methoxy-2,3-di-p-tolyl-7,8-dihydropyrido[2,3-b]pyrazin-5(6H)-yl)heptanoic acid;
(R)-7-(8-methoxy-2,3-di-p-tolyl-7,8-dihydropyrido[2,3-b]pyrazin-5(6H)-yl)heptanoic acid;
(S)-7-(8-methoxy-2,3-di-p-tolyl-7,8-dihydropyrido[2,3-b]pyrazin-5(6H)-yl)heptanoic acid;
7-(2,3-Bis(2,4-difluorophenyl)-7,8-dihydropyrido[2,3-b]pyrazin-5(6H)-yl)heptanoic acid;
7-(2,3-Bis(6-methylpyridin-3-yl)-7,8-dihydropyrido[2,3-b]pyrazin-5(6H)-yl)heptanoic acid;
7-(2-(6-Methylpyridin-3-yl)-3-p-tolyl-7,8-dihydropyrido[2,3-b]pyrazin-5(6H)-yl)heptanoic acid;
7-(3-(6-Methylpyridin-3-yl)-2-p-tolyl-7,8-dihydropyrido[2,3-b]pyrazin-5(6H)-yl)heptanoic acid;
9-(6-Oxo-2,3-di-p-tolyl-7,8-dihydropyrido[2,3-b]pyrazin-5(6H)-yl)nonanoic acid;
9-(2,3-Di-p-tolyl-7,8-dihydropyrido[2,3-b]pyrazin-5(6H)-yl)nonanoic acid;
(rac)-7-(7-(2-hydroxypropan-2-yl)-2,3-di-p-tolyl-7,8-dihydropyrido[2,3-b]pyrazin-5(6H)-yl)heptanoic acid;
(R)-7-(7-(2-hydroxypropan-2-yl)-2,3-di-p-tolyl-7,8-dihydropyrido[2,3-b]pyrazin-5(6H)-yl)heptanoic acid;
(S)-7-(7-(2-hydroxypropan-2-yl)-2,3-di-p-tolyl-7,8-dihydropyrido[2,3-b]pyrazin-5(6H)-yl)heptanoic acid;
6-(2,3-Di-p-tolyl-7,8-dihydropyrido[2,3-b]pyrazin-5(6H)-yl)hexanoic acid;
(R)-7-(7-hydroxy-6-oxo-2,3-di-p-tolyl-7,8-dihydropyrido[2,3-b]pyrazin-5(6H)-yl)heptanoic acid;
(S)-7-(7-hydroxy-6-oxo-2,3-di-p-tolyl-7,8-dihydropyrido[2,3-b]pyrazin-5(6H)-yl)heptanoic acid;
8-(6-Oxo-2,3-di-p-tolyl-7,8-dihydropyrido[2,3-b]pyrazin-5(6H)-yl)octanoic acid;
7-(2,3-Di-p-tolyl-7,8-dihydropyrido[2,3-b]pyrazin-5(6H)-yl)-N-methoxyheptanamide;
7-(2,3-Di-p-tolyl-7,8-dihydropyrido[2,3-b]pyrazin-5(6H)-yl)-N,N-dimethylheptanamide;
7-(2,3-Di-p-tolyl-7,8-dihydropyrido[2,3-b]pyrazin-5(6H)-yl)-N-hydroxy-N-methylheptanamide;
6-(2,3-Di-p-tolyl-7,8-dihydropyrido[2,3-b]pyrazin-5(6H)-yl)-N-hydroxyhexanamide;
(R)-7-(8-Hydroxy-2,3-di-p-tolyl-7,8-dihydropyrido[3,2-b]pyrazin-5(6H)-yl)-N-(methylsulfonyl)heptanamide;
(S)-7-(8-Hydroxy-2,3-di-p-tolyl-7,8-dihydropyrido[3,2-b]pyrazin-5(6H)-yl)-N-(methylsulfonyl)heptanamide;
(R)—N-(Benzylsulfonyl)-7-(8-hydroxy-2,3-di-p-tolyl-7,8-dihydropyrido[3,2-b]pyrazin-5(6H)-yl)heptanamide;
(S)—N-(Benzylsulfonyl)-7-(8-hydroxy-2,3-di-p-tolyl-7,8-dihydropyrido[3,2-b]pyrazin-5(6H)-yl)heptanamide;
7-(2,3-Di-p-tolyl-7,8-dihydropyrido[2,3-b]pyrazin-5(6H)-yl)-N-(methylsulfonyl)heptanamide;
7-(7-Piperidin-1-yl)-2,3-di-p-tolyl-7,8-dihydropyrido[2,3-b]pyrazin-5(6H)-yl)heptanoic acid;
rac-7-(8-Methoxy-8-methyl-2,3-di-p-tolyl-7,8-dihydropyrido[2,3-b]pyrazin-5(6H)-yl)heptanoic acid;
7-(8-Hydroxy-8-methyl-2,3-di-p-tolyl-7,8-dihydropyrido[2,3-b]pyrazin-5(6H)-yl)heptanoic acid;
rac-7-(2,3-Di-p-tolyl-7,8-dihydropyrido[2,3-b]pyrazin-5(6H)-yl)-3-hydroxyheptanoic acid;
(R)-7-(8-Methoxy-8-methyl-2,3-di-p-tolyl-7,8-dihydropyrido[2,3-b]pyrazin-5(6H)-yl)heptanoic acid;
(S)-7-(8-Methoxy-8-methyl-2,3-di-p-tolyl-7,8-dihydropyrido[2,3-b]pyrazin-5(6H)-yl)heptanoic acid;
(R)-7-(2,3-di-p-tolyl-7,8-dihydropyrido[2,3-b]pyrazin-5(6H)-yl)-3-hydroxyheptanoic acid;
(S)-7-(2,3-di-p-tolyl-7,8-dihydropyrido[2,3-b]pyrazin-5(6H)-yl)-3-hydroxyheptanoic acid;
7-(2,3-Bis(4-chlorophenyl)-6-oxo-7,8-dihydropyrido[2,3-b]pyrazin-5(6H)-yl)heptanoic acid;
7-(2-(4-Chlorophenyl)-6-oxo-3-p-tolyl-7,8-dihydropyrido[2,3-b]pyrazin-5(6H)-yl)heptanoic acid;
7-(3-(4-Chlorophenyl)-6-oxo-2-p-tolyl-7,8-dihydropyrido[2,3-b]pyrazin-5(6H)-yl)heptanoic acid;
N-(Benzylsulfonyl)-7-(2,3-di-p-tolyl-7,8-dihydropyrido[2,3-b]pyrazin-5(6H)-yl)heptanamide;
N-Benzyl-7-(2,3-di-p-tolyl-7,8-dihydro pyrido[2,3-b]pyrazin-5(6H)-yl)heptanamide;
7-(2,3-Di-p-tolyl-7,8-dihydro pyrido[2,3-b]pyrazin-5(6H)-yl)-N-(phenyl sulfonyl)heptanamide;
7-(2,3-Di-p-tolyl-7,8-dihydropyrido[2,3-b]pyrazin-5(6H)-yl)-N-isopropylheptanamide;
7-(2,3-Di-p-tolyl-7,8-dihydropyrido[2,3-b]pyrazin-5(6H)-yl)-N-methylheptanamide;
7-(2,3-Di-p-tolyl-7,8-dihydropyrido[2,3-b]pyrazin-5(6H)-yl)-N-phenylheptanamide;
7-(2,3-Di-p-tolyl-7,8-dihydropyrido[2,3-b]pyrazin-5(6H)-yl)-N-hydroxyheptanamide;
7-(2,3-Di-p-tolyl-7,8-dihydropyrido[2,3-b]pyrazin-5(6H)-yl)-N-(isopropylsulfonyl)heptanamide;
(rac)-7-(7-hydroxy-7-methyl-2,3-di-p-tolyl-7,8-dihydropyrido[2,3-b]pyrazin-5(6H)-yl)heptanoic acid;
(R)-7-(7-hydroxy-7-methyl-2,3-di-p-tolyl-7,8-dihydropyrido[2,3-b]pyrazin-5(6H)-yl)heptanic acid;

(S)-7-(7-hydroxy-7-mehtyl-2,3-di-p-tolyl-7,8-dihydropyrido[2,3-b]pyrazin-5(6H)-yl)heptanix acid;
(rac)-7-(7-(dimethylamino)-2,3-di-p-tolyl-7,8-dihydropyrido[2,3-b]pyrazin-5(6H)-yl)heptanoic acid;
(R)-7-(7-(dimethylamino)-2,3-di-p-tolyl-7,8-dihydropyrido[2,3-b]pyrazin-5(6H)-yl) heptanic acid;
(S)-7-(7-dimethylamino)-2,3-di-p-tolyl-7,8-dihydropyrido[2,3-b]pyrazin-5(6H)-yl)heptanic acid;
7-(3-(4-chlorophenyl)-2-(p-tolyl)-7,8-dihydropyrido[2,3-b]pyrazin-5(6H)-yl)heptanoic acid;
7-(2-(4-chlorophenyl)-3-(p-tolyl)-7,8-dihydropyrido[2,3-b]pyrazin-5(6H)-yl)heptanoic acid;
7-(2,3-bis(4-chlorophenyl)-7,8-dihydropyrido[2,3-b]pyrazin-5(6H)-yl)heptanoic acid;
7-(6-oxo-2,3-di-p-tolyl-7,8-dihydropyrido[2,3-b]pyrazin-5(6H)-yl)heptanoic acid;
7-(2-(4-chlorophenyl)-6-oxo-3-(p-tolyl)-7,8-dihydropyrido[2,3-b]pyrazin-5(6H)-yl)heptanoic acid;
7-(3-(4-chlorophenyl)-6-oxo-2-(p-tolyl)-7,8-dihydropyrido[2,3-b]pyrazin-5(6H)-yl)heptanoic acid;
7-(7-hydroxy-6-oxo-2,3-di-p-tolyl-7,8-dihydropyrido[2,3-b]pyrazin-5(6H)-yl)heptanoic acid;
7-(2-(4-chlorophenyl)-7-hydroxy-6-oxo-3-(p-tolyl)-7,8-dihydropyrido[2,3-b]pyrazin-5(6H)-yl)heptanoic acid;
7-(3-(4-chlorophenyl)-7-hydroxy-6-oxo-2-(p-tolyl)-7,8-dihydropyrido[2,3-b]pyrazin-5(6H)-yl)heptanoic acid;
7-(2,3-bis(4-chlorophenyl)-7-hydroxy-6-oxo-7,8-dihydropyrido[2,3-b]pyrazin-5(6H)-yl)heptanoic acid;
7-(7-hydroxy-2,3-di-p-tolyl-7,8-dihydropyrido[2,3-b]pyrazin-5(6H)-yl)heptanoic acid;
7-(2-(4-chlorophenyl)-7-hydroxy-3-(p-tolyl)-7,8-dihydropyrido[2,3-b]pyrazin-5(6H)-yl)heptanoic acid;
7-(3-(4-chlorophenyl)-7-hydroxy-2-(p-tolyl)-7,8-dihydropyrido[2,3-b]pyrazin-5(6H)-yl)heptanoic acid;
7-(2,3-bis(4-chlorophenyl)-7-hydroxy-7,8-dihydropyrido[2,3-b]pyrazin-5(6H)-yl)heptanoic acid;
7-(8-hydroxy-2,3-di-p-tolyl-7,8-dihydropyrido[2,3-b]pyrazin-5(6H)-yl)heptanoic acid;
7-(2-(4-chlorophenyl)-8-hydroxy-3-(p-tolyl)-7,8-dihydropyrido[2,3-b]pyrazin-5(6H)-yl)heptanoic acid;
7-(3-(4-chlorophenyl)-8-hydroxy-2-(p-tolyl)-7,8-dihydropyrido[2,3-b]pyrazin-5(6H)-yl)heptanoic acid;
7-(2,3-bis(4-chlorophenyl)-8-hydroxy-7,8-dihydropyrido[2,3-b]pyrazin-5(6H)-yl)heptanoic acid;
7-(2,3-di-p-tolyl-7,8-dihydropyrido[2,3-b]pyrazin-5(6H)-yl)-N-(phenylsulfonyl)heptanamide;
7-(2-(4-chlorophenyl)-3-(p-tolyl)-7,8-dihydropyrido[2,3-b]pyrazin-5(6H)-yl)-N-(phenylsulfonyl)heptanamide;
7-(3-(4-chlorophenyl)-2-(p-tolyl)-7,8-dihydropyrido[2,3-b]pyrazin-5(6H)-yl)-N-(phenylsulfonyl)heptanamide;
7-(2,3-bis(4-chlorophenyl)-7,8-dihydropyrido[2,3-b]pyrazin-5(6H)-yl)-N-(phenylsulfonyl)heptanamide;
7-(6-oxo-2,3-di-p-tolyl-7,8-dihydropyrido[2,3-b]pyrazin-5(6H)-yl)-N-(phenylsulfonyl)heptanamide;
7-(2-(4-chlorophenyl)-6-oxo-3-(p-tolyl)-7,8-dihydropyrido[2,3-b]pyrazin-5(6H)-yl)-N-(phenylsulfonyl)heptanamide;
7-(3-(4-chlorophenyl)-6-oxo-2-(p-tolyl)-7,8-dihydropyrido[2,3-b]pyrazin-5(6H)-yl)-N-(phenylsulfonyl)heptanamide;
7-(2,3-bis(4-chlorophenyl)-6-oxo-7,8-dihydropyrido[2,3-b]pyrazin-5(6H)-yl)-N-(phenylsulfonyl)heptanamide;
7-(7-hydroxy-6-oxo-2,3-di-p-tolyl-7,8-dihydropyrido[2,3-b]pyrazin-5(6H)-yl)-N-(phenylsulfonyl)heptanamide;
7-(2-(4-chlorophenyl)-7-hydroxy-6-oxo-3-(p-tolyl)-7,8-dihydropyrido[2,3-b]pyrazin-5(6H)-yl)-N-(phenylsulfonyl)heptanamide;
7-(3-(4-chlorophenyl)-7-hydroxy-6-oxo-2-(p-tolyl)-7,8-dihydropyrido[2,3-b]pyrazin-5(6H)-yl)-N-(phenylsulfonyl)heptanamide;
7-(2,3-bis(4-chlorophenyl)-7-hydroxy-6-oxo-7,8-dihydropyrido[2,3-b]pyrazin-5(6H)-yl)-N-(phenylsulfonyl)heptanamide;
7-(7-hydroxy-2,3-di-p-tolyl-7,8-dihydropyrido[2,3-b]pyrazin-5(6H)-yl)-N-(phenylsulfonyl)heptanamide;
7-(2-(4-chlorophenyl)-7-hydroxy-3-(p-tolyl)-7,8-dihydropyrido[2,3-b]pyrazin-5(6H)-yl)-N-(phenylsulfonyl)heptanamide;
7-(3-(4-chlorophenyl)-7-hydroxy-2-(p-tolyl)-7,8-dihydropyrido[2,3-b]pyrazin-5(6H)-yl)-N-(phenylsulfonyl)heptanamide;
7-(2,3-bis(4-chlorophenyl)-7-hydroxy-7,8-dihydropyrido[2,3-b]pyrazin-5(6H)-yl)-N-(phenylsulfonyl)heptanamide;
7-(8-hydroxy-2,3-di-p-tolyl-7,8-dihydropyrido[2,3-b]pyrazin-5(6H)-yl)-N-(phenylsulfonyl)heptanamide;
7-(2-(4-chlorophenyl)-8-hydroxy-3-(p-tolyl)-7,8-dihydropyrido[2,3-b]pyrazin-5(6H)-yl)-N-(phenylsulfonyl)heptanamide;
7-(3-(4-chlorophenyl)-8-hydroxy-2-(p-tolyl)-7,8-dihydropyrido[2,3-b]pyrazin-5(6H)-yl)-N-(phenylsulfonyl)heptanamide;
7-(2,3-bis(4-chlorophenyl)-8-hydroxy-7,8-dihydropyrido[2,3-b]pyrazin-5(6H)-yl)-N-(phenylsulfonyl)heptanamide;
N-(benzylsulfonyl)-7-(2,3-bis(4-chlorophenyl)-7,8-dihydropyrido[2,3-b]pyrazin-5(6H)-yl)heptanamide;
N-(benzylsulfonyl)-7-(2-(4-chlorophenyl)-3-(p-tolyl)-7,8-dihydropyrido[2,3-b]pyrazin-5(6H)-yl)heptanamide;
N-(benzylsulfonyl)-7-(3-(4-chlorophenyl)-2-(p-tolyl)-7,8-dihydropyrido[2,3-b]pyrazin-5(6H)-yl)heptanamide;
N-(benzylsulfonyl)-7-(6-oxo-2,3-di-p-tolyl-7,8-dihydropyrido[2,3-b]pyrazin-5(6H)-yl)heptanamide;
N-(benzylsulfonyl)-7-(3-(4-chlorophenyl)-6-oxo-2-(p-tolyl)-7,8-dihydropyrido[2,3-b]pyrazin-5(6H)-yl)heptanamide;
N-(benzylsulfonyl)-7-(7-hydroxy-6-oxo-2,3-di-p-tolyl-7,8-dihydropyrido[2,3-b]pyrazin-5(6H)-yl)heptanamide;
N-(benzylsulfonyl)-7-(3-(4-chlorophenyl)-7-hydroxy-6-oxo-2-(p-tolyl)-7,8-dihydropyrido[2,3-b]pyrazin-5(6H)-yl)heptanamide;
N-(benzylsulfonyl)-7-(7-hydroxy-2,3-di-p-tolyl-7,8-dihydropyrido[2,3-b]pyrazin-5(6H)-yl)heptanamide;
N-(benzylsulfonyl)-7-(3-(4-chlorophenyl)-7-hydroxy-2-(p-tolyl)-7,8-dihydropyrido[2,3-b]pyrazin-5(6H)-yl)heptanamide;
N-(benzylsulfonyl)-7-(8-hydroxy-2,3-di-p-tolyl-7,8-dihydropyrido[2,3-b]pyrazin-5(6H)-yl)heptanamide;
N-(benzylsulfonyl)-7-(3-(4-chlorophenyl)-8-hydroxy-2-(p-tolyl)-7,8-dihydropyrido[2,3-b]pyrazin-5(6H)-yl)heptanamide;
7-(2-(4-chlorophenyl)-3-(p-tolyl)-7,8-dihydropyrido[2,3-b]pyrazin-5(6H)-yl)-N-phenylheptanamide;
7-(3-(4-chlorophenyl)-2-(p-tolyl)-7,8-dihydropyrido[2,3-b]pyrazin-5(6H)-yl)-N-phenylheptanamide;
7-(2,3-bis(4-chlorophenyl)-7,8-dihydropyrido[2,3-b]pyrazin-5(6H)-yl)-N-phenylheptanamide;
7-(6-oxo-2,3-di-p-tolyl-7,8-dihydropyrido[2,3-b]pyrazin-5(6H)-yl)-N-phenylheptanamide;
7-(2-(4-chlorophenyl)-6-oxo-3-(p-tolyl)-7,8-dihydropyrido[2,3-b]pyrazin-5(6H)-yl)-N-phenylheptanamide;

7-(3-(4-chlorophenyl)-6-oxo-2-(p-tolyl)-7,8-dihydropyrido[2,3-b]pyrazin-5(6H)-yl)-N-phenylheptanamide;

7-(2,3-bis(4-chlorophenyl)-6-oxo-7,8-dihydropyrido[2,3-b]pyrazin-5(6H)-yl)-N-phenylheptanamide;

7-(7-hydroxy-6-oxo-2,3-di-p-tolyl-7,8-dihydropyrido[2,3-b]pyrazin-5(6H)-yl)-N-phenylheptanamide;

7-(2-(4-chlorophenyl)-7-hydroxy-6-oxo-3-(p-tolyl)-7,8-dihydropyrido[2,3-b]pyrazin-5(6H)-yl)-N-phenylheptanamide;

7-(3-(4-chlorophenyl)-7-hydroxy-6-oxo-2-(p-tolyl)-7,8-dihydropyrido[2,3-b]pyrazin-5(6H)-yl)-N-phenylheptanamide;

7-(2,3-bis(4-chlorophenyl)-7-hydroxy-6-oxo-7,8-dihydropyrido[2,3-b]pyrazin-5(6H)-yl)-N-phenylheptanamide;

7-(7-hydroxy-2,3-di-p-tolyl-7,8-dihydropyrido[2,3-b]pyrazin-5(6H)-yl)-N-phenylheptanamide;

7-(2-(4-chlorophenyl)-7-hydroxy-3-(p-tolyl)-7,8-dihydropyrido[2,3-b]pyrazin-5(6H)-yl)-N-phenylheptanamide;

7-(3-(4-chlorophenyl)-7-hydroxy-2-(p-tolyl)-7,8-dihydropyrido[2,3-b]pyrazin-5(6H)-yl)-N-phenylheptanamide;

7-(2,3-bis(4-chlorophenyl)-7-hydroxy-7,8-dihydropyrido[2,3-b]pyrazin-5(6H)-yl)-N-phenylheptanamide;

7-(8-hydroxy-2,3-di-p-tolyl-7,8-dihydropyrido[2,3-b]pyrazin-5(6H)-yl)-N-phenylheptanamide;

7-(2-(4-chlorophenyl)-8-hydroxy-3-(p-tolyl)-7,8-dihydropyrido[2,3-b]pyrazin-5(6H)-yl)-N-phenylheptanamide;

7-(3-(4-chlorophenyl)-8-hydroxy-2-(p-tolyl)-7,8-dihydropyrido[2,3-b]pyrazin-5(6H)-yl)-N-phenylheptanamide;

7-(2,3-bis(4-chlorophenyl)-8-hydroxy-7,8-dihydropyrido[2,3-b]pyrazin-5(6H)-yl)-N-phenylheptanamide;

N-benzyl-7-(2,3-di-p-tolyl-7,8-dihydropyrido[2,3-b]pyrazin-5(6H)-yl)heptanamide;

N-benzyl-7-(2-(4-chlorophenyl)-3-(p-tolyl)-7,8-dihydropyrido[2,3-b]pyrazin-5(6H)-yl)heptanamide;

N-benzyl-7-(3-(4-chlorophenyl)-2-(p-tolyl)-7,8-dihydropyrido[2,3-b]pyrazin-5(6H)-yl)heptanamide;

N-benzyl-7-(2,3-bis(4-chlorophenyl)-7,8-dihydropyrido[2,3-b]pyrazin-5(6H)-yl)heptanamide;

N-benzyl-7-(6-oxo-2,3-di-p-tolyl-7,8-dihydropyrido[2,3-b]pyrazin-5(6H)-yl)heptanamide;

N-benzyl-7-(2-(4-chlorophenyl)-6-oxo-3-(p-tolyl)-7,8-dihydropyrido[2,3-b]pyrazin-5(6H)-yl)heptanamide;

N-benzyl-7-(3-(4-chlorophenyl)-6-oxo-2-(p-tolyl)-7,8-dihydropyrido[2,3-b]pyrazin-5(6H)-yl)heptanamide;

N-benzyl-7-(2,3-bis(4-chlorophenyl)-6-oxo-7,8-dihydropyrido[2,3-b]pyrazin-5(6H)-yl)heptanamide;

N-benzyl-7-(7-hydroxy-6-oxo-2,3-di-p-tolyl-7,8-dihydropyrido[2,3-b]pyrazin-5(6H)-yl)heptanamide;

N-benzyl-7-(2-(4-chlorophenyl)-7-hydroxy-6-oxo-3-(p-tolyl)-7,8-dihydropyrido[2,3-b]pyrazin-5(6H)-yl)heptanamide;

N-benzyl-7-(3-(4-chlorophenyl)-7-hydroxy-6-oxo-2-(p-tolyl)-7,8-dihydropyrido[2,3-b]pyrazin-5(6H)-yl)heptanamide;

N-benzyl-7-(2,3-bis(4-chlorophenyl)-7-hydroxy-6-oxo-7,8-dihydropyrido[2,3-b]pyrazin-5(6H)-yl)heptanamide;

N-benzyl-7-(7-hydroxy-2,3-di-p-tolyl-7,8-dihydropyrido[2,3-b]pyrazin-5(6H)-yl)heptanamide;

N-benzyl-7-(2-(4-chlorophenyl)-7-hydroxy-3-(p-tolyl)-7,8-dihydropyrido[2,3-b]pyrazin-5(6H)-yl)heptanamide;

N-benzyl-7-(3-(4-chlorophenyl)-7-hydroxy-2-(p-tolyl)-7,8-dihydropyrido[2,3-b]pyrazin-5(6H)-yl)heptanamide;

N-benzyl-7-(2,3-bis(4-chlorophenyl)-7-hydroxy-7,8-dihydropyrido[2,3-b]pyrazin-5(6H)-yl)heptanamide;

N-benzyl-7-(8-hydroxy-2,3-di-p-tolyl-7,8-dihydropyrido[2,3-b]pyrazin-5(6H)-yl)heptanamide;

N-benzyl-7-(2-(4-chlorophenyl)-8-hydroxy-3-(p-tolyl)-7,8-dihydropyrido[2,3-b]pyrazin-5(6H)-yl)heptanamide;

N-benzyl-7-(3-(4-chlorophenyl)-8-hydroxy-2-(p-tolyl)-7,8-dihydropyrido[2,3-b]pyrazin-5(6H)-yl)heptanamide;

N-benzyl-7-(2,3-bis(4-chlorophenyl)-8-hydroxy-7,8-dihydropyrido[2,3-b]pyrazin-5(6H)-yl)heptanamide;

7-(2-(4-chlorophenyl)-3-(p-tolyl)-7,8-dihydropyrido[2,3-b]pyrazin-5(6H)-yl)-N-(methylsulfonyl)heptanamide;

7-(3-(4-chlorophenyl)-2-(p-tolyl)-7,8-dihydropyrido[2,3-b]pyrazin-5(6H)-yl)-N-(methylsulfonyl)heptanamide;

7-(2,3-bis(4-chlorophenyl)-7,8-dihydropyrido[2,3-b]pyrazin-5(6H)-yl)-N-(methylsulfonyl)heptanamide;

7-(2-(4-chlorophenyl)-3-(p-tolyl)-7,8-dihydropyrido[2,3-b]pyrazin-5(6H)-yl)-N-(isopropylsulfonyl)heptanamide;

7-(3-(4-chlorophenyl)-2-(p-tolyl)-7,8-dihydropyrido[2,3-b]pyrazin-5(6H)-yl)-N-(isopropylsulfonyl)heptanamide;

7-(2,3-bis(4-chlorophenyl)-7,8-dihydropyrido[2,3-b]pyrazin-5(6H)-yl)-N-(isopropylsulfonyl)heptanamide;

7-(2-(4-chlorophenyl)-3-(p-tolyl)-7,8-dihydropyrido[2,3-b]pyrazin-5(6H)-yl)-N-methylheptanamide;

7-(3-(4-chlorophenyl)-2-(p-tolyl)-7,8-dihydropyrido[2,3-b]pyrazin-5(6H)-yl)-N-methylheptanamide;

7-(2,3-bis(4-chlorophenyl)-7,8-dihydropyrido[2,3-b]pyrazin-5(6H)-yl)-N-methylheptanamide;

7-(2-(4-chlorophenyl)-3-(p-tolyl)-7,8-dihydropyrido[2,3-b]pyrazin-5(6H)-yl)-N-isopropylheptanamide;

7-(3-(4-chlorophenyl)-2-(p-tolyl)-7,8-dihydropyrido[2,3-b]pyrazin-5(6H)-yl)-N-isopropylheptanamide;

7-(2,3-bis(4-chlorophenyl)-7,8-dihydropyrido[2,3-b]pyrazin-5(6H)-yl)-N-isopropylheptanamide;

7-(2-(4-chlorophenyl)-3-(p-tolyl)-7,8-dihydropyrido[2,3-b]pyrazin-5(6H)-yl)-N-hydroxyheptanamide;

7-(3-(4-chlorophenyl)-2-(p-tolyl)-7,8-dihydropyrido[2,3-b]pyrazin-5(6H)-yl)-N-hydroxyheptanamide;

6-(5-methyl-2,3-di-p-tolyl-5,6,7,8-tetrahydropyrido[2,3-b]pyrazin-6-yl)hexanoic acid;

6-(5-isopropyl-2,3-di-p-tolyl-5,6,7,8-tetrahydropyrido[2,3-b]pyrazin-6-yl)hexanoic acid;

5-(2,3-di-p-tolyl-5,6,7,8-tetrahydropyrido[2,3-b]pyrazin-6-yl)pentanoic acid;

5-(5-methyl-2,3-di-p-tolyl-5,6,7,8-tetrahydropyrido[2,3-b]pyrazin-6-yl)pentanoic acid;

5-(5-isopropyl-2,3-di-p-tolyl-5,6,7,8-tetrahydropyrido[2,3-b]pyrazin-6-yl)pentanoic acid;

7-(2,3-di-p-tolyl-5,6,7,8-tetrahydropyrido[2,3-b]pyrazin-6-yl)heptanoic acid;

7-(5-methyl-2-phenyl-3-(p-tolyl)-5,6,7,8-tetrahydropyrido[2,3-b]pyrazin-6-yl)heptanoic acid;

7-(5-isopropyl-2,3-di-p-tolyl-5,6,7,8-tetrahydropyrido[2,3-b]pyrazin-6-yl)heptanoic acid;

6-(7-hydroxy-2,3-di-p-tolyl-5,6,7,8-tetrahydropyrido[2,3-b]pyrazin-6-yl)hexanoic acid;

6-(7-hydroxy-5-methyl-2,3-di-p-tolyl-5,6,7,8-tetrahydropyrido[2,3-b]pyrazin-6-yl)hexanoic acid;

6-(7-hydroxy-5-isopropyl-2,3-di-p-tolyl-5,6,7,8-tetrahydropyrido[2,3-b]pyrazin-6-yl)hexanoic acid;

5-(7-hydroxy-2,3-di-p-tolyl-5,6,7,8-tetrahydropyrido[2,3-b]pyrazin-6-yl)pentanoic acid;

5-(7-hydroxy-5-methyl-2,3-di-p-tolyl-5,6,7,8-tetrahydropyrido[2,3-b]pyrazin-6-yl)pentanoic acid;

5-(7-hydroxy-5-isopropyl-2,3-di-p-tolyl-5,6,7,8-tetrahydropyrido[2,3-b]pyrazin-6-yl)pentanoic acid;
7-(7-hydroxy-2,3-di-p-tolyl-5,6,7,8-tetrahydropyrido[2,3-b]pyrazin-6-yl)heptanoic acid;
7-(7-hydroxy-5-methyl-2-phenyl-3-(p-tolyl)-5,6,7,8-tetrahydropyrido[2,3-b]pyrazin-6-yl)heptanoic acid;
7-(7-hydroxy-5-isopropyl-2,3-di-p-tolyl-5,6,7,8-tetrahydropyrido[2,3-b]pyrazin-6-yl)heptanoic acid;
6-(8-hydroxy-2,3-di-p-tolyl-5,6,7,8-tetrahydropyrido[2,3-b]pyrazin-6-yl)hexanoic acid;
6-(8-hydroxy-5-methyl-2,3-di-p-tolyl-5,6,7,8-tetrahydropyrido[2,3-b]pyrazin-6-yl)hexanoic acid;
6-(8-hydroxy-5-isopropyl-2,3-di-p-tolyl-5,6,7,8-tetrahydropyrido[2,3-b]pyrazin-6-yl)hexanoic acid;
5-(8-hydroxy-2,3-di-p-tolyl-5,6,7,8-tetrahydropyrido[2,3-b]pyrazin-6-yl)pentanoic acid;
5-(8-hydroxy-5-methyl-2,3-di-p-tolyl-5,6,7,8-tetrahydropyrido[2,3-b]pyrazin-6-yl)pentanoic acid;
5-(8-hydroxy-5-isopropyl-2,3-di-p-tolyl-5,6,7,8-tetrahydropyrido[2,3-b]pyrazin-6-yl)pentanoic acid;
7-(8-hydroxy-2,3-di-p-tolyl-5,6,7,8-tetrahydropyrido[2,3-b]pyrazin-6-yl)heptanoic acid;
7-(8-hydroxy-5-methyl-2,3-di-p-tolyl-5,6,7,8-tetrahydropyrido[2,3-b]pyrazin-6-yl)heptanoic acid;
7-(8-hydroxy-5-isopropyl-2,3-di-p-tolyl-5,6,7,8-tetrahydropyrido[2,3-b]pyrazin-6-yl)heptanoic acid; and
7-(2,3-bis(4-chlorophenyl)-7,8-dihydropyrido[2,3-b]pyrazin-5(6H)-yl)-N-hydroxyheptanamide;
or a pharmaceutically acceptable salt thereof.

2. The compound according to claim 1, which is selected from the group consisting of
(rac)-6-(2,3-di-p-tolyl-5,6,7,8-tetrahydropyrido[2,3-b]pyrazin-6-yl)hexanoic acid;
(S)-6-(2,3-di-p-tolyl-5,6,7,8-tetrahydropyrido[2,3-b]pyrazin-6-yl)hexanoic acid;
(R)-6-(2,3-di-p-tolyl-5,6,7,8-tetrahydropyrido[2,3-b]pyrazin-6-yl)hexanoic acid;
(rac)-7-(7-(2-Hydroxypropan-2-yl)-6-oxo-2,3-di-p-tolyl-7,8-dihydropyrido[2,3-b]pyrazin-5(6H)-yl)heptanoic acid;
(R)-7-(7-(2-hydroxypropan-2-yl)-6-oxo-2,3-di-p-tolyl-7,8-dihydropyrido[2,3-b]pyrazin-5(6H)-yl)heptanoic acid;
(S)-7-(7-(2-hydroxypropan-2-yl)-6-oxo-2,3-di-p-tolyl-7,8-dihydropyrido[2,3-b]pyrazin-5(6H)-yl)heptanoic acid;
7-(7-Ethyl-2,3-di-p-tolyl-7,8-dihydropyrido[2,3-b]pyrazin-5(6H)-yl)heptanoic acid;
7-(7-Methyl-2-phenyl-3-(p-tolyl)-7,8-dihydropyrido[2,3-b]pyrazin-5(6H)-yl)heptanoic acid;
(rac)-7-(6-Ethyl-2,3-di-p-tolyl-7,8-dihydropyrido[2,3-b]pyrazin-5(6H)-yl)heptanoic acid;
(R)-7-(6-Ethyl-2,3-di-p-tolyl-7,8-dihydropyrido[2,3-b]pyrazin-5(6H)-yl)heptanoic acid;
(S)-7-(6-Ethyl-2,3-di-p-tolyl-7,8-dihydropyrido[2,3-b]pyrazin-5(6H)-yl)heptanoic acid;
7-(6-Methyl-2-phenyl-3-p-tolyl-7,8-dihydropyrido[2,3-b]pyrazin-5(6H)-yl)heptanoic acid;
7-(3-o-Tolyl-2-p-tolyl-7,8-dihydropyrido[3,2-b]pyrazin-5(6H)-yl)heptanoic acid;
7-(2-o-Tolyl-3-p-tolyl-7,8-dihydropyrido[3,2-b]pyrazin-5(6H)-yl)heptanoic acid;
7-(2-(2-Fluorophenyl)-3-p-tolyl-7,8-dihydropyrido[2,3-b]pyrazin-5(6H)-yl)heptanoic acid;
7-(2-(4-Fluorophenyl)-3-p-tolyl-7,8-dihydropyrido[2,3-b]pyrazin-5(6H)-yl)heptanoic acid;
7-(2-(3-Fluorophenyl)-3-p-tolyl-7,8-dihydropyrido[2,3-b]pyrazin-5(6H)-yl)heptanoic acid;
7-(2-(4-Methoxyphenyl)-3-p-tolyl-7,8-dihydropyrido[2,3-b]pyrazin-5(6H)-yl)heptanoic acid;
(rac)-7-(8-Methoxy-2,3-di-p-tolyl-7,8-dihydropyrido[2,3-b]pyrazin-5(6H)-yl)heptanoic acid;
(R)-7-(8-methoxy-2,3-di-p-tolyl-7,8-dihydropyrido[2,3-b]pyrazin-5(6H)-yl)heptanoic acid;
(S)-7-(8-methoxy-2,3-di-p-tolyl-7,8-dihydropyrido[2,3-b]pyrazin-5(6H)-yl)heptanoic acid;
7-(2,3-Bis(2,4-difluorophenyl)-7,8-dihydropyrido[2,3-b]pyrazin-5(6H)-yl)heptanoic acid;
7-(2,3-Bis(6-methylpyridin-3-yl)-7,8-dihydropyrido[2,3-b]pyrazin-5(6H)-yl)heptanoic acid;
7-(2-(6-Methylpyridin-3-yl)-3-p-tolyl-7,8-dihydropyrido[2,3-b]pyrazin-5(6H)-yl)heptanoic acid;
7-(3-(6-Methylpyridin-3-yl)-2-p-tolyl-7,8-dihydropyrido[2,3-b]pyrazin-5(6H)-yl)heptanoic acid;
9-(6-Oxo-2,3-di-p-tolyl-7,8-dihydropyrido[2,3-b]pyrazin-5(6H)-yl)nonanoic acid;
9-(2,3-Di-p-tolyl-7,8-dihydropyrido[2,3-b]pyrazin-5(6H)-yl)nonanoic acid;
(rac)-7-(7-(2-hydroxypropan-2-yl)-2,3-di-p-tolyl-7,8-dihydropyrido[2,3-b]pyrazin-5(6H)-yl)heptanoic acid;
(R)-7-(7-(2-hydroxypropan-2-yl)-2,3-di-p-tolyl-7,8-dihydropyrido[2,3-b]pyrazin-5(6H)-yl)heptanoic acid;
(S)-7-(7-(2-hydroxypropan-2-yl)-2,3-di-p-tolyl-7,8-dihydropyrido[2,3-b]pyrazin-5(6H)-yl)heptanoic acid;
6-(2,3-Di-p-tolyl-7,8-dihydropyrido[2,3-b]pyrazin-5(6H)-yl)hexanoic acid;
(R)-7-(7-hydroxy-6-oxo-2,3-di-p-tolyl-7,8-dihydropyrido[2,3-b]pyrazin-5(6H)-yl)heptanoic acid;
(S)-7-(7-hydroxy-6-oxo-2,3-di-p-tolyl-7,8-dihydropyrido[2,3-b]pyrazin-5(6H)-yl)heptanoic acid;
8-(6-Oxo-2,3-di-p-tolyl-7,8-dihydropyrido[2,3-b]pyrazin-5(6H)-yl)octanoic acid;
7-(2,3-Di-p-tolyl-7,8-dihydropyrido[2,3-b]pyrazin-5(6H)-yl)-N-methoxyheptanamide;
7-(2,3-Di-p-tolyl-7,8-dihydropyrido[2,3-b]pyrazin-5(6H)-yl)-N,N-dimethylheptanamide;
7-(2,3-Di-p-tolyl-7,8-dihydropyrido[2,3-b]pyrazin-5(6H)-yl)-N-hydroxy-N-methylheptanamide;
6-(2,3-Di-p-tolyl-7,8-dihydropyrido[2,3-b]pyrazin-5(6H)-yl)-N-hydroxyhexanamide;
(R)-7-(8-Hydroxy-2,3-di-p-tolyl-7,8-dihydropyrido[3,2-b]pyrazin-5(6H)-yl)-N-(methylsulfonyl)heptanamide;
(S)-7-(8-Hydroxy-2,3-di-p-tolyl-7,8-dihydropyrido[3,2-b]pyrazin-5(6H)-yl)-N-(methylsulfonyl)heptanamide;
(R)—N-(Benzylsulfonyl)-7-(8-hydroxy-2,3-di-p-tolyl-7,8-dihydropyrido[3,2-b]pyrazin-5(6H)-yl)heptanamide;
(S)—N-(Benzylsulfonyl)-7-(8-hydroxy-2,3-di-p-tolyl-7,8-dihydropyrido[3,2-b]pyrazin-5(6H)-yl)heptanamide;
7-(2,3-Di-p-tolyl-7,8-dihydropyrido[2,3-b]pyrazin-5(6H)-yl)-N-(methylsulfonyl)heptanamide;
7-(7-Piperidin-1-yl)-2,3-di-p-tolyl-7,8-dihydropyrido[2,3-b]pyrazin-5(6H)-yl)heptanoic acid;
rac-7-(8-Methoxy-8-methyl-2,3-di-p-tolyl-7,8-dihydropyrido[2,3-b]pyrazin-5(6H)-yl)heptanoic acid;
7-(8-Hydroxy-8-methyl-2,3-di-p-tolyl-7,8-dihydropyrido[2,3-b]pyrazin-5(6H)-yl)heptanoic acid;
rac-7-(2,3-Di-p-tolyl-7,8-dihydropyrido[2,3-b]pyrazin-5(6H)-yl)-3-hydroxyheptanoic acid;
(R)-7-(8-Methoxy-8-methyl-2,3-di-p-tolyl-7,8-dihydropyrido[2,3-b]pyrazin-5(6H)-yl)heptanoic acid;
(S)-7-(8-Methoxy-8-methyl-2,3-di-p-tolyl-7,8-dihydropyrido[2,3-b]pyrazin-5(6H)-yl)heptanoic acid;

(R)-7-(2,3-di-p-tolyl-7,8-dihydropyrido[2,3-b]pyrazin-5(6H)-yl)-3-hydroxyheptanoic acid;
(S)-7-(2,3-di-p-tolyl-7,8-dihydropyrido[2,3-b]pyrazin-5(6H)-yl)-3-hydroxyheptanoic acid;
7-(2,3-Bis(4-chlorophenyl)-6-oxo-7,8-dihydropyrido[2,3-b]pyrazin-5(6H)-yl)heptanoic acid;
7-(2-(4-Chlorophenyl)-6-oxo-3-p-tolyl-7,8-dihydropyrido[2,3-b]pyrazin-5(6H)-yl)heptanoic acid;
7-(3-(4-Chlorophenyl)-6-oxo-2-p-tolyl-7,8-dihydropyrido[2,3-b]pyrazin-5(6H)-yl)heptanoic acid;
N-(Benzylsulfonyl)-7-(2,3-di-p-tolyl-7,8-dihydropyrido[2,3-b]pyrazin-5(6H)-yl)heptanamide;
N-Benzyl-7-(2,3-di-p-tolyl-7,8-dihydro pyrido[2,3-b]pyrazin-5(6H)-yl)heptanamide;
7-(2,3-Di-p-tolyl-7,8-dihydro pyrido[2,3-b]pyrazin-5(6H)-yl)-N-(phenyl sulfonyl) heptanamide;
7-(2,3-Di-p-tolyl-7,8-dihydropyrido[2,3-b]pyrazin-5(6H)-yl)-N-isopropylheptanamide;
7-(2,3-Di-p-tolyl-7,8-dihydropyrido[2,3-b]pyrazin-5(6H)-yl)-N-methylheptanamide;
7-(2,3-Di-p-tolyl-7,8-dihydropyrido[2,3-b]pyrazin-5(6H)-yl)-N-phenylheptanamide;
7-(2,3-Di-p-tolyl-7,8-dihydropyrido[2,3-b]pyrazin-5(6H)-yl)-N-hydroxyheptanamide; and
7-(2,3-Di-p-tolyl-7,8-dihydropyrido[2,3-b]pyrazin-5(6H)-yl)-N-(isopropylsulfonyl)heptanamide;
or a pharmaceutically acceptable salt thereof.

3. The compound according to claim 1 selected from the group consisting of
(rac)-6-(2,3-di-p-tolyl-5,6,7,8-tetrahydropyrido[2,3-b]pyrazin-6-yl)hexanoic acid;
(R)-6-(2,3-di-p-tolyl-5,6,7,8-tetrahydropyrido[2,3-b]pyrazin-6-yl)hexanoic acid;
(S)-6-(2,3-di-p-tolyl-5,6,7,8-tetrahydropyrido[2,3-b]pyrazin-6-yl)hexanoic acid;
(rac)-7-(7-(2-Hydroxypropan-2-yl)-6-oxo-2,3-di-p-tolyl-7,8-dihydropyrido[2,3-b]pyrazin-5(6H)-yl)heptanoic acid;
(R)-7-(7-(2-hydroxypropan-2-yl)-6-oxo-2,3-di-p-tolyl-7,8-dihydropyrido[2,3-b]pyrazin-5(6H)-yl)heptanoic acid;
(S)-7-(7-(2-hydroxypropan-2-yl)-6-oxo-2,3-di-p-tolyl-7,8-dihydropyrido[2,3-b]pyrazin-5(6H)-yl)heptanoic acid;
7-(7-Ethyl-2,3-di-p-tolyl-7,8-dihydropyrido[2,3-b]pyrazin-5(6H)-yl)heptanoic acid;
7-(7-Methyl-2-phenyl-3-(p-tolyl)-7,8-dihydropyrido[2,3-b]pyrazin-5(6H)-yl)heptanoic acid;
(rac)-7-(6-Ethyl-2,3-di-p-tolyl-7,8-dihydropyrido[2,3-b]pyrazin-5(6H)-yl)heptanoic acid;
(R)-7-(6-Ethyl-2,3-di-p-tolyl-7,8-dihydropyrido[2,3-b]pyrazin-5(6H)-yl)heptanoic acid;
(S)-7-(6-Ethyl-2,3-di-p-tolyl-7,8-dihydropyrido[2,3-b]pyrazin-5(6H)-yl)heptanoic acid;
7-(6-Methyl-2-phenyl-3-p-tolyl-7,8-dihydropyrido[2,3-b]pyrazin-5(6H)-yl)heptanoic acid;
7-(3-o-Tolyl-2-p-tolyl-7,8-dihydropyrido[3,2-b]pyrazin-5(6H)-yl)heptanoic acid;
7-(2-o-Tolyl-3-p-tolyl-7,8-dihydropyrido[3,2-b]pyrazin-5(6H)-yl)heptanoic acid;
7-(2-(2-Fluorophenyl)-3-p-tolyl-7,8-dihydropyrido[2,3-b]pyrazin-5(6H)-yl)heptanoic acid;
7-(2-(4-Fluorophenyl)-3-p-tolyl-7,8-dihydropyrido[2,3-b]pyrazin-5(6H)-yl)heptanoic acid;
7-(2-(3-Fluorophenyl)-3-p-tolyl-7,8-dihydropyrido[2,3-b]pyrazin-5(6H)-yl)heptanoic acid;
7-(2-(4-Methoxyphenyl)-3-p-tolyl-7,8-dihydropyrido[2,3-b]pyrazin-5(6H)-yl)heptanoic acid;
(rac)-7-(8-Methoxy-2,3-di-p-tolyl-7,8-dihydropyrido[2,3-b]pyrazin-5(6H)-yl)heptanoic acid;
(R)-7-(8-methoxy-2,3-di-p-tolyl-7,8-dihydropyrido[2,3-b]pyrazin-5(6H)-yl)heptanoic acid;
(S)-7-(8-methoxy-2,3-di-p-tolyl-7,8-dihydropyrido[2,3-b]pyrazin-5(6H)-yl)heptanoic acid;
7-(2,3-Bis(2,4-difluorophenyl)-7,8-dihydropyrido[2,3-b]pyrazin-5(6H)-yl)heptanoic acid;
7-(2,3-Bis(6-methylpyridin-3-yl)-7,8-dihydropyrido[2,3-b]pyrazin-5(6H)-yl)heptanoic acid;
7-(2-(6-Methylpyridin-3-yl)-3-p-tolyl-7,8-dihydropyrido[2,3-b]pyrazin-5(6H)-yl)heptanoic acid;
7-(3-(6-Methylpyridin-3-yl)-2-p-tolyl-7,8-dihydropyrido[2,3-b]pyrazin-5(6H)-yl)heptanoic acid;
9-(6-Oxo-2,3-di-p-tolyl-7,8-dihydropyrido[2,3-b]pyrazin-5(6H)-yl)nonanoic acid; 9-(2,3-Di-p-tolyl-7,8-dihydropyrido[2,3-b]pyrazin-5(6H)-yl)nonanoic acid;
(rac)-7-(7-(2-hydroxypropan-2-yl)-2,3-di-p-tolyl-7,8-dihydropyrido[2,3-b]pyrazin-5(6H)-yl)heptanoic acid;
(R)-7-(7-(2-hydroxypropan-2-yl)-2,3-di-p-tolyl-7,8-dihydropyrido[2,3-b]pyrazin-5(6H)-yl)heptanoic acid;
(S)-7-(7-(2-hydroxypropan-2-yl)-2,3-di-p-tolyl-7,8-dihydropyrido[2,3-b]pyrazin-5(6H)-yl)heptanoic acid;
6-(2,3-Di-p-tolyl-7,8-dihydropyrido[2,3-b]pyrazin-5(6H)-yl)hexanoic acid;
(R)-7-(7-hydroxy-6-oxo-2,3-di-p-tolyl-7,8-dihydropyrido[2,3-b]pyrazin-5(6H)-yl)heptanoic acid; and
(S)-7-(7-hydroxy-6-oxo-2,3-di-p-tolyl-7,8-dihydropyrido[2,3-b]pyrazin-5(6H)-yl)heptanoic acid;
or a pharmaceutically acceptable salt thereof.

4. A pharmaceutical composition, comprising:
a therapeutically effective amount of the compound according to claim 1, or a pharmaceutically acceptable salt thereof, and one or more pharmaceutically acceptable carriers.

5. The pharmaceutical composition according to claim 4, further comprising: a second active agent.

6. A method of activating prostacyclin receptor activity in a subject in need thereof, comprising:
administering to said subject a therapeutically effective amount of the compound according to claim 1, or a pharmaceutically acceptable salt thereof.

7. The method according to claim 6, wherein said subject has a disorder or disease selected from the group consisting of pulmonary arterial hypertension, cystic fibrosis and fibrotic diseases.

* * * * *